US011434265B2

(12) United States Patent
Liu

(10) Patent No.: US 11,434,265 B2
(45) Date of Patent: Sep. 6, 2022

(54) CHIMERIC NEUROTOXINS

(71) Applicant: Ipsen Biopharm Limited, Wrexham (GB)

(72) Inventor: Sai Man Liu, Oxford (GB)

(73) Assignee: IPSEN BIOPHARM LIMITED, Wrexham (GB)

( * ) Notice: Subject to any disclaimer, the term of this patent is extended or adjusted under 35 U.S.C. 154(b) by 324 days.

(21) Appl. No.: 16/094,254

(22) PCT Filed: May 5, 2017

(86) PCT No.: PCT/EP2017/060821
§ 371 (c)(1),
(2) Date: Oct. 17, 2018

(87) PCT Pub. No.: WO2017/191315
PCT Pub. Date: Nov. 9, 2017

(65) Prior Publication Data
US 2019/0127427 A1  May 2, 2019

(30) Foreign Application Priority Data
May 5, 2016 (GB) ..................................... 1607901

(51) Int. Cl.
*C07K 14/33* (2006.01)
*C12N 9/52* (2006.01)
*A61K 38/00* (2006.01)

(52) U.S. Cl.
CPC ............... *C07K 14/33* (2013.01); *C12N 9/52* (2013.01); *C12Y 304/24069* (2013.01); *A61K 38/00* (2013.01); *C07K 2319/55* (2013.01)

(58) Field of Classification Search
None
See application file for complete search history.

(56) References Cited

U.S. PATENT DOCUMENTS

| | | | | |
|---|---|---|---|---|
| 6,545,126 B1 * | 4/2003 | Johnson | ................. | C07K 14/33 424/94.6 |
| 7,172,764 B2 * | 2/2007 | Li | ..................... | A61K 47/6895 424/239.1 |
| 7,465,457 B2 * | 12/2008 | Johnson | ................. | C07K 14/33 424/239.1 |
| 7,514,088 B2 * | 4/2009 | Steward | ............. | A61K 38/4886 424/184.1 |
| 9,598,685 B2 * | 3/2017 | Dong | ....................... | A61P 25/04 |
| 9,849,163 B2 * | 12/2017 | Chaddock | ...... | C12Y 304/24069 |
| 9,920,310 B2 * | 3/2018 | Anderson | .......... | A61K 38/4886 |
| 10,190,110 B2 * | 1/2019 | Dong | ........................ | A61P 1/00 |
| 10,266,816 B2 * | 4/2019 | Rummel | ................ | A61P 19/00 |
| 10,307,468 B2 * | 6/2019 | Palan | .................... | A61P 25/16 |
| 10,329,543 B2 * | 6/2019 | Ostertag | ............. | C12N 5/0636 |
| 10,451,621 B2 * | 10/2019 | Wang | ...................... | C12Q 1/37 |
| 10,457,927 B2 * | 10/2019 | Dolly | ................. | A61K 38/4893 |
| 10,501,731 B2 * | 12/2019 | Steward | ................ | A61P 25/04 |
| 10,647,750 B2 * | 5/2020 | Anderson | ............. | C07K 14/33 |
| 10,704,035 B2 * | 7/2020 | Collier | .................... | C12N 9/52 |
| 10,709,772 B2 * | 7/2020 | Csikos | ................ | A61K 9/0053 |
| 10,786,438 B2 * | 9/2020 | Krishnan | ................ | A61K 8/65 |
| 10,808,236 B2 * | 10/2020 | Rummel | ................ | C12N 9/52 |
| 10,844,362 B2 * | 11/2020 | Dong | ....................... | A61P 21/00 |
| 10,883,096 B2 * | 1/2021 | Rummel | ............... | C07K 14/33 |
| 11,104,891 B2 * | 8/2021 | Dong | ...................... | A61P 25/04 |
| 11,117,935 B2 * | 9/2021 | Dong | ...................... | C12N 9/52 |
| 2012/0128649 A1 * | 5/2012 | Chaddock | ...... | C12Y 304/24069 424/94.3 |
| 2014/0147429 A1 | 5/2014 | Chaddock et al. | | |
| 2016/0279208 A1 * | 9/2016 | Chaddock | ...... | C12Y 304/24069 |
| 2018/0080016 A1 * | 3/2018 | Dong | ....................... | C07K 14/33 |
| 2018/0117128 A1 * | 5/2018 | Palan | .................... | C12P 21/06 |
| 2019/0127427 A1 * | 5/2019 | Liu | ........................ | C07K 14/33 |
| 2019/0185524 A1 * | 6/2019 | Dong | ....................... | C07K 14/33 |
| 2019/0201505 A1 * | 7/2019 | Palan | ............. | C12Y 304/24069 |
| 2019/0256834 A1 * | 8/2019 | Dong | ............. | C12Y 304/24069 |
| 2019/0300869 A1 * | 10/2019 | Dong | ...................... | A61P 25/08 |
| 2020/0224185 A9 * | 7/2020 | Dong | ................... | A61K 9/0019 |
| 2021/0040467 A1 * | 2/2021 | Dong | ....................... | C07K 14/33 |
| 2022/0033447 A1 * | 2/2022 | Dong | ............. | C12Y 304/24069 |

FOREIGN PATENT DOCUMENTS

WO     2015097087       7/2015
WO     WO-2017191315 A1 *  11/2017 ..... C12Y 304/24069

OTHER PUBLICATIONS

Foster et al., Neurotoxicity Research, 2006, 9(2,3):101-107 (Year: 2006).*
Gil et al., PLoS ONE, 2013, 8/7:e69692,9 pages . . . doi:10.1371/journal.one.0069692 published: Jul. 31, 2013 (Year: 2013).*
International Search Report dated Aug. 1, 2017, in PCT/EP2017/060821.
Written Opinion issued by International Searching Authority in PCT/EP2017/060821.
Wang et al., Biochem J., 444:59-67 (2012).
Wang et al., The FASEB Journal, 26:5035-5048 (2012).

* cited by examiner

*Primary Examiner* — Nita M. Minnifield
(74) *Attorney, Agent, or Firm* — Gene J. Yao; Barnes & Thornburg LLP

(57) ABSTRACT

The present invention relates to chimeric neurotoxins with enhanced properties and their use in therapy.

17 Claims, 33 Drawing Sheets
Specification includes a Sequence Listing.

| | | |
|---|---|---|
| D_P19321 | LSKPPR--PT--SKYQSYYDPSYLSIDEQKDTFLKGIIKLFKRINERDIGKKLINYLVVGSP | 115 |
| DC_AR745660 | LSKPPR--PT--SKYQSYYDPSYLSIDEQKDTFLKGIIKLFKRINERDIGKKLINYLVVGSP | 115 |
| C1_P18640 | LNKPPR-VT--SPKSGYYDPNLSTDSDKDTFLKEIIKLFKRINSREIGEELIYRLSTDIP | 115 |
| CD_AB200360 | LNKPPR-VT--SPKSGYYDPNLSTDSDKDTFLKEIIKLFKRINSREIGEELIYRLATDIP | 115 |
| G_Q60393 | QFNASTGVFSKDVYEYYDPTYLKTDAEKDKFLKTMIKLFNRINSKPSGQRLLDMIVDAIP | 117 |
| B4_EF051570 | DFNKSSGIFNRDVCEYYDPDYLNTNDKKNIFLQTMIKLFNRIRSKPLGEKLLEMIINGIP | 117 |
| B8_JQ964806 | DFNKSSGIFNRDVCEYYDPDYLNTNDKKNIFLQTMIKLFNRIRSKPLGEKLLEMIINGIP | 117 |
| B7_JC354985 | DFNKSSGIFNRDVCEYYDPDYLNTNDKKNIFLQTMIKLFNRIRSKPLGEKLLEMIINGIP | 117 |
| B6_AB302852 | DFNKSSGIFNRDVCEYYDPDYLNTNDKKNIFLQTMIKLFNRIRSKPLGEKLLEMIINGIP | 117 |
| B2_AB084152 | DFNKSSGIFNRDVCEYYDPDYLNTNDKKNIFLQTMIKLFNRIRSKPLGEKLLEMIINGIP | 117 |
| B3_EF028400 | DFNKSSGIFNRDVCEYYDPDYLNTNDKKNIFLQTMIKLFNRIRSKPLGEKLLEMIINGIP | 117 |
| B1_B1INP5 | DFNKSSGIFNRDVCEYYDPDYLNTNDKKNIFLQTMIKLFNRIRSKPLGEKLLEMIINGIP | 117 |
| B5_EF033130 | DFNKSSGIFNRDVCEYYDPDYLNTNDKKNIFLQTMIKLFNRIRSKPLGEKLLEMIINGIP | 117 |
| A4_EU341307 | DLNPPPEAK-QVPISYYDSAYLSTDNEKDNYLKGVIKLFERIYSTDLGRMLLISIVRGIP | 116 |
| A7_JQ954969 | DLNPPPEAK-QVPVSYYDSTVLSTDNEKDNYLKGVTKLFERIYSTDLGRMLLTSIVRGIP | 116 |
| A6_FJ981696 | DLNPPPEAK-QVPVSYYDSTVLSTDNEKDNYLKGVTKLFERIYSTDLGRMLLTSIVRGIP | 116 |
| A1_A5HZZ9 | DLNPPPEAK-QVPVSYYDSTVLSTDNEKDNYLKGVTKLFERIYSTDLGRMLLTSIVRGIP | 116 |
| A5_EU679004 | DLNPPPEAK-QVPVSYYDSIVLSTDNEKDNYLKFERIYSTELGRMLLTSIVRGIP | 116 |
| A3_DQ185900 | DLNPPPEAK-QVPVSYYDSIVLSTDNEKDNYLKGVTKLFEDRIYSTGLGRMLLSFIVKGIP | 116 |
| A2_X73423 | DLNPPPEAK-QVPVSYYDSTVLSTDNEKDNYLKLFERIYSTDLGRMLLTSIVRGIP | 116 |
| A8_KM233166 | DLNPPPEAK-QVPVSYYDSTVLSTNTEKNKYLQIMIKLFKRINSKPAGQILLEEIKNAIP | 116 |
| H_KGC15617 | LFNPPVSLK-AGSDGYFDPNYLSTNTEKNKYLQIMIKLFKRINSKPAGQILLEEIKNAIP | 112 |
| E9_JX424534 | NFLPPTSLK-NGDSSYYDPNLQNDQEKDRFLKIVTRVFNRINDNLSGRILEELSKANP | 115 |
| E12_KM370319 | DFQPPTSLK-NGDSSYYDPNLQSNEEKDRFLKIVTKIFNRINDNLSGGILEELSKANP | 112 |
| E11_KF861875 | DFLPPTSLK-NGDSSYYDPNLQSNEEKDRFLKIVTKIFNRINDNLSGGILEELSKANP | 112 |
| E10_KF861917 | DFLPPTSLK-NGDSSYYDPNLQSNEEKDRFLKIVTKIFNRINDNLSGGILEELSKANP | 112 |
| E7_JN695729 | DFLPPTSLK-NGDSSYYDPNLQSNEEKDRFLKIVTKIFNRINDNLSGGILEELSKANP | 112 |
| E8_JN695730 | DFLPPTSLK-NGDSSYYDPNLQSNEEKDRFLKIVTKIFNRINDNLSGRILEELSKANP | 112 |
| E5_AB037711 | DFHPPTSLK-NGDSSYYDPNLQSNEEKDRFLKIVTKIFNRINDNLSGGILEELSKANP | 112 |
| E6_AM695759 | DFHPPTSLK-NGDSSYYDPNLQSDEEKDRFLKIVTKIFNRINNNLSGGILEELSKANP | 112 |
| E4_AB088207 | DFHPPTSLK-NGDSSYYDPNLQSDQEKDFLKIVTKIFNRINDNLSGGILEELSKANP | 112 |
| E3_EF028403 | DFHPPTSLK-NGDSSYYDPNLQSDEEKDRFLKIVTKIFNRINNNLSGGILEELSKANP | 112 |
| E1_Q00496 | DFHPPTSLK-NGDSSYYDPNLQSDEEKDRFLKIVTKIFNRINNNLSGGILEELSKANP | 112 |
| E2_EF028404 | DFHPPTSLK-NGDSSYYDPNLQSDEEKDRFLKIVTKIFNRINNNLSGGILEELSKANP | 112 |
| F7_GU213233 | DFYFPISLD-SGSSAYYDPNVLTTDAEKDRFLKTVIKLFNRINSNPAGQVLLEEIKNGKP | 116 |
| F5_GU213211 | KFDPPDSLK-AGSDGYFDPNVLSTNTEKNRYLQIMIKLFKRINSNEAGKILLNQIKDAIP | 116 |
| F1_Q57236 | DFDPPASLE-NGSSAYYDPNVLTTDAEKDRYLKTTIKLFKRINSNPAGEVLLQEISYAKP | 116 |
| F4_GU213214 | DFDPPASLK-NGSSAYYDPNVLTTDAEKDRYLKTTIKLFKRINSNPAGEVLLQEISYAKP | 116 |
| F2_GU213209 | EFQVPDSLK-NGSSAYYDPNVLTTDAEKDRYLKTTIKLFNRINSNPTGKVLLEEVSNARP | 116 |
| F3_GU213227 | DFQVPDSLK-NGSSAYYDPNVLTTDAEKDRYLKTTIKLFNRINSNPTGKVLLEEVSNARP | 116 |
| F6_M92906 | DFDPPASLK-NGSSAYYDPNVLTTDAEKDRYLKTTIKLFKRINSNPAGKVLLQEISYAKP | 116 |
| T_P04958 | DFNPPSSLI-EGASEYYDPNVLRTDSDKDRFLQTMVKLFNRIKNNVAGEALLDKIINAIP | 116 |
| | * * * : : *.* : * | |

```
D_P19321       KLLSTSSFWKFISDPGWVE------------                               1275
DC_AB745660    LLESTSTHWVFVPASF------------                                  1285
C1_P18640      LLESTSTHWGFVFVSF------------                                  1291
CD_AB200360    KLLSTSSFWKFISDFGWVE---------                                  1280
G_Q60393       NKLRLGCNWQFIPVDEGWTE--------                                  1297
B4_EF051570    YKSNLGCNWQFIPKDEGWTE--------                                  1291
B8_JQ964806    YMPDLGCNWQFIPKDEGWTE--------                                  1292
B7_JQ354985    YSSNLGCNWQFIPKDEGWTE--------                                  1291
B6_AB302852    YNPNLGCNWQFIPKDEGWIE--------                                  1291
B2_AB084152    YNPNLGCNWQFIPKDEGWIE--------                                  1291
B3_EF028400    YNPNLGCNWQFIPKDEGWIE--------                                  1291
B1_B1INP5      YNLKLGCNWQFIPKDEGWTE--------                                  1291
B5_EF033130    YNSKLGCNWQFIPKDEGWTE--------                                  1291
A4_EU341307    ---RTLGCSWEFIPVDEGMRERPL                                      1296
A7_JQ954969    ---VTLGCSWELIPVDYGMGESSL                                      1296
A6_FJ981696    ---RTFGCSWEFIPVDEGMGEKPL                                      1296
A1_A5HZZ9      ---RTLGCSWEFIPVDLGMGERPL                                      1296
A5_EU679004    ---RTFGCSWEFIPVDLGMGESPL                                      1296
A3_DQ185900    ---RTFGCSWEFIPVDDGMGESSL                                      1292
A2_X73423      ---RTFGCSWEFIPVDDGMGESSL                                      1296
A8_KM233166    ---RTFGCSWEFIPVDDGMGESSQ                                      1297
H_KGO15617     ---RTFGCSWEFIPVDDGMGESSL                                      1288
E9_JX424534    ---NSNGCFWSFIPENGMQEH---                                      1251
E12_KM370319   ---NSNGCFWNFISEEHGMQEK---                                     1254
E11_KF861875   ---NSNGCFWNFISEEHGMQEK---                                     1252
E10_KF861917   ---NSNGCFWNFISEEHGMQEK---                                     1252
E7_JN695729    ---NSNGCFWNFISEEHGMQEK---                                     1252
E8_JN695730    ---NSNGCFWNFISEEHGMQEK---                                     1252
E5_AB037711    ---NSNGCFWNFISEEHGMQEK---                                     1251
E6_AM695759    ---NSNGFFWNFISEEHGMQEK---                                     1252
E4_AB088207    ---NSNGFFWNFISEEHGMQEK---                                     1252
E3_EF028403    ---NSNGCFWNFISEEHGMQEK---                                     1252
E1_Q00496      ---NSNGCFWNFISEEHGMQEK---                                     1252
E2_EF028404    ---MSNGCFWNFISEEHGMQEK---                                     1252
F7_GU213233    ---RNNGCFWSFISKEHGMQE----                                     1268
F5_GU213211    ---SSNGCFWSFISKEHGMQE----                                     1277
F1_Q57236      ---SSNGCFWSFISKEHGMQEN---                                     1278
F4_GU213214    ---SSNGCFWSFISKEHGMQE----                                     1277
F2_GU213209    ---SSNGCFWSFISKEHGMWKE---                                     1280
F3_GU213227    ---SSNGCFWSFISKEHGMQE----                                     1279
F6_M92906      ---SSNGCFWSSISKENGMWKE---                                     1274
T_P04958       ------ILGCDWYFVPTDEGWTND                                      1315
                                 *   .
```

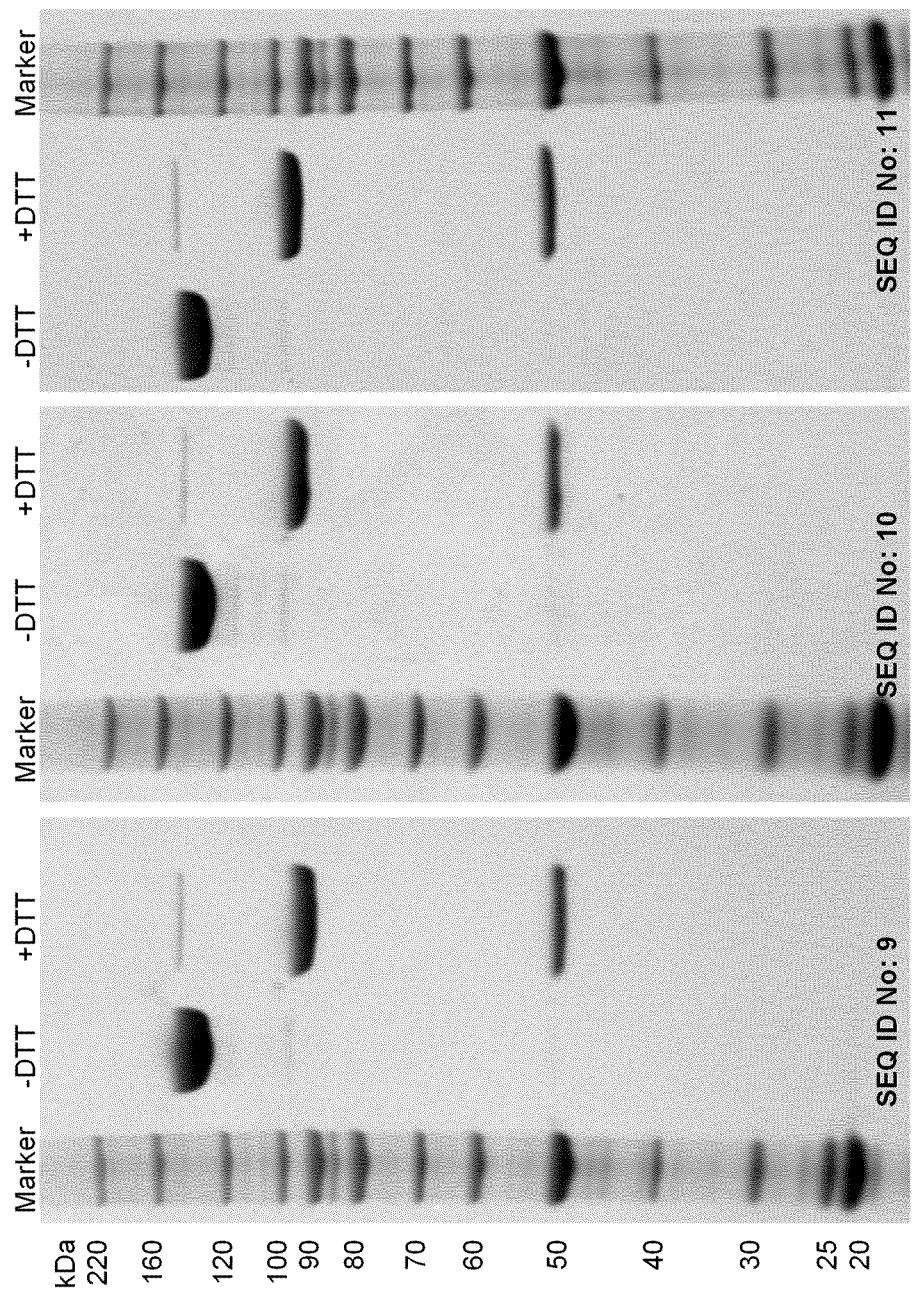

SEQUENCE LISTING

```
<160> NUMBER OF SEQ ID NOS: 91

<210> SEQ ID NO 1
<211> LENGTH: 1296
<212> TYPE: PRT
<213> ORGANISM: Clostridium botulinum

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
```

```
            290                 295                 300
Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720
```

```
Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
        1025                1030                1035

Lys Pro Ile Ser Asn Leu Gly Asn Ile His Ala Ser Asn Asn Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080

Ile Lys Asp Leu Tyr Asp Asn Gln Ser Asn Ser Gly Ile Leu Lys
        1085                1090                1095

Asp Phe Trp Gly Asp Tyr Leu Gln Tyr Asp Lys Pro Tyr Tyr Met
        1100                1105                1110

Leu Asn Leu Tyr Asp Pro Asn Lys Tyr Val Asp Val Asn Asn Val
        1115                1120                1125
```

Gly Ile Arg Gly Tyr Met Tyr Leu Lys Gly Pro Arg Gly Ser Val
1130                1135                1140

Met Thr Thr Asn Ile Tyr Leu Asn Ser Ser Leu Tyr Arg Gly Thr
1145                1150                1155

Lys Phe Ile Ile Lys Lys Tyr Ala Ser Gly Asn Lys Asp Asn Ile
1160                1165                1170

Val Arg Asn Asn Asp Arg Val Tyr Ile Asn Val Val Lys Asn
1175                1180                1185

Lys Glu Tyr Arg Leu Ala Thr Asn Ala Ser Gln Ala Gly Val Glu
1190                1195                1200

Lys Ile Leu Ser Ala Leu Glu Ile Pro Asp Val Gly Asn Leu Ser
1205                1210                1215

Gln Val Val Met Lys Ser Lys Asn Asp Gln Gly Ile Thr Asn
1220                1225                1230

Lys Cys Lys Met Asn Leu Gln Asp Asn Asn Gly Asn Asp Ile Gly
1235                1240                1245

Phe Ile Gly Phe His Gln Phe Asn Asn Ile Ala Lys Leu Val Ala
1250                1255                1260

Ser Asn Trp Tyr Asn Arg Gln Ile Glu Arg Ser Ser Arg Thr Leu
1265                1270                1275

Gly Cys Ser Trp Glu Phe Ile Pro Val Asp Asp Gly Trp Gly Glu
1280                1285                1290

Arg Pro Leu
1295

<210> SEQ ID NO 2
<211> LENGTH: 1291
<212> TYPE: PRT
<213> ORGANISM: Clostridium botulinum

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

```
Met Lys Phe Cys Pro Glu Tyr Val Ser Val Phe Asn Val Gln Glu
            195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Pro Asn Glu Lys Phe
                245                 250                 255

Phe Met Gln Ser Thr Asp Ala Ile Gln Ala Glu Leu Tyr Thr Phe
            260                 265                 270

Gly Gly Gln Asp Pro Ser Ile Ile Thr Pro Ser Thr Asp Lys Ser Ile
                275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605
```

-continued

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
            645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu
            1010                1015                1020

Ser Asn Thr Asp Ile Lys Asp Ile Arg Glu Val Ile Ala Asn Gly

-continued

```
                1025                1030                1035
Glu Ile Ile Phe Lys Leu Asp Gly Asp Ile Asp Arg Thr Gln Phe
            1040                1045                1050
Ile Trp Met Lys Tyr Phe Ser Ile Phe Asn Thr Glu Leu Ser Gln
            1055                1060                1065
Ser Asn Ile Glu Glu Arg Tyr Lys Ile Gln Ser Tyr Ser Glu Tyr
            1070                1075                1080
Leu Lys Asp Phe Trp Gly Asn Pro Leu Met Tyr Asn Lys Glu Tyr
            1085                1090                1095
Tyr Met Phe Asn Ala Gly Asn Lys Asn Ser Tyr Ile Lys Leu Lys
            1100                1105                1110
Lys Asp Ser Pro Val Gly Glu Ile Leu Thr Arg Ser Lys Tyr Asn
            1115                1120                1125
Gln Asn Ser Lys Tyr Ile Asn Tyr Arg Asp Leu Tyr Ile Gly Glu
            1130                1135                1140
Lys Phe Ile Ile Arg Arg Lys Ser Asn Ser Gln Ser Ile Asn Asp
            1145                1150                1155
Asp Ile Val Arg Lys Glu Asp Tyr Ile Tyr Leu Asp Phe Phe Asn
            1160                1165                1170
Leu Asn Gln Glu Trp Arg Val Tyr Thr Tyr Lys Tyr Phe Lys Lys
            1175                1180                1185
Glu Glu Glu Lys Leu Phe Leu Ala Pro Ile Ser Asp Ser Asp Glu
            1190                1195                1200
Phe Tyr Asn Thr Ile Gln Ile Lys Glu Tyr Asp Glu Gln Pro Thr
            1205                1210                1215
Tyr Ser Cys Gln Leu Leu Phe Lys Lys Asp Glu Glu Ser Thr Asp
            1220                1225                1230
Glu Ile Gly Leu Ile Gly Ile His Arg Phe Tyr Glu Ser Gly Ile
            1235                1240                1245
Val Phe Glu Glu Tyr Lys Asp Tyr Phe Cys Ile Ser Lys Trp Tyr
            1250                1255                1260
Leu Lys Glu Val Lys Arg Lys Pro Tyr Asn Leu Lys Leu Gly Cys
            1265                1270                1275
Asn Trp Gln Phe Ile Pro Lys Asp Glu Gly Trp Thr Glu
            1280                1285                1290
```

<210> SEQ ID NO 3
<211> LENGTH: 1291
<212> TYPE: PRT
<213> ORGANISM: Clostridium botulinum

<400> SEQUENCE: 3

```
Met Pro Ile Thr Ile Asn Asn Phe Asn Tyr Ser Asp Pro Val Asp Asn
1               5                   10                  15
Lys Asn Ile Leu Tyr Leu Asp Thr His Leu Asn Thr Leu Ala Asn Glu
            20                  25                  30
Pro Glu Lys Ala Phe Arg Ile Thr Gly Asn Ile Trp Val Ile Pro Asp
        35                  40                  45
Arg Phe Ser Arg Asn Ser Asn Pro Asn Leu Asn Lys Pro Pro Arg Val
    50                  55                  60
Thr Ser Pro Lys Ser Gly Tyr Tyr Asp Pro Asn Tyr Leu Ser Thr Asp
65                  70                  75                  80
Ser Asp Lys Asp Pro Phe Leu Lys Glu Ile Ile Lys Leu Phe Lys Arg
                85                  90                  95
```

-continued

```
Ile Asn Ser Arg Glu Ile Gly Glu Glu Leu Ile Tyr Arg Leu Ser Thr
                100                 105                 110
Asp Ile Pro Phe Pro Gly Asn Asn Thr Pro Ile Asn Thr Phe Asp
        115                 120                 125
Phe Asp Val Asp Phe Asn Ser Val Asp Val Lys Thr Arg Gln Gly Asn
    130                 135                 140
Asn Trp Val Lys Thr Gly Ser Ile Asn Pro Ser Val Ile Ile Thr Gly
145                 150                 155                 160
Pro Arg Glu Asn Ile Ile Asp Pro Glu Thr Ser Thr Phe Lys Leu Thr
                165                 170                 175
Asn Asn Thr Phe Ala Ala Gln Glu Gly Phe Gly Ala Leu Ser Ile Ile
            180                 185                 190
Ser Ile Ser Pro Arg Phe Met Leu Thr Tyr Ser Asn Ala Thr Asn Asp
        195                 200                 205
Val Gly Glu Gly Arg Phe Ser Lys Ser Glu Phe Cys Met Asp Pro Ile
    210                 215                 220
Leu Ile Leu Met His Glu Leu Asn His Ala Met His Asn Leu Tyr Gly
225                 230                 235                 240
Ile Ala Ile Pro Asn Asp Gln Thr Ile Ser Ser Val Thr Ser Asn Ile
                245                 250                 255
Phe Tyr Ser Gln Tyr Asn Val Lys Leu Glu Tyr Ala Glu Ile Tyr Ala
            260                 265                 270
Phe Gly Gly Pro Thr Ile Asp Leu Ile Pro Lys Ser Ala Arg Lys Tyr
        275                 280                 285
Phe Glu Glu Lys Ala Leu Asp Tyr Tyr Arg Ser Ile Ala Lys Arg Leu
    290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Thr Val Asn Arg Asn Lys Phe Val Glu Leu Tyr Asn
            340                 345                 350
Glu Leu Thr Gln Ile Phe Thr Glu Phe Asn Tyr Ala Lys Ile Tyr Asn
        355                 360                 365
Val Gln Asn Arg Lys Ile Tyr Leu Ser Asn Val Tyr Thr Pro Val Thr
    370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg Ser Leu Tyr Asn
        435                 440                 445
Lys Thr Leu Asp Cys Arg Glu Leu Leu Val Lys Asn Thr Asp Leu Pro
    450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
                485                 490                 495
Val Asp Gln Val Ile Leu Ser Lys Asn Thr Ser Glu His Gly Gln Leu
            500                 505                 510
Asp Leu Leu Tyr Pro Ser Ile Asp Ser Glu Ser Glu Ile Leu Pro Gly
```

-continued

```
                515                 520                 525
Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
                580                 585                 590

Val Gln Gly Gly Leu Phe Leu Met Trp Ala Asn Asp Val Val Glu Asp
                595                 600                 605

Phe Thr Thr Asn Ile Leu Arg Lys Asp Thr Leu Asp Lys Ile Ser Asp
                610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
                660                 665                 670

Ala Phe Val Ile Tyr Ser Lys Val Gln Glu Arg Asn Glu Ile Ile Lys
                675                 680                 685

Thr Ile Asp Asn Cys Leu Glu Gln Arg Ile Lys Arg Trp Lys Asp Ser
                690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
                755                 760                 765

Asp Val Lys Ile Ser Glu Ala Met Asn Asn Ile Asn Lys Phe Ile Arg
                770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
                820                 825                 830

Lys Ala Lys Val Asn Asn Ser Phe Gln Asn Thr Ile Pro Phe Asn Ile
                835                 840                 845

Phe Ser Tyr Thr Asn Asn Ser Leu Leu Lys Asp Ile Ile Asn Glu Tyr
                850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
                900                 905                 910

Ser Ser Gly Glu Asp Arg Gly Lys Val Ile Val Thr Gln Asn Glu Asn
                915                 920                 925

Ile Val Tyr Asn Ser Met Tyr Glu Ser Phe Ser Ile Ser Phe Trp Ile
                930                 935                 940
```

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn  Ala Pro Gly Tyr Asn Lys Trp Phe
        995                 1000                1005

Phe Val Thr Val Thr Asn Asn  Met Met Gly Asn Met  Lys Ile Tyr
    1010                1015                1020

Ile Asn Gly Lys Leu Ile Asp  Thr Ile Lys Val Lys  Glu Leu Thr
    1025                1030                1035

Gly Ile Asn Phe Ser Lys Thr  Ile Thr Phe Glu Ile  Asn Lys Ile
    1040                1045                1050

Pro Asp Thr Gly Leu Ile Thr  Ser Asp Ser Asp Asn  Ile Asn Met
    1055                1060                1065

Trp Ile Arg Asp Phe Tyr Ile  Phe Ala Lys Glu Leu  Asp Gly Lys
    1070                1075                1080

Asp Ile Asn Ile Leu Phe Asn  Ser Leu Gln Tyr Thr  Asn Val Val
    1085                1090                1095

Lys Asp Tyr Trp Gly Asn Asp  Leu Arg Tyr Asn Lys  Glu Tyr Tyr
    1100                1105                1110

Met Val Asn Ile Asp Tyr Leu  Asn Arg Tyr Met Tyr  Ala Asn Ser
    1115                1120                1125

Arg Gln Ile Val Phe Asn Thr  Arg Arg Asn Asn Asn  Asp Phe Asn
    1130                1135                1140

Glu Gly Tyr Lys Ile Ile Ile  Lys Arg Ile Arg Gly  Asn Thr Asn
    1145                1150                1155

Asp Thr Arg Val Arg Gly Gly  Asp Ile Leu Tyr Phe  Asp Met Thr
    1160                1165                1170

Ile Asn Asn Lys Ala Tyr Asn  Leu Phe Met Lys Asn  Glu Thr Met
    1175                1180                1185

Tyr Ala Asp Asn His Ser Thr  Glu Asp Ile Tyr Ala  Ile Gly Leu
    1190                1195                1200

Arg Glu Gln Thr Lys Asp Ile  Asn Asp Asn Ile Ile  Phe Gln Ile
    1205                1210                1215

Gln Pro Met Asn Asn Thr Tyr  Tyr Tyr Ala Ser Gln  Ile Phe Lys
    1220                1225                1230

Ser Asn Phe Asn Gly Glu Asn  Ile Ser Gly Ile Cys  Ser Ile Gly
    1235                1240                1245

Thr Tyr Arg Phe Arg Leu Gly  Gly Asp Trp Tyr Arg  His Asn Tyr
    1250                1255                1260

Leu Val Pro Thr Val Lys Gln  Gly Asn Tyr Ala Ser  Leu Leu Glu
    1265                1270                1275

Ser Thr Ser Thr His Trp Gly  Phe Val Pro Val Ser  Glu
    1280                1285                1290

<210> SEQ ID NO 4
<211> LENGTH: 1276
<212> TYPE: PRT
<213> ORGANISM: Clostridium botulinum

<400> SEQUENCE: 4

Met Thr Trp Pro Val Lys Asp Phe Asn Tyr Ser Asp Pro Val Asn Asp

-continued

```
  1               5                  10                 15
Asn Asp Ile Leu Tyr Leu Arg Ile Pro Gln Asn Lys Leu Ile Thr Thr
                 20                 25                 30
Pro Val Lys Ala Phe Met Ile Thr Gln Asn Ile Trp Val Ile Pro Glu
                 35                 40                 45
Arg Phe Ser Ser Asp Thr Asn Pro Ser Leu Ser Lys Pro Pro Arg Pro
     50                 55                 60
Thr Ser Lys Tyr Gln Ser Tyr Tyr Asp Pro Ser Tyr Leu Ser Thr Asp
 65                 70                 75                 80
Glu Gln Lys Asp Thr Phe Leu Lys Gly Ile Ile Lys Leu Phe Lys Arg
                 85                 90                 95
Ile Asn Glu Arg Asp Ile Gly Lys Lys Leu Ile Asn Tyr Leu Val Val
                100                105                110
Gly Ser Pro Phe Met Gly Asp Ser Ser Thr Pro Glu Asp Thr Phe Asp
                115                120                125
Phe Thr Arg His Thr Thr Asn Ile Ala Val Glu Lys Phe Glu Asn Gly
                130                135                140
Ser Trp Lys Val Thr Asn Ile Ile Thr Pro Ser Val Leu Ile Phe Gly
145                150                155                160
Pro Leu Pro Asn Ile Leu Asp Tyr Thr Ala Ser Leu Thr Leu Gln Gly
                165                170                175
Gln Gln Ser Asn Pro Ser Phe Glu Gly Phe Gly Thr Leu Ser Ile Leu
                180                185                190
Lys Val Ala Pro Glu Phe Leu Leu Thr Phe Ser Asp Val Thr Ser Asn
                195                200                205
Gln Ser Ser Ala Val Leu Gly Lys Ser Ile Phe Cys Met Asp Pro Val
                210                215                220
Ile Ala Leu Met His Glu Leu Thr His Ser Leu His Gln Leu Tyr Gly
225                230                235                240
Ile Asn Ile Pro Ser Asp Lys Arg Ile Arg Pro Gln Val Ser Glu Gly
                245                250                255
Phe Phe Ser Gln Asp Gly Pro Asn Val Gln Phe Glu Glu Leu Tyr Thr
                260                265                270
Phe Gly Gly Leu Asp Val Glu Ile Ile Pro Gln Ile Glu Arg Ser Gln
                275                280                285
Leu Arg Glu Lys Ala Leu Gly His Tyr Lys Asp Ile Ala Lys Arg Leu
                290                295                300
Asn Asn Ile Asn Lys Thr Ile Pro Ser Ser Trp Ile Ser Asn Ile Asp
305                310                315                320
Lys Tyr Lys Lys Ile Phe Ser Glu Lys Tyr Asn Phe Asp Lys Asp Asn
                325                330                335
Thr Gly Asn Phe Val Val Asn Ile Asp Lys Phe Asn Ser Leu Tyr Ser
                340                345                350
Asp Leu Thr Asn Val Met Ser Glu Val Val Tyr Ser Ser Gln Tyr Asn
                355                360                365
Val Lys Asn Arg Thr His Tyr Phe Ser Arg His Tyr Leu Pro Val Phe
                370                375                380
Ala Asn Ile Leu Asp Asp Asn Ile Tyr Thr Ile Arg Asp Gly Phe Asn
385                390                395                400
Leu Thr Asn Lys Gly Phe Asn Ile Glu Asn Ser Gly Gln Asn Ile Glu
                405                410                415
Arg Asn Pro Ala Leu Gln Lys Leu Ser Ser Glu Ser Val Val Asp Leu
                420                425                430
```

-continued

Phe Thr Lys Val Cys Leu Arg Leu Thr Lys Asn Ser Arg Asp Asp Ser
            435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
                500                 505                 510

Pro Asn Val Asn Met Glu Pro Leu Asn Leu Pro Gly Glu Glu Ile Val
            515                 520                 525

Phe Tyr Asp Asp Ile Thr Lys Tyr Val Asp Tyr Leu Asn Ser Tyr Tyr
        530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
            595                 600                 605

Ile Met Lys Lys Asp Thr Leu Asp Lys Ile Ser Asp Val Ser Val Ile
        610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
        690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
        770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
                820                 825                 830

Asn Glu Ser Phe Glu Asn Thr Met Pro Phe Asn Ile Phe Ser Tyr Thr
            835                 840                 845

```
Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
                900                 905                 910

Lys Ile Ile Val Asn Leu Asn Asn Ile Leu Tyr Ser Ala Ile Tyr
            915                 920                 925

Glu Asn Ser Ser Val Ser Phe Trp Ile Lys Ile Ser Lys Asp Leu Thr
930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
                980                 985                 990

Leu Ser His Thr Gly Tyr Thr Asn Lys Trp Phe Phe Val Thr Ile Thr
                995                 1000                1005

Asn Asn Ile Met Gly Tyr Met Lys Leu Tyr Ile Asn Gly Glu Leu
1010                1015                1020

Lys Gln Ser Gln Lys Ile Glu Asp Leu Asp Glu Val Lys Leu Asp
1025                1030                1035

Lys Thr Ile Val Phe Gly Ile Asp Glu Asn Ile Asp Glu Asn Gln
1040                1045                1050

Met Leu Trp Ile Arg Asp Phe Asn Ile Phe Ser Lys Glu Leu Ser
1055                1060                1065

Asn Glu Asp Ile Asn Ile Val Tyr Glu Gly Gln Ile Leu Arg Asn
1070                1075                1080

Val Ile Lys Asp Tyr Trp Gly Asn Pro Leu Lys Phe Asp Thr Glu
1085                1090                1095

Tyr Tyr Ile Ile Asn Asp Asn Tyr Ile Asp Arg Tyr Ile Ala Pro
1100                1105                1110

Glu Ser Asn Val Leu Val Leu Val Gln Tyr Pro Asp Arg Ser Lys
1115                1120                1125

Leu Tyr Thr Gly Asn Pro Ile Thr Ile Lys Ser Val Ser Asp Lys
1130                1135                1140

Asn Pro Tyr Ser Arg Ile Leu Asn Gly Asp Asn Ile Ile Leu His
1145                1150                1155

Met Leu Tyr Asn Ser Arg Lys Tyr Met Ile Ile Arg Asp Thr Asp
1160                1165                1170

Thr Ile Tyr Ala Thr Gln Gly Gly Glu Cys Ser Gln Asn Cys Val
1175                1180                1185

Tyr Ala Leu Lys Leu Gln Ser Asn Leu Gly Asn Tyr Gly Ile Gly
1190                1195                1200

Ile Phe Ser Ile Lys Asn Ile Val Ser Lys Asn Lys Tyr Cys Ser
1205                1210                1215

Gln Ile Phe Ser Ser Phe Arg Glu Asn Thr Met Leu Leu Ala Asp
1220                1225                1230

Ile Tyr Lys Pro Trp Arg Phe Ser Phe Lys Asn Ala Tyr Thr Pro
1235                1240                1245

Val Ala Val Thr Asn Tyr Glu Thr Lys Leu Leu Ser Thr Ser Ser
```

```
                    1250                1255                1260
       Phe Trp Lys Phe Ile Ser Arg Asp Pro Gly Trp Val Glu
          1265                1270                1275

<210> SEQ ID NO 5
<211> LENGTH: 1252
<212> TYPE: PRT
<213> ORGANISM: Clostridium botulinum

<400> SEQUENCE: 5

Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Thr Ser Leu Lys Asn Gly
     50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350
```

-continued

```
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Cys Ile Glu Ile Asn Asn Gly
                420                 425                 430
Glu Leu Phe Phe Val Ala Ser Glu Asn Ser Tyr Asn Asp Asn Ile
        435                 440                 445
Asn Thr Pro Lys Glu Ile Asp Asp Thr Val Thr Ser Asn Asn Tyr
        450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
        515                 520                 525
Pro Glu Gly Glu Asn Asn Val Asn Leu Thr Ser Ser Ile Asp Thr Ala
        530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
                580                 585                 590
Val Asp Lys Ile Ala Asp Ile Ser Ile Val Val Pro Tyr Ile Gly Leu
        595                 600                 605
Ala Leu Asn Ile Gly Asn Glu Ala Gln Lys Gly Asn Phe Lys Asp Ala
        610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
        675                 680                 685
Trp Met Thr Lys Ile Asn Thr Gln Phe Asn Lys Arg Lys Glu Gln Met
        690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
        755                 760                 765
Tyr Leu Met Lys Leu Ile Asn Glu Val Lys Ile Asn Lys Leu Arg Glu
```

```
            770              775              780
Tyr Asp Glu Asn Val Lys Thr Tyr Leu Leu Asn Tyr Ile Ile Gln His
785              790              795              800

Gly Ser Ile Leu Gly Glu Ser Gln Gln Glu Leu Asn Ser Met Val Thr
                 805              810              815

Asp Thr Leu Asn Asn Ser Ile Pro Phe Lys Leu Ser Ser Tyr Thr Asp
                 820              825              830

Asp Lys Ile Leu Ile Ser Tyr Phe Asn Lys Phe Phe Lys Arg Ile Lys
                 835              840              845

Ser Ser Ser Val Leu Asn Met Arg Tyr Lys Asn Asp Lys Tyr Val Asp
850              855              860

Thr Ser Gly Tyr Asp Ser Asn Ile Asn Ile Asn Gly Asp Val Tyr Lys
865              870              875              880

Tyr Pro Thr Asn Lys Asn Gln Phe Gly Ile Tyr Asn Asp Lys Leu Ser
                 885              890              895

Glu Val Asn Ile Ser Gln Asn Asp Tyr Ile Ile Tyr Asp Asn Lys Tyr
                 900              905              910

Lys Asn Phe Ser Ile Ser Phe Trp Val Arg Ile Pro Asn Tyr Asp Asn
                 915              920              925

Lys Ile Val Asn Val Asn Asn Glu Tyr Thr Ile Ile Asn Cys Met Arg
930              935              940

Asp Asn Asn Ser Gly Trp Lys Val Ser Leu Asn His Asn Glu Ile Ile
945              950              955              960

Trp Thr Leu Gln Asp Asn Ala Gly Ile Asn Gln Lys Leu Ala Phe Asn
                 965              970              975

Tyr Gly Asn Ala Asn Gly Ile Ser Asp Tyr Ile Asn Lys Trp Ile Phe
                 980              985              990

Val Thr Ile Thr Asn Asp Arg Leu  Gly Asp Ser Lys Leu  Tyr Ile Asn
                 995               1000              1005

Gly Asn  Leu Ile Asp Gln Lys  Ser Ile Leu Asn Leu  Gly Asn Ile
1010              1015              1020

His Val  Ser Asp Asn Ile Leu  Phe Lys Ile Val Asn  Cys Ser Tyr
1025              1030              1035

Thr Arg  Tyr Ile Gly Ile Arg  Tyr Phe Asn Ile Phe  Asp Lys Glu
1040              1045              1050

Leu Asp  Glu Thr Glu Ile Gln  Thr Leu Tyr Ser Asn  Glu Pro Asn
1055              1060              1065

Thr Asn  Ile Leu Lys Asp Phe  Trp Gly Asn Tyr Leu  Leu Tyr Asp
1070              1075              1080

Lys Glu  Tyr Tyr Leu Leu Asn  Val Leu Lys Pro Asn  Asn Phe Ile
1085              1090              1095

Asp Arg  Arg Lys Asp Ser Thr  Leu Ser Ile Asn Asn  Ile Arg Ser
1100              1105              1110

Thr Ile  Leu Leu Ala Asn Arg  Leu Tyr Ser Gly Ile  Lys Val Lys
1115              1120              1125

Ile Gln  Arg Val Asn Asn Ser  Ser Thr Asn Asp Asn  Leu Val Arg
1130              1135              1140

Lys Asn  Asp Gln Val Tyr Ile  Asn Phe Val Ala Ser  Lys Thr His
1145              1150              1155

Leu Phe  Pro Leu Tyr Ala Asp  Thr Ala Thr Thr Asn  Lys Glu Lys
1160              1165              1170

Thr Ile  Lys Ile Ser Ser Ser  Gly Asn Arg Phe Asn  Gln Val Val
1175              1180              1185
```

-continued

```
Val Met Asn Ser Val Gly Asn Asn Cys Thr Met Asn Phe Lys Asn
    1190            1195                1200

Asn Asn Gly Asn Asn Ile Gly Leu Leu Gly Phe Lys Ala Asp Thr
    1205            1210                1215

Val Val Ala Ser Thr Trp Tyr Tyr Thr His Met Arg Asp His Thr
    1220            1225                1230

Asn Ser Asn Gly Cys Phe Trp Asn Phe Ile Ser Glu Glu His Gly
    1235            1240                1245

Trp Gln Glu Lys
    1250

<210> SEQ ID NO 6
<211> LENGTH: 1278
<212> TYPE: PRT
<213> ORGANISM: Clostridium botulinum

<400> SEQUENCE: 6

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asp Pro Ser Asp Phe Asp Pro Pro Ala Ser
        50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
```

```
            290                 295                 300
Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
                340                 345                 350

Glu Ile Asp Leu Ala Asn Lys Phe Lys Val Lys Cys Arg Asn Thr Tyr
                355                 360                 365

Phe Ile Lys Tyr Gly Phe Leu Lys Val Pro Asn Leu Leu Asp Asp Asp
                370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
                420                 425                 430

Ile Pro Arg Lys Gly Thr Lys Ala Pro Pro Arg Leu Cys Ile Arg Val
                435                 440                 445

Asn Asn Arg Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Gln Thr Leu Asn Thr Leu Val Gln
                500                 505                 510

Asp Asp Ser Tyr Val Pro Arg Tyr Asp Ser Asn Gly Thr Ser Glu Ile
                515                 520                 525

Glu Glu His Asn Val Val Asp Leu Asn Val Phe Phe Tyr Leu His Ala
                530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
                565                 570                 575

Glu Phe Ile Asn Thr Ile Asn Lys Pro Val His Ala Ala Leu Phe Ile
                580                 585                 590

Ser Trp Ile Asn Gln Val Ile Arg Asp Phe Thr Thr Glu Ala Thr Gln
                595                 600                 605

Lys Ser Thr Phe Asp Lys Ile Ala Asp Ile Ser Leu Val Val Pro Tyr
610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
                645                 650                 655

Pro Glu Leu Leu Ile Pro Thr Ile Leu Val Phe Thr Ile Lys Ser Phe
                660                 665                 670

Ile Gly Ser Ser Glu Asn Lys Asn Lys Ile Ile Lys Ala Ile Asn Asn
                675                 680                 685

Ser Leu Met Glu Arg Glu Thr Lys Trp Lys Glu Ile Tyr Ser Trp Ile
                690                 695                 700

Val Ser Asn Trp Leu Thr Arg Ile Asn Thr Gln Phe Asn Lys Arg Lys
705                 710                 715                 720
```

-continued

Glu Gln Met Tyr Gln Ala Leu Gln Asn Gln Val Asp Ala Ile Lys Thr
              725                 730                 735

Val Ile Glu Tyr Lys Tyr Asn Asn Tyr Thr Ser Asp Glu Arg Asn Arg
          740                 745                 750

Leu Glu Ser Glu Tyr Asn Ile Asn Asn Ile Arg Glu Glu Leu Asn Lys
      755                 760                 765

Lys Val Ser Leu Ala Met Glu Asn Ile Glu Arg Phe Ile Thr Glu Ser
770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
              805                 810                 815

Ser Glu His Arg Ser Ile Leu Gly Asn Ser Val Gln Glu Leu Asn Asp
          820                 825                 830

Leu Val Thr Ser Thr Leu Asn Asn Ser Ile Pro Phe Glu Leu Ser Ser
      835                 840                 845

Tyr Thr Asn Asp Lys Ile Leu Ile Leu Tyr Phe Asn Lys Leu Tyr Lys
  850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
              885                 890                 895

Val Tyr Ile Tyr Ser Thr Asn Arg Asn Gln Phe Gly Ile Tyr Ser Ser
          900                 905                 910

Lys Pro Ser Glu Val Asn Ile Ala Gln Asn Asn Asp Ile Ile Tyr Asn
      915                 920                 925

Gly Arg Tyr Gln Asn Phe Ser Ile Ser Phe Trp Val Arg Ile Pro Lys
  930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
              965                 970                 975

Ile Ile Trp Thr Leu Gln Asp Thr Ala Gly Asn Asn Gln Lys Leu Val
          980                 985                 990

Phe Asn Tyr Thr Gln Met Ile Ser Ile Ser Asp Tyr Ile Asn Lys Trp
      995                 1000                1005

Ile Phe Val Thr Ile Thr Asn Asn Arg Leu Gly Asn Ser Arg Ile
    1010                1015                1020

Tyr Ile Asn Gly Asn Leu Ile Asp Glu Lys Ser Ile Ser Asn Leu
    1025                1030                1035

Gly Asp Ile His Val Ser Asp Asn Ile Leu Phe Lys Ile Val Gly
    1040                1045                1050

Cys Asn Asp Thr Arg Tyr Val Gly Ile Arg Tyr Phe Lys Val Phe
    1055                1060                1065

Asp Thr Glu Leu Gly Lys Thr Glu Ile Glu Thr Leu Tyr Ser Asp
    1070                1075                1080

Glu Pro Asp Pro Ser Ile Leu Lys Asp Phe Trp Gly Asn Tyr Leu
    1085                1090                1095

Leu Tyr Asn Lys Arg Tyr Tyr Leu Leu Asn Leu Leu Arg Thr Asp
    1100                1105                1110

Lys Ser Ile Thr Gln Asn Ser Asn Phe Leu Asn Ile Asn Gln Gln
    1115                1120                1125

```
Arg Gly Val Tyr Gln Lys Pro Asn Ile Phe Ser Asn Thr Arg Leu
    1130                1135                1140

Tyr Thr Gly Val Glu Val Ile Ile Arg Lys Asn Gly Ser Thr Asp
1145                1150                1155

Ile Ser Asn Thr Asp Asn Phe Val Arg Lys Asn Asp Leu Ala Tyr
    1160                1165                1170

Ile Asn Val Val Asp Arg Asp Val Glu Tyr Arg Leu Tyr Ala Asp
    1175                1180                1185

Ile Ser Ile Ala Lys Pro Glu Lys Ile Ile Lys Leu Ile Arg Thr
    1190                1195                1200

Ser Asn Ser Asn Asn Ser Leu Gly Gln Ile Ile Val Met Asp Ser
    1205                1210                1215

Ile Gly Asn Asn Cys Thr Met Asn Phe Gln Asn Asn Asn Gly Gly
    1220                1225                1230

Asn Ile Gly Leu Leu Gly Phe His Ser Asn Asn Leu Val Ala Ser
    1235                1240                1245

Ser Trp Tyr Tyr Asn Asn Ile Arg Lys Asn Thr Ser Ser Asn Gly
    1250                1255                1260

Cys Phe Trp Ser Phe Ile Ser Lys Glu His Gly Trp Gln Glu Asn
    1265                1270                1275

<210> SEQ ID NO 7
<211> LENGTH: 1297
<212> TYPE: PRT
<213> ORGANISM: Clostridium botulinum

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
        50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220
```

```
Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
            245                 250                 255

Phe Met Gln His Ser Asp Pro Val Gln Ala Glu Glu Leu Tyr Thr Phe
        260                 265                 270

Gly Gly His Asp Pro Ser Val Ile Ser Pro Ser Thr Asp Met Asn Ile
    275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
610                 615                 620

Ile Ile Pro Tyr Ile Gly Pro Ala Leu Asn Val Gly Asn Glu Thr Ala
625                 630                 635                 640
```

-continued

```
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
            660                 665                 670
Leu Glu Ser Tyr Val Gly Asn Lys Gly His Ile Ile Met Thr Ile Ser
        675                 680                 685
Asn Ala Leu Lys Lys Arg Asp Gln Lys Trp Thr Asp Met Tyr Gly Leu
    690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                725                 730                 735
Lys Ile Ile Glu Asp Gln Tyr Asn Arg Tyr Ser Glu Glu Asp Lys Met
            740                 745                 750
Asn Ile Asn Ile Asp Phe Asn Asp Ile Asp Phe Lys Leu Asn Gln Ser
        755                 760                 765
Ile Asn Leu Ala Ile Asn Asn Ile Asp Asp Phe Ile Asn Gln Cys Ser
    770                 775                 780
Ile Ser Tyr Leu Met Asn Arg Met Ile Pro Leu Ala Val Lys Lys Leu
785                 790                 795                 800
Lys Asp Phe Asp Asp Asn Leu Lys Arg Asp Leu Leu Glu Tyr Ile Asp
                805                 810                 815
Thr Asn Glu Leu Tyr Leu Leu Asp Glu Val Asn Ile Leu Lys Ser Lys
            820                 825                 830
Val Asn Arg His Leu Lys Asp Ser Ile Pro Phe Asp Leu Ser Leu Tyr
        835                 840                 845
Thr Lys Asp Thr Ile Leu Ile Gln Val Phe Asn Asn Tyr Ile Ser Asn
    850                 855                 860
Ile Ser Ser Asn Ala Ile Leu Ser Leu Ser Tyr Arg Gly Gly Arg Leu
865                 870                 875                 880
Ile Asp Ser Ser Gly Tyr Gly Ala Thr Met Asn Val Gly Ser Asp Val
                885                 890                 895
Ile Phe Asn Asp Ile Gly Asn Gly Gln Phe Lys Leu Asn Asn Ser Glu
            900                 905                 910
Asn Ser Asn Ile Thr Ala His Gln Ser Lys Phe Val Val Tyr Asp Ser
        915                 920                 925
Met Phe Asp Asn Phe Ser Ile Asn Phe Trp Val Arg Thr Pro Lys Tyr
    930                 935                 940
Asn Asn Asn Asp Ile Gln Thr Tyr Leu Gln Asn Glu Tyr Thr Ile Ile
945                 950                 955                 960
Ser Cys Ile Lys Asn Asp Ser Gly Trp Lys Val Ser Ile Lys Gly Asn
                965                 970                 975
Arg Ile Ile Trp Thr Leu Ile Asp Val Asn Ala Lys Ser Lys Ser Ile
            980                 985                 990
Phe Phe Glu Tyr Ser Ile Lys Asp Asn Ile Ser Asp Tyr Ile Asn Lys
        995                 1000                1005
Trp Phe Ser Ile Thr Ile Thr Asn Asp Arg Leu Gly Asn Ala Asn
    1010                1015                1020
Ile Tyr Ile Asn Gly Ser Leu Lys Lys Ser Glu Lys Ile Leu Asn
    1025                1030                1035
Leu Asp Arg Ile Asn Ser Ser Asn Asp Ile Asp Phe Lys Leu Ile
    1040                1045                1050
Asn Cys Thr Asp Thr Thr Lys Phe Val Trp Ile Lys Asp Phe Asn
```

```
        1055                1060                1065

Ile Phe Gly Arg Glu Leu Asn Ala Thr Glu Val Ser Ser Leu Tyr
        1070                1075                1080

Trp Ile Gln Ser Ser Thr Asn Thr Leu Lys Asp Phe Trp Gly Asn
        1085                1090                1095

Pro Leu Arg Tyr Asp Thr Gln Tyr Tyr Leu Phe Asn Gln Gly Met
        1100                1105                1110

Gln Asn Ile Tyr Ile Lys Tyr Phe Ser Lys Ala Ser Met Gly Glu
        1115                1120                1125

Thr Ala Pro Arg Thr Asn Phe Asn Asn Ala Ala Ile Asn Tyr Gln
        1130                1135                1140

Asn Leu Tyr Leu Gly Leu Arg Phe Ile Ile Lys Lys Ala Ser Asn
        1145                1150                1155

Ser Arg Asn Ile Asn Asn Asp Asn Ile Val Arg Glu Gly Asp Tyr
        1160                1165                1170

Ile Tyr Leu Asn Ile Asp Asn Ile Ser Asp Glu Ser Tyr Arg Val
        1175                1180                1185

Tyr Val Leu Val Asn Ser Lys Glu Ile Gln Thr Gln Leu Phe Leu
        1190                1195                1200

Ala Pro Ile Asn Asp Asp Pro Thr Phe Tyr Asp Val Leu Gln Ile
        1205                1210                1215

Lys Lys Tyr Tyr Glu Lys Thr Thr Tyr Asn Cys Gln Ile Leu Cys
        1220                1225                1230

Glu Lys Asp Thr Lys Thr Phe Gly Leu Phe Gly Ile Gly Lys Phe
        1235                1240                1245

Val Lys Asp Tyr Gly Tyr Val Trp Asp Thr Tyr Asp Asn Tyr Phe
        1250                1255                1260

Cys Ile Ser Gln Trp Tyr Leu Arg Arg Ile Ser Glu Asn Ile Asn
        1265                1270                1275

Lys Leu Arg Leu Gly Cys Asn Trp Gln Phe Ile Pro Val Asp Glu
        1280                1285                1290

Gly Trp Thr Glu
        1295

<210> SEQ ID NO 8
<211> LENGTH: 1315
<212> TYPE: PRT
<213> ORGANISM: Clostridium tetani

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110
```

-continued

```
Asn Ala Ile Pro Tyr Leu Gly Asn Ser Tyr Ser Leu Leu Asp Lys Phe
            115                 120                 125
Asp Thr Asn Ser Asn Ser Val Ser Phe Asn Leu Leu Glu Gln Asp Pro
            130                 135                 140
Ser Gly Ala Thr Thr Lys Ser Ala Met Leu Thr Asn Leu Ile Ile Phe
145                 150                 155                 160
Gly Pro Gly Pro Val Leu Asn Lys Asn Glu Val Arg Gly Ile Val Leu
                165                 170                 175
Arg Val Asp Asn Lys Asn Tyr Phe Pro Cys Arg Asp Gly Phe Gly Ser
            180                 185                 190
Ile Met Gln Met Ala Phe Cys Pro Glu Tyr Val Pro Thr Phe Asp Asn
            195                 200                 205
Val Ile Glu Asn Ile Thr Ser Leu Thr Ile Gly Lys Ser Lys Tyr Phe
            210                 215                 220
Gln Asp Pro Ala Leu Leu Leu Met His Glu Leu Ile His Val Leu His
225                 230                 235                 240
Gly Leu Tyr Gly Met Gln Val Ser Ser His Glu Ile Ile Pro Ser Lys
                245                 250                 255
Gln Glu Ile Tyr Met Gln His Thr Tyr Pro Ile Ser Ala Glu Glu Leu
            260                 265                 270
Phe Thr Phe Gly Gly Gln Asp Ala Asn Leu Ile Ser Ile Asp Ile Lys
            275                 280                 285
Asn Asp Leu Tyr Glu Lys Thr Leu Asn Asp Tyr Lys Ala Ile Ala Asn
            290                 295                 300
Lys Leu Ser Gln Val Thr Ser Cys Asn Asp Pro Asn Ile Asp Ile Asp
305                 310                 315                 320
Ser Tyr Lys Gln Ile Tyr Gln Gln Lys Tyr Gln Phe Asp Lys Asp Ser
                325                 330                 335
Asn Gly Gln Tyr Ile Val Asn Glu Asp Lys Phe Gln Ile Leu Tyr Asn
            340                 345                 350
Ser Ile Met Tyr Gly Phe Thr Glu Ile Glu Leu Gly Lys Lys Phe Asn
            355                 360                 365
Ile Lys Thr Arg Leu Ser Tyr Phe Ser Met Asn His Asp Pro Val Lys
            370                 375                 380
Ile Pro Asn Leu Leu Asp Asp Thr Ile Tyr Asn Asp Thr Glu Gly Phe
385                 390                 395                 400
Asn Ile Glu Ser Lys Asp Leu Lys Ser Glu Tyr Lys Gly Gln Asn Met
                405                 410                 415
Arg Val Asn Thr Asn Ala Phe Arg Asn Val Asp Gly Ser Gly Leu Val
            420                 425                 430
Ser Lys Leu Ile Gly Leu Cys Lys Lys Ile Ile Pro Pro Thr Asn Ile
            435                 440                 445
Arg Glu Asn Leu Tyr Asn Arg Thr Ala Ser Leu Thr Asp Leu Gly Gly
            450                 455                 460
Glu Leu Cys Ile Lys Ile Lys Asn Glu Asp Leu Thr Phe Ile Ala Glu
465                 470                 475                 480
Lys Asn Ser Phe Ser Glu Glu Pro Phe Gln Asp Glu Ile Val Ser Tyr
                485                 490                 495
Asn Thr Lys Asn Lys Pro Leu Asn Phe Asn Tyr Ser Leu Asp Lys Ile
            500                 505                 510
Ile Val Asp Tyr Asn Leu Gln Ser Lys Ile Thr Leu Pro Asn Asp Arg
            515                 520                 525
Thr Thr Pro Val Thr Lys Gly Ile Pro Tyr Ala Pro Glu Tyr Lys Ser
```

```
                530                 535                 540
Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
                595                 600                 605

Gly Ile Leu Phe Leu Gln Trp Val Arg Asp Ile Ile Asp Asp Phe Thr
                610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
                675                 680                 685

Ser Ile Ala Glu Ser Ser Thr Gln Lys Glu Lys Ile Ile Lys Thr Ile
690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
                740                 745                 750

Lys Lys Ile Ile Asp Tyr Glu Tyr Lys Ile Tyr Ser Gly Pro Asp Lys
                755                 760                 765

Glu Gln Ile Ala Asp Glu Ile Asn Asn Leu Lys Asn Lys Leu Glu Glu
                770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
                820                 825                 830

Lys Ala Asn Ser Lys Phe Ile Gly Ile Thr Glu Leu Lys Lys Leu Glu
                835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
                900                 905                 910

Gln Leu Val Pro Gly Ile Asn Gly Lys Ala Ile His Leu Val Asn Asn
                915                 920                 925

Glu Ser Ser Glu Val Ile Val His Lys Ala Met Asp Ile Glu Tyr Asn
930                 935                 940

Asp Met Phe Asn Asn Phe Thr Val Ser Phe Trp Leu Arg Val Pro Lys
945                 950                 955                 960
```

Val Ser Ala Ser His Leu Glu Gln Tyr Gly Thr Asn Glu Tyr Ser Ile
            965                 970                 975

Ile Ser Ser Met Lys Lys His Ser Leu Ser Ile Gly Ser Gly Trp Ser
        980                 985                 990

Val Ser Leu Lys Gly Asn Asn Leu Ile Trp Thr Leu Lys Asp Ser Ala
    995                 1000                1005

Gly Glu Val Arg Gln Ile Thr Phe Arg Asp Leu Pro Asp Lys Phe
1010                1015                1020

Asn Ala Tyr Leu Ala Asn Lys Trp Val Phe Ile Thr Ile Thr Asn
1025                1030                1035

Asp Arg Leu Ser Ser Ala Asn Leu Tyr Ile Asn Gly Val Leu Met
1040                1045                1050

Gly Ser Ala Glu Ile Thr Gly Leu Gly Ala Ile Arg Glu Asp Asn
1055                1060                1065

Asn Ile Thr Leu Lys Leu Asp Arg Cys Asn Asn Asn Gln Tyr
1070                1075                1080

Val Ser Ile Asp Lys Phe Arg Ile Phe Cys Lys Ala Leu Asn Pro
1085                1090                1095

Lys Glu Ile Glu Lys Leu Tyr Thr Ser Tyr Leu Ser Ile Thr Phe
1100                1105                1110

Leu Arg Asp Phe Trp Gly Asn Pro Leu Arg Tyr Asp Thr Glu Tyr
1115                1120                1125

Tyr Leu Ile Pro Val Ala Ser Ser Ser Lys Asp Val Gln Leu Lys
1130                1135                1140

Asn Ile Thr Asp Tyr Met Tyr Leu Thr Asn Ala Pro Ser Tyr Thr
1145                1150                1155

Asn Gly Lys Leu Asn Ile Tyr Tyr Arg Arg Leu Tyr Asn Gly Leu
1160                1165                1170

Lys Phe Ile Ile Lys Arg Tyr Thr Pro Asn Asn Glu Ile Asp Ser
1175                1180                1185

Phe Val Lys Ser Gly Asp Phe Ile Lys Leu Tyr Val Ser Tyr Asn
1190                1195                1200

Asn Asn Glu His Ile Val Gly Tyr Pro Lys Asp Gly Asn Ala Phe
1205                1210                1215

Asn Asn Leu Asp Arg Ile Leu Arg Val Gly Tyr Asn Ala Pro Gly
1220                1225                1230

Ile Pro Leu Tyr Lys Lys Met Glu Ala Val Lys Leu Arg Asp Leu
1235                1240                1245

Lys Thr Tyr Ser Val Gln Leu Lys Leu Tyr Asp Asp Lys Asn Ala
1250                1255                1260

Ser Leu Gly Leu Val Gly Thr His Asn Gly Gln Ile Gly Asn Asp
1265                1270                1275

Pro Asn Arg Asp Ile Leu Ile Ala Ser Asn Trp Tyr Phe Asn His
1280                1285                1290

Leu Lys Asp Lys Ile Leu Gly Cys Asp Trp Tyr Phe Val Pro Thr
1295                1300                1305

Asp Glu Gly Trp Thr Asn Asp
1310                1315

<210> SEQ ID NO 9
<211> LENGTH: 1315
<212> TYPE: PRT
<213> ORGANISM: Artificfial Sequence
<220> FEATURE:

<223> OTHER INFORMATION: Synthetic

<400> SEQUENCE: 9

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

```
Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
```

-continued

```
                820                 825                 830
    Gln Val Asp Arg Leu Lys Asp Lys Val Asn Asn Thr Leu Ser Thr Asp
            835                 840                 845
    Ile Pro Phe Gln Leu Ser Lys Tyr Val Asp Asn Gln Arg Leu Leu Ser
            850                 855                 860
    Thr Phe Thr Glu Tyr Ile Lys Ser Glu Ile Leu Asn Asn Ile Ile Leu
    865                 870                 875                 880
    Asn Leu Arg Tyr Lys Asp Asn Asn Leu Ile Asp Leu Ser Gly Tyr Gly
                    885                 890                 895
    Ala Lys Val Glu Val Tyr Asp Gly Val Glu Leu Asn Asp Lys Asn Gln
                900                 905                 910
    Phe Lys Leu Thr Ser Ser Ala Asn Ser Lys Ile Arg Val Thr Gln Asn
            915                 920                 925
    Gln Asn Ile Ile Phe Asn Ser Val Phe Leu Asp Phe Ser Val Ser Phe
            930                 935                 940
    Trp Ile Arg Ile Pro Lys Tyr Lys Asn Asp Gly Ile Gln Asn Tyr Ile
    945                 950                 955                 960
    His Asn Glu Tyr Thr Ile Ile Asn Cys Met Lys Asn Asn Ser Gly Trp
                    965                 970                 975
    Lys Ile Ser Ile Arg Gly Asn Arg Ile Ile Trp Thr Leu Ile Asp Ile
                980                 985                 990
    Asn Gly Lys Thr Lys Ser Val Phe Phe Glu Tyr Asn Ile Arg Glu Asp
                995                 1000                1005
    Ile Ser Glu Tyr Ile Asn Arg Trp Phe Phe Val Thr Ile Thr Asn
            1010                1015                1020
    Asn Leu Asn Asn Ala Lys Ile Tyr Ile Asn Gly Lys Leu Glu Ser
            1025                1030                1035
    Asn Thr Asp Ile Lys Asp Ile Arg Glu Val Ile Ala Asn Gly Glu
            1040                1045                1050
    Ile Ile Phe Lys Leu Asp Gly Asp Ile Asp Arg Thr Gln Phe Ile
            1055                1060                1065
    Trp Met Lys Tyr Phe Ser Ile Phe Asn Thr Glu Leu Ser Gln Ser
            1070                1075                1080
    Asn Ile Glu Glu Arg Tyr Lys Ile Gln Ser Tyr Ser Glu Tyr Leu
            1085                1090                1095
    Lys Asp Phe Trp Gly Asn Pro Leu Met Tyr Asn Lys Glu Tyr Tyr
            1100                1105                1110
    Met Phe Asn Ala Gly Asn Lys Asn Ser Tyr Ile Lys Leu Lys Lys
            1115                1120                1125
    Asp Ser Pro Val Gly Glu Ile Leu Thr Arg Ser Lys Tyr Asn Gln
            1130                1135                1140
    Asn Ser Lys Tyr Ile Asn Tyr Arg Asp Leu Tyr Ile Gly Glu Lys
            1145                1150                1155
    Phe Ile Ile Arg Arg Lys Ser Asn Ser Gln Ser Ile Asn Asp Asp
            1160                1165                1170
    Ile Val Arg Lys Glu Asp Tyr Ile Tyr Leu Asp Phe Phe Asn Leu
            1175                1180                1185
    Asn Gln Glu Trp Arg Val Tyr Thr Tyr Lys Tyr Phe Lys Lys Glu
            1190                1195                1200
    Glu Met Lys Leu Phe Leu Ala Pro Ile Tyr Asp Ser Asp Glu Phe
            1205                1210                1215
    Tyr Asn Thr Ile Gln Ile Lys Glu Tyr Asp Glu Gln Pro Thr Tyr
            1220                1225                1230
```

```
Ser Cys Gln Leu Leu Phe Lys Lys Asp Glu Glu Ser Thr Asp Glu
    1235                1240                1245

Ile Gly Leu Ile Gly Ile His Arg Phe Tyr Glu Ser Gly Ile Val
    1250                1255                1260

Phe Glu Glu Tyr Lys Asp Tyr Phe Cys Ile Ser Lys Trp Tyr Leu
    1265                1270                1275

Lys Glu Val Lys Arg Lys Pro Tyr Asn Leu Lys Leu Gly Cys Asn
    1280                1285                1290

Trp Gln Phe Ile Pro Lys Asp Glu Gly Trp Thr Glu His His His
    1295                1300                1305

His His His His His His His
    1310            1315
```

<210> SEQ ID NO 10  
<211> LENGTH: 1327  
<212> TYPE: PRT  
<213> ORGANISM: Artificial Sequence  
<220> FEATURE:  
<223> OTHER INFORMATION: Synthetic

<400> SEQUENCE: 10

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

-continued

```
Phe Ile Asp Ser Leu Gln Glu Asn Glu Phe Arg Leu Tyr Tyr Asn
        275                 280                 285
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
                370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
                435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
                500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
        530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
                580                 585                 590
Lys Val Asn Lys Ala Thr Glu Ala Ala Met Phe Leu Gly Trp Val Glu
                595                 600                 605
Gln Leu Val Tyr Asp Phe Thr Asp Glu Thr Ser Glu Val Ser Thr Thr
        610                 615                 620
Asp Lys Ile Ala Asp Ile Thr Ile Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
                660                 665                 670
Ile Pro Val Leu Gly Thr Phe Ala Leu Val Ser Tyr Ile Ala Asn Lys
                675                 680                 685
```

-continued

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
        740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Glu Leu Gly Gly Gly Gly
865                 870                 875                 880

Ser Glu Leu Ser Glu Ile Leu Asn Asn Ile Ile Leu Asn Leu Arg Tyr
            885                 890                 895

Lys Asp Asn Asn Leu Ile Asp Leu Ser Gly Tyr Gly Ala Lys Val Glu
        900                 905                 910

Val Tyr Asp Gly Val Glu Leu Asn Asp Lys Asn Gln Phe Lys Leu Thr
    915                 920                 925

Ser Ser Ala Asn Ser Lys Ile Arg Val Thr Gln Asn Gln Asn Ile Ile
930                 935                 940

Phe Asn Ser Val Phe Leu Asp Phe Ser Val Ser Phe Trp Ile Arg Ile
945                 950                 955                 960

Pro Lys Tyr Lys Asn Asp Gly Ile Gln Asn Tyr Ile His Asn Glu Tyr
            965                 970                 975

Thr Ile Ile Asn Cys Met Lys Asn Asn Ser Gly Trp Lys Ile Ser Ile
        980                 985                 990

Arg Gly Asn Arg Ile Ile Trp Thr Leu Ile Asp Ile Asn Gly Lys Thr
    995                 1000                1005

Lys Ser Val Phe Phe Glu Tyr Asn Ile Arg Glu Asp Ile Ser Glu
    1010                1015                1020

Tyr Ile Asn Arg Trp Phe Phe Val Thr Ile Thr Asn Asn Leu Asn
    1025                1030                1035

Asn Ala Lys Ile Tyr Ile Asn Gly Lys Leu Glu Ser Asn Thr Asp
    1040                1045                1050

Ile Lys Asp Ile Arg Glu Val Ile Ala Asn Gly Glu Ile Ile Phe
    1055                1060                1065

Lys Leu Asp Gly Asp Ile Asp Arg Thr Gln Phe Ile Trp Met Lys
    1070                1075                1080

Tyr Phe Ser Ile Phe Asn Thr Glu Leu Ser Gln Ser Asn Ile Glu
    1085                1090                1095

Glu Arg Tyr Lys Ile Gln Ser Tyr Ser Glu Tyr Leu Lys Asp Phe

```
              1100                1105                1110
Trp Gly Asn Pro Leu Met Tyr Asn Lys Glu Tyr Tyr Met Phe Asn
         1115                1120                1125

Ala Gly Asn Lys Asn Ser Tyr Ile Lys Leu Lys Lys Asp Ser Pro
         1130                1135                1140

Val Gly Glu Ile Leu Thr Arg Ser Lys Tyr Asn Gln Asn Ser Lys
         1145                1150                1155

Tyr Ile Asn Tyr Arg Asp Leu Tyr Ile Gly Glu Lys Phe Ile Ile
         1160                1165                1170

Arg Arg Lys Ser Asn Ser Gln Ser Ile Asn Asp Asp Ile Val Arg
         1175                1180                1185

Lys Glu Asp Tyr Ile Tyr Leu Asp Phe Phe Asn Leu Asn Gln Glu
         1190                1195                1200

Trp Arg Val Tyr Thr Tyr Lys Tyr Phe Lys Lys Glu Glu Met Lys
         1205                1210                1215

Leu Phe Leu Ala Pro Ile Tyr Asp Ser Asp Glu Phe Tyr Asn Thr
         1220                1225                1230

Ile Gln Ile Lys Glu Tyr Asp Glu Gln Pro Thr Tyr Ser Cys Gln
         1235                1240                1245

Leu Leu Phe Lys Lys Asp Glu Glu Ser Thr Asp Glu Ile Gly Leu
         1250                1255                1260

Ile Gly Ile His Arg Phe Tyr Glu Ser Gly Ile Val Phe Glu Glu
         1265                1270                1275

Tyr Lys Asp Tyr Phe Cys Ile Ser Lys Trp Tyr Leu Lys Glu Val
         1280                1285                1290

Lys Arg Lys Pro Tyr Asn Leu Lys Leu Gly Cys Asn Trp Gln Phe
         1295                1300                1305

Ile Pro Lys Asp Glu Gly Trp Thr Glu His His His His His His
         1310                1315                1320

His His His His
         1325

<210> SEQ ID NO 11
<211> LENGTH: 1314
<212> TYPE: PRT
<213> ORGANISM: Artificial Sequence
<220> FEATURE:
<223> OTHER INFORMATION: Synthetic

<400> SEQUENCE: 11

Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
                 20                  25                  30

Val Lys Ala Phe Lys Ile His Asn Lys Ile Trp Val Ile Pro Glu Arg
             35                  40                  45

Asp Thr Phe Thr Asn Pro Glu Glu Gly Asp Leu Asn Pro Pro Pro Glu
         50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
```

-continued

```
                115                 120                 125
Val Ile Asp Thr Asn Cys Ile Asn Val Ile Gln Pro Asp Gly Ser Tyr
130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
                180                 185                 190
Thr Phe Gly Phe Glu Glu Ser Leu Glu Val Asp Thr Asn Pro Leu Leu
                195                 200                 205
Gly Ala Gly Lys Phe Ala Thr Asp Pro Ala Val Thr Leu Ala His Glu
210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
                290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
                370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
                435                 440                 445
Ala Leu Asn Asp Leu Cys Ile Lys Val Asn Asn Trp Asp Leu Phe Phe
                450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
                500                 505                 510
Glu Asn Ile Ser Ile Glu Asn Leu Ser Ser Asp Ile Ile Gly Gln Leu
                515                 520                 525
Glu Leu Met Pro Asn Ile Glu Arg Phe Pro Asn Gly Lys Lys Tyr Glu
530                 535                 540
```

```
Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
                885                 890                 895

Lys Val Glu Val Tyr Asp Gly Val Glu Leu Asn Asp Lys Asn Gln Phe
            900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960
```

Asn Glu Tyr Thr Ile Ile Asn Cys Met Lys Asn Asn Ser Gly Trp Lys
            965                 970                 975

Ile Ser Ile Arg Gly Asn Arg Ile Ile Trp Thr Leu Ile Asp Ile Asn
        980                 985                 990

Gly Lys Thr Lys Ser Val Phe Phe Glu Tyr Asn Ile Arg Glu Asp Ile
        995                 1000                1005

Ser Glu Tyr Ile Asn Arg Trp Phe Phe Val Thr Ile Thr Asn Asn
    1010                1015                1020

Leu Asn Asn Ala Lys Ile Tyr Ile Asn Gly Lys Leu Glu Ser Asn
    1025                1030                1035

Thr Asp Ile Lys Asp Ile Arg Glu Val Ile Ala Asn Gly Glu Ile
    1040                1045                1050

Ile Phe Lys Leu Asp Gly Asp Ile Asp Arg Thr Gln Phe Ile Trp
    1055                1060                1065

Met Lys Tyr Phe Ser Ile Phe Asn Thr Glu Leu Ser Gln Ser Asn
    1070                1075                1080

Ile Glu Glu Arg Tyr Lys Ile Gln Ser Tyr Ser Glu Tyr Leu Lys
    1085                1090                1095

Asp Phe Trp Gly Asn Pro Leu Met Tyr Asn Lys Glu Tyr Tyr Met
    1100                1105                1110

Phe Asn Ala Gly Asn Lys Asn Ser Tyr Ile Lys Leu Lys Lys Asp
    1115                1120                1125

Ser Pro Val Gly Glu Ile Leu Thr Arg Ser Lys Tyr Asn Gln Asn
    1130                1135                1140

Ser Lys Tyr Ile Asn Tyr Arg Asp Leu Tyr Ile Gly Glu Lys Phe
    1145                1150                1155

Ile Ile Arg Arg Lys Ser Asn Ser Gln Ser Ile Asn Asp Asp Ile
    1160                1165                1170

Val Arg Lys Glu Asp Tyr Ile Tyr Leu Asp Phe Phe Asn Leu Asn
    1175                1180                1185

Gln Glu Trp Arg Val Tyr Thr Tyr Lys Tyr Phe Lys Lys Glu Glu
    1190                1195                1200

Met Lys Leu Phe Leu Ala Pro Ile Tyr Asp Ser Asp Glu Phe Tyr
    1205                1210                1215

Asn Thr Ile Gln Ile Lys Glu Tyr Asp Glu Gln Pro Thr Tyr Ser
    1220                1225                1230

Cys Gln Leu Leu Phe Lys Lys Asp Glu Glu Ser Thr Asp Glu Ile
    1235                1240                1245

Gly Leu Ile Gly Ile His Arg Phe Tyr Glu Ser Gly Ile Val Phe
    1250                1255                1260

Glu Glu Tyr Lys Asp Tyr Phe Cys Ile Ser Lys Trp Tyr Leu Lys
    1265                1270                1275

Glu Val Lys Arg Lys Pro Tyr Asn Leu Lys Leu Gly Cys Asn Trp
    1280                1285                1290

Gln Phe Ile Pro Lys Asp Glu Gly Trp Thr Glu His His His
    1295                1300                1305

His His His His His His
    1310

<210> SEQ ID NO 12
<211> LENGTH: 1304
<212> TYPE: PRT
<213> ORGANISM: Artificial Sequence
<220> FEATURE:
<223> OTHER INFORMATION: Synthetic

```
<400> SEQUENCE: 12

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Gly Asp Leu Asn Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
```

-continued

```
                    405                 410                 415
Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Met Phe Leu Gly Trp Val Glu
                595                 600                 605

Gln Leu Val Tyr Asp Phe Thr Asp Glu Thr Ser Glu Val Ser Thr Thr
                610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830
```

```
Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Leu Asn Asn Ile Ile Leu Asn
865                 870                 875                 880

Leu Arg Tyr Lys Asp Asn Asn Leu Ile Asp Leu Ser Gly Tyr Gly Ala
        885                 890                 895

Lys Val Glu Val Tyr Asp Gly Val Glu Leu Asn Asp Lys Asn Gln Phe
        900                 905                 910

Lys Leu Thr Ser Ser Ala Asn Ser Lys Ile Arg Val Thr Gln Asn Gln
        915                 920                 925

Asn Ile Ile Phe Asn Ser Val Phe Leu Asp Phe Ser Val Ser Phe Trp
    930                 935                 940

Ile Arg Ile Pro Lys Tyr Lys Asn Asp Gly Ile Gln Asn Tyr Ile His
945                 950                 955                 960

Asn Glu Tyr Thr Ile Ile Asn Cys Met Lys Asn Asn Ser Gly Trp Lys
            965                 970                 975

Ile Ser Ile Arg Gly Asn Arg Ile Ile Trp Thr Leu Ile Asp Ile Asn
        980                 985                 990

Gly Lys Thr Lys Ser Val Phe Phe  Glu Tyr Asn Ile Arg  Glu Asp Ile
        995                 1000                1005

Ser Glu  Tyr Ile Asn Arg Trp  Phe Phe Val Thr Ile  Thr Asn Asn
    1010                1015                1020

Leu Asn  Asn Ala Lys Ile Tyr  Ile Asn Gly Lys Leu  Glu Ser Asn
    1025                1030                1035

Thr Asp  Ile Lys Asp Ile Arg  Glu Val Ile Ala Asn  Gly Glu Ile
    1040                1045                1050

Ile Phe  Lys Leu Asp Gly Asp  Ile Asp Arg Thr Gln  Phe Ile Trp
    1055                1060                1065

Met Lys  Tyr Phe Ser Ile Phe  Asn Thr Glu Leu Ser  Gln Ser Asn
    1070                1075                1080

Ile Glu  Glu Arg Tyr Lys Ile  Gln Ser Tyr Ser Glu  Tyr Leu Lys
    1085                1090                1095

Asp Phe  Trp Gly Asn Pro Leu  Met Tyr Asn Lys Glu  Tyr Tyr Met
    1100                1105                1110

Phe Asn  Ala Gly Asn Lys Asn  Ser Tyr Ile Lys Leu  Lys Lys Asp
    1115                1120                1125

Ser Pro  Val Gly Glu Ile Leu  Thr Arg Ser Lys Tyr  Asn Gln Asn
    1130                1135                1140

Ser Lys  Tyr Ile Asn Tyr Arg  Asp Leu Tyr Ile Gly  Glu Lys Phe
    1145                1150                1155

Ile Ile  Arg Arg Lys Ser Asn  Ser Gln Ser Ile Asn  Asp Asp Ile
    1160                1165                1170

Val Arg  Lys Glu Asp Tyr Ile  Tyr Leu Asp Phe Phe  Asn Leu Asn
    1175                1180                1185

Gln Glu  Trp Arg Val Tyr Thr  Tyr Lys Tyr Phe Lys  Lys Glu Glu
    1190                1195                1200

Met Lys  Leu Phe Leu Ala Pro  Ile Tyr Asp Ser Asp  Glu Phe Tyr
    1205                1210                1215

Asn Thr  Ile Gln Ile Lys Glu  Tyr Asp Glu Gln Pro  Thr Tyr Ser
    1220                1225                1230
```

```
Cys Gln Leu Leu Phe Lys Lys Asp Glu Glu Ser Thr Asp Glu Ile
    1235                1240                1245

Gly Leu Ile Gly Ile His Arg Phe Tyr Glu Ser Gly Ile Val Phe
    1250                1255                1260

Glu Glu Tyr Lys Asp Tyr Phe Cys Ile Ser Lys Trp Tyr Leu Lys
    1265                1270                1275

Glu Val Lys Arg Lys Pro Tyr Asn Leu Lys Leu Gly Cys Asn Trp
    1280                1285                1290

Gln Phe Ile Pro Lys Asp Gly Trp Thr Glu
    1295                1300
```

<210> SEQ ID NO 13
<211> LENGTH: 1304
<212> TYPE: PRT
<213> ORGANISM: Artificial Sequence
<220> FEATURE:
<223> OTHER INFORMATION: Synthetic

<400> SEQUENCE: 13

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285
```

```
Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                    325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
        515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
```

-continued

```
            705                 710                 715                 720
        Val Asn Thr Gln Ile Asp Leu Ile Arg Lys Lys Met Lys Glu Ala Leu
                        725                 730                 735
        Glu Asn Gln Ala Glu Ala Thr Lys Ala Ile Ile Asn Tyr Gln Tyr Asn
                        740                 745                 750
        Gln Tyr Thr Glu Glu Lys Asn Asn Ile Asn Phe Asn Ile Asp Asp
                        755                 760                 765
        Leu Ser Ser Lys Leu Asn Glu Ser Ile Asn Lys Ala Met Ile Asn Ile
                        770                 775                 780
        Asn Lys Phe Leu Asn Gln Cys Ser Val Ser Tyr Leu Met Asn Ser Met
        785                 790                 795                 800
        Ile Pro Tyr Gly Val Lys Arg Leu Glu Asp Phe Asp Ala Ser Leu Lys
                        805                 810                 815
        Asp Ala Leu Leu Lys Tyr Ile Tyr Asp Asn Arg Gly Thr Leu Ile Gly
                        820                 825                 830
        Gln Val Asp Arg Leu Lys Asp Lys Val Asn Asn Thr Leu Ser Thr Asp
                        835                 840                 845
        Ile Pro Phe Gln Leu Ser Lys Tyr Val Asp Asn Gln Arg Leu Leu Ser
                        850                 855                 860
        Thr Phe Thr Glu Tyr Ile Lys Asn Ile Leu Asn Asn Ile Ile Leu Asn
        865                 870                 875                 880
        Leu Arg Tyr Lys Asp Asn Asn Leu Ile Asp Leu Ser Gly Tyr Gly Ala
                        885                 890                 895
        Lys Val Glu Val Tyr Asp Gly Val Glu Leu Asn Asp Lys Asn Gln Phe
                        900                 905                 910
        Lys Leu Thr Ser Ser Ala Asn Ser Lys Ile Arg Val Thr Gln Asn Gln
                        915                 920                 925
        Asn Ile Ile Phe Asn Ser Val Phe Leu Asp Phe Ser Val Ser Phe Trp
                        930                 935                 940
        Ile Arg Ile Pro Lys Tyr Lys Asn Asp Gly Ile Gln Asn Tyr Ile His
        945                 950                 955                 960
        Asn Glu Tyr Thr Ile Ile Asn Cys Met Lys Asn Asn Ser Gly Trp Lys
                        965                 970                 975
        Ile Ser Ile Arg Gly Asn Arg Ile Ile Trp Thr Leu Ile Asp Ile Asn
                        980                 985                 990
        Gly Lys Thr Lys Ser Val Phe Phe Glu Tyr Asn Ile Arg Glu Asp Ile
                        995                 1000                1005
        Ser Glu Tyr Ile Asn Arg Trp Phe Phe Val Thr Ile Thr Asn Asn
                        1010                1015                1020
        Leu Asn Asn Ala Lys Ile Tyr Ile Asn Gly Lys Leu Glu Ser Asn
                        1025                1030                1035
        Thr Asp Ile Lys Asp Ile Arg Glu Val Ile Ala Asn Gly Glu Ile
                        1040                1045                1050
        Ile Phe Lys Leu Asp Gly Asp Ile Asp Arg Thr Gln Phe Ile Trp
                        1055                1060                1065
        Met Lys Tyr Phe Ser Ile Phe Asn Thr Glu Leu Ser Gln Ser Asn
                        1070                1075                1080
        Ile Glu Glu Arg Tyr Lys Ile Gln Ser Tyr Ser Glu Tyr Leu Lys
                        1085                1090                1095
        Asp Phe Trp Gly Asn Pro Leu Met Tyr Asn Lys Glu Tyr Tyr Met
                        1100                1105                1110
        Phe Asn Ala Gly Asn Lys Asn Ser Tyr Ile Lys Leu Lys Lys Asp
                        1115                1120                1125
```

-continued

```
Ser Pro Val Gly Glu Ile Leu Thr Arg Ser Lys Tyr Asn Gln Asn
    1130                1135                1140

Ser Lys Tyr Ile Asn Tyr Arg Asp Leu Tyr Ile Gly Glu Lys Phe
    1145                1150                1155

Ile Ile Arg Arg Lys Ser Asn Ser Gln Ser Ile Asn Asp Asp Ile
    1160                1165                1170

Val Arg Lys Glu Asp Tyr Ile Tyr Leu Asp Phe Phe Asn Leu Asn
    1175                1180                1185

Gln Glu Trp Arg Val Tyr Thr Tyr Lys Tyr Phe Lys Lys Glu Glu
    1190                1195                1200

Glu Lys Leu Phe Leu Ala Pro Ile Ser Asp Ser Asp Glu Phe Tyr
    1205                1210                1215

Asn Thr Ile Gln Ile Lys Glu Tyr Asp Glu Gln Pro Thr Tyr Ser
    1220                1225                1230

Cys Gln Leu Leu Phe Lys Lys Asp Glu Glu Ser Thr Asp Glu Ile
    1235                1240                1245

Gly Leu Ile Gly Ile His Arg Phe Tyr Glu Ser Gly Ile Val Phe
    1250                1255                1260

Glu Glu Tyr Lys Asp Tyr Phe Cys Ile Ser Lys Trp Tyr Leu Lys
    1265                1270                1275

Glu Val Lys Arg Lys Pro Tyr Asn Leu Lys Leu Gly Cys Asn Trp
    1280                1285                1290

Gln Phe Ile Pro Lys Asp Glu Gly Trp Thr Glu
    1295                1300
```

<210> SEQ ID NO 14
<211> LENGTH: 6
<212> TYPE: PRT
<213> ORGANISM: Clostridium botulinum

<400> SEQUENCE: 14

```
Asn Ile Ile Asn Thr Ser
1               5
```

<210> SEQ ID NO 15
<211> LENGTH: 6
<212> TYPE: PRT
<213> ORGANISM: Clostridium botulinum

<400> SEQUENCE: 15

```
Asn Ile Val Asn Thr Ser
1               5
```

<210> SEQ ID NO 16
<211> LENGTH: 6
<212> TYPE: PRT
<213> ORGANISM: Clostridium botulinum

<400> SEQUENCE: 16

```
Asn Ile Val Asn Thr Ser
1               5
```

<210> SEQ ID NO 17
<211> LENGTH: 6
<212> TYPE: PRT
<213> ORGANISM: Clostridium botulinum

<400> SEQUENCE: 17

```
Asn Ile Thr Asn Ala Ser
```

```
1               5

<210> SEQ ID NO 18
<211> LENGTH: 6
<212> TYPE: PRT
<213> ORGANISM: Artificial Sequence
<220> FEATURE:
<223> OTHER INFORMATION: artificial

<400> SEQUENCE: 18

Asn Ile Ile Asn Thr Ser
1               5

<210> SEQ ID NO 19
<211> LENGTH: 6
<212> TYPE: PRT
<213> ORGANISM: Clostridium botulinum

<400> SEQUENCE: 19

Asn Ile Ile Asn Thr Ser
1               5

<210> SEQ ID NO 20
<211> LENGTH: 6
<212> TYPE: PRT
<213> ORGANISM: Clostridium botulinum

<400> SEQUENCE: 20

Asn Ile Ile Asn Thr Ser
1               5

<210> SEQ ID NO 21
<211> LENGTH: 6
<212> TYPE: PRT
<213> ORGANISM: Clostridium botulinum

<400> SEQUENCE: 21

Asn Ile Thr Asn Thr Ser
1               5

<210> SEQ ID NO 22
<211> LENGTH: 6
<212> TYPE: PRT
<213> ORGANISM: Clostridium botulinum

<400> SEQUENCE: 22

Glu Ile Leu Asn Asn Ile
1               5

<210> SEQ ID NO 23
<211> LENGTH: 6
<212> TYPE: PRT
<213> ORGANISM: Clostridium botulinum

<400> SEQUENCE: 23

Glu Ile Leu Asn Asn Ile
1               5

<210> SEQ ID NO 24
<211> LENGTH: 6
<212> TYPE: PRT
<213> ORGANISM: Clostridium botulinum

<400> SEQUENCE: 24

Glu Ile Leu Asn Asn Ile
```

```
1               5

<210> SEQ ID NO 25
<211> LENGTH: 6
<212> TYPE: PRT
<213> ORGANISM: Clostridium botulinum

<400> SEQUENCE: 25

Glu Ile Leu Asn Asn Ile
1               5

<210> SEQ ID NO 26
<211> LENGTH: 6
<212> TYPE: PRT
<213> ORGANISM: Clostridium botulinum

<400> SEQUENCE: 26

Asp Ile Leu Asn Asn Ile
1               5

<210> SEQ ID NO 27
<211> LENGTH: 6
<212> TYPE: PRT
<213> ORGANISM: Clostridium botulinum

<400> SEQUENCE: 27

Glu Ile Leu Asn Asn Ile
1               5

<210> SEQ ID NO 28
<211> LENGTH: 6
<212> TYPE: PRT
<213> ORGANISM: Clostridium botulinum

<400> SEQUENCE: 28

Glu Ile Leu Asn Asn Ile
1               5

<210> SEQ ID NO 29
<211> LENGTH: 6
<212> TYPE: PRT
<213> ORGANISM: Clostridium botulinum

<400> SEQUENCE: 29

Glu Ile Leu Asn Asn Ile
1               5

<210> SEQ ID NO 30
<211> LENGTH: 6
<212> TYPE: PRT
<213> ORGANISM: Clostridium botulinum

<400> SEQUENCE: 30

Asn Ile Asn Asp Ser Lys
1               5

<210> SEQ ID NO 31
<211> LENGTH: 6
<212> TYPE: PRT
<213> ORGANISM: Clostridium botulinum

<400> SEQUENCE: 31

Ser Ile Asn Asp Ser Lys
1               5
```

```
<210> SEQ ID NO 32
<211> LENGTH: 6
<212> TYPE: PRT
<213> ORGANISM: Clostridium botulinum

<400> SEQUENCE: 32

Ser Ile Asn Asp Ser Lys
1               5

<210> SEQ ID NO 33
<211> LENGTH: 6
<212> TYPE: PRT
<213> ORGANISM: Clostridium botulinum

<400> SEQUENCE: 33

Ser Ile Asn Asp Ser Lys
1               5

<210> SEQ ID NO 34
<211> LENGTH: 6
<212> TYPE: PRT
<213> ORGANISM: Clostridium botulinum

<400> SEQUENCE: 34

Arg Ile Lys Ser Ser Ser
1               5

<210> SEQ ID NO 35
<211> LENGTH: 6
<212> TYPE: PRT
<213> ORGANISM: Clostridium botulinum

<400> SEQUENCE: 35

Arg Ile Lys Ser Ser Ser
1               5

<210> SEQ ID NO 36
<211> LENGTH: 6
<212> TYPE: PRT
<213> ORGANISM: Clostridium botulinum

<400> SEQUENCE: 36

Arg Ile Lys Ser Ser Ser
1               5

<210> SEQ ID NO 37
<211> LENGTH: 6
<212> TYPE: PRT
<213> ORGANISM: Clostridium botulinum

<400> SEQUENCE: 37

Arg Ile Lys Ser Ser Ser
1               5

<210> SEQ ID NO 38
<211> LENGTH: 6
<212> TYPE: PRT
<213> ORGANISM: Clostridium botulinum

<400> SEQUENCE: 38

Arg Ile Lys Ser Ser Ser
1               5

<210> SEQ ID NO 39
```

```
<211> LENGTH: 6
<212> TYPE: PRT
<213> ORGANISM: Clostridium botulinum

<400> SEQUENCE: 39

Arg Ile Lys Ser Ser Ser
1               5

<210> SEQ ID NO 40
<211> LENGTH: 6
<212> TYPE: PRT
<213> ORGANISM: Clostridium botulinum

<400> SEQUENCE: 40

Arg Ile Lys Ser Ser Ser
1               5

<210> SEQ ID NO 41
<211> LENGTH: 6
<212> TYPE: PRT
<213> ORGANISM: Clostridium botulinum

<400> SEQUENCE: 41

Arg Ile Lys Ser Ser Ser
1               5

<210> SEQ ID NO 42
<211> LENGTH: 6
<212> TYPE: PRT
<213> ORGANISM: Clostridium botulinum

<400> SEQUENCE: 42

Arg Ile Lys Ser Ser Ser
1               5

<210> SEQ ID NO 43
<211> LENGTH: 6
<212> TYPE: PRT
<213> ORGANISM: Clostridium botulinum

<400> SEQUENCE: 43

Arg Ile Lys Ser Ser Ser
1               5

<210> SEQ ID NO 44
<211> LENGTH: 6
<212> TYPE: PRT
<213> ORGANISM: Clostridium botulinum

<400> SEQUENCE: 44

Arg Ile Lys Ser Ser Ser
1               5

<210> SEQ ID NO 45
<211> LENGTH: 6
<212> TYPE: PRT
<213> ORGANISM: Clostridium botulinum

<400> SEQUENCE: 45

Arg Ile Lys Ser Ser Ser
1               5

<210> SEQ ID NO 46
<211> LENGTH: 6
<212> TYPE: PRT
```

<213> ORGANISM: Clostridium botulinum

<400> SEQUENCE: 46

Arg Ile Lys Ser Ser Ser
1               5

<210> SEQ ID NO 47
<211> LENGTH: 6
<212> TYPE: PRT
<213> ORGANISM: Clostridium botulinum

<400> SEQUENCE: 47

Lys Ile Lys Asp Ser Ser
1               5

<210> SEQ ID NO 48
<211> LENGTH: 6
<212> TYPE: PRT
<213> ORGANISM: Clostridium botulinum

<400> SEQUENCE: 48

Lys Ile Lys Asp Ser Ser
1               5

<210> SEQ ID NO 49
<211> LENGTH: 6
<212> TYPE: PRT
<213> ORGANISM: Clostridium botulinum

<400> SEQUENCE: 49

Lys Ile Lys Asp Asn Cys
1               5

<210> SEQ ID NO 50
<211> LENGTH: 6
<212> TYPE: PRT
<213> ORGANISM: Clostridium botulinum

<400> SEQUENCE: 50

Lys Ile Lys Asp Ser Ser
1               5

<210> SEQ ID NO 51
<211> LENGTH: 6
<212> TYPE: PRT
<213> ORGANISM: Clostridium botulinum

<400> SEQUENCE: 51

Lys Ile Lys Asp Ser Ser
1               5

<210> SEQ ID NO 52
<211> LENGTH: 6
<212> TYPE: PRT
<213> ORGANISM: Clostridium botulinum

<400> SEQUENCE: 52

Lys Ile Lys Asp Ser Ser
1               5

<210> SEQ ID NO 53
<211> LENGTH: 6
<212> TYPE: PRT
<213> ORGANISM: Clostridium botulinum

```
<400> SEQUENCE: 53

Asn Ile Ser Ser Asn Ala
1               5

<210> SEQ ID NO 54
<211> LENGTH: 6
<212> TYPE: PRT
<213> ORGANISM: Clostridium botulinum

<400> SEQUENCE: 54

Glu Leu Lys Tyr Asn Cys
1               5

<210> SEQ ID NO 55
<211> LENGTH: 6
<212> TYPE: PRT
<213> ORGANISM: Clostridium botulinum

<400> SEQUENCE: 55

Ile Leu Lys Lys Ser Thr
1               5

<210> SEQ ID NO 56
<211> LENGTH: 1286
<212> TYPE: PRT
<213> ORGANISM: Artificial Sequence
<220> FEATURE:
<223> OTHER INFORMATION: Synthetic

<400> SEQUENCE: 56

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220
```

-continued

```
Ala Leu Ile Leu Met His Glu Leu Ile His Val His Gly Leu Tyr
225                 230                 235                 240

Gly Ile Lys Val Asp Asp Leu Pro Ile Val Pro Asn Glu Lys Lys Phe
            245                 250                 255

Phe Met Gln Ser Thr Asp Ala Ile Gln Ala Glu Glu Leu Tyr Thr Phe
        260                 265                 270

Gly Gly Gln Asp Pro Ser Ile Ile Thr Pro Ser Thr Asp Lys Ser Ile
    275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
        340                 345                 350

Met Phe Gly Phe Thr Glu Thr Asn Ile Ala Glu Asn Tyr Lys Ile Lys
    355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
        420                 425                 430

Lys Ile Gln Met Cys Lys Ser Val Lys Ala Pro Gly Ile Cys Ile Asp
    435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
            485                 490                 495

Leu Ile Ser Lys Ile Glu Leu Pro Ser Glu Asn Thr Glu Ser Leu Thr
        500                 505                 510

Asp Phe Asn Val Asp Val Pro Val Tyr Glu Lys Gln Pro Ala Ile Lys
    515                 520                 525

Lys Ile Phe Thr Asp Glu Asn Thr Ile Phe Gln Tyr Leu Tyr Ser Gln
530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
            565                 570                 575

Tyr Ile Lys Thr Ala Asn Lys Val Val Glu Ala Gly Leu Phe Ala Gly
        580                 585                 590

Trp Val Lys Gln Ile Val Asn Asp Phe Val Ile Glu Ala Asn Lys Ser
    595                 600                 605

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
```

-continued

```
                645                 650                 655
Glu Leu Leu Ile Pro Val Val Gly Ala Phe Leu Leu Glu Ser Tyr Ile
                    660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                    725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Ile Asn
850                 855                 860

Asp Ser Lys Ile Leu Ser Leu Gln Asn Arg Lys Asn Thr Leu Val Asp
865                 870                 875                 880

Thr Ser Gly Tyr Asn Ala Glu Val Ser Glu Glu Gly Asp Val Gln Leu
                885                 890                 895

Asn Pro Ile Phe Pro Phe Asp Phe Lys Leu Gly Ser Ser Gly Glu Asp
                900                 905                 910

Arg Gly Lys Val Ile Val Thr Gln Asn Glu Asn Ile Val Tyr Asn Ser
                915                 920                 925

Met Tyr Glu Ser Phe Ser Ile Ser Phe Trp Ile Arg Ile Asn Lys Trp
                930                 935                 940

Val Ser Asn Leu Pro Gly Tyr Thr Ile Ile Asp Ser Val Lys Asn Asn
945                 950                 955                 960

Ser Gly Trp Ser Ile Gly Ile Ile Ser Asn Phe Leu Val Phe Thr Leu
                    965                 970                 975

Lys Gln Asn Glu Asp Ser Glu Gln Ser Ile Asn Phe Ser Tyr Asp Ile
                980                 985                 990

Ser Asn Asn Ala Pro Gly Tyr Asn  Lys Trp Phe Phe Val  Thr Val Thr
                995                 1000                1005

Asn Asn  Met Met Gly Asn Met  Lys Ile Tyr Ile Asn  Gly Lys Leu
                1010                1015               1020

Ile Asp  Thr Ile Lys Val Lys  Glu Leu Thr Gly Ile  Asn Phe Ser
                1025                1030               1035

Lys Thr  Ile Thr Phe Glu Ile  Asn Lys Ile Pro Asp  Thr Gly Leu
                1040                1045               1050

Ile Thr  Ser Asp Ser Asp Asn  Ile Asn Met Trp Ile  Arg Asp Phe
                1055                1060               1065
```

Tyr Ile Phe Ala Lys Glu Leu Asp Gly Lys Asp Ile Asn Ile Leu
        1070                1075                1080

Phe Asn Ser Leu Gln Tyr Thr Asn Val Val Lys Asp Tyr Trp Gly
    1085                1090                1095

Asn Asp Leu Arg Tyr Asn Lys Glu Tyr Tyr Met Val Asn Ile Asp
    1100                1105                1110

Tyr Leu Asn Arg Tyr Met Tyr Ala Asn Ser Arg Gln Ile Val Phe
    1115                1120                1125

Asn Thr Arg Arg Asn Asn Asn Asp Phe Asn Glu Gly Tyr Lys Ile
    1130                1135                1140

Ile Ile Lys Arg Ile Arg Gly Asn Thr Asn Asp Thr Arg Val Arg
    1145                1150                1155

Gly Gly Asp Ile Leu Tyr Phe Asp Met Thr Ile Asn Asn Lys Ala
    1160                1165                1170

Tyr Asn Leu Phe Met Lys Asn Glu Thr Met Tyr Ala Asp Asn His
    1175                1180                1185

Ser Thr Glu Asp Ile Tyr Ala Ile Gly Leu Arg Glu Gln Thr Lys
    1190                1195                1200

Asp Ile Asn Asp Asn Ile Ile Phe Gln Ile Gln Pro Met Asn Asn
    1205                1210                1215

Thr Tyr Tyr Tyr Ala Ser Gln Ile Phe Lys Ser Asn Phe Asn Gly
    1220                1225                1230

Glu Asn Ile Ser Gly Ile Cys Ser Ile Gly Thr Tyr Arg Phe Arg
    1235                1240                1245

Leu Gly Gly Asp Trp Tyr Arg His Asn Tyr Leu Val Pro Thr Val
    1250                1255                1260

Lys Gln Gly Asn Tyr Ala Ser Leu Leu Glu Ser Thr Ser Thr His
    1265                1270                1275

Trp Gly Phe Val Pro Val Ser Glu
    1280                1285

<210> SEQ ID NO 57
<211> LENGTH: 1291
<212> TYPE: PRT
<213> ORGANISM: Artificial Sequence
<220> FEATURE:
<223> OTHER INFORMATION: Synthetic

<400> SEQUENCE: 57

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
            85                  90                  95

Asn Arg Ile Lys Ser Lys Pro Leu Gly Glu Lys Leu Leu Glu Met Ile
        100                 105                 110

Ile Asn Gly Ile Pro Tyr Leu Gly Asp Arg Arg Val Pro Leu Glu Glu
    115                 120                 125

```
Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
            165                 170                 175

Ile Gln Asn His Phe Ala Ser Arg Glu Gly Phe Gly Gly Ile Met Gln
                180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
            210                 215                 220

Ala Leu Ile Leu Met His Gln Leu Ile Tyr Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
530                 535                 540
```

```
Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
            565                 570                 575

Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
            850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
```

```
                  965                 970                 975
Asp Ile Asn Gly Lys Thr Lys Ser Val Phe Glu Tyr Asn Ile Arg
                980                 985                 990

Glu Asp Ile Ser Glu Tyr Ile Asn Arg Trp Phe Phe Val Thr Ile Thr
            995                1000                1005

Asn Asn Leu Asn Asn Ala Lys Ile Tyr Ile Asn Gly Lys Leu Glu
           1010                1015                1020

Ser Asn Thr Asp Ile Lys Asp Ile Arg Glu Val Ile Ala Asn Gly
           1025                1030                1035

Glu Ile Ile Phe Lys Leu Asp Gly Asp Ile Asp Arg Thr Gln Phe
           1040                1045                1050

Ile Trp Met Lys Tyr Phe Ser Ile Phe Asn Thr Glu Leu Ser Gln
           1055                1060                1065

Ser Asn Ile Glu Glu Arg Tyr Lys Ile Gln Ser Tyr Ser Glu Tyr
           1070                1075                1080

Leu Lys Asp Phe Trp Gly Asn Pro Leu Met Tyr Asn Lys Glu Tyr
           1085                1090                1095

Tyr Met Phe Asn Ala Gly Asn Lys Asn Ser Tyr Ile Lys Leu Lys
           1100                1105                1110

Lys Asp Ser Pro Val Gly Glu Ile Leu Thr Arg Ser Lys Tyr Asn
           1115                1120                1125

Gln Asn Ser Lys Tyr Ile Asn Tyr Arg Asp Leu Tyr Ile Gly Glu
           1130                1135                1140

Lys Phe Ile Ile Arg Arg Lys Ser Asn Ser Gln Ser Ile Asn Asp
           1145                1150                1155

Asp Ile Val Arg Lys Glu Asp Tyr Ile Tyr Leu Asp Phe Phe Asn
           1160                1165                1170

Leu Asn Gln Glu Trp Arg Val Tyr Thr Tyr Lys Tyr Phe Lys Lys
           1175                1180                1185

Glu Glu Glu Lys Leu Phe Leu Ala Pro Ile Ser Asp Ser Asp Glu
           1190                1195                1200

Phe Tyr Asn Thr Ile Gln Ile Lys Glu Tyr Asp Glu Gln Pro Thr
           1205                1210                1215

Tyr Ser Cys Gln Leu Leu Phe Lys Lys Asp Glu Glu Ser Thr Asp
           1220                1225                1230

Glu Ile Gly Leu Ile Gly Ile His Arg Phe Tyr Glu Ser Gly Ile
           1235                1240                1245

Val Phe Glu Glu Tyr Lys Asp Tyr Phe Cys Ile Ser Lys Trp Tyr
           1250                1255                1260

Leu Lys Glu Val Lys Arg Lys Pro Tyr Asn Leu Lys Leu Gly Cys
           1265                1270                1275

Asn Trp Gln Phe Ile Pro Lys Asp Glu Gly Trp Thr Glu
           1280                1285                1290

<210> SEQ ID NO 58
<211> LENGTH: 1285
<212> TYPE: PRT
<213> ORGANISM: Clostridium botulinum

<400> SEQUENCE: 58

Met Thr Trp Pro Val Lys Asp Phe Asn Tyr Ser Asp Pro Val Asn Asp
1               5                  10                  15

Asn Asp Ile Leu Tyr Leu Arg Ile Pro Gln Asn Lys Leu Ile Thr Thr
            20                  25                  30
```

Pro Val Lys Ala Phe Met Ile Thr Gln Asn Ile Trp Val Ile Pro Glu
              35                  40                  45
Arg Phe Ser Ser Asp Thr Asn Pro Ser Leu Ser Lys Pro Pro Arg Pro
 50                  55                  60
Thr Ser Lys Tyr Gln Ser Tyr Tyr Asp Pro Ser Tyr Leu Ser Thr Asp
 65                  70                  75                  80
Glu Gln Lys Asp Thr Phe Leu Lys Gly Ile Ile Lys Leu Phe Lys Arg
                  85                  90                  95
Ile Asn Glu Arg Asp Ile Gly Lys Lys Leu Ile Asn Tyr Leu Val Val
             100                 105                 110
Gly Ser Pro Phe Met Gly Asp Ser Ser Thr Pro Glu Asp Thr Phe Asp
         115                 120                 125
Phe Thr Arg His Thr Thr Asn Ile Ala Val Glu Lys Phe Glu Asn Gly
     130                 135                 140
Ser Trp Lys Val Thr Asn Ile Ile Thr Pro Ser Val Leu Ile Phe Gly
 145                 150                 155                 160
Pro Leu Pro Asn Ile Leu Asp Tyr Thr Ala Ser Leu Thr Leu Gln Gly
                 165                 170                 175
Gln Gln Ser Asn Pro Ser Phe Glu Gly Phe Gly Thr Leu Ser Ile Leu
             180                 185                 190
Lys Val Ala Pro Glu Phe Leu Leu Thr Phe Ser Asp Val Thr Ser Asn
         195                 200                 205
Gln Ser Ser Ala Val Leu Gly Lys Ser Ile Phe Cys Met Asp Pro Val
     210                 215                 220
Ile Ala Leu Met His Glu Leu Thr His Ser Leu His Gln Leu Tyr Gly
 225                 230                 235                 240
Ile Asn Ile Pro Ser Asp Lys Arg Ile Arg Pro Gln Val Ser Glu Gly
                 245                 250                 255
Phe Phe Ser Gln Asp Gly Pro Asn Val Gln Phe Glu Glu Leu Tyr Thr
             260                 265                 270
Phe Gly Gly Ser Asp Val Glu Ile Ile Pro Gln Ile Glu Arg Leu Gln
         275                 280                 285
Leu Arg Glu Lys Ala Leu Gly His Tyr Lys Asp Ile Ala Lys Arg Leu
     290                 295                 300
Asn Asn Ile Asn Lys Thr Ile Pro Ser Ser Trp Ser Ser Asn Ile Asp
 305                 310                 315                 320
Lys Tyr Lys Lys Ile Phe Ser Glu Lys Tyr Asn Phe Asp Lys Asp Asn
                 325                 330                 335
Thr Gly Asn Phe Val Val Asn Ile Asp Lys Phe Asn Ser Leu Tyr Ser
             340                 345                 350
Asp Leu Thr Asn Val Met Ser Glu Val Val Tyr Ser Ser Gln Tyr Asn
         355                 360                 365
Val Lys Asn Arg Thr His Tyr Phe Ser Lys His Tyr Leu Pro Val Phe
     370                 375                 380
Ala Asn Ile Leu Asp Asp Asn Ile Tyr Thr Ile Ile Asn Gly Phe Asn
 385                 390                 395                 400
Leu Thr Thr Lys Gly Phe Asn Ile Glu Asn Ser Gly Gln Asn Ile Glu
                 405                 410                 415
Arg Asn Pro Ala Leu Gln Lys Leu Ser Ser Glu Ser Val Val Asp Leu
             420                 425                 430
Phe Thr Lys Val Cys Leu Arg Leu Thr Arg Asn Ser Arg Asp Asp Ser
         435                 440                 445
Thr Cys Ile Gln Val Lys Asn Asn Thr Leu Pro Tyr Val Ala Asp Lys

```
                450                 455                 460
Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
                500                 505                 510

Pro Asn Val Asn Met Glu Pro Leu Asn Val Pro Gly Glu Glu Val
515                 520                 525

Phe Tyr Asp Asp Ile Thr Lys Asp Val Asp Tyr Leu Asn Ser Tyr Tyr
    530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
                595                 600                 605

Ile Met Lys Lys Asp Thr Leu Asp Lys Ile Ser Asp Val Ser Ala Ile
                610                 615                 620

Ile Pro Tyr Ile Gly Pro Ala Leu Asn Ile Gly Asn Ser Ala Leu Arg
625                 630                 635                 640

Gly Asn Phe Lys Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
                675                 680                 685

Cys Leu Glu Gln Arg Val Lys Arg Trp Lys Asp Ser Tyr Gln Trp Met
                690                 695                 700

Val Ser Asn Trp Leu Ser Arg Ile Thr Thr Gln Phe Asn His Ile Ser
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
                755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Lys Thr Lys Thr Glu Leu Ile Asn Leu Ile Asp Ser
                805                 810                 815

His Asn Ile Ile Leu Val Gly Glu Val Asp Arg Leu Lys Ala Lys Val
                820                 825                 830

Asn Glu Ser Phe Glu Asn Thr Ile Pro Phe Asn Ile Phe Ser Tyr Thr
                835                 840                 845

Asn Asn Ser Leu Leu Lys Asp Met Ile Asn Glu Tyr Phe Asn Ser Ile
                850                 855                 860

Asn Asp Ser Lys Ile Leu Ser Leu Gln Asn Lys Lys Asn Thr Leu Met
865                 870                 875                 880
```

-continued

```
Asp Thr Ser Gly Tyr Asn Ala Glu Val Arg Val Gly Asn Val Gln
            885                 890                 895

Leu Asn Pro Ile Phe Pro Phe Asp Phe Lys Leu Gly Ser Ser Gly Asp
            900                 905                 910

Asp Arg Gly Lys Val Ile Val Thr Gln Asn Glu Asn Ile Val Tyr Asn
            915                 920                 925

Ala Met Tyr Glu Ser Phe Ser Ile Ser Phe Trp Ile Arg Ile Asn Lys
    930                 935                 940

Trp Val Ser Asn Leu Pro Gly Tyr Thr Ile Ile Asp Ser Val Lys Asn
945                 950                 955                 960

Asn Ser Gly Trp Ser Ile Gly Ile Ile Ser Asn Phe Leu Val Phe Thr
                965                 970                 975

Leu Lys Gln Asn Glu Asn Ser Glu Gln Asp Ile Asn Phe Ser Tyr Asp
            980                 985                 990

Ile Ser Lys Asn Ala Ala Gly Tyr Asn Lys Trp Phe Phe Val Thr Ile
            995                1000                1005

Thr Thr Asn Met Met Gly Asn Met Met Ile Tyr Ile Asn Gly Lys
           1010                1015                1020

Leu Ile Asp Thr Ile Lys Val Lys Glu Leu Thr Gly Ile Asn Phe
           1025                1030                1035

Ser Lys Thr Ile Thr Phe Gln Met Asn Lys Ile Pro Asn Thr Gly
           1040                1045                1050

Leu Ile Thr Ser Asp Ser Asp Asn Ile Asn Met Trp Ile Arg Asp
           1055                1060                1065

Phe Tyr Ile Phe Ala Lys Glu Leu Asp Asp Lys Asp Ile Asn Ile
           1070                1075                1080

Leu Phe Asn Ser Leu Gln Tyr Thr Asn Val Val Lys Asp Tyr Trp
           1085                1090                1095

Gly Asn Asp Leu Arg Tyr Asp Lys Glu Tyr Tyr Met Ile Asn Val
           1100                1105                1110

Asn Tyr Met Asn Arg Tyr Met Ser Lys Lys Gly Asn Gly Ile Val
           1115                1120                1125

Phe Asn Thr Arg Lys Asn Asn Asn Asp Phe Asn Glu Gly Tyr Lys
           1130                1135                1140

Ile Ile Ile Lys Arg Ile Ile Gly Asn Thr Asn Asp Thr Arg Val
           1145                1150                1155

Arg Gly Glu Asn Val Leu Tyr Phe Asn Thr Thr Ile Asp Asn Lys
           1160                1165                1170

Gln Tyr Ser Leu Gly Met Tyr Lys Pro Ser Arg Asn Leu Gly Thr
           1175                1180                1185

Asp Leu Val Pro Leu Gly Ala Leu Asp Gln Pro Met Asp Glu Ile
           1190                1195                1200

Arg Lys Tyr Gly Ser Phe Ile Ile Gln Pro Cys Asn Thr Phe Asp
           1205                1210                1215

Tyr Tyr Ala Ser Gln Leu Phe Leu Ser Ser Asn Ala Thr Thr Asn
           1220                1225                1230

Arg Ile Gly Ile Leu Ser Ile Gly Ser Tyr Ser Phe Lys Leu Gly
           1235                1240                1245

Asp Asp Tyr Trp Phe Asn His Glu Tyr Leu Ile Pro Val Ile Lys
           1250                1255                1260

Ile Glu His Tyr Ala Ser Leu Leu Glu Ser Thr Ser Thr His Trp
           1265                1270                1275
```

```
Val Phe Val Pro Ala Ser Glu
    1280            1285

<210> SEQ ID NO 59
<211> LENGTH: 1280
<212> TYPE: PRT
<213> ORGANISM: Clostridium botulinum

<400> SEQUENCE: 59

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Ile Gly Asn Ile Trp Val Ile Pro Asp
            35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
                100                 105                 110

Asp Ile Pro Phe Pro Gly Asn Asn Asn Thr Pro Ile Asn Thr Phe Asp
            115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
                180                 185                 190

Ser Ile Ser Pro Arg Phe Met Leu Thr Tyr Ser Asn Ala Thr Asn Asn
            195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Asn Val Lys Leu Glu Tyr Ala Glu Ile Tyr Ala
                260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
            340                 345                 350

Glu Leu Thr Gln Ile Phe Thr Glu Phe Asn Tyr Ala Lys Ile Tyr Asn
    355                 360                 365
```

```
Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
    450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
            500                 505                 510

Asp Leu Leu Tyr Pro Ile Ile Glu Gly Glu Ser Gln Val Leu Pro Gly
        515                 520                 525

Glu Asn Gln Val Phe Tyr Asp Asn Arg Thr Gln Asn Val Asp Tyr Leu
    530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
    690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Ile Lys Ile Ser Glu Ala Met Asn Asn Ile Asn Lys Phe Ile Arg
    770                 775                 780
```

-continued

```
Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
            820                 825                 830

Lys Ala Lys Ile Asn Glu Ser Phe Glu Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
            900                 905                 910

Ser Ser Gly Asp Lys Ile Ile Val Asn Leu Asn Asn Asn Ile Leu Tyr
        915                 920                 925

Ser Ala Ile Tyr Glu Asn Ser Ser Val Ser Phe Trp Ile Lys Ile Ser
    930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
            980                 985                 990

Tyr Ser Glu Ser Leu Ser His Thr Gly Tyr Thr Asn Lys Trp Phe Phe
        995                 1000                1005

Val Thr Ile Thr Asn Asn Ile Met Gly Tyr Met Lys Leu Tyr Ile
    1010                1015                1020

Asn Gly Glu Leu Lys Gln Ser Glu Arg Ile Glu Asp Leu Asp Glu
    1025                1030                1035

Val Lys Leu Asp Lys Thr Ile Val Phe Gly Ile Asp Glu Asn Ile
    1040                1045                1050

Asp Glu Asn Gln Met Leu Trp Ile Arg Asp Phe Asn Ile Phe Ser
    1055                1060                1065

Lys Glu Leu Ser Asn Glu Asp Ile Asn Ile Val Tyr Glu Gly Gln
    1070                1075                1080

Ile Leu Arg Asn Val Ile Lys Asp Tyr Trp Gly Asn Pro Leu Lys
    1085                1090                1095

Phe Asp Thr Glu Tyr Tyr Met Ile Asn Tyr Asn Tyr Ile Asp Arg
    1100                1105                1110

Tyr Ile Ala Pro Lys Asn Asn Ile Leu Val Leu Val Gln Tyr Ser
    1115                1120                1125

Asp Ile Ser Lys Leu Tyr Thr Lys Asn Pro Ile Thr Ile Lys Ser
    1130                1135                1140

Ala Ala Asn Lys Asn Pro Tyr Ser Arg Ile Leu Asn Gly Asp Asp
    1145                1150                1155

Ile Met Phe His Met Leu Tyr Asp Ser Arg Glu Tyr Met Ile Ile
    1160                1165                1170

Arg Asp Thr Asp Thr Ile Tyr Ala Thr Gln Gly Gly Gln Cys Ser
    1175                1180                1185

Lys Asn Cys Val Tyr Ala Leu Lys Leu Gln Ser Asn Leu Gly Asn
```

```
                    1190                1195                1200

Tyr Gly Ile Gly Ile Phe Ser Ile Lys Asn Ile Val Ser Gln Asn
            1205                1210                1215

Lys Tyr Cys Ser Gln Ile Phe Ser Ser Phe Met Lys Asn Thr Met
            1220                1225                1230

Leu Leu Ala Asp Ile Tyr Lys Pro Trp Arg Phe Ser Phe Glu Asn
            1235                1240                1245

Ala Tyr Thr Pro Val Ala Val Thr Asn Tyr Glu Thr Lys Leu Leu
            1250                1255                1260

Ser Thr Ser Ser Phe Trp Lys Phe Ile Ser Arg Asp Pro Gly Trp
            1265                1270                1275

Val Glu
    1280

<210> SEQ ID NO 60
<211> LENGTH: 1291
<212> TYPE: PRT
<213> ORGANISM: Clostridium botulinum

<400> SEQUENCE: 60

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Gln Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270
```

-continued

```
Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
                340                 345                 350

Met Phe Gly Phe Thr Glu Ile Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Val Pro Gly Ile Cys Ile Asp
            435                 440                 445

Val Asp Asn Glu Asn Leu Phe Phe Ile Ala Asp Lys Asn Ser Phe Ser
    450                 455                 460

Asp Asp Leu Ser Lys Asn Glu Arg Val Glu Tyr Asn Thr Gln Asn Asn
465                 470                 475                 480

Tyr Ile Gly Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Val Phe Thr Asp Glu Asn Thr Ile Phe Gln Tyr Leu Tyr Ser Gln
530                 535                 540

Thr Phe Pro Leu Asn Ile Arg Asp Ile Ser Leu Thr Ser Ser Phe Asp
545                 550                 555                 560

Asp Ala Leu Leu Val Ser Ser Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
            595                 600                 605

Ser Thr Met Asp Lys Ile Ala Asp Ile Ser Leu Ile Val Pro Tyr Ile
    610                 615                 620

Gly Leu Ala Leu Asn Val Gly Asp Glu Thr Ala Lys Gly Asn Phe Glu
625                 630                 635                 640

Ser Ala Phe Glu Ile Ala Gly Ser Ser Ile Leu Leu Glu Phe Ile Pro
                645                 650                 655

Glu Leu Leu Ile Pro Val Val Gly Val Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Val Glu Lys Trp Ile Asp Met Tyr Gly Leu Ile Val Ala Gln Trp
```

```
                690             695             700
Leu Ser Thr Val Asn Thr Gln Phe Tyr Thr Ile Lys Glu Gly Met Tyr
705             710             715             720
Lys Ala Leu Asn Tyr Gln Ala Gln Ala Leu Glu Ile Ile Lys Tyr
            725             730             735
Lys Tyr Asn Ile Tyr Ser Glu Glu Lys Ser Asn Ile Asn Ile Asn
            740             745             750
Phe Asn Asp Ile Asn Ser Lys Leu Asn Asp Gly Ile Asn Gln Ala Met
            755             760             765
Asp Asn Ile Asn Asp Phe Ile Asn Glu Cys Ser Val Ser Tyr Leu Met
770             775             780
Lys Lys Met Ile Pro Leu Ala Val Lys Lys Leu Leu Asp Phe Asp Asn
785             790             795             800
Thr Leu Lys Lys Asn Leu Leu Asn Tyr Ile Asp Glu Asn Lys Leu Tyr
            805             810             815
Leu Ile Gly Ser Val Glu Asp Glu Lys Ser Lys Val Asp Lys Tyr Leu
            820             825             830
Lys Thr Ile Ile Pro Phe Asp Leu Ser Thr Tyr Thr Asn Asn Glu Ile
            835             840             845
Leu Ile Lys Ile Phe Asn Lys Tyr Asn Ser Glu Ile Leu Asn Asn Ile
            850             855             860
Ile Leu Asn Leu Arg Tyr Arg Asp Asn Asn Leu Ile Asp Leu Ser Gly
865             870             875             880
Tyr Gly Ala Lys Val Glu Val Tyr Asp Gly Val Lys Leu Asn Asp Lys
            885             890             895
Asn Gln Phe Lys Leu Thr Ser Ser Ala Asp Ser Lys Ile Arg Val Thr
            900             905             910
Gln Asn Gln Asn Ile Ile Phe Asn Ser Met Phe Leu Asp Phe Ser Val
            915             920             925
Ser Phe Trp Ile Arg Ile Pro Lys Tyr Arg Asn Asp Asp Ile Gln Asn
            930             935             940
Tyr Ile His Asn Glu Tyr Thr Ile Ile Asn Cys Met Lys Asn Asn Ser
945             950             955             960
Gly Trp Lys Ile Ser Ile Arg Gly Asn Arg Ile Ile Trp Thr Leu Ile
            965             970             975
Asp Ile Asn Gly Lys Thr Lys Ser Val Phe Phe Glu Tyr Asn Ile Arg
            980             985             990
Glu Asp Ile Ser Glu Tyr Ile Asn Arg Trp Phe Phe Val Thr Ile Thr
            995             1000            1005
Asn Asn Leu Asp Asn Ala Lys Ile Tyr Ile Asn Gly Thr Leu Glu
            1010            1015            1020
Ser Asn Met Asp Ile Lys Asp Ile Gly Glu Val Ile Val Asn Gly
            1025            1030            1035
Glu Ile Thr Phe Lys Leu Asp Gly Asp Val Asp Arg Thr Gln Phe
            1040            1045            1050
Ile Trp Met Lys Tyr Phe Ser Ile Phe Asn Thr Gln Leu Asn Gln
            1055            1060            1065
Ser Asn Ile Lys Glu Ile Tyr Lys Ile Gln Ser Tyr Ser Glu Tyr
            1070            1075            1080
Leu Lys Asp Phe Trp Gly Asn Pro Leu Met Tyr Asn Lys Glu Tyr
            1085            1090            1095
Tyr Met Phe Asn Ala Gly Asn Lys Asn Ser Tyr Ile Lys Leu Val
            1100            1105            1110
```

```
Lys Asp Ser Ser Val Gly Glu Ile Leu Ile Arg Ser Lys Tyr Asn
1115                1120                1125

Gln Asn Ser Asn Tyr Ile Asn Tyr Arg Asn Leu Tyr Ile Gly Glu
1130                1135                1140

Lys Phe Ile Ile Arg Arg Lys Ser Asn Ser Gln Ser Ile Asn Asp
1145                1150                1155

Asp Ile Val Arg Lys Glu Asp Tyr Ile His Leu Asp Phe Val Asn
1160                1165                1170

Ser Asn Glu Glu Trp Arg Val Tyr Ala Tyr Lys Asn Phe Lys Glu
1175                1180                1185

Gln Glu Gln Lys Leu Phe Leu Ser Ile Ile Tyr Asp Ser Asn Glu
1190                1195                1200

Phe Tyr Lys Thr Ile Gln Ile Lys Glu Tyr Asp Glu Gln Pro Thr
1205                1210                1215

Tyr Ser Cys Gln Leu Leu Phe Lys Lys Asp Glu Glu Ser Thr Asp
1220                1225                1230

Asp Ile Gly Leu Ile Gly Ile His Arg Phe Tyr Glu Ser Gly Val
1235                1240                1245

Leu Arg Lys Lys Tyr Lys Asp Tyr Phe Cys Ile Ser Lys Trp Tyr
1250                1255                1260

Leu Lys Glu Val Lys Arg Lys Pro Tyr Lys Ser Asn Leu Gly Cys
1265                1270                1275

Asn Trp Gln Phe Ile Pro Lys Asp Glu Gly Trp Thr Glu
1280                1285                1290

<210> SEQ ID NO 61
<211> LENGTH: 1292
<212> TYPE: PRT
<213> ORGANISM: Clostridium botulinum

<400> SEQUENCE: 61

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Gly Glu Glu Arg Lys Glu Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
```

-continued

```
            180             185             190
Met Lys Phe Cys Pro Glu Tyr Val Ser Val Phe Asn Asn Val Gln Glu
            195             200             205

Asn Lys Gly Ala Ser Ile Phe Asn Arg Arg Gly Tyr Phe Ser Asp Pro
    210             215             220

Ala Leu Ile Leu Met His Glu Leu Ile His Val Leu His Gly Leu Tyr
225             230             235             240

Gly Ile Lys Val Asp Asp Leu Pro Ile Val Pro Asn Gly Lys Lys Phe
            245             250             255

Phe Met Gln Ser Thr Asp Ala Ile Gln Ala Glu Glu Leu Tyr Thr Phe
            260             265             270

Gly Gly Gln Asp Pro Ser Ile Ile Thr Pro Ser Thr Asp Lys Ser Ile
            275             280             285

Tyr Asp Lys Val Leu Gln Asn Phe Arg Gly Ile Val Asp Arg Leu Asn
    290             295             300

Lys Val Leu Val Cys Ile Ser Asp Pro Asn Ile Asn Ile Asn Ile Tyr
305             310             315             320

Lys Asn Lys Phe Lys Asp Lys Tyr Lys Phe Val Glu Asp Ser Glu Gly
            325             330             335

Lys Tyr Ser Ile Asp Val Glu Ser Phe Asp Lys Leu Tyr Lys Ser Leu
            340             345             350

Met Phe Gly Phe Thr Glu Thr Asn Ile Ala Glu Asn Tyr Lys Ile Lys
            355             360             365

Thr Arg Ala Ser Tyr Phe Ser Asp Ser Leu Pro Pro Val Lys Ile Lys
    370             375             380

Asn Leu Leu Asp Asp Glu Ile Tyr Thr Ile Glu Glu Gly Phe Asn Ile
385             390             395             400

Ser Asp Lys Asn Met Gly Lys Glu Tyr Arg Gly Gln Asn Lys Ala Ile
            405             410             415

Asn Lys Gln Ala Tyr Glu Glu Ile Ser Lys Glu His Leu Ala Val Tyr
            420             425             430

Lys Ile Gln Met Cys Lys Ser Val Arg Ala Pro Gly Ile Cys Ile Asp
            435             440             445

Val Asp Asn Glu Asp Leu Phe Phe Ile Ala Asp Lys Asn Ser Phe Ser
    450             455             460

Asp Asp Leu Ser Lys Asn Glu Arg Ile Glu Tyr Asn Thr Gln Ser Asn
465             470             475             480

Tyr Ile Glu Asn Asp Phe Ser Ile Asn Glu Leu Ile Leu Asp Thr Asp
            485             490             495

Leu Ile Ser Lys Ile Glu Leu Pro Ser Glu Asn Thr Glu Ser Leu Thr
            500             505             510

Asp Phe Asn Val Asp Val Pro Val Tyr Glu Lys Gln Pro Ala Ile Lys
            515             520             525

Lys Ile Phe Thr Asp Glu Asn Thr Ile Phe Gln Tyr Leu Tyr Ser Gln
    530             535             540

Thr Phe Pro Leu Asp Ile Arg Asp Ile Ser Leu Thr Ser Ser Phe Asp
545             550             555             560

Asp Ala Leu Leu Phe Ser Asn Lys Val Tyr Ser Phe Phe Ser Met Asp
            565             570             575

Tyr Ile Lys Thr Ala Asn Lys Val Val Glu Ala Gly Leu Phe Ala Gly
            580             585             590

Trp Val Lys Gln Ile Val Asp Asp Phe Val Ile Glu Ala Asn Lys Ser
            595             600             605
```

-continued

```
Asn Thr Met Asp Lys Ile Ala Asp Ile Ser Leu Ile Val Pro Tyr Ile
    610             615                 620
Gly Leu Ala Leu Asn Val Gly Asn Glu Thr Ala Lys Gly Asn Phe Glu
625             630                 635                 640
Asn Ala Phe Glu Ile Ala Gly Ser Ser Ile Leu Leu Glu Phe Ile Pro
            645                 650                 655
Glu Leu Leu Ile Pro Val Val Gly Ala Phe Leu Leu Glu Ser Tyr Ile
            660                 665                 670
Asp Asn Lys Asn Lys Ile Ile Lys Thr Ile Asp Asn Ala Leu Thr Lys
        675                 680                 685
Arg Asp Glu Lys Trp Ile Asp Met Tyr Gly Leu Ile Val Ala Gln Trp
690                 695                 700
Leu Ser Thr Val Asn Thr Gln Phe Tyr Thr Ile Lys Glu Gly Met Tyr
705             710                 715                 720
Lys Ala Leu Asn Tyr Gln Ala Gln Ala Leu Glu Glu Ile Ile Lys Tyr
            725                 730                 735
Lys Tyr Asn Ile Tyr Ser Glu Lys Glu Lys Ser Asn Ile Ser Ile Asp
            740                 745                 750
Phe Asn Asp Ile Asn Ser Lys Leu Asn Glu Gly Ile Asn Gln Ala Ile
        755                 760                 765
Asp Asn Ile Asn Asp Phe Ile Asn Glu Cys Ser Val Ser Tyr Leu Met
770                 775                 780
Lys Lys Met Ile Pro Leu Ala Val Glu Lys Leu Leu Asp Phe Asp Asn
785             790                 795                 800
Thr Leu Lys Lys Asn Leu Leu Asn Tyr Ile Asp Glu Asn Lys Leu Tyr
            805                 810                 815
Leu Ile Gly Ser Ala Glu Tyr Glu Lys Ser Lys Val Asp Lys His Leu
            820                 825                 830
Lys Thr Ile Met Thr Phe Asp Leu Ser Met Tyr Thr Asn Asn Thr Ile
        835                 840                 845
Leu Ile Lys Met Val Asn Lys Tyr Asn Ser Glu Ile Leu Asn Asn Ile
850                 855                 860
Ile Leu Asn Leu Arg Tyr Arg Asp Asn Asn Leu Ile Asp Leu Ser Gly
865             870                 875                 880
Tyr Gly Ala Asn Val Glu Val Tyr Asp Gly Val Glu Leu Asn Asp Lys
            885                 890                 895
Asn Gln Phe Lys Leu Thr Ser Ser Thr Asn Ser Glu Ile Arg Val Thr
        900                 905                 910
Gln Asn Gln Asn Ile Ile Val Asn Ser Met Phe Leu Asp Phe Ser Val
        915                 920                 925
Ser Phe Trp Ile Arg Ile Pro Lys Tyr Lys Asn Asp Gly Ile Gln Asn
930             935                 940
Tyr Ile His Asn Glu Tyr Thr Ile Ile Asn Cys Met Lys Asn Asn Ser
945             950                 955                 960
Gly Trp Lys Ile Ser Ile Arg Gly Asn Arg Ile Ile Trp Thr Leu Ile
            965                 970                 975
Asp Ile Asn Gly Lys Ile Lys Ser Val Phe Phe Glu Tyr Ser Ile Arg
            980                 985                 990
Lys Asp Val Ser Glu Tyr Ile Asn Arg Trp Phe Phe Val Thr Ile Thr
        995                 1000                1005
Asn Asn Leu Asp Asn Ala Lys Ile Tyr Ile Asn Gly Lys Leu Glu
    1010            1015                1020
```

-continued

Ser Asn Met Asp Ile Arg Asp Ile Arg Glu Val Ile Ala Asn Gly
    1025                1030                1035

Glu Ile Ile Phe Lys Leu Asp Gly Asp Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Ile Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Ser Lys Asn Ser Tyr Ile Lys Leu Lys
    1100                1105                1110

Lys Asp Ser Ser Val Gly Glu Ile Leu Thr Arg Ser Lys Tyr Asn
    1115                1120                1125

Gln Asn Ser Gln Tyr Ile Asn Tyr Arg Asp Leu Tyr Ile Gly Glu
    1130                1135                1140

Lys Phe Ile Ile Lys Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Ala Tyr Lys Asp Phe Lys Gly
    1175                1180                1185

Gln Lys Glu Gln Lys Leu Phe Leu Ala Asn Ile His Asp Ser Asn
    1190                1195                1200

Glu Phe Tyr Lys Thr Ile Gln Ile Lys Glu Tyr Asp Glu Gln Pro
    1205                1210                1215

Thr Tyr Ser Cys Gln Leu Leu Phe Lys Lys Asp Glu Glu Ser Thr
    1220                1225                1230

Asp Glu Ile Gly Leu Ile Gly Ile His Arg Phe Tyr Glu Ser Gly
    1235                1240                1245

Phe Val Phe Gln Glu Tyr Lys Tyr Tyr Phe Cys Ile Ser Lys Trp
    1250                1255                1260

Tyr Leu Lys Glu Val Lys Lys Pro Tyr Asn Pro Asp Leu Gly
    1265                1270                1275

Cys Asn Trp Gln Phe Ile Pro Lys Asp Glu Gly Trp Thr Glu
    1280                1285                1290

<210> SEQ ID NO 62
<211> LENGTH: 1291
<212> TYPE: PRT
<213> ORGANISM: Clostridium botulinum

<400> SEQUENCE: 62

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

```
Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Lys Asn Ile
465                 470                 475                 480

Tyr Ile Glu Asn Tyr Phe Ser Ile Asn Glu Leu Ile Leu Asp Thr Asp
                485                 490                 495

Leu Ile Ser Gly Ile Glu Leu Pro Ser Glu Asn Thr Glu Ser Leu Thr
            500                 505                 510
```

-continued

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
            565                 570                 575

Tyr Ile Lys Thr Ala Asn Lys Val Val Glu Ala Gly Leu Phe Ala Gly
            580                 585                 590

Trp Val Lys Gln Ile Ile Asp Asp Phe Val Ile Glu Ala Asn Lys Ser
        595                 600                 605

Ser Thr Met Asp Lys Ile Ala Asp Ile Ser Leu Ile Val Pro Tyr Ile
        610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
            645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
            675                 680                 685

Arg Val Glu Lys Trp Ile Asp Met Tyr Gly Leu Ile Val Ala Gln Trp
        690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Leu Asn Ile Asn Ile Asp
            740                 745                 750

Phe Asn Asp Ile Asn Ser Lys Leu Asn Glu Gly Ile Asn Gln Ala Ile
        755                 760                 765

Asp Asn Ile Asn Asn Phe Ile Asn Glu Cys Ser Val Ser Tyr Leu Met
        770                 775                 780

Lys Lys Met Ile Pro Leu Ala Ile Glu Lys Leu Leu Asp Phe Asp Asn
785                 790                 795                 800

Ala Leu Lys Lys Asn Leu Leu Asn Tyr Ile Asp Glu Asn Lys Leu Tyr
                805                 810                 815

Leu Ile Gly Ser Val Glu Glu Lys Ser Lys Val Asp Lys Phe Phe
            820                 825                 830

Lys Thr Ile Ile Pro Phe Asp Leu Ser Met Tyr Thr Asn Asn Thr Ile
        835                 840                 845

Leu Ile Glu Met Val Asn Lys Tyr Asn Ser Glu Ile Leu Asn Asn Ile
850                 855                 860

Ile Leu Asn Leu Arg Tyr Arg Asp Asn Leu Ile Asp Ser Ser Gly
865                 870                 875                 880

Tyr Gly Ala Lys Val Glu Val Tyr Asn Gly Val Glu Leu Asn Asp Lys
            885                 890                 895

Asn Gln Phe Lys Leu Thr Ser Ser Ala Asn Ser Lys Ile Lys Val Thr
        900                 905                 910

Gln Asn Gln Asn Ile Thr Phe Asn Ser Met Phe Leu Asp Phe Ser Val
        915                 920                 925

Ser Phe Trp Ile Arg Ile Pro Lys Tyr Lys Asn Asp Gly Ile Gln Asn

-continued

```
                930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Thr
                965                 970                 975

Asp Ile Asn Gly Lys Thr Lys Ser Val Phe Phe Glu Tyr Ser Ile Arg
                980                 985                 990

Glu Asp Ile Ser Asp Tyr Ile Asn Arg Trp Phe Phe Val Thr Ile Thr
                995                 1000                1005

Asn Asn Leu Asp Asn Ala Lys Ile Tyr Ile Asn Gly Lys Leu Glu
        1010                1015                1020

Ser Asn Ile Asp Ile Arg Asp Ile Arg Glu Val Ile Val Asn Gly
        1025                1030                1035

Glu Ile Ile Phe Lys Leu Asp Gly Glu Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Val Lys Glu Ile Tyr Lys Ile Gln Ser Tyr Ser Lys Tyr
        1070                1075                1080

Leu Lys Asp Phe Trp Gly Asn Pro Leu Met Tyr Asn Lys Glu Tyr
        1085                1090                1095

Tyr Met Phe Asn Ala Gly Asn Lys Asn Ser Tyr Ile Lys Leu Val
        1100                1105                1110

Lys Asp Ser Ser Val Gly Glu Ile Leu Thr Arg Ser Lys Tyr Asn
        1115                1120                1125

Gln Asn Ser Asn Tyr Ile Asn Tyr Arg Asn Leu Tyr Ile Gly Glu
        1130                1135                1140

Lys Phe Ile Ile Arg Arg Lys Ser Ser Ser Gln Ser Ile Ser Asp
        1145                1150                1155

Asp Ile Val Arg Lys Glu Asp Tyr Ile Tyr Leu Asp Phe Phe Asn
        1160                1165                1170

Ser Asn Arg Glu Trp Arg Val Tyr Ala Tyr Lys Asn Phe Lys Gly
        1175                1180                1185

Gln Glu Glu Lys Leu Phe Leu Ala Asn Ile Tyr Asp Ser Asn Glu
        1190                1195                1200

Phe Tyr Lys Thr Ile Gln Ile Lys Glu Tyr Asp Glu Gln Pro Thr
        1205                1210                1215

Tyr Ser Cys Gln Leu Leu Phe Lys Lys Asp Glu Glu Ser Thr Asp
        1220                1225                1230

Glu Ile Gly Leu Ile Gly Ile His Asn Phe Tyr Glu Ser Gly Ile
        1235                1240                1245

Leu Phe Lys Asp Tyr Lys Asp Tyr Phe Cys Ile Ser Lys Trp Tyr
        1250                1255                1260

Leu Lys Glu Val Lys Lys Lys Pro Tyr Ser Ser Asn Leu Gly Cys
        1265                1270                1275

Asn Trp Gln Phe Ile Pro Lys Asp Glu Gly Trp Thr Glu
        1280                1285                1290
```

<210> SEQ ID NO 63
<211> LENGTH: 1291
<212> TYPE: PRT
<213> ORGANISM: Clostridium botulinum

<400> SEQUENCE: 63

```
Met Pro Val Thr Ile Asn Asn Phe Asn Tyr Asn Asp Pro Ile Asp Asn
1               5                   10                  15
Asn Asn Ile Ile Met Met Glu Pro Pro Phe Ala Arg Gly Thr Gly Arg
            20                  25                  30
Tyr Tyr Lys Ala Phe Lys Ile Thr Asp Arg Ile Trp Ile Ile Pro Glu
            35                  40                  45
Arg Tyr Thr Phe Gly Tyr Lys Pro Glu Asp Phe Asn Lys Ser Ser Gly
    50                  55                  60
Ile Phe Asn Arg Asp Val Cys Glu Tyr Tyr Asp Pro Asp Tyr Leu Asn
65                  70                  75                  80
Thr Asn Asp Lys Lys Asn Ile Phe Leu Gln Thr Met Ile Lys Leu Phe
            85                  90                  95
Asn Arg Ile Lys Ser Lys Pro Leu Gly Glu Lys Leu Leu Glu Met Ile
            100                 105                 110
Ile Asn Gly Ile Pro Tyr Leu Gly Asp Arg Arg Val Pro Leu Glu Glu
            115                 120                 125
Phe Asn Thr Asn Ile Ala Ser Val Thr Val Asn Lys Leu Ile Ser Asn
    130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Glu Thr Ile Asp Ile Gly
            165                 170                 175
Ile Gln Asn His Phe Ala Ser Arg Glu Gly Phe Gly Gly Ile Met Gln
            180                 185                 190
Met Lys Phe Cys Pro Glu Tyr Val Ser Val Phe Asn Asn Val Gln Glu
            195                 200                 205
Asn Lys Gly Ala Ser Ile Phe Asn Arg Arg Gly Tyr Phe Ser Asp Pro
    210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
            245                 250                 255
Phe Met Gln Ser Thr Asp Ala Ile Gln Ala Glu Glu Leu Tyr Thr Phe
            260                 265                 270
Gly Gly Gln Asp Pro Ser Ile Ile Thr Pro Ser Thr Asp Lys Ser Ile
            275                 280                 285
Tyr Asp Lys Val Leu Gln Asn Phe Arg Gly Ile Val Asp Arg Leu Asn
    290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
            325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
            355                 360                 365
Thr Arg Ala Ser Tyr Phe Ser Asp Ser Leu Pro Pro Val Lys Ile Lys
    370                 375                 380
Asn Leu Leu Asp Asn Glu Ile Tyr Thr Ile Glu Gly Phe Asn Ile
385                 390                 395                 400
Ser Asp Lys Asn Met Glu Lys Glu Tyr Arg Gly Gln Asn Lys Ala Ile
            405                 410                 415
Asn Lys Gln Ala Tyr Glu Glu Ile Ser Lys Glu His Leu Ala Val Tyr
```

```
                420             425             430
Lys Ile Gln Met Cys Lys Ser Val Arg Ala Pro Gly Ile Cys Ile Asp
            435             440             445
Val Asp Asn Glu Asp Leu Phe Phe Ile Ala Asp Lys Asn Ser Phe Ser
450             455             460
Asp Asp Leu Ser Lys Asn Glu Arg Ile Glu Tyr Asp Thr Gln Ser Asn
465             470             475             480
Tyr Ile Glu Asn Arg Ser Ser Ile Asp Glu Leu Ile Leu Asp Thr Asn
            485             490             495
Leu Ile Ser Lys Ile Glu Leu Pro Ser Glu Asn Thr Glu Ser Leu Thr
            500             505             510
Asp Phe Asn Val Asp Val Pro Val Tyr Glu Lys Gln Pro Ala Ile Lys
            515             520             525
Lys Phe Phe Thr Asp Glu Asn Thr Ile Phe Gln Tyr Leu Tyr Ser Gln
            530             535             540
Thr Phe Pro Leu Asp Ile Arg Asp Ile Ser Leu Thr Ser Ser Phe Asp
545             550             555             560
Asp Ala Leu Leu Phe Ser Asn Lys Val Tyr Ser Phe Ser Met Asp
            565             570             575
Tyr Ile Lys Thr Ala Asn Lys Val Val Glu Ala Gly Leu Phe Ala Gly
            580             585             590
Trp Val Lys Gln Ile Val Asp Asp Phe Val Ile Glu Ala Asn Lys Ser
            595             600             605
Asn Thr Met Asp Lys Leu Ala Asp Ile Ser Leu Ile Val Pro Tyr Ile
            610             615             620
Gly Leu Ala Leu Asn Val Gly Asn Glu Thr Ala Lys Gly Asn Phe Glu
625             630             635             640
Asn Ala Phe Glu Ile Ala Gly Ala Ser Ile Leu Leu Glu Phe Ile Pro
            645             650             655
Glu Leu Leu Ile Pro Val Val Gly Ala Phe Leu Leu Glu Ser Tyr Ile
            660             665             670
Asp Asn Lys Asn Lys Ile Ile Lys Thr Ile Asp Asn Ala Leu Thr Lys
            675             680             685
Arg Asp Glu Lys Trp Arg Asp Met Tyr Gly Leu Ile Val Ala Gln Trp
            690             695             700
Leu Ser Thr Val Asn Thr Gln Phe Tyr Thr Ile Lys Glu Gly Met Tyr
705             710             715             720
Lys Ala Leu Asn Tyr Gln Ala Gln Ala Leu Glu Glu Ile Ile Lys Tyr
            725             730             735
Lys Tyr Asn Ile Tyr Ser Glu Lys Glu Lys Ser Asn Ile Asn Ile Asp
            740             745             750
Phe Asn Asp Ile Asn Ser Lys Leu Asn Glu Gly Ile Asn Gln Ala Ile
            755             760             765
Asp Asn Ile Asn Asn Phe Ile Asn Glu Cys Ser Val Ser Tyr Leu Met
            770             775             780
Lys Lys Met Ile Pro Leu Ala Val Glu Lys Leu Leu Asp Phe Asp Asn
785             790             795             800
Thr Leu Lys Lys Asn Leu Leu Asn Tyr Ile Asp Glu Asn Lys Leu Tyr
            805             810             815
Leu Ile Gly Ser Ala Glu Tyr Glu Lys Ser Lys Val Asp Lys His Leu
            820             825             830
Lys Thr Ile Ile Pro Phe Asp Leu Ser Met Tyr Thr Asn Asn Thr Ile
            835             840             845
```

```
Leu Ile Glu Ile Phe Lys Lys Tyr Asn Ser Glu Ile Leu Asn Asn Ile
    850                 855                 860

Ile Leu Asn Leu Arg Tyr Arg Asp Asn Asn Leu Ile Asp Leu Ser Gly
865                 870                 875                 880

Tyr Gly Ala Asn Val Glu Val Tyr Asp Gly Val Glu Leu Asn Asp Lys
                885                 890                 895

Asn Gln Phe Lys Leu Thr Ser Ser Thr Asn Ser Glu Ile Arg Val Thr
            900                 905                 910

Gln Asn Gln Asn Ile Ile Phe Asn Ser Met Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Ile Lys Asn Asn Ser
945                 950                 955                 960

Gly Trp Lys Ile Ser Ile Arg Gly Asn Arg Ile Ile Trp Thr Leu Thr
                965                 970                 975

Asp Ile Asn Gly Lys Thr Lys Ser Val Phe Phe Glu Tyr Ser Ile Arg
            980                 985                 990

Glu Asp Ile Ser Asp Tyr Ile Asn Arg Trp Phe Phe Val Thr Ile Thr
        995                 1000                1005

Asn Asn Ser Asp Asn Ala Lys Ile Tyr Ile Asn Gly Lys Leu Glu
    1010                1015                1020

Ser Asn Ile Asp Ile Lys Asp Ile Gly Glu Val Ile Ala Asn Gly
    1025                1030                1035

Glu Ile Ile Phe Lys Leu Asp Gly Asp Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Lys Glu Ile Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Pro Val Gly Glu Ile Leu Thr Arg Ser Lys Tyr Asn
    1115                1120                1125

Gln Asn Ser Asn Tyr Ile Asn Tyr Arg Asn Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Ala Leu Lys Asn Phe Lys Lys
    1175                1180                1185

Lys Glu Glu Lys Leu Phe Leu Ala Pro Ile Ser Asp Ser Asp Glu
    1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245
```

```
Val Phe Lys Asp Tyr Lys Tyr Tyr Phe Cys Ile Ser Lys Trp Tyr
1250                1255                1260

Leu Lys Glu Val Lys Arg Lys Pro Tyr Asn Pro Asn Leu Gly Cys
1265                1270                1275

Asn Trp Gln Phe Ile Pro Lys Asp Glu Gly Trp Ile Glu
1280                1285                1290

<210> SEQ ID NO 64
<211> LENGTH: 1291
<212> TYPE: PRT
<213> ORGANISM: Clostridium botulinum

<400> SEQUENCE: 64

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335
```

```
Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
            435                 440                 445

Val Asp Asn Glu Asp Leu Phe Phe Ile Ala Asp Lys Asn Ser Phe Ser
            450                 455                 460

Asp Asp Leu Ser Lys Asn Glu Arg Ile Glu Tyr Asp Thr Gln Ser Asn
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
            595                 600                 605

Ser Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asp Glu Lys Trp Ile Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Lys Ser Asn Ile Asn Ile Asp
            740                 745                 750
```

Phe Asn Asp Ile Asn Ser Lys Leu Asn Glu Gly Ile Asn Gln Ala Val
        755                 760                 765
Asp Asn Ile Asn Asn Phe Ile Asn Glu Cys Ser Val Ser Tyr Leu Met
        770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
            805                 810                 815
Leu Ile Gly Ser Ala Glu Tyr Glu Lys Ser Lys Val Asp Lys His Leu
            820                 825                 830
Lys Thr Ile Ile Pro Phe Asp Leu Ser Met Tyr Thr Asn Asn Thr Ile
            835                 840                 845
Leu Ile Glu Ile Phe Asn Lys Tyr Asn Ser Glu Ile Leu Asn Asn Ile
        850                 855                 860
Ile Leu Asn Leu Arg Tyr Arg Asp Asn Asn Leu Ile Asp Leu Ser Gly
865                 870                 875                 880
Tyr Gly Ala Asn Val Glu Val Tyr Asp Gly Val Glu Leu Asn Asp Lys
            885                 890                 895
Asn Gln Phe Lys Leu Thr Ser Ser Thr Asn Ser Glu Ile Arg Val Thr
            900                 905                 910
Gln Asn Gln Asn Ile Ile Phe Asn Ser Met Phe Leu Asp Phe Ser Val
            915                 920                 925
Ser Phe Trp Ile Arg Ile Pro Lys Tyr Lys Asn Asp Gly Ile Gln Asn
        930                 935                 940
Tyr Ile His Asn Glu Tyr Thr Ile Ile Asn Cys Ile Lys Asn Asn Ser
945                 950                 955                 960
Gly Trp Lys Ile Ser Ile Arg Gly Asn Arg Ile Ile Trp Thr Leu Thr
            965                 970                 975
Asp Ile Asn Gly Lys Thr Lys Ser Val Phe Phe Glu Tyr Ser Ile Arg
            980                 985                 990
Glu Asp Ile Ser Asp Tyr Ile Asn Arg Trp Phe Phe Val Thr Ile Thr
            995                 1000                1005
Asn Asn Ser Asp Asn Ala Lys Ile Tyr Ile Asn Gly Lys Leu Glu
        1010                1015                1020
Ser Asn Ile Asp Ile Lys Asp Ile Gly Glu Val Ile Ala Asn Gly
        1025                1030                1035
Glu Ile Ile Phe Lys Leu Asp Gly Asp Ile Asp Arg Thr Gln Phe
        1040                1045                1050
Ile Trp Met Lys Tyr Phe Ser Ile Phe Asn Thr Glu Leu Ser Gln
        1055                1060                1065
Ser Asn Ile Lys Glu Ile Tyr Lys Ile Gln Ser Tyr Ser Glu Tyr
        1070                1075                1080
Leu Lys Asp Phe Trp Gly Asn Pro Leu Met Tyr Asn Lys Glu Tyr
        1085                1090                1095
Tyr Met Phe Asn Ala Gly Asn Lys Asn Ser Tyr Ile Lys Leu Lys
        1100                1105                1110
Lys Asp Ser Ser Val Gly Glu Ile Leu Thr Arg Ser Lys Tyr Asn
        1115                1120                1125
Gln Asn Ser Asn Tyr Ile Asn Tyr Arg Asn Leu Tyr Ile Gly Glu
        1130                1135                1140
Lys Phe Ile Ile Arg Arg Lys Ser Asn Ser Gln Ser Ile Asn Asp
        1145                1150                1155
Asp Ile Val Arg Lys Glu Asp Tyr Ile Tyr Leu Asp Phe Phe Asn

```
                  1160                1165                1170

Ser  Asn  Arg  Glu  Trp  Arg  Val  Tyr  Ala  Tyr  Lys  Asp  Phe  Lys  Glu
     1175                1180                1185

Glu  Glu  Lys  Lys  Leu  Phe  Leu  Ala  Asn  Ile  Tyr  Asp  Ser  Asn  Glu
     1190                1195                1200

Phe  Tyr  Lys  Thr  Ile  Gln  Ile  Lys  Glu  Tyr  Asp  Glu  Gln  Pro  Thr
     1205                1210                1215

Tyr  Ser  Cys  Gln  Leu  Leu  Phe  Lys  Lys  Asp  Glu  Glu  Ser  Thr  Asp
     1220                1225                1230

Glu  Ile  Gly  Leu  Ile  Gly  Ile  His  Arg  Phe  Tyr  Glu  Ser  Gly  Ile
     1235                1240                1245

Val  Leu  Lys  Asp  Tyr  Lys  Asn  Tyr  Phe  Cys  Ile  Ser  Lys  Trp  Tyr
     1250                1255                1260

Leu  Lys  Glu  Val  Lys  Arg  Lys  Pro  Tyr  Asn  Pro  Asn  Leu  Gly  Cys
     1265                1270                1275

Asn  Trp  Gln  Phe  Ile  Pro  Lys  Asp  Glu  Gly  Trp  Ile  Glu
     1280                1285                1290

<210> SEQ ID NO 65
<211> LENGTH: 1291
<212> TYPE: PRT
<213> ORGANISM: Clostridium botulinum

<400> SEQUENCE: 65

Met  Pro  Val  Thr  Ile  Asn  Asn  Phe  Asn  Tyr  Asn  Asp  Pro  Ile  Asp  Asn
1                   5                   10                  15

Asp  Asn  Ile  Ile  Met  Met  Glu  Pro  Pro  Phe  Ala  Arg  Gly  Thr  Gly  Arg
                20                  25                  30

Tyr  Tyr  Lys  Ala  Phe  Lys  Ile  Thr  Asp  Arg  Ile  Trp  Ile  Ile  Pro  Glu
            35                  40                  45

Arg  Tyr  Thr  Phe  Gly  Tyr  Lys  Pro  Glu  Asp  Phe  Asn  Lys  Ser  Ser  Gly
        50                  55                  60

Ile  Phe  Asn  Arg  Asp  Val  Cys  Glu  Tyr  Tyr  Asp  Pro  Asp  Tyr  Leu  Asn
65                  70                  75                  80

Thr  Asn  Asp  Lys  Lys  Asn  Ile  Phe  Leu  Gln  Thr  Met  Ile  Lys  Leu  Phe
                85                  90                  95

Asn  Arg  Ile  Lys  Ser  Lys  Pro  Leu  Gly  Glu  Lys  Leu  Leu  Glu  Met  Ile
            100                 105                 110

Ile  Asn  Gly  Ile  Pro  Tyr  Leu  Gly  Asp  Arg  Arg  Val  Pro  Leu  Glu  Glu
        115                 120                 125

Phe  Asn  Thr  Asn  Ile  Ala  Ser  Val  Thr  Val  Asn  Lys  Leu  Ile  Ser  Asn
130                 135                 140

Pro  Gly  Glu  Val  Glu  Arg  Lys  Lys  Gly  Ile  Phe  Ala  Asn  Leu  Ile  Ile
145                 150                 155                 160

Phe  Gly  Pro  Gly  Pro  Val  Leu  Asn  Glu  Asn  Glu  Thr  Ile  Asp  Ile  Gly
                165                 170                 175

Ile  Gln  Asn  His  Phe  Ala  Ser  Arg  Glu  Gly  Phe  Gly  Ile  Met  Gln
            180                 185                 190

Met  Lys  Phe  Cys  Pro  Glu  Tyr  Val  Ser  Val  Phe  Asn  Asn  Val  Gln  Glu
        195                 200                 205

Asn  Lys  Gly  Ala  Ser  Ile  Phe  Asn  Arg  Arg  Gly  Tyr  Phe  Ser  Asp  Pro
210                 215                 220

Ala  Leu  Ile  Leu  Met  His  Glu  Leu  Ile  His  Val  Leu  His  Gly  Leu  Tyr
225                 230                 235                 240
```

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Arg Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Arg Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asp Thr Gln Ser Asn
465                 470                 475                 480

Tyr Ile Glu Asn Arg Ser Ser Ile Asp Glu Leu Ile Leu Asp Thr Asn
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
        595                 600                 605

Ser Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile 660                 665                 670
Asp Asn Lys Asn Lys Ile Ile Lys Thr Ile Asp Asn Ala Leu Thr Lys
            675                 680                 685
Arg Asp Glu Lys Trp Ile Asp Met Tyr Gly Leu Ile Val Ala Gln Trp
        690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
            725                 730                 735
Lys Tyr Asn Ile Tyr Ser Glu Lys Glu Lys Ser Asn Ile Asn Ile Asp
            740                 745                 750
Phe Asn Asp Ile Asn Ser Lys Leu Asn Glu Gly Ile Asn Gln Ala Ile
        755                 760                 765
Asp Asn Ile Asn Asn Phe Ile Asn Glu Cys Ser Val Ser Tyr Leu Met
        770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
            805                 810                 815
Leu Ile Gly Ser Ala Glu Tyr Glu Lys Ser Lys Val Asp Lys His Leu
            820                 825                 830
Lys Thr Ile Ile Pro Phe Asp Leu Ser Met Tyr Thr Asn Asn Thr Ile
        835                 840                 845
Leu Ile Glu Ile Phe Asn Lys Tyr Asn Ser Glu Ile Leu Asn Asn Ile
        850                 855                 860
Ile Leu Asn Leu Arg Tyr Arg Asp Asn Asn Leu Ile Asp Leu Ser Gly
865                 870                 875                 880
Tyr Gly Ala Lys Val Glu Val Tyr Asn Gly Val Glu Leu Asn Asp Lys
            885                 890                 895
Asn Gln Phe Lys Leu Thr Ser Ser Ala Asn Ser Lys Ile Arg Val Thr
            900                 905                 910
Gln Asn Gln Asp Ile Ile Phe Asn Ser Met Phe Leu Asp Phe Ser Val
        915                 920                 925
Ser Phe Trp Ile Arg Ile Pro Lys Tyr Lys Asn Asp Gly Ile Gln Asn
    930                 935                 940
Tyr Ile His Asn Glu Tyr Thr Ile Ile Asn Cys Ile Lys Asn Asn Ser
945                 950                 955                 960
Gly Trp Lys Ile Ser Ile Arg Gly Asn Lys Ile Ile Trp Thr Leu Thr
            965                 970                 975
Asp Ile Asn Gly Lys Thr Lys Ser Val Phe Phe Glu Tyr Ser Ile Arg
            980                 985                 990
Lys Asp Val Ser Glu Tyr Ile Asn Arg Trp Phe Phe Val Thr Ile Thr
        995                 1000                1005
Asn Asn Ser Asp Asn Ala Lys Ile Tyr Ile Asn Gly Lys Leu Glu
        1010                1015                1020
Ser Asn Ile Asp Ile Lys Asp Ile Gly Glu Val Ile Ala Asn Gly
        1025                1030                1035
Glu Ile Ile Phe Lys Leu Asp Gly Asp Ile Asp Arg Thr Gln Phe
        1040                1045                1050
Ile Trp Met Lys Tyr Phe Ser Ile Phe Asn Thr Glu Leu Ser Gln
        1055                1060                1065
Ser Asn Ile Lys Glu Ile Tyr Lys Ile Gln Ser Tyr Ser Glu Tyr
        1070                1075                1080

```
Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Ser Val Gly Glu Ile Leu Thr Arg Ser Lys Tyr Asn
    1115                1120                1125

Gln Asn Ser Asn Tyr Ile Asn Tyr Arg Asn Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Ala Tyr Lys Asp Phe Lys Lys
    1175                1180                1185

Lys Glu Glu Lys Leu Phe Leu Ala Asn Ile Tyr Asp Ser Asn Glu
    1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245

Val Phe Lys Asp Tyr Lys Asp Tyr Phe Cys Ile Ser Lys Trp Tyr
    1250                1255                1260

Leu Lys Glu Val Lys Arg Lys Pro Tyr Asn Pro Asn Leu Gly Cys
    1265                1270                1275

Asn Trp Gln Phe Ile Pro Lys Asp Glu Gly Trp Ile Glu
    1280                1285                1290

<210> SEQ ID NO 66
<211> LENGTH: 1291
<212> TYPE: PRT
<213> ORGANISM: Clostridium botulinum

<400> SEQUENCE: 66

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Met Gly Arg
                20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
```

```
            145                 150                 155                 160
        Phe Gly Pro Gly Pro Val Leu Asn Glu Asn Glu Thr Ile Asp Ile Gly
                        165                 170                 175

Ile Gln Asn His Phe Ala Ser Arg Glu Gly Phe Gly Gly Ile Met Gln
                        180                 185                 190

Met Lys Phe Cys Pro Glu Tyr Val Ser Val Phe Asn Asn Val Gln Glu
                        195                 200                 205

Asn Lys Gly Ala Ser Ile Phe Asn Arg Arg Gly Tyr Phe Ser Asp Pro
                        210                 215                 220

Ala Leu Ile Leu Met His Glu Leu Ile His Val Leu His Gly Leu Tyr
        225                 230                 235                 240

Gly Ile Lys Val Asn Asp Leu Pro Ile Val Pro Asn Glu Lys Lys Phe
                            245                 250                 255

Phe Met Gln Ser Thr Asp Ala Ile Gln Ala Glu Glu Leu Tyr Thr Phe
                        260                 265                 270

Gly Gly Gln Asp Pro Ser Ile Ile Ser Pro Ser Thr Asp Lys Ser Ile
                        275                 280                 285

Tyr Asp Lys Val Leu Gln Asn Phe Arg Gly Ile Val Asp Arg Leu Asn
                        290                 295                 300

Lys Val Leu Val Cys Ile Ser Asp Pro Asn Ile Asn Ile Asn Ile Tyr
        305                 310                 315                 320

Lys Asn Lys Phe Lys Asp Lys Tyr Lys Phe Val Glu Asp Ser Glu Gly
                        325                 330                 335

Lys Tyr Ser Ile Asp Val Glu Ser Phe Asp Lys Leu Tyr Lys Ser Leu
                        340                 345                 350

Met Phe Gly Phe Thr Glu Thr Asn Ile Ala Glu Asn Tyr Lys Ile Lys
                        355                 360                 365

Thr Arg Ala Ser Tyr Phe Ser Asp Ser Leu Pro Pro Val Lys Ile Lys
                        370                 375                 380

Asn Leu Leu Asp Asn Glu Ile Tyr Thr Ile Glu Glu Gly Phe Asn Ile
        385                 390                 395                 400

Ser Asp Lys Asn Met Glu Lys Glu Tyr Arg Gly Gln Asn Lys Ala Ile
                        405                 410                 415

Asn Lys Gln Ala Tyr Glu Glu Ile Ser Lys Glu His Leu Ala Val Tyr
                        420                 425                 430

Lys Ile Gln Met Cys Lys Ser Val Lys Ala Pro Gly Ile Cys Ile Asp
                        435                 440                 445

Val Asp Asn Glu Asp Leu Phe Phe Ile Ala Asp Lys Asn Ser Phe Ser
        450                 455                 460

Asp Asp Leu Ser Lys Asn Glu Arg Ile Ala Tyr Asn Thr Gln Asn Asn
        465                 470                 475                 480

Tyr Ile Glu Asn Asp Phe Ser Ile Asn Glu Leu Ile Leu Asp Thr Asp
                        485                 490                 495

Leu Ile Ser Lys Ile Glu Leu Pro Ser Glu Asn Thr Glu Ser Leu Thr
                        500                 505                 510

Asp Phe Asn Val Tyr Val Pro Val Tyr Lys Lys Gln Pro Ala Ile Lys
                        515                 520                 525

Lys Ile Phe Thr Asp Glu Asn Thr Ile Phe Gln Tyr Leu Tyr Ser Gln
                        530                 535                 540

Thr Phe Pro Leu Asp Ile Arg Asp Ile Ser Leu Thr Ser Ser Phe Asp
        545                 550                 555                 560

Asp Ala Leu Leu Phe Ser Asn Lys Val Tyr Ser Phe Phe Ser Met Asp
                        565                 570                 575
```

-continued

Tyr Ile Lys Thr Ala Asn Lys Val Val Glu Ala Gly Leu Phe Ala Gly
            580                 585                 590

Trp Val Lys Gln Ile Val Asp Asp Phe Val Ile Glu Ala Asn Lys Ser
            595                 600                 605

Ser Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Glu Thr Ile Asn Ser Ala Leu Thr Lys
            675                 680                 685

Arg Asp Glu Lys Trp Ile Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
            740                 745                 750

Phe Asn Asp Val Asn Ser Lys Leu Asn Glu Gly Ile Asn Gln Ala Ile
            755                 760                 765

Asp Asn Ile Asn Asn Phe Ile Asn Glu Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Arg Lys Asn Leu Leu Asn Tyr Ile Asp Glu Asn Lys Leu Tyr
            805                 810                 815

Leu Ile Gly Ser Ala Glu Tyr Glu Lys Ser Lys Val Asp Lys Tyr Leu
            820                 825                 830

Lys Thr Ser Ile Pro Phe Asp Leu Ser Thr Tyr Thr Asn Asn Thr Ile
            835                 840                 845

Leu Ile Glu Ile Phe Asn Lys Tyr Asn Ser Asp Ile Leu Asn Asn Ile
            850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Ile
            900                 905                 910

Gln Asn Gln Asn Ile Ile Phe Asn Ser Met Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
            980                 985                 990

```
Glu Asp Ile Ser Glu Tyr Ile Asn Arg Trp Phe Phe Val Thr Ile Thr
            995                 1000                1005

Asn Asn Ser Asp Asn Ala Lys Ile Tyr Ile Asn Gly Lys Leu Glu
    1010                1015                1020

Ser His Ile Asp Ile Arg Asp Ile Arg Glu Val Ile Ala Asn Asp
    1025                1030                1035

Glu Ile Ile Phe Lys Leu Asp Gly Asn Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Ile Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Ser Val Gly Glu Ile Leu Thr Arg Ser Lys Tyr Asn
    1115                1120                1125

Gln Asn Ser Lys Tyr Ile Asn Tyr Arg Asp Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Met Tyr Lys Tyr Phe Lys Lys
    1175                1180                1185

Glu Glu Glu Lys Leu Phe Leu Ala Pro Ile Ser Asp Ser Asp Glu
    1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245

Val Phe Lys Glu Tyr Lys Asp Tyr Phe Cys Ile Ser Lys Trp Tyr
    1250                1255                1260

Leu Lys Glu Val Lys Arg Lys Pro Tyr Asn Ser Lys Leu Gly Cys
    1265                1270                1275

Asn Trp Gln Phe Ile Pro Lys Asp Glu Gly Trp Thr Glu
    1280                1285                1290

<210> SEQ ID NO 67
<211> LENGTH: 1296
<212> TYPE: PRT
<213> ORGANISM: Clostridium botulinum

<400> SEQUENCE: 67

Met Pro Leu Val Asn Gln Gln Ile Asn Tyr Tyr Asp Pro Val Asn Gly
1               5                   10                  15

Val Asp Ile Ala Tyr Ile Lys Ile Pro Asn Ala Gly Lys Met Gln Pro
            20                  25                  30

Val Lys Ala Phe Lys Ile His Asn Lys Val Trp Val Ile Pro Glu Arg
        35                  40                  45

Asp Ile Phe Thr Asn Pro Glu Glu Val Asp Leu Asn Pro Pro Glu
    50                  55                  60
```

```
Ala Lys Gln Val Pro Ile Ser Tyr Tyr Asp Ser Ala Tyr Leu Ser Thr
 65                  70                  75                  80

Asp Asn Glu Lys Asp Asn Tyr Leu Lys Gly Val Ile Lys Leu Phe Glu
                 85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Lys Ile Asp Thr Glu Leu Lys
        115                 120                 125

Val Ile Asp Thr Asn Cys Ile Asn Ile Ile Gln Leu Asp Asp Ser Tyr
130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                    165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
            195                 200                 205

Gly Ala Gly Lys Phe Ala Gln Asp Pro Ala Val Ala Leu Ala His Glu
210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                245                 250                 255

Glu Val Ser Leu Glu Glu Leu Ile Thr Phe Gly Gly Asn Asp Ala Lys
                260                 265                 270

Phe Ile Asp Ser Leu Gln Lys Lys Glu Phe Ser Leu Tyr Tyr Tyr Asn
            275                 280                 285

Lys Phe Lys Asp Ile Ala Ser Thr Leu Asn Lys Ala Lys Ser Ile Val
        290                 295                 300

Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Asp Val Asn Tyr
        370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Glu Leu Cys Ile Lys Val Asn Asn Trp Asp Leu Phe Phe
        450                 455                 460

Ser Pro Ser Glu Asp Asn Phe Thr Asn Asp Leu Asp Lys Val Glu Glu
465                 470                 475                 480
```

```
Ile Thr Ser Asp Thr Asn Ile Glu Ala Ala Glu Asn Ile Ser Leu
                485                 490                 495

Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
            515                 520                 525

Glu Pro Met Pro Asn Ile Glu Arg Phe Pro Asn Gly Lys Lys Tyr Glu
            530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
            595                 600                 605

Asn Leu Val Tyr Asp Phe Thr Asp Glu Thr Asn Glu Val Ser Thr Met
            610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
                660                 665                 670

Leu Pro Val Leu Gly Thr Phe Ala Leu Val Ser Tyr Val Ser Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Ser Ala Met Ile Asn Ile
            770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
            805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
            835                 840                 845

Ile Pro Phe Gln Leu Ser Lys Tyr Val Asp Asn Lys Lys Leu Leu Ser
            850                 855                 860

Thr Phe Thr Glu Tyr Ile Lys Asn Ile Thr Asn Ala Ser Ile Leu Ser
865                 870                 875                 880

Ile Val Tyr Lys Asp Asp Leu Ile Asp Leu Ser Arg Tyr Gly Ala
                885                 890                 895

Glu Ile Tyr Asn Gly Asp Lys Val Tyr Tyr Asn Ser Ile Asp Lys Asn
```

```
                    900             905             910
Gln Ile Arg Leu Ile Asn Leu Glu Ser Ser Thr Ile Glu Val Ile Leu
                915             920             925

Lys Lys Ala Ile Val Tyr Asn Ser Met Tyr Glu Asn Phe Ser Thr Ser
    930             935             940

Phe Trp Ile Arg Ile Pro Lys Tyr Phe Asn Ser Ile Ser Leu Asn Asn
945             950             955             960

Glu Tyr Thr Ile Ile Asn Cys Met Glu Asn Asn Ser Gly Trp Lys Val
                965             970             975

Ser Leu Asn Tyr Gly Glu Ile Ile Trp Thr Phe Gln Asp Thr Gln Glu
                980             985             990

Ile Lys Gln Arg Val Val Phe Lys Tyr Ser Gln Met Ile Asn Ile Ser
                995             1000            1005

Asp Tyr Ile Asn Arg Trp Ile Phe Val Thr Ile Thr Asn Asn Arg
    1010            1015            1020

Ile Thr Lys Ser Lys Ile Tyr Ile Asn Gly Arg Leu Ile Asp Gln
    1025            1030            1035

Lys Pro Ile Ser Asn Leu Gly Asn Ile His Ala Ser Asn Lys Ile
    1040            1045            1050

Met Phe Lys Leu Asp Gly Cys Arg Asp Pro His Arg Tyr Ile Val
    1055            1060            1065

Ile Lys Tyr Phe Asn Leu Phe Asp Lys Glu Leu Ser Glu Lys Glu
    1070            1075            1080

Ile Lys Asp Leu Tyr Asp Asn Gln Ser Asn Ser Gly Ile Leu Lys
    1085            1090            1095

Asp Phe Trp Gly Asp Tyr Leu Gln Tyr Asp Lys Ser Tyr Tyr Met
    1100            1105            1110

Leu Asn Leu Tyr Asp Pro Asn Lys Tyr Val Asp Val Asn Asn Val
    1115            1120            1125

Gly Ile Arg Gly Tyr Met Tyr Leu Lys Gly Pro Arg Asp Asn Val
    1130            1135            1140

Met Thr Thr Asn Ile Tyr Leu Asn Ser Ser Leu Tyr Met Gly Thr
    1145            1150            1155

Lys Phe Ile Ile Lys Lys Tyr Ala Ser Gly Asn Lys Asp Asn Ile
    1160            1165            1170

Val Arg Asn Asn Asp Arg Val Tyr Ile Asn Val Val Val Lys Asn
    1175            1180            1185

Lys Glu Tyr Arg Leu Ala Thr Asn Ala Ser Gln Ala Gly Val Glu
    1190            1195            1200

Lys Ile Leu Ser Ala Leu Glu Ile Pro Asp Val Gly Asn Leu Ser
    1205            1210            1215

Gln Val Val Val Met Lys Ser Lys Asn Asp Gln Gly Ile Thr Asn
    1220            1225            1230

Lys Cys Lys Met Asn Leu Gln Asp Asn Asn Gly Asn Asp Ile Gly
    1235            1240            1245

Phe Ile Gly Phe His Gln Phe Asn Asn Ile Ala Lys Leu Val Ala
    1250            1255            1260

Ser Asn Trp Tyr Asn Arg Gln Ile Glu Arg Ser Ser Arg Thr Leu
    1265            1270            1275

Gly Cys Ser Trp Glu Phe Ile Pro Val Asp Asp Gly Trp Arg Glu
    1280            1285            1290

Arg Pro Leu
    1295
```

<210> SEQ ID NO 68
<211> LENGTH: 1296
<212> TYPE: PRT
<213> ORGANISM: Clostridium botulinum

<400> SEQUENCE: 68

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Ile Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Asn Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Ile Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Glu Val Ala Ser Ile Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Arg Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Met Asn Ile Val Pro Glu Val Asn Tyr
```

```
              370                 375                 380
Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Glu Gly Tyr Asn Lys
                435                 440                 445

Ala Leu Asn Asp Leu Cys Ile Lys Val Asn Asn Trp Asp Leu Phe Phe
                450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Ser
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560

Tyr Gly Asn Ser Arg Ile Val Leu Ile Asn Ser Val Asn Glu Ala Leu
                565                 570                 575

Leu Asn Pro Ser Ser Val Tyr Thr Phe Phe Ser Ser Asp Tyr Val Lys
                580                 585                 590

Lys Ala Asn Glu Ala Thr Glu Ala Ala Met Phe Leu Gly Trp Val Glu
                595                 600                 605

Gln Leu Val Tyr Asp Phe Thr Asp Glu Thr Ser Glu Val Ser Thr Met
                610                 615                 620

Asp Lys Ile Ala Asp Ile Thr Ile Ile Val Pro Tyr Ile Gly Pro Ala
625                 630                 635                 640

Leu Asn Ile Gly Asn Met Val Tyr Lys Lys Phe Glu Glu Ala Leu
                645                 650                 655

Ile Phe Ser Gly Ala Val Ile Leu Leu Glu Phe Val Pro Glu Ile Val
                660                 665                 670

Leu Pro Ile Leu Gly Thr Phe Ala Leu Val Ser Tyr Thr Ser Asn Lys
                675                 680                 685

Val Leu Thr Val Arg Thr Ile Asp Asn Ala Leu Ser Lys Arg Asn Glu
                690                 695                 700

Lys Trp Glu Glu Val Tyr Lys Tyr Ile Val Thr Asn Trp Leu Ala Lys
705                 710                 715                 720

Val Asn Thr Gln Ile Asn Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Gly Asp
                755                 760                 765

Leu Ser Ser Lys Leu Asn Asp Ser Ile Asn Lys Ala Met Ile Asn Ile
                770                 775                 780

Asn Lys Phe Leu Asp Gln Cys Ser Val Ser Tyr Leu Met Asn Ser Met
785                 790                 795                 800
```

-continued

Ile Pro Gln Gly Val Lys Gln Leu Lys Asp Phe Asp Thr Ser Leu Arg
            805                 810                 815

Asp Ser Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Ala Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Arg Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
            930                 935                 940

Phe Trp Ile Lys Ile Pro Lys Tyr Phe Ser Lys Ile Asn Leu Asn Asn
945                 950                 955                 960

Glu Tyr Thr Ile Ile Asn Cys Ile Glu Asn Asn Ser Gly Trp Lys Val
            965                 970                 975

Ser Leu Asn Tyr Gly Glu Ile Ile Trp Thr Leu Gln Asp Asn Glu Gln
            980                 985                 990

Asn Ile Gln Arg Val Val Phe Lys Tyr Ser Gln Met Val Asn Ile Ser
            995                 1000                1005

Asp Tyr Ile Asn Arg Trp Ile Phe Val Thr Ile Thr Asn Asn Arg
        1010            1015            1020

Leu Thr Lys Ser Lys Ile Tyr Ile Asn Gly Arg Leu Ile Asp Gln
        1025            1030            1035

Lys Pro Ile Ser Asn Leu Gly Asn Ile His Ala Ser Asn Lys Ile
        1040            1045            1050

Met Phe Lys Leu Asp Gly Cys Arg Asp Pro His Arg Tyr Ile Leu
        1055            1060            1065

Ile Lys Tyr Phe Asn Leu Phe Asp Lys Glu Leu Asn Glu Lys Glu
        1070            1075            1080

Ile Lys Asp Leu Tyr Asp Asn Gln Ser Asn Ser Gly Ile Leu Lys
        1085            1090            1095

Asp Phe Trp Gly Asp Tyr Leu Gln Tyr Asp Lys Pro Tyr Tyr Met
        1100            1105            1110

Leu Asn Leu Tyr Asp Pro Asn Lys Tyr Ile Asp Val Asn Asn Ile
        1115            1120            1125

Gly Ile Arg Gly Tyr Met Tyr Leu Lys Gly Pro Arg Gly Ser Val
        1130            1135            1140

Thr Thr Thr Asn Ile Tyr Leu Asn Ser Met Leu Tyr Met Gly Thr
        1145            1150            1155

Lys Phe Ile Ile Lys Lys His Ala Ser Gly Asn Lys Asp Asn Ile
        1160            1165            1170

Val Arg Asn Asn Asp Arg Val Tyr Ile Asn Val Leu Val Lys Asn
        1175            1180            1185

Lys Glu Tyr Arg Leu Ala Thr Asn Ala Ser Gln Ala Gly Gly Glu
        1190            1195            1200

-continued

```
Lys Ile Leu Ser Ala Val Glu Ile Pro Asp Val Gly Asn Leu Ser
    1205                1210                1215

Gln Val Val Met Lys Ser Lys Asn Asp Gln Gly Ile Arg Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Gly Lys Thr Ser Val Thr Leu
    1265                1270                1275

Gly Cys Ser Trp Glu Leu Ile Pro Val Asp Tyr Gly Trp Gly Glu
    1280                1285                1290

Ser Ser Leu
    1295

<210> SEQ ID NO 69
<211> LENGTH: 1296
<212> TYPE: PRT
<213> ORGANISM: Clostridium botulinum

<400> SEQUENCE: 69

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270
```

-continued

```
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
        290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Ala Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
        435                 440                 445
Ala Leu Asn Asp Leu Cys Ile Lys Val Asn Asn Trp Asp Leu Phe Phe
    450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
        515                 520                 525
Glu Leu Met Pro Asn Ile Glu Arg Phe Pro Asn Gly Lys Lys Tyr Glu
    530                 535                 540
Leu Asp Lys Tyr Thr Met Phe His Tyr Leu Ser Ala Gln Glu Phe Glu
545                 550                 555                 560
His Gly Lys Ser Arg Ile Asp Leu Thr Asn Ser Val Asn Glu Ala Leu
                565                 570                 575
Leu Asn Pro Ser His Val Tyr Thr Phe Phe Ser Ser Asp Tyr Val Lys
            580                 585                 590
Lys Val Asn Lys Ala Thr Glu Ala Met Phe Leu Gly Trp Val Glu
        595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Ile Val Ser Tyr Ile Ala Asn Lys
        675                 680                 685
```

-continued

Val Leu Thr Val Gln Thr Ile Asn Asn Ala Leu Ser Lys Arg Asn Glu
690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
        755                 760                 765

Leu Ser Ser Lys Leu Asn Glu Ser Ile Asn Ser Ala Met Ile Asn Ile
770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
            805                 810                 815

Asp Val Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Ser
865                 870                 875                 880

Leu Arg Tyr Glu Asn Asn His Leu Ile Asp Leu Ser Arg Tyr Ala Ser
            885                 890                 895

Lys Ile Asn Ile Gly Ser Arg Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Lys Ile Pro Lys Tyr Phe Ser Glu Ile Ser Leu Asn Asn
945                 950                 955                 960

Glu Tyr Thr Ile Ile Asn Cys Ile Glu Asn Asn Ser Gly Trp Lys Val
            965                 970                 975

Ser Leu Asn Tyr Gly Glu Ile Ile Trp Thr Leu Gln Asp Asn Lys Gln
            980                 985                 990

Asn Ile Gln Arg Val Val Phe Lys Tyr Ser Gln Met Val Ala Ile Ser
            995                 1000                1005

Asp Tyr Ile Asn Arg Trp Ile Phe Ile Thr Ile Thr Asn Asn Arg
    1010                1015                1020

Leu Thr Lys Ser Lys Ile Tyr Ile Asn Gly Arg Leu Ile Asp Gln
    1025                1030                1035

Lys Pro Ile Ser Asn Leu Gly Asn Ile His Ala Ser Asn Lys Ile
    1040                1045                1050

Met Phe Lys Leu Asp Gly Cys Arg Asp Pro Arg Arg Tyr Ile Met
    1055                1060                1065

Ile Lys Tyr Phe Asn Leu Phe Asp Lys Glu Leu Asn Glu Lys Glu
    1070                1075                1080

Ile Lys Asp Leu Tyr Asp Ser Gln Ser Asn Ser Gly Ile Leu Lys
    1085                1090                1095

Asp Phe Trp Gly Asn Tyr Leu Gln Tyr Asp Lys Pro Tyr Tyr Met

```
                    1100                1105                1110
Leu Asn  Leu Phe  Asp Pro  Asn  Lys Tyr  Val Asp  Asn Asn Val
        1115                 1120                1125
Gly Ile  Arg Gly  Tyr Met  Tyr  Leu Lys  Gly Ser  Arg  Ser Thr Leu
        1130                 1135                1140
Leu Thr  Thr Asn  Ile Tyr  Leu  Asn Ser  Gly Leu  Tyr  Met Gly Thr
        1145                 1150                1155
Lys Phe  Ile Ile  Lys Lys  Tyr  Ala Ser  Gly Asn  Lys  Asp Asn Ile
        1160                 1165                1170
Val Arg  Asn Asn  Asp Arg  Val  Tyr Ile  Asn Val  Val  Val Asn Asn
        1175                 1180                1185
Lys Glu  Tyr Arg  Leu Ala  Thr  Asn Ala  Ser Gln  Ala  Gly Val Glu
        1190                 1195                1200
Lys Ile  Leu Ser  Ala Leu  Glu  Ile Pro  Asp Ile  Gly  Asn Leu Ser
        1205                 1210                1215
Gln Val  Val Val  Met Lys  Ser  Lys Asn  Asp Gln  Gly  Ile Arg Asn
        1220                 1225                1230
Lys Cys  Lys Met  Asn Leu  Gln  Asp Asn  Asn Gly  Asn  Asp Ile Gly
        1235                 1240                1245
Phe Ile  Gly Phe  His Lys  Phe  Asn Asp  Ile Tyr  Lys  Leu Val Ala
        1250                 1255                1260
Ser Asn  Trp Tyr  Asn Arg  Gln  Ile Glu  Ile Ser  Arg  Thr Phe
        1265                 1270                1275
Gly Cys  Ser Trp  Glu Phe  Ile  Pro Val  Asp Asp  Gly  Trp Gly Glu
        1280                 1285                1290
Lys Pro  Leu
        1295
```

<210> SEQ ID NO 70
<211> LENGTH: 1296
<212> TYPE: PRT
<213> ORGANISM: Clostridium botulinum

<400> SEQUENCE: 70

```
Met Leu Phe  Val Asn  Lys Gln  Phe  Asn Tyr  Lys Asp  Pro Val Asn Gly
1               5                     10                    15
Val Asp Ile  Ala Tyr  Ile Lys  Ile  Pro Asn  Ala Gly  Gln Met Gln Pro
                20                    25                    30
Val Lys Ala  Phe Lys  Ile His  Asn  Lys Ile  Trp Val  Ile Pro Glu Arg
            35                    40                    45
Asp Thr Phe  Thr Asn  Pro Glu  Glu  Gly Asp  Leu Asn  Pro Pro Pro Glu
        50                    55                    60
Ala Lys Gln  Val Pro  Val Ser  Tyr  Tyr Asp  Ser Thr  Tyr Leu Ser Thr
65                    70                    75                    80
Asp Asn Glu  Lys Asp  Asn Tyr  Leu  Lys Gly  Val Thr  Lys Leu Phe Glu
                85                    90                    95
Arg Ile Tyr  Ser Thr  Glu Leu  Gly  Arg Met  Leu Leu  Thr Ser Ile Val
                100                   105                   110
Arg Gly Ile  Pro Phe  Trp Gly  Gly  Ser Thr  Ile Asp  Thr Glu Leu Lys
            115                   120                   125
Val Ile Asp  Thr Asn  Cys Ile  Asn  Val Ile  Gln Pro  Asp Gly Ser Tyr
        130                   135                   140
Arg Ser Glu  Glu Leu  Asn Leu  Val  Ile Ile  Gly Pro  Ser Ala Asp Ile
145                   150                   155                   160
```

-continued

Ile Gln Phe Glu Cys Lys Ser Phe Gly His Asp Val Leu Asn Leu Thr
            165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
            210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Glu His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Glu Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Val Leu Thr Asn Ser Val Asn Glu Ala Leu
            565                 570                 575

Leu Asn Pro Ser Ser Val Tyr Thr Phe Phe Ser Ser Asp Tyr Val Arg

```
                580             585             590
Lys Val Asn Lys Ala Thr Glu Ala Met Phe Leu Gly Trp Val Glu
            595             600             605
Gln Leu Val Tyr Asp Phe Thr Asp Glu Thr Ser Glu Val Ser Thr Thr
            610             615             620
Asp Lys Ile Ala Asp Ile Thr Ile Ile Pro Tyr Ile Gly Pro Ala
625             630             635             640
Leu Asn Ile Gly Asn Met Leu Tyr Lys Asp Asp Phe Val Gly Ala Leu
            645             650             655
Ile Phe Ser Gly Ala Val Ile Leu Leu Glu Phe Ile Pro Glu Ile Ala
            660             665             670
Ile Pro Val Leu Gly Thr Phe Ala Leu Val Ser Tyr Ile Ala Asn Lys
            675             680             685
Val Leu Thr Val Gln Thr Ile Asp Asn Ala Leu Ser Lys Arg Asn Glu
            690             695             700
Lys Trp Gly Glu Val Tyr Lys Tyr Ile Val Thr Asn Trp Leu Ala Lys
705             710             715             720
Val Asn Thr Gln Ile Asp Leu Ile Arg Lys Lys Met Lys Glu Ala Leu
            725             730             735
Glu Asn Gln Ala Glu Ala Thr Lys Ala Ile Ile Asn Tyr Gln Tyr Asn
            740             745             750
Gln Tyr Thr Glu Glu Lys Asn Asn Ile Asn Phe Asn Ile Gly Asp
            755             760             765
Leu Ser Ser Lys Leu Asn Asp Ser Ile Asn Lys Ala Met Ile Asn Ile
            770             775             780
Asn Lys Phe Leu Asn Gln Cys Ser Val Ser Tyr Leu Met Asn Ser Met
785             790             795             800
Ile Pro Tyr Gly Val Lys Arg Leu Glu Asp Phe Asp Ala Ser Leu Lys
            805             810             815
Asp Ala Leu Leu Lys Tyr Ile Tyr Asp Asn Arg Gly Thr Leu Ile Gly
            820             825             830
Gln Val Asp Arg Leu Lys Asp Lys Val Asn Asn Thr Leu Ser Thr Asp
            835             840             845
Ile Pro Phe Gln Leu Ser Lys Tyr Val Asp Asn Gln Arg Leu Leu Ser
850             855             860
Thr Phe Thr Glu Tyr Ile Lys Asn Ile Ile Asn Thr Ser Ile Leu Asn
865             870             875             880
Leu Arg Tyr Glu Ser Asn His Leu Ile Asp Leu Ser Arg Tyr Ala Ser
            885             890             895
Glu Ile Asn Ile Gly Ser Lys Val Asn Phe Asp Pro Ile Asp Lys Asn
            900             905             910
Gln Ile Gln Leu Phe Asn Leu Glu Ser Ser Lys Ile Glu Ile Ile Leu
            915             920             925
Lys Asn Ala Ile Val Tyr Asn Ser Met Tyr Glu Asn Phe Ser Thr Ser
            930             935             940
Phe Trp Ile Lys Ile Pro Lys Tyr Phe Ser Lys Ile Asn Leu Asn Asn
945             950             955             960
Glu Tyr Thr Ile Ile Asn Cys Ile Glu Asn Asn Ser Gly Trp Lys Val
            965             970             975
Ser Leu Asn Tyr Gly Glu Ile Ile Trp Thr Leu Gln Asp Asn Lys Gln
            980             985             990
Asn Ile Gln Arg Val Val Phe Lys  Tyr Ser Gln Met Val  Ala Ile Ser
            995             1000             1005
```

-continued

```
Asp Tyr Ile Asn Arg Trp Ile Phe Ile Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Pro His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asn Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Ile
    1130                1135                1140

Val Thr Thr Asn Ile Tyr Leu Asn Ser Ser Leu Tyr Met Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Val Leu Glu Ile Pro Asp Val Gly Asn Leu Ser
    1205                1210                1215

Gln Val Val Val Met Lys Ser Lys Asn Asp Gln Gly Ile Arg Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Asp Lys Leu Val Ala
    1250                1255                1260

Ser Asn Trp Tyr Asn Arg Gln Ile Glu Arg Ser Ser Arg Thr Phe
    1265                1270                1275

Gly Cys Ser Trp Glu Phe Ile Pro Val Asp Asp Gly Trp Gly Glu
    1280                1285                1290

Ser Pro Leu
    1295

<210> SEQ ID NO 71
<211> LENGTH: 1292
<212> TYPE: PRT
<213> ORGANISM: Clostridium botulinum

<400> SEQUENCE: 71

Met Pro Phe Val Asn Lys Pro Phe Asn Tyr Arg Asp Pro Gly Asn
1               5                   10                  15

Val Asp Ile Ala Tyr Ile Lys Ile Pro Asn Ala Gly Gln Met Gln Pro
                20                  25                  30

Val Lys Ala Phe Lys Ile His Glu Gly Val Trp Val Ile Pro Glu Arg
            35                  40                  45

Asp Thr Phe Thr Asn Pro Glu Glu Gly Asp Leu Asn Pro Pro Pro Glu
```

-continued

```
          50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Ile Lys Leu Phe Asp
                 85                  90                  95
Arg Ile Tyr Ser Thr Gly Leu Gly Arg Met Leu Leu Ser Phe Ile Val
                100                 105                 110
Lys Gly Ile Pro Phe Trp Gly Gly Ser Thr Ile Asp Thr Glu Leu Lys
                115                 120                 125
Val Ile Asp Thr Asn Cys Ile Asn Val Ile Glu Pro Gly Gly Ser Tyr
130                 135                 140
Arg Ser Glu Glu Leu Asn Leu Val Ile Thr Gly Pro Ser Ala Asp Ile
145                 150                 155                 160
Ile Gln Phe Glu Cys Lys Ser Phe Gly His Asp Val Phe Asn Leu Thr
                165                 170                 175
Arg Asn Gly Tyr Gly Ser Thr Gln Tyr Ile Arg Phe Ser Pro Asp Phe
                180                 185                 190
Thr Phe Gly Phe Glu Glu Ser Leu Glu Val Asp Thr Asn Pro Leu Leu
                195                 200                 205
Gly Ala Gly Thr Phe Ala Thr Asp Pro Ala Val Thr Leu Ala His Glu
                210                 215                 220
Leu Ile His Ala Ala His Arg Leu Tyr Gly Ile Ala Ile Asn Pro Asn
225                 230                 235                 240
Arg Val Leu Lys Val Lys Thr Asn Ala Tyr Tyr Glu Met Ser Gly Leu
                245                 250                 255
Glu Val Ser Phe Glu Glu Leu Arg Thr Phe Gly Gly Asn Asp Thr Asn
                260                 265                 270
Phe Ile Asp Ser Leu Trp Gln Lys Lys Phe Ser Arg Asp Ala Tyr Asp
                275                 280                 285
Asn Leu Gln Asn Ile Ala Arg Ile Leu Asn Glu Ala Lys Thr Ile Val
                290                 295                 300
Gly Thr Thr Thr Pro Leu Gln Tyr Met Lys Asn Ile Phe Ile Arg Lys
305                 310                 315                 320
Tyr Phe Leu Ser Glu Asp Ala Ser Gly Lys Ile Ser Val Asn Lys Ala
                325                 330                 335
Ala Phe Lys Glu Phe Tyr Arg Val Leu Thr Arg Gly Phe Thr Glu Leu
                340                 345                 350
Glu Phe Val Asn Pro Phe Lys Val Ile Asn Arg Lys Thr Tyr Leu Asn
                355                 360                 365
Phe Asp Lys Ala Val Phe Arg Ile Asn Ile Val Pro Asp Glu Asn Tyr
                370                 375                 380
Thr Ile Asn Glu Gly Phe Asn Leu Glu Gly Ala Asn Ser Asn Gly Gln
385                 390                 395                 400
Asn Thr Glu Ile Asn Ser Arg Asn Phe Thr Arg Leu Lys Asn Phe Thr
                405                 410                 415
Gly Leu Phe Glu Phe Tyr Lys Leu Leu Cys Val Arg Gly Ile Ile Pro
                420                 425                 430
Phe Lys Thr Lys Ser Leu Asp Glu Gly Tyr Asn Lys Ala Leu Asn Tyr
                435                 440                 445
Leu Cys Ile Lys Val Asn Asn Trp Asp Leu Phe Phe Ser Pro Ser Glu
                450                 455                 460
Asp Asn Phe Thr Asn Asp Leu Asp Lys Val Glu Glu Ile Thr Ala Asp
465                 470                 475                 480
```

```
Thr Asn Ile Glu Ala Ala Glu Asn Ile Ser Ser Asp Leu Ile Gln
            485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Gln Leu Glu Pro Met Pro
            515                 520                 525

Asn Ile Glu Arg Phe Pro Asn Gly Lys Lys Tyr Glu Leu Asp Lys Tyr
            530                 535                 540

Thr Met Phe His Tyr Leu Arg Ala Gln Glu Phe Glu His Gly Asp Ser
545                 550                 555                 560

Arg Ile Ile Leu Thr Asn Ser Ala Glu Glu Ala Leu Leu Lys Pro Asn
                565                 570                 575

Val Ala Tyr Thr Phe Phe Ser Ser Lys Tyr Val Lys Ile Asn Lys
            580                 585                 590

Ala Val Glu Ala Val Ile Phe Leu Ser Trp Ala Glu Glu Leu Val Tyr
            595                 600                 605

Asp Phe Thr Asp Glu Thr Asn Glu Val Thr Thr Met Asp Lys Ile Ala
            610                 615                 620

Asp Ile Thr Ile Ile Val Pro Tyr Ile Gly Pro Ala Leu Asn Ile Gly
625                 630                 635                 640

Asn Met Val Ser Lys Gly Glu Phe Val Glu Ala Ile Leu Phe Thr Gly
                645                 650                 655

Val Val Ala Leu Leu Glu Phe Ile Pro Glu Tyr Ser Leu Pro Val Phe
            660                 665                 670

Gly Thr Phe Ala Ile Val Ser Tyr Ile Ala Asn Lys Val Leu Thr Val
            675                 680                 685

Gln Thr Ile Asn Asn Ala Leu Ser Lys Arg Asn Glu Lys Trp Asp Glu
            690                 695                 700

Val Tyr Lys Tyr Thr Val Thr Asn Trp Leu Ala Lys Val Asn Thr Gln
705                 710                 715                 720

Ile Asp Leu Ile Arg Glu Lys Met Lys Lys Ala Leu Glu Asn Gln Ala
                725                 730                 735

Glu Ala Thr Arg Ala Ile Ile Asn Tyr Gln Tyr Asn Gln Tyr Thr Glu
            740                 745                 750

Glu Glu Lys Asn Asn Ile Asn Phe Asn Ile Asp Asp Leu Ser Ser Lys
            755                 760                 765

Leu Asn Arg Ser Ile Asn Arg Ala Met Ile Asn Ile Asn Lys Phe Leu
            770                 775                 780

Asp Gln Cys Ser Val Ser Tyr Leu Met Asn Ser Met Ile Pro Tyr Ala
785                 790                 795                 800

Val Lys Arg Leu Lys Asp Phe Asp Ala Ser Val Arg Asp Val Leu Leu
                805                 810                 815

Lys Tyr Ile Tyr Asp Asn Arg Gly Thr Leu Ile Leu Gln Val Asp Arg
            820                 825                 830

Leu Lys Asp Glu Val Asn Asn Thr Leu Ser Ala Asp Ile Pro Phe Gln
            835                 840                 845

Leu Ser Lys Tyr Val Asn Asp Lys Lys Leu Leu Ser Thr Phe Thr Glu
            850                 855                 860

Tyr Ile Lys Asn Ile Val Asn Thr Ser Ile Leu Ser Ile Val Tyr Lys
865                 870                 875                 880

Lys Asp Asp Leu Ile Asp Leu Ser Arg Tyr Gly Ala Lys Ile Asn Ile
                885                 890                 895
```

```
Gly Asp Arg Val Tyr Tyr Asp Ser Ile Asp Lys Asn Gln Ile Lys Leu
            900                 905                 910

Ile Asn Leu Glu Ser Ser Thr Ile Glu Val Ile Leu Lys Asn Ala Ile
        915                 920                 925

Val Tyr Asn Ser Met Tyr Glu Asn Phe Ser Thr Ser Phe Trp Ile Lys
    930                 935                 940

Ile Pro Lys Tyr Phe Ser Lys Ile Asn Leu Asn Asn Glu Tyr Thr Ile
945                 950                 955                 960

Ile Asn Cys Ile Glu Asn Asn Ser Gly Trp Lys Val Ser Leu Asn Tyr
            965                 970                 975

Gly Glu Ile Ile Trp Thr Leu Gln Asp Asn Lys Gln Asn Ile Gln Arg
        980                 985                 990

Val Val Phe Lys Tyr Ser Gln Met Val Asn Ile Ser Asp Tyr Ile Asn
    995                 1000                1005

Arg Trp Met Phe Val Thr Ile Thr Asn Asn Arg Leu Thr Lys Ser
        1010                1015                1020

Lys Ile Tyr Ile Asn Gly Arg Leu Ile Asp Gln Lys Pro Ile Ser
        1025                1030                1035

Asn Leu Gly Asn Ile His Ala Ser Asn Lys Ile Met Phe Lys Leu
        1040                1045                1050

Asp Gly Cys Arg Asp Pro Arg Arg Tyr Ile Met Ile Lys Tyr Phe
        1055                1060                1065

Asn Leu Phe Asp Lys Glu Leu Asn Glu Lys Glu Ile Lys Asp Leu
        1070                1075                1080

Tyr Asp Ser Gln Ser Asn Pro Gly Ile Leu Lys Asp Phe Trp Gly
        1085                1090                1095

Asn Tyr Leu Gln Tyr Asp Lys Pro Tyr Tyr Met Leu Asn Leu Phe
        1100                1105                1110

Asp Pro Asn Lys Tyr Val Asp Val Asn Asn Ile Gly Ile Arg Gly
        1115                1120                1125

Tyr Met Tyr Leu Lys Gly Pro Arg Gly Ser Val Met Thr Thr Asn
        1130                1135                1140

Ile Tyr Leu Asn Ser Thr Leu Tyr Met Gly Thr Lys Phe Ile Ile
        1145                1150                1155

Lys Lys Tyr Ala Ser Gly Asn Glu Asp Asn Ile Val Arg Asn Asn
        1160                1165                1170

Asp Arg Val Tyr Ile Asn Val Val Val Lys Asn Lys Glu Tyr Arg
        1175                1180                1185

Leu Ala Thr Asn Ala Ser Gln Ala Gly Val Glu Lys Ile Leu Ser
        1190                1195                1200

Ala Leu Glu Ile Pro Asp Val Gly Asn Leu Ser Gln Val Val Val
        1205                1210                1215

Met Lys Ser Lys Asp Asp Gln Gly Ile Arg Asn Lys Cys Lys Met
        1220                1225                1230

Asn Leu Gln Asp Asn Asn Gly Asn Asp Ile Gly Phe Val Gly Phe
        1235                1240                1245

His Leu Tyr Asp Asn Ile Ala Lys Leu Val Ala Ser Asn Trp Tyr
        1250                1255                1260

Asn Arg Gln Val Gly Lys Ala Ser Arg Thr Phe Gly Cys Ser Trp
        1265                1270                1275

Glu Phe Ile Pro Val Asp Asp Gly Trp Gly Glu Ser Ser Leu
        1280                1285                1290
```

<210> SEQ ID NO 72
<211> LENGTH: 1296
<212> TYPE: PRT
<213> ORGANISM: Clostridium botulinum

<400> SEQUENCE: 72

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Val Ala Ser Thr Leu Asn Lys Ala Lys Ser Ile Ile
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Asn Phe Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380
```

```
Thr Ile Lys Asp Gly Phe Asn Leu Lys Gly Ala Asn Leu Ser Thr Asn
385                 390                 395                 400

Phe Asn Gly Gln Asn Thr Glu Ile Asn Ser Arg Asn Phe Thr Arg Leu
            405                 410                 415

Lys Asn Phe Thr Gly Leu Phe Glu Phe Tyr Lys Leu Leu Cys Val Arg
            420                 425                 430

Gly Ile Ile Pro Phe Lys Thr Lys Ser Leu Asp Glu Gly Tyr Asn Lys
            435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asp Lys Val Glu Glu
465                 470                 475                 480

Ile Thr Ala Asp Thr Asn Ile Glu Ala Ala Glu Glu Asn Ile Ser Leu
            485                 490                 495

Asp Leu Ile Gln Gln Tyr Tyr Leu Thr Phe Asp Phe Asp Asn Glu Pro
            500                 505                 510

Glu Asn Ile Ser Ile Glu Asn Leu Ser Ser Asp Ile Ile Gly Gln Leu
            515                 520                 525

Glu Pro Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Asp Ser Arg Ile Ile Leu Thr Asn Ser Ala Glu Glu Ala Leu
            565                 570                 575

Leu Lys Pro Asn Val Ala Tyr Thr Phe Phe Ser Ser Lys Tyr Val Lys
            580                 585                 590

Lys Ile Asn Lys Ala Val Glu Ala Phe Met Phe Leu Asn Trp Ala Glu
            595                 600                 605

Glu Leu Val Tyr Asp Phe Thr Asp Glu Thr Asn Glu Val Thr Thr Met
        610                 615                 620

Asp Lys Ile Ala Asp Ile Thr Ile Ile Val Pro Tyr Ile Gly Pro Ala
625                 630                 635                 640

Leu Asn Ile Gly Asn Met Leu Ser Lys Gly Glu Phe Val Glu Ala Ile
            645                 650                 655

Ile Phe Thr Gly Val Val Ala Met Leu Glu Phe Ile Pro Glu Tyr Ala
            660                 665                 670

Leu Pro Val Phe Gly Thr Phe Ala Ile Val Ser Tyr Ile Ala Asn Lys
            675                 680                 685

Val Leu Thr Val Gln Thr Ile Asn Asn Ala Leu Ser Lys Arg Asn Glu
        690                 695                 700

Lys Trp Asp Glu Val Tyr Lys Tyr Thr Val Thr Asn Trp Leu Ala Lys
705                 710                 715                 720

Val Asn Thr Gln Ile Asp Leu Ile Arg Glu Lys Met Lys Lys Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Ser Ala Met Ile Asn Ile
            770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
```

```
            805                 810                 815
Asp Val Leu Leu Lys Tyr Ile Tyr Asp Asn Arg Gly Thr Leu Val Leu
            820                 825                 830

Gln Val Asp Arg Leu Lys Asp Glu Val Asn Asn Thr Leu Ser Ala Asp
            835                 840                 845

Ile Pro Phe Gln Leu Ser Lys Tyr Val Asp Asn Lys Lys Leu Leu Ser
    850                 855                 860

Thr Phe Thr Glu Tyr Ile Lys Asn Ile Val Asn Thr Ser Ile Leu Ser
865                 870                 875                 880

Ile Val Tyr Lys Lys Asp Asp Leu Ile Asp Leu Ser Arg Tyr Gly Ala
                885                 890                 895

Lys Ile Asn Ile Gly Asp Arg Val Tyr Tyr Asp Ser Ile Asp Lys Asn
                900                 905                 910

Gln Ile Lys Leu Ile Asn Leu Glu Ser Ser Thr Ile Glu Val Ile Leu
            915                 920                 925

Lys Asn Ala Ile Val Tyr Asn Ser Met Tyr Glu Asn Phe Ser Thr Ser
        930                 935                 940

Phe Trp Ile Lys Ile Pro Lys Tyr Phe Ser Lys Ile Asn Leu Asn Asn
945                 950                 955                 960

Glu Tyr Thr Ile Ile Asn Cys Ile Glu Asn Asn Ser Gly Trp Lys Val
                965                 970                 975

Ser Leu Asn Tyr Gly Glu Ile Ile Trp Thr Leu Gln Asp Asn Lys Gln
        980                 985                 990

Asn Ile Gln Arg Val Val Phe Lys Tyr Ser Gln Met Val Asn Ile Ser
        995                 1000                1005

Asp Tyr Ile Asn Arg Trp Ile Phe Val Thr Ile Thr Asn Asn Arg
    1010                1015                1020

Leu Thr Lys Ser Lys Ile Tyr Ile Asn Gly Arg Leu Ile Asp Gln
    1025                1030                1035

Lys Pro Ile Ser Asn Leu Gly Asn Ile His Ala Ser Asn Lys Ile
    1040                1045                1050

Met Phe Lys Leu Asp Gly Cys Arg Asp Pro Arg Arg Tyr Ile Met
    1055                1060                1065

Ile Lys Tyr Phe Asn Leu Phe Asp Lys Glu Leu Asn Glu Lys Glu
    1070                1075                1080

Ile Lys Asp Leu Tyr Asp Ser Gln Ser Asn Ser Gly Ile Leu Lys
    1085                1090                1095

Asp Phe Trp Gly Asn Tyr Leu Gln Tyr Asp Lys Pro Tyr Tyr Met
    1100                1105                1110

Leu Asn Leu Phe Asp Pro Asn Lys Tyr Val Asp Val Asn Asn Ile
    1115                1120                1125

Gly Ile Arg Gly Tyr Met Tyr Leu Lys Gly Pro Arg Gly Ser Val
    1130                1135                1140

Val Thr Thr Asn Ile Tyr Leu Asn Ser Thr Leu Tyr Glu Gly Thr
    1145                1150                1155

Lys Phe Ile Ile Lys Lys Tyr Ala Ser Gly Asn Glu Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215
```

```
Gln Val Val Val Met Lys Ser Lys Asp Asp Gln Gly Ile Arg Asn
    1220            1225            1230

Lys Cys Lys Met Asn Leu Gln Asp Asn Asn Gly Asn Asp Ile Gly
    1235            1240            1245

Phe Ile Gly Phe His Leu Tyr Asp Asn Ile Ala Lys Leu Val Ala
    1250            1255            1260

Ser Asn Trp Tyr Asn Arg Gln Val Gly Lys Ala Ser Arg Thr Phe
    1265            1270            1275

Gly Cys Ser Trp Glu Phe Ile Pro Val Asp Asp Gly Trp Gly Glu
    1280            1285            1290

Ser Ser Leu
    1295

<210> SEQ ID NO 73
<211> LENGTH: 1297
<212> TYPE: PRT
<213> ORGANISM: Clostridium botulinum

<400> SEQUENCE: 73

Met Pro Phe Val Asn Lys Gln Phe Asn Tyr Lys Asp Thr Val Asn Gly
1               5                   10                  15

Ile Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Lys Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Glu His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asn Ala Lys
            260                 265                 270

Phe Ile Asp Ser Leu Gln Glu Asn Glu Phe Arg Leu Tyr Tyr Tyr Asn
```

```
                275                 280                 285
Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Lys Val Leu Asn Arg Lys Thr Tyr Leu Asn
                355                 360                 365

Phe Asp Lys Ala Val Phe Lys Ile Asn Ile Val Pro Asp Glu Asn Tyr
                370                 375                 380

Thr Ile Lys Asp Gly Phe Asn Leu Lys Asn Thr Asn Leu Ala Ala Asn
385                 390                 395                 400

Phe Asn Gly Gln Asn Thr Glu Ile Asn Ser Arg Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Pro Phe Lys Thr Lys Ser Leu Asp Glu Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asp Phe Asn Glu Pro
                500                 505                 510

Glu Asn Ile Ser Ile Glu Asn Leu Ser Ser Asp Ile Ile Gly Gln Leu
                515                 520                 525

Glu Pro Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Ser Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
                610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
690                 695                 700
```

```
Lys Trp Asp Glu Val Tyr Lys Tyr Ile Val Thr Asn Trp Leu Ala Lys
705                 710                 715                 720

Val Asn Thr Gln Ile Asp Leu Val Arg Lys Met Lys Glu Ala Leu
        725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Ser Ala Met Thr Asn Ile
770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Glu Val Leu Leu Lys Tyr Ile Tyr Asp Asn Arg Gly Thr Leu Ile Leu
                820                 825                 830

Gln Val Asp Arg Leu Lys Asp Lys Val Asn Asn Thr Leu Ser Ala Asp
            835                 840                 845

Ile Pro Phe Gln Leu Ser Lys Tyr Val Asp Asn Lys Lys Leu Leu Ser
850                 855                 860

Thr Phe Thr Glu Tyr Ile Lys Asn Ile Thr Asn Thr Ser Ile Leu Ser
865                 870                 875                 880

Ile Val Val Asp Lys Asp Gly Arg Leu Ile Asp Leu Ser Arg Tyr Gly
                885                 890                 895

Ala Glu Ile Tyr Asn Gly Asp Lys Ser Tyr Asn Ser Ile Asp Lys
            900                 905                 910

Asn Gln Ile Lys Leu Ile Asn Leu Glu Ser Ser Ala Ile Glu Val Ile
            915                 920                 925

Leu Lys Asn Ala Ile Val Tyr Asn Ser Met Tyr Glu Asn Phe Ser Thr
930                 935                 940

Ser Phe Trp Ile Lys Ile Pro Lys Tyr Phe Ser Lys Ile Asn Leu Asn
945                 950                 955                 960

Asn Glu Tyr Thr Ile Ile Asn Cys Ile Glu Asn Asn Ser Gly Trp Lys
                965                 970                 975

Val Ser Leu Asn Tyr Gly Glu Ile Ile Trp Thr Leu Gln Asp Asn Gln
            980                 985                 990

Gln Asn Ile Gln Arg Val Val Phe Lys Tyr Ser Gln Met Val Asn Ile
        995                 1000                1005

Ser Asp Tyr Ile Asn Arg Trp Ile Phe Val Thr Ile Thr Asn Asn
    1010                1015                1020

Arg Leu Asp Lys Ser Lys Ile Tyr Ile Asn Gly Arg Leu Ile Asp
    1025                1030                1035

Gln Lys Pro Ile Ser Asn Leu Gly Asn Ile His Ala Ser Asn Asn
    1040                1045                1050

Ile Met Phe Lys Leu Asp Gly Cys Arg Asp Pro Arg Arg Tyr Ile
    1055                1060                1065

Val Ile Lys Tyr Phe Asn Leu Phe Asp Lys Glu Leu Asn Glu Lys
    1070                1075                1080

Glu Ile Lys Asp Leu Tyr Asp Asn Gln Ser Asn Ser Gly Ile Leu
    1085                1090                1095

Lys Asp Phe Trp Gly Asp Tyr Leu Gln Tyr Asp Lys Pro Tyr Tyr
    1100                1105                1110
```

```
Met Leu Asn Leu Tyr Asp Pro Asn Lys Tyr Val Asp Val Asn Asn
    1115                1120                1125

Ile Gly Ile Arg Gly Tyr Met Tyr Leu Lys Gly Pro Arg Gly Ser
    1130                1135                1140

Val Val Thr Thr Asn Ile Tyr Leu Asn Ser Thr Leu Tyr Met Gly
    1145                1150                1155

Thr Lys Phe Ile Ile Lys Lys Tyr Ala Ser Gly Asn Lys Asp Asn
    1160                1165                1170

Ile Val Arg Asn Asn Asp Arg Val Tyr Ile Asn Val Val Val Lys
    1175                1180                1185

Asn Lys Glu Tyr Arg Leu Ala Thr Asn Ala Leu Gln Ala Gly Val
    1190                1195                1200

Glu Lys Ile Leu Ser Ala Leu Glu Ile Pro Asp Val Gly Asn Leu
    1205                1210                1215

Ser Gln Val Val Val Met Lys Ser Lys Asn Asp Gln Gly Ile Arg
    1220                1225                1230

Asn Lys Cys Lys Met Asn Leu Gln Asp Asn Asn Gly Asn Asp Ile
    1235                1240                1245

Gly Leu Ile Gly Phe His Gln Phe Asn Asn Ile Ala Lys Leu Val
    1250                1255                1260

Ala Ser Asn Trp Tyr Asn Arg Gln Val Gly Lys Ala Ser Arg Thr
    1265                1270                1275

Phe Gly Cys Ser Trp Glu Phe Ile Pro Val Asp Asp Gly Trp Gly
    1280                1285                1290

Glu Ser Ser Gln
    1295

<210> SEQ ID NO 74
<211> LENGTH: 1288
<212> TYPE: PRT
<213> ORGANISM: Clostridium botulinum

<400> SEQUENCE: 74

Met Pro Val Val Ile Asn Ser Phe Asn Tyr Asp Asp Pro Val Asn Asp
1               5                   10                  15

Asn Thr Ile Ile Tyr Ile Arg Pro Pro Tyr Tyr Glu Thr Ser Asn Thr
                20                  25                  30

Tyr Phe Lys Ala Phe Gln Ile Met Asp Asn Val Trp Ile Ile Pro Glu
            35                  40                  45

Arg Tyr Arg Leu Gly Ile Asp Pro Ser Leu Phe Asn Pro Pro Val Ser
        50                  55                  60

Leu Lys Ala Gly Ser Asp Gly Tyr Phe Asp Pro Asn Tyr Leu Ser Thr
65                  70                  75                  80

Asn Thr Glu Lys Asn Lys Tyr Leu Gln Ile Met Ile Lys Leu Phe Lys
                85                  90                  95

Arg Ile Asn Ser Lys Pro Ala Gly Gln Ile Leu Leu Glu Glu Ile Lys
            100                 105                 110

Asn Ala Ile Pro Tyr Leu Gly Asn Ser Tyr Thr Gln Glu Glu Gln Phe
        115                 120                 125

Thr Thr Asn Asn Arg Thr Val Ser Phe Asn Val Lys Leu Ala Asn Gly
    130                 135                 140

Asn Ile Val Gln Gln Met Ala Asn Leu Ile Ile Trp Gly Pro Gly Pro
145                 150                 155                 160

Asp Leu Thr Thr Asn Lys Thr Gly Gly Ile Ile Tyr Ser Pro Tyr Gln
                165                 170                 175
```

```
Ser Met Glu Ala Thr Pro Tyr Lys Asp Gly Phe Gly Ser Ile Met Thr
        180                 185                 190

Val Glu Phe Ser Pro Glu Tyr Ala Thr Ala Phe Asn Asp Ile Ser Ile
        195                 200                 205

Ala Ser His Ser Pro Ser Leu Phe Ile Lys Asp Pro Ala Leu Ile Leu
        210                 215                 220

Met His Glu Leu Ile His Val Leu His Gly Leu Tyr Gly Thr Tyr Ile
225                 230                 235                 240

Thr Glu Tyr Lys Ile Thr Pro Asn Val Val Gln Ser Tyr Met Lys Val
                245                 250                 255

Thr Lys Pro Ile Thr Ser Ala Glu Phe Leu Thr Phe Gly Gly Arg Asp
        260                 265                 270

Arg Asn Ile Val Pro Gln Ser Ile Gln Ser Gln Leu Tyr Asn Lys Val
        275                 280                 285

Leu Ser Asp Tyr Lys Arg Ile Ala Ser Arg Leu Asn Lys Val Asn Thr
        290                 295                 300

Ala Thr Ala Leu Ile Asn Ile Asp Glu Phe Lys Asn Leu Tyr Glu Trp
305                 310                 315                 320

Lys Tyr Gln Phe Ala Lys Asp Ser Asn Gly Val Tyr Ser Val Asp Leu
                325                 330                 335

Asn Lys Phe Glu Gln Leu Tyr Lys Lys Ile Tyr Ser Phe Thr Glu Phe
        340                 345                 350

Asn Leu Ala Tyr Glu Phe Lys Ile Lys Thr Arg Leu Gly Tyr Leu Ala
        355                 360                 365

Glu Asn Phe Gly Pro Phe Tyr Leu Pro Asn Leu Leu Asp Asp Ser Ile
        370                 375                 380

Tyr Thr Glu Val Asp Gly Phe Asn Ile Gly Ala Leu Ser Ile Asn Tyr
385                 390                 395                 400

Gln Gly Gln Asn Ile Gly Ser Asp Ile Asn Ser Ile Lys Lys Leu Gln
                405                 410                 415

Gly Gln Gly Val Val Ser Arg Val Val Arg Leu Cys Ser Asn Ser Asn
        420                 425                 430

Thr Lys Asn Ser Leu Cys Ile Thr Val Asn Asn Arg Asp Leu Phe Phe
        435                 440                 445

Ile Ala Ser Gln Glu Ser Tyr Gly Glu Asn Thr Ile Asn Thr Tyr Lys
450                 455                 460

Glu Ile Asp Asp Thr Thr Thr Leu Asp Pro Ser Phe Glu Asp Ile Leu
465                 470                 475                 480

Asp Lys Val Ile Leu Asn Phe Asn Glu Gln Val Ile Pro Gln Met Pro
                485                 490                 495

Asn Arg Asn Val Ser Thr Asp Ile Gln Lys Asp Asn Tyr Ile Pro Lys
        500                 505                 510

Tyr Asp Tyr Asn Arg Thr Asp Ile Ile Asp Ser Tyr Glu Val Gly Arg
        515                 520                 525

Asn Tyr Asn Thr Phe Phe Tyr Leu Asn Ala Gln Lys Phe Ser Pro Asn
        530                 535                 540

Glu Ser Asn Ile Thr Leu Thr Ser Ser Phe Asp Thr Gly Leu Leu Glu
545                 550                 555                 560

Gly Ser Lys Val Tyr Thr Phe Phe Ser Ser Asp Phe Ile Asn Asn Ile
                565                 570                 575

Asn Lys Pro Val Gln Ala Leu Leu Phe Ile Glu Trp Val Lys Gln Val
        580                 585                 590
```

-continued

```
Ile Arg Asp Phe Thr Thr Glu Ala Thr Lys Thr Ser Thr Val Asp Lys
            595                 600                 605

Leu Lys Asp Ile Ser Leu Val Val Pro Tyr Ile Gly Leu Ala Leu Asn
610                 615                 620

Ile Gly Asp Glu Ile Tyr Lys Gln His Phe Ala Glu Ala Val Glu Leu
625                 630                 635                 640

Val Gly Ala Gly Leu Leu Leu Glu Phe Ser Pro Glu Phe Leu Ile Pro
                645                 650                 655

Thr Leu Leu Ile Phe Thr Ile Lys Gly Tyr Leu Thr Gly Ser Ile Arg
            660                 665                 670

Asp Lys Asp Lys Ile Ile Lys Thr Leu Asp Asn Ala Leu Asn Val Arg
        675                 680                 685

Asp Gln Lys Trp Lys Glu Leu Tyr Arg Trp Val Val Ser Lys Trp Leu
    690                 695                 700

Thr Thr Ile Asn Thr Gln Phe Asn Lys Arg Lys Glu Gln Met Tyr Lys
705                 710                 715                 720

Ala Leu Lys Asn Gln Ala Thr Ala Ile Lys Lys Ile Ile Glu Asn Lys
                725                 730                 735

Tyr Asn Asn Tyr Thr Thr Asp Glu Lys Ser Lys Ile Asp Ser Ser Tyr
            740                 745                 750

Asn Ile Asn Glu Ile Glu Arg Thr Leu Asn Glu Lys Ile Asn Leu Ala
        755                 760                 765

Met Lys Asn Ile Glu Gln Phe Ile Thr Glu Ser Ser Ile Ala Tyr Leu
    770                 775                 780

Ile Asn Ile Ile Asn Asn Glu Thr Ile Gln Lys Leu Lys Ser Tyr Asp
785                 790                 795                 800

Asp Leu Val Arg Arg Tyr Leu Leu Gly Tyr Ile Arg Asn His Ser Ser
                805                 810                 815

Ile Leu Gly Asn Ser Val Glu Glu Leu Asn Ser Lys Val Asn Asn His
            820                 825                 830

Leu Asp Asn Gly Ile Pro Phe Glu Leu Ser Ser Tyr Thr Asn Asp Ser
        835                 840                 845

Leu Leu Ile Arg Tyr Phe Asn Lys Asn Tyr Gly Glu Leu Lys Tyr Asn
    850                 855                 860

Cys Ile Leu Asn Ile Lys Tyr Glu Met Asp Arg Asp Lys Leu Val Asp
865                 870                 875                 880

Ser Ser Gly Tyr Arg Ser Arg Ile Asn Ile Gly Thr Gly Val Lys Phe
                885                 890                 895

Ser Glu Ile Asp Lys Asn Gln Val Gln Leu Ser Asn Leu Glu Ser Ser
            900                 905                 910

Lys Ile Glu Val Ile Leu Asn Asn Gly Val Ile Tyr Asn Ser Met Tyr
        915                 920                 925

Glu Asn Phe Ser Thr Ser Phe Trp Ile Arg Ile Pro Lys Tyr Phe Arg
    930                 935                 940

Asn Ile Asn Asn Glu Tyr Lys Ile Ile Ser Cys Met Gln Asn Asn Ser
945                 950                 955                 960

Gly Trp Glu Val Ser Leu Asn Phe Ser Asn Met Asn Ser Lys Ile Ile
                965                 970                 975

Trp Thr Leu Gln Asp Thr Glu Gly Ile Lys Lys Thr Val Val Phe Gln
            980                 985                 990

Tyr Thr Gln Asn Ile Asn Ile Ser  Asp Tyr Ile Asn Arg  Trp Ile Phe
        995                 1000                 1005

Val Thr  Ile Thr Asn Asn Arg  Leu Ser Asn Ser Lys  Ile Tyr Ile
```

```
              1010                1015                1020

Asn Gly Arg Leu Ile Asn Glu Glu Ser Ile Ser Asp Leu Gly Asn
        1025                1030                1035

Ile His Ala Ser Asn Asn Ile Met Phe Lys Leu Asp Gly Cys Arg
        1040                1045                1050

Asp Pro His Arg Tyr Ile Trp Ile Lys Tyr Phe Asn Leu Phe Asp
        1055                1060                1065

Lys Glu Leu Asn Lys Lys Glu Ile Lys Asp Leu Tyr Asp Asn Gln
        1070                1075                1080

Ser Asn Ser Gly Ile Leu Lys Asp Phe Trp Gly Asp Tyr Leu Gln
        1085                1090                1095

Tyr Asp Lys Pro Tyr Tyr Met Leu Asn Leu Tyr Asp Pro Asn Lys
        1100                1105                1110

Tyr Leu Asp Val Asn Asn Val Gly Ile Arg Gly Tyr Met Tyr Leu
        1115                1120                1125

Lys Gly Pro Arg Gly Arg Ile Val Thr Thr Asn Ile Tyr Leu Asn
        1130                1135                1140

Ser Thr Leu Tyr Met Gly Thr Lys Phe Ile Ile Lys Lys Tyr Ala
        1145                1150                1155

Ser Gly Asn Lys Asp Asn Ile Val Arg Asn Asn Asp Arg Val Tyr
        1160                1165                1170

Ile Asn Val Val Val Lys Asn Lys Glu Tyr Arg Leu Ala Thr Asn
        1175                1180                1185

Ala Ser Gln Ala Gly Val Glu Lys Ile Leu Ser Ala Val Glu Ile
        1190                1195                1200

Pro Asp Val Gly Asn Leu Ser Gln Val Val Val Met Lys Ser Glu
        1205                1210                1215

Asn Asp Gln Gly Ile Arg Asn Lys Cys Lys Met Asn Leu Gln Asp
        1220                1225                1230

Asn Asn Gly Asn Asp Ile Gly Phe Ile Gly Phe His Gln Phe Asn
        1235                1240                1245

Asn Ile Ala Lys Leu Val Ala Ser Asn Trp Tyr Asn Arg Gln Ile
        1250                1255                1260

Gly Lys Ala Ser Arg Thr Phe Gly Cys Ser Trp Glu Phe Ile Pro
        1265                1270                1275

Val Asp Asp Gly Trp Gly Glu Ser Ser Leu
        1280                1285

<210> SEQ ID NO 75
<211> LENGTH: 1251
<212> TYPE: PRT
<213> ORGANISM: Clostridium botulinum

<400> SEQUENCE: 75

Met Pro Lys Ile Asn Ser Phe Asn Tyr Asn Asp Pro Val Asn Asp
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asn Phe Leu Pro Pro Thr Ser Leu Lys Asn Gly
        50                  55                  60

Asp Ser Ser Tyr Tyr Asp Pro Asn Tyr Leu Gln Asn Asp Gln Glu Lys
65                  70                  75                  80
```

```
Asp Arg Phe Leu Lys Ile Val Thr Lys Val Phe Asn Arg Ile Asn Asp
            85                  90                  95

Asn Leu Ser Gly Arg Ile Leu Leu Glu Glu Leu Ser Lys Ala Asn Pro
        100                 105                 110

Tyr Leu Gly Asn Asp Asn Thr Arg Asp Asp Phe Ile Ile Asn Asp
        115                 120                 125

Gly Ser Ala Val Pro Ile Gln Phe Ser Asn Gly Ser Gln Ser Ile Leu
        130                 135                 140

Leu Pro Thr Val Ile Ile Met Gly Ala Glu Pro Asp Leu Phe Glu Thr
145                 150                 155                 160

Asn Ser Ser Asn Val Ser Leu Ile Asn Asn Tyr Ser Pro Ser Asn His
                165                 170                 175

Gly Phe Gly Ser Ile Ala Ile Val Thr Phe Ser Pro Glu Tyr Ser Phe
        180                 185                 190

Arg Phe Asn Asp Asn Ser Met Asn Glu Phe Ile Gln Asp Pro Ala Leu
        195                 200                 205

Thr Leu Ile His Glu Leu Ile His Ser Leu His Gly Leu Tyr Gly Ala
        210                 215                 220

Lys Gly Ile Thr Thr Lys Tyr Thr Ile Thr Gln Gln Gln Asn Pro Leu
225                 230                 235                 240

Ile Thr Asn Ile Arg Gly Ile Asn Ile Glu Glu Phe Leu Thr Phe Gly
                245                 250                 255

Gly Asn Asn Leu Asn Ile Ile Thr Ser Ser Gln Leu Asn Asp Ile Tyr
        260                 265                 270

Thr Asn Leu Leu Asp Asp Tyr Lys Lys Ile Ala Ser Lys Leu Ser Lys
        275                 280                 285

Val Gln Val Ser Asn Pro Gln Leu Asn Pro Tyr Lys Asp Val Phe Gln
        290                 295                 300

Glu Lys Tyr Gly Leu Asp Lys Asn Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Glu Thr Tyr Ile
        340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Thr Leu Asn Val Asn Phe
        370                 375                 380

Arg Gly Gln Asn Pro Asn Leu Asn Pro Arg Ile Ile Thr Pro Ile Thr
385                 390                 395                 400

Asp Arg Gly Leu Val Lys Lys Ile Ile Arg Phe Cys Lys Asn Ile Val
                405                 410                 415

Ser Val Lys Gly Ile Arg Lys Ser Ile Cys Ile Glu Val Asn Asn Gly
        420                 425                 430

Asp Leu Phe Phe Val Ala Ser Glu Lys Ser Tyr Asn Asn Asp Ser Ile
        435                 440                 445

Asn Ile Pro Lys Glu Ile Asp Asp Thr Val Thr Leu Asn Asn Asn Tyr
        450                 455                 460

Glu Asn Asp Leu Asp Gln Val Ile Leu Asn Phe Asn Ser Glu Ser Ala
465                 470                 475                 480

Pro Gly Leu Ser Asp Lys Lys Leu Asn Ile Ser Ile Gln Asp Val
        485                 490                 495

Tyr Ile Pro Lys Tyr Asp Ser Asn Gly Thr Ser Asp Ile Glu Gln Tyr
```

```
                500              505              510
Asp Val Ser Glu Leu Asn Val Phe Phe Tyr Leu Asp Ala Gln Lys Val
            515              520              525
Pro Glu Gly Glu Asn Asn Val Asn Leu Thr Ser Ser Ile Asp Thr Ala
            530              535              540
Leu Leu Glu Gln Ser Lys Ile Tyr Thr Phe Phe Ser Ser Glu Phe Ile
545             550              555              560
Asn Asn Val Asn Lys Pro Val Gln Ala Ala Leu Phe Val Gly Trp Ile
            565              570              575
Gln Gln Val Leu Val Asp Phe Thr Thr Glu Ala Thr Gln Lys Ser Thr
            580              585              590
Val Asp Lys Ile Ala Asp Ile Ser Ile Val Val Pro Tyr Ile Gly Leu
            595              600              605
Ala Leu Asn Ile Gly Asn Glu Ser Gln Lys Gly Asn Phe Lys Asp Ala
            610              615              620
Leu Glu Leu Leu Gly Ala Gly Ile Leu Leu Glu Phe Val Pro Glu Leu
625             630              635              640
Leu Ile Pro Thr Ile Leu Val Phe Thr Ile Lys Ser Phe Leu Gly Ser
            645              650              655
Ser Asp Asn Lys Asn Lys Val Ile Lys Ala Ile Asn Asn Ala Leu Lys
            660              665              670
Glu Arg Asp Glu Lys Trp Lys Glu Val Tyr Ser Phe Ile Val Ser Asn
            675              680              685
Trp Ile Thr Lys Ile Asn Thr Gln Phe Asn Lys Arg Lys Glu Gln Met
            690              695              700
Tyr Gln Ala Leu Gln Asn Gln Val Asn Ala Leu Lys Thr Ile Ile Glu
705             710              715              720
Ser Lys Tyr Asn Ser Tyr Thr Leu Glu Glu Lys Asn Glu Leu Thr Asn
            725              730              735
Lys Tyr Asp Ile Glu Gln Ile Glu Asn Glu Leu Asn Gln Lys Val Ser
            740              745              750
Ile Ala Met Asn Asn Ile Asp Arg Phe Leu Thr Glu Ser Ser Ile Ser
            755              760              765
Tyr Leu Met Lys Leu Ile Asn Glu Val Lys Ile Asn Lys Leu Arg Glu
            770              775              780
Tyr Asp Glu Asn Val Lys Thr Tyr Leu Leu Asp Tyr Ile Thr Lys His
785             790              795              800
Gly Ser Ile Leu Gly Glu Ser Gln Gln Glu Leu Asn Ser Met Ile Ile
            805              810              815
Asp Thr Leu Asn Asn Ser Ile Pro Phe Lys Leu Ser Ser Tyr Thr Asp
            820              825              830
Asp Lys Ile Leu Ile Ser Tyr Phe Asn Lys Phe Lys Thr Ile Lys
            835              840              845
Ser Ser Ser Val Leu Ser Met Arg Tyr Lys Asn Asp Lys Tyr Ile Asp
850             855              860
Thr Ser Gly Tyr Asp Ser Asn Ile Asn Ile Asn Gly Asp Val Phe Ile
865             870              875              880
Tyr Pro Thr Asn Lys Asn Gln Phe Gly Ile Tyr Asn Ser Lys Leu Ser
            885              890              895
Glu Val Asn Ile Ser Gln Asn Asp Tyr Ile Ile Tyr Asp Asn Lys Tyr
            900              905              910
Lys Asn Phe Ser Ile Ser Phe Trp Val Arg Ile Pro Asn Tyr Asn Asn
            915              920              925
```

```
Lys Ile Val Asn Val Asn Asn Glu Tyr Thr Ile Ile Asn Cys Met Arg
            930                 935                 940

Asp Asn Asn Ser Gly Trp Lys Ile Ser Leu Asn His Asn Glu Ile Ile
945                 950                 955                 960

Trp Thr Leu Gln Asp Asn Ala Gly Ile Asn Gln Lys Leu Val Phe Lys
            965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Tyr Ser Lys Leu Tyr Ile Asn
        995                1000                1005

Gly His Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Met Arg Tyr Phe Asn Ile Phe Asp Lys Glu
    1040                1045                1050

Leu Asp Glu Thr Glu Ile Gln Thr Leu Tyr Asn Asn Glu Pro Asn
    1055                1060                1065

Ala Asn Val Leu Lys Asp Phe Trp Gly Asn Tyr Leu Leu Tyr Asn
    1070                1075                1080

Lys Glu Tyr Tyr Leu Leu Asn Met Leu Lys Pro Ser Lys Thr Ile
    1085                1090                1095

Ser His Asn Arg Asp Leu Thr Phe Ser Ile Tyr Asn Asn Arg Asn
    1100                1105                1110

Ile Val Asn Gly Leu Tyr Arg Leu Tyr Ser Gly Ile Lys Val Lys
    1115                1120                1125

Ile Gln Lys Ile Asn Asp Ser Asp Thr Arg Asp Asn Ile Val Arg
    1130                1135                1140

Asp Asn Asp Gln Val Tyr Val Asn Tyr Ile Asn Gly Asn Val Tyr
    1145                1150                1155

Tyr Ser Leu Tyr Ala Asp Thr Asn Ala Thr Asn Lys Glu Lys Thr
    1160                1165                1170

Ile Lys Ser Ser Thr Ser Gly Asn Arg Phe Asn Gln Val Val Val
    1175                1180                1185

Met Asn Ser Val Arg Asn Asn Cys Thr Met Asn Phe Lys Asn Asn
    1190                1195                1200

Asn Gly His Asp Ile Gly Leu Leu Gly Phe Lys Ser Asn Ala Leu
    1205                1210                1215

Val Ala Ser Thr Trp Tyr Tyr Thr Asn Met Arg Asp His Thr Asn
    1220                1225                1230

Ser Asn Gly Cys Phe Trp Ser Phe Ile Pro Glu Glu Asn Gly Trp
    1235                1240                1245

Gln Glu His
    1250

<210> SEQ ID NO 76
<211> LENGTH: 1254
<212> TYPE: PRT
<213> ORGANISM: Clostridium botulinum

<400> SEQUENCE: 76

Met Leu Tyr Met Pro Lys Ile Asn Ser Phe Asn Tyr Asn Asp Pro Val
1               5                   10                  15

Asn Asp Arg Thr Ile Leu Tyr Ile Lys Pro Gly Gly Cys Gln Gln Phe
```

```
                20                  25                  30
Tyr Lys Ser Phe Asn Ile Met Lys Asn Ile Trp Ile Ile Pro Glu Arg
            35                  40                  45

Asn Val Ile Gly Thr Ile Pro Gln Asp Phe Gln Pro Pro Thr Ser Leu
 50                  55                  60

Lys Asn Gly Asp Ser Ser Tyr Tyr Asp Pro Asn Tyr Leu Gln Ser Asn
 65                  70                  75                  80

Glu Glu Lys Asp Arg Phe Leu Lys Ile Val Thr Lys Ile Phe Asn Arg
                85                  90                  95

Ile Asn Asp Asn Leu Ser Gly Gly Ile Leu Glu Glu Leu Ser Lys
            100                 105                 110

Ala Asn Pro Tyr Leu Gly Asn Asp Asn Thr Pro Asp Gly Asp Phe Ile
            115                 120                 125

Ile Asn Asp Ala Ser Ala Val Pro Ile Gln Phe Ser Asn Gly Ser Gln
            130                 135                 140

Ser Ile Leu Leu Pro Asn Val Ile Ile Met Gly Ala Glu Pro Asp Leu
145                 150                 155                 160

Phe Glu Thr Asn Ser Ser Asn Ile Ser Leu Ile Asn Asn Tyr Arg Pro
                165                 170                 175

Ser Asn His Gly Phe Gly Ser Ile Ala Ile Val Thr Phe Ser Pro Glu
            180                 185                 190

Tyr Ser Phe Arg Phe Asn Asp Asn Ser Met Asn Glu Phe Ile Gln Asp
            195                 200                 205

Pro Ala Leu Thr Leu Met His Glu Leu Ile His Ser Leu His Gly Leu
            210                 215                 220

Tyr Gly Ala Lys Gly Ile Thr Thr Lys Tyr Thr Ile Thr Gln Gln Gln
225                 230                 235                 240

Asn Ser Leu Ile Thr Asn Ile Arg Gly Ile Asn Ile Glu Glu Phe Leu
                245                 250                 255

Thr Phe Gly Gly Asn Asp Leu Asn Ile Ile Thr Ser Ser Gln Phe Asn
            260                 265                 270

Asp Ile Tyr Thr Asn Leu Leu Asp Asp Tyr Lys Lys Ile Ala Ser Lys
            275                 280                 285

Leu Ser Gln Val Arg Val Ser Asn Pro Gln Leu Asn Pro Tyr Lys Asp
            290                 295                 300

Val Phe Gln Glu Lys Tyr Gly Leu Asp Lys Asp Ala Ser Gly Ile Tyr
305                 310                 315                 320

Ser Val Asn Ile Asn Lys Phe Asn Asp Ile Phe Lys Lys Leu Tyr Ser
                325                 330                 335

Phe Thr Glu Phe Asp Leu Ala Thr Lys Phe Gln Val Lys Cys Arg Glu
            340                 345                 350

Thr Tyr Ile Gly Gln Tyr Lys Tyr Phe Gln Leu Ser Asn Leu Leu Asn
            355                 360                 365

Asp Ser Ile Tyr Asn Ile Ser Glu Gly Tyr Asn Ile Asn Asn Leu Lys
            370                 375                 380

Val Asn Phe Arg Gly Gln Asn Ala Asn Leu Asn Pro Arg Ile Ile Thr
385                 390                 395                 400

Pro Ile Thr Gly Arg Gly Leu Val Lys Lys Ile Arg Phe Cys Lys
                405                 410                 415

Asn Ile Val Ser Val Lys Gly Ile Arg Lys Ser Ile Cys Ile Glu Val
            420                 425                 430

Asn Asn Gly Glu Leu Phe Phe Val Ala Ser Glu Asn Ser Tyr Asn Asp
            435                 440                 445
```

```
Asp Asn Ile Asn Thr Pro Lys Glu Ile Asp Asp Thr Val Thr Ser Asn
450                 455                 460
Asn Asn Tyr Glu Asn Asp Leu Asp Gln Val Ile Leu Asn Phe Asn Ser
465                 470                 475                 480
Glu Ser Ala Pro Gly Leu Ser Asp Glu Lys Leu Asn Leu Thr Ile Gln
                485                 490                 495
Asp Asp Ala Tyr Ile Pro Lys Tyr Asp Ser Asn Gly Thr Ser Asp Ile
                500                 505                 510
Glu Gln His Asp Val Asn Glu Leu Asn Val Phe Phe Tyr Leu Asp Ala
            515                 520                 525
Gln Lys Val Pro Glu Gly Glu Asn Asn Val Asn Leu Thr Ser Ser Ile
530                 535                 540
Asp Thr Ala Leu Leu Glu Gln Pro Lys Ile Tyr Thr Phe Phe Ser Ser
545                 550                 555                 560
Glu Phe Ile Asn Asn Val Asn Lys Pro Val Gln Ala Val Leu Phe Val
                565                 570                 575
Ser Trp Ile Gln Gln Val Leu Val Asp Phe Thr Thr Glu Ala Thr Gln
                580                 585                 590
Lys Ser Thr Val Asp Lys Ile Ala Asp Ile Ser Ile Val Val Pro Tyr
            595                 600                 605
Ile Gly Leu Ala Leu Asn Ile Gly Asn Glu Ala Gln Lys Gly Asn Phe
610                 615                 620
Lys Asp Ala Leu Glu Leu Leu Gly Ala Gly Ile Leu Leu Glu Phe Val
625                 630                 635                 640
Pro Glu Leu Leu Ile Pro Thr Ile Leu Val Phe Thr Ile Lys Ser Phe
                645                 650                 655
Leu Gly Ser Ser Asp Asn Lys Asn Lys Ile Ile Lys Ala Ile Asn Asn
                660                 665                 670
Ala Leu Lys Glu Arg Asp Glu Lys Trp Lys Glu Val Tyr Ser Phe Ile
            675                 680                 685
Val Ser Asn Trp Ile Thr Lys Ile Asn Thr Gln Phe Asn Lys Arg Lys
690                 695                 700
Glu Gln Met Tyr Gln Ala Leu Gln Asn Gln Val Asn Ala Ile Lys Thr
705                 710                 715                 720
Ile Ile Glu Ser Lys Tyr Asn Ser Tyr Thr Leu Glu Glu Lys Asn Glu
                725                 730                 735
Leu Thr Asn Lys Tyr Asp Ile Lys Gln Ile Glu Asn Glu Leu Asn Gln
                740                 745                 750
Lys Val Ser Ile Ala Met Asn Asn Ile Asp Arg Phe Leu Thr Glu Ser
            755                 760                 765
Ser Ile Ser Tyr Leu Met Lys Leu Ile Asn Glu Val Lys Ile Asn Lys
770                 775                 780
Leu Arg Glu Tyr Asp Glu Asn Val Lys Thr Tyr Leu Leu Asn Tyr Ile
785                 790                 795                 800
Ile Gln His Gly Ser Thr Leu Gly Glu Ser Gln Gln Glu Leu Asn Ser
                805                 810                 815
Met Val Ile Asn Thr Leu Asn Asn Ser Ile Pro Phe Lys Leu Ser Ser
                820                 825                 830
Tyr Thr Asp Asp Lys Ile Leu Ile Ser Tyr Phe Asn Lys Phe Phe Lys
            835                 840                 845
Arg Ile Lys Ser Ser Ser Val Leu Asn Met Arg Tyr Lys Asn Asp Lys
850                 855                 860
```

-continued

```
Tyr Val Asp Thr Ser Gly Tyr Asp Ser Asn Ile Asn Ile Asn Gly Glu
865                 870                 875                 880

Ile Phe Ile Tyr Pro Thr Asn Lys Asn Gln Phe Ser Ile Phe Asn Ser
                885                 890                 895

Lys Pro Ser Glu Val Asn Ile Ser Gln Asn Asp Tyr Ile Ile Tyr Asp
            900                 905                 910

Asn Lys Tyr Lys Asn Phe Ser Ile Ser Phe Trp Val Arg Ile Pro Asn
        915                 920                 925

Tyr Asp Asn Lys Ile Val Asn Val Asn Asn Glu Tyr Thr Ile Ile Asn
    930                 935                 940

Cys Met Arg Asp Asn Asn Ser Gly Trp Lys Val Ser Leu Asn His Asn
945                 950                 955                 960

Glu Ile Ile Trp Thr Leu Gln Asp Asn Ala Gly Ile Asn Gln Lys Leu
                965                 970                 975

Ala Phe Asn Tyr Gly Asn Ser Asn Gly Ile Ser Asp Tyr Ile Asn Lys
                980                 985                 990

Trp Ile Phe Val Thr Ile Thr Asn Asp Arg Leu Gly Asp Ser Lys Leu
            995                 1000                1005

Tyr Ile Asn Gly Asn Leu Ile Asp Gln Lys Ser Ile Leu Asn Leu
    1010                1015                1020

Gly Asn Ile His Val Ser Asp Asn Ile Leu Phe Lys Ile Val Asn
    1025                1030                1035

Cys Ser Tyr Thr Arg Tyr Ile Gly Ile Arg Tyr Phe Asn Ile Phe
    1040                1045                1050

Asp Lys Glu Leu Asp Glu Thr Glu Ile Gln Thr Leu Tyr Ser Asn
    1055                1060                1065

Glu Pro Asn Thr Asn Ile Leu Lys Asp Phe Trp Gly Asn Tyr Leu
    1070                1075                1080

Leu Tyr Asp Lys Glu Tyr Tyr Leu Leu Asn Val Leu Lys Pro Asn
    1085                1090                1095

Ser Ile Ile Ser His Arg Arg Asp Leu Thr Phe Ser Phe Tyr Asn
    1100                1105                1110

His Arg Tyr Ile Val Asn Gly Leu Tyr Arg Leu Tyr Ser Gly Ile
    1115                1120                1125

Lys Val Lys Ile Gln Arg Val Asn Asp Ser Ser Thr Asn Asp Gln
    1130                1135                1140

Phe Val Arg Lys Asn Asp Gln Val Tyr Ile Asn Tyr Ile Tyr Asn
    1145                1150                1155

Asn Leu Ser Tyr Ser Leu Tyr Ala Asp Thr Asn Ile Lys Asp Lys
    1160                1165                1170

Glu Lys Thr Ile Lys Ser Ser Leu Ser Gly Asn Ile Phe Asn Gln
    1175                1180                1185

Val Val Val Met Asn Ser Val Gly Asn Asn Cys Thr Met Asn Phe
    1190                1195                1200

Lys Asn Asn Asn Gly Asn Asn Ile Gly Leu Leu Gly Phe Lys Asp
    1205                1210                1215

Asn Thr Leu Val Ala Ser Trp Tyr Tyr Thr His Met Arg Asp
    1220                1225                1230

Asn Thr Asn Ser Asn Gly Cys Phe Trp Asn Phe Ile Ser Glu Glu
    1235                1240                1245

His Gly Trp Gln Glu Lys
    1250
```

<210> SEQ ID NO 77
<211> LENGTH: 1252
<212> TYPE: PRT
<213> ORGANISM: Clostridium botulinum

<400> SEQUENCE: 77

| Met | Pro | Lys | Ile | Asn | Ser | Phe | Asn | Tyr | Asn | Asp | Pro | Val | Asn | Asp | Lys |
|---|---|---|---|---|---|---|---|---|---|---|---|---|---|---|---|
| 1 | | | | 5 | | | | | 10 | | | | | 15 | |

| Thr | Ile | Leu | Tyr | Ile | Lys | Pro | Gly | Gly | Cys | Gln | Gln | Phe | Tyr | Lys | Ser |
|---|---|---|---|---|---|---|---|---|---|---|---|---|---|---|---|
| | | | 20 | | | | | 25 | | | | | 30 | | |

| Phe | Asn | Ile | Met | Lys | Asn | Ile | Trp | Ile | Ile | Pro | Glu | Arg | Asn | Val | Ile |
|---|---|---|---|---|---|---|---|---|---|---|---|---|---|---|---|
| | | | 35 | | | | | 40 | | | | | 45 | | |

| Gly | Thr | Ile | Pro | Gln | Asp | Phe | Leu | Pro | Pro | Thr | Ser | Leu | Lys | Asn | Gly |
|---|---|---|---|---|---|---|---|---|---|---|---|---|---|---|---|
| | 50 | | | | | 55 | | | | | 60 | | | | |

| Asp | Ser | Ser | Tyr | Tyr | Asp | Pro | Asn | Tyr | Leu | Gln | Ser | Asn | Glu | Glu | Lys |
|---|---|---|---|---|---|---|---|---|---|---|---|---|---|---|---|
| 65 | | | | | 70 | | | | | 75 | | | | | 80 |

| Asp | Arg | Phe | Leu | Lys | Ile | Val | Thr | Lys | Ile | Phe | Asn | Arg | Ile | Asn | Asp |
|---|---|---|---|---|---|---|---|---|---|---|---|---|---|---|---|
| | | | | 85 | | | | | 90 | | | | | 95 | |

| Asn | Leu | Ser | Gly | Gly | Ile | Leu | Leu | Glu | Glu | Leu | Ser | Lys | Ala | Asn | Pro |
|---|---|---|---|---|---|---|---|---|---|---|---|---|---|---|---|
| | | | 100 | | | | | 105 | | | | | 110 | | |

| Tyr | Leu | Gly | Asn | Asp | Asn | Thr | Pro | Asn | Asn | Gln | Phe | His | Ile | Gly | Asp |
|---|---|---|---|---|---|---|---|---|---|---|---|---|---|---|---|
| | | 115 | | | | | 120 | | | | | 125 | | | |

| Ala | Ser | Ala | Val | Glu | Ile | Lys | Phe | Ser | Asn | Gly | Ser | Gln | Ser | Ile | Leu |
|---|---|---|---|---|---|---|---|---|---|---|---|---|---|---|---|
| 130 | | | | | 135 | | | | | 140 | | | | | |

| Leu | Pro | Thr | Val | Ile | Ile | Met | Gly | Ala | Glu | Pro | Asp | Leu | Phe | Glu | Thr |
|---|---|---|---|---|---|---|---|---|---|---|---|---|---|---|---|
| 145 | | | | | 150 | | | | | 155 | | | | | 160 |

| Asn | Ser | Ser | Asn | Ile | Ser | Leu | Lys | Asn | Asn | Tyr | Met | Pro | Ser | Asn | His |
|---|---|---|---|---|---|---|---|---|---|---|---|---|---|---|---|
| | | | | 165 | | | | | 170 | | | | | 175 | |

| Gly | Phe | Gly | Ser | Ile | Ala | Ile | Val | Thr | Phe | Ser | Pro | Glu | Tyr | Ser | Phe |
|---|---|---|---|---|---|---|---|---|---|---|---|---|---|---|---|
| | | | 180 | | | | | 185 | | | | | 190 | | |

| Arg | Phe | Asn | Asp | Asn | Ser | Met | Asn | Glu | Phe | Ile | Gln | Asp | Pro | Ala | Leu |
|---|---|---|---|---|---|---|---|---|---|---|---|---|---|---|---|
| | | 195 | | | | | 200 | | | | | 205 | | | |

| Thr | Leu | Met | His | Glu | Leu | Ile | His | Ser | Leu | His | Gly | Leu | Tyr | Gly | Ala |
|---|---|---|---|---|---|---|---|---|---|---|---|---|---|---|---|
| 210 | | | | | 215 | | | | | 220 | | | | | |

| Lys | Gly | Ile | Thr | Thr | Lys | Tyr | Thr | Ile | Thr | Gln | Gln | Asn | Pro | Leu |
|---|---|---|---|---|---|---|---|---|---|---|---|---|---|---|
| 225 | | | | | 230 | | | | | 235 | | | | | 240 |

| Ile | Thr | Asn | Ile | Arg | Gly | Thr | Asn | Ile | Glu | Glu | Phe | Leu | Thr | Phe | Gly |
|---|---|---|---|---|---|---|---|---|---|---|---|---|---|---|---|
| | | | | 245 | | | | | 250 | | | | | 255 | |

| Gly | Thr | Asp | Leu | Asn | Ile | Ile | Thr | Asn | Ala | Gln | Ser | Asn | Asp | Ile | Tyr |
|---|---|---|---|---|---|---|---|---|---|---|---|---|---|---|---|
| | | | 260 | | | | | 265 | | | | | 270 | | |

| Thr | Asn | Leu | Leu | Asp | Asp | Tyr | Lys | Lys | Ile | Ala | Ser | Lys | Leu | Ser | Gln |
|---|---|---|---|---|---|---|---|---|---|---|---|---|---|---|---|
| | | 275 | | | | | 280 | | | | | 285 | | | |

| Val | Gln | Val | Ser | Asn | Pro | Gln | Leu | Asn | Pro | Tyr | Lys | Asp | Val | Phe | Gln |
|---|---|---|---|---|---|---|---|---|---|---|---|---|---|---|---|
| 290 | | | | | 295 | | | | | 300 | | | | | |

| Glu | Lys | Tyr | Gly | Leu | Asp | Lys | Asp | Ala | Asn | Gly | Ile | Tyr | Ser | Val | Asn |
|---|---|---|---|---|---|---|---|---|---|---|---|---|---|---|---|
| 305 | | | | | 310 | | | | | 315 | | | | | 320 |

| Ile | Asn | Lys | Phe | Asn | Asp | Ile | Phe | Lys | Lys | Leu | Tyr | Ser | Phe | Thr | Glu |
|---|---|---|---|---|---|---|---|---|---|---|---|---|---|---|---|
| | | | | 325 | | | | | 330 | | | | | 335 | |

| Phe | Asp | Leu | Ala | Thr | Lys | Phe | Gln | Val | Lys | Cys | Arg | Lys | Thr | Tyr | Ile |
|---|---|---|---|---|---|---|---|---|---|---|---|---|---|---|---|
| | | | 340 | | | | | 345 | | | | | 350 | | |

| Gly | His | His | Lys | Tyr | Phe | Arg | Leu | Ser | Asp | Leu | Leu | Asn | Asp | Ser | Ile |
|---|---|---|---|---|---|---|---|---|---|---|---|---|---|---|---|
| | | 355 | | | | | 360 | | | | | 365 | | | |

| Tyr | Asn | Ile | Ser | Asp | Gly | Tyr | Asn | Ile | Asn | Thr | Leu | Lys | Val | Asn | Phe |
|---|---|---|---|---|---|---|---|---|---|---|---|---|---|---|---|
| | | 370 | | | | | 375 | | | | | 380 | | | |

-continued

Arg Gly Gln Asn Thr Asn Leu Asn Thr Arg Ile Ile Thr Pro Ile Thr
385                 390                 395                 400

Gly Arg Gly Val Val Arg Lys Ile Ile Arg Phe Cys Thr Asn Ile Phe
            405                 410                 415

Ser Pro Lys Gly Ile Arg Lys Ser Ile Cys Ile Glu Val Asn Asn Gly
            420                 425                 430

Glu Leu Phe Phe Val Ala Ser Glu Asn Ser Tyr Asn Asp Asp Asn Ile
        435                 440                 445

Asn Thr Ser Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asp Asp Ala
            485                 490                 495

Tyr Ile Pro Lys Tyr Asp Ser Asn Gly Thr Ser Asp Ile Glu Gln Tyr
            500                 505                 510

Asp Val Ser Glu Leu Asn Val Phe Phe Tyr Leu Asp Ala Gln Lys Val
        515                 520                 525

Pro Glu Gly Glu Asn Asn Val Asp Phe Thr Ser Ser Ile Asp Thr Ala
530                 535                 540

Leu Leu Glu Gln Pro Lys Ile Tyr Thr Phe Phe Ser Ser Lys Phe Ile
545                 550                 555                 560

Ser Asn Leu Asn Lys Thr Met Gln Ala Ala Leu Phe Val Ser Trp Ile
            565                 570                 575

Gln Gln Val Leu Val Asp Phe Thr Thr Glu Ala Thr Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Ile Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Asn Trp Lys Glu Val Tyr Ser Phe Ile Val Ser Asn
            675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Lys Asn
            725                 730                 735

Lys Tyr Asp Ile Glu Gln Ile Glu Asn Glu Leu Asn Gln Thr Val Ser
            740                 745                 750

Ile Ala Met Asn Asn Ile Glu Ile Phe Leu Thr Glu Ser Ser Ile Ser
            755                 760                 765

Tyr Leu Met Lys Leu Ile Asn Glu Val Lys Ile Asn Lys Leu Lys Glu
            770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile

```
                805                 810                 815
Asp Thr Leu Asn Asn Ser Ile Pro Phe Lys Leu Ser Ser Tyr Thr Asp
            820                 825                 830
Asp Lys Ile Leu Ile Ser Tyr Phe Asn Lys Phe Phe Lys Thr Ile Lys
            835                 840                 845
Ser Ser Ser Val Leu Asn Met Arg Tyr Lys Asn Asp Lys Tyr Ile Asp
    850                 855                 860
Thr Ser Gly Tyr Asp Ser Asn Ile Asn Ile Lys Gly Asp Val Phe Ile
865                 870                 875                 880
Tyr Pro Thr Asn Lys Asn Gln Phe Gly Ile Tyr Asn Asn Lys Leu Ser
                885                 890                 895
Glu Val Asn Ile Ser Gln Asn Asp Tyr Ile Ile Tyr Asp Asn Lys Tyr
            900                 905                 910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Ile Asn Cys Met Arg
        930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Val Phe Lys
                965                 970                 975
Tyr Gly Asn Ala Asn Gly Ile Ser Asp Tyr Ile Asn Lys Trp Ile Phe
            980                 985                 990
Val Thr Ile Thr Asn Asp Arg Leu  Gly Asp Ser Lys Leu  Tyr Ile Asn
            995                 1000                1005
Gly Asn  Leu Ile Asp Lys Lys  Ser Ile Leu Asn Leu  Gly Asn Ile
    1010                1015                1020
His Val  Ser Asp Asn Ile Leu  Phe Lys Ile Val Asn  Cys Ser Tyr
    1025                1030                1035
Thr Arg  Tyr Ile Gly Met Arg  Tyr Phe Asn Ile Phe  Asp Lys Glu
    1040                1045                1050
Leu Asp  Lys Thr Glu Ile Glu  Thr Leu Tyr Asn Asn  Glu Pro Asn
    1055                1060                1065
Thr Asn  Ile Leu Lys Asp Phe  Trp Gly Asn Tyr Leu  Leu Tyr Asp
    1070                1075                1080
Lys Glu  Tyr Tyr Leu Leu Asn  Val Leu Lys Pro Asn  Asn Val Ile
    1085                1090                1095
Asp Ser  Asn Arg Asp Ser Thr  Phe Ser Ile His Asn  Ile Arg Ser
    1100                1105                1110
Thr Ile  Val Leu Ala Asn Arg  Leu Tyr Ser Gly Ile  Lys Val Lys
    1115                1120                1125
Ile Gln  Arg Val Asn Asn Ser  Ser Thr Asn Asp Asn  Leu Val Arg
    1130                1135                1140
Lys Asn  Asp Gln Val Tyr Ile  Asn Phe Val Ala Ser  Lys Thr His
    1145                1150                1155
Leu Phe  Pro Leu Tyr Ala Asp  Thr Asn Thr Thr Asn  Lys Glu Lys
    1160                1165                1170
Thr Ile  Lys Ser Ser Ser Ser  Gly Asn Arg Phe Asn  Gln Val Val
    1175                1180                1185
Val Met  Asn Ser Val Gly Asn  Asn Cys Thr Met Asn  Phe Lys Asn
    1190                1195                1200
Asn Asn  Gly Asn Asn Ile Gly  Met Leu Gly Phe Lys  Asp Asn Thr
    1205                1210                1215
```

Leu Val Ala Ser Thr Trp Tyr Tyr Thr His Met Arg Asp Asn Thr
    1220            1225                1230

Asn Ser Asn Gly Cys Phe Trp Asn Phe Ile Ser Glu Glu His Gly
    1235            1240                1245

Trp Gln Glu Lys
    1250

<210> SEQ ID NO 78
<211> LENGTH: 1252
<212> TYPE: PRT
<213> ORGANISM: Clostridium botulinum

<400> SEQUENCE: 78

Met Pro Lys Ile Asn Ser Phe Asn Tyr Asn Asp Pro Val Asn Asp Lys
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asn Glu Glu Lys
65                  70                  75                  80

Asp Arg Phe Leu Lys Ile Val Thr Lys Ile Phe Asn Arg Ile Asn Asp
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asn Asn Gln Phe His Ile Gly Asp
        115                 120                 125

Ala Ser Ala Val Glu Ile Lys Phe Ser Asn Gly Ser Gln Ser Ile Leu
    130                 135                 140

Leu Pro Thr Val Ile Ile Met Gly Ala Glu Pro Asp Leu Phe Glu Thr
145                 150                 155                 160

Asn Ser Ser Asn Ile Ser Leu Lys Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Asn Ala Gln Ser Asn Asp Ile Tyr
            260                 265                 270

Thr Asn Leu Leu Ala Asp Tyr Lys Lys Ile Ala Ser Lys Leu Ser Gln
        275                 280                 285

Val Gln Val Ser Asn Pro Gln Leu Asn Pro Tyr Lys Asp Ile Phe Gln
    290                 295                 300

Glu Lys Tyr Gly Leu Asp Lys Asn Ala Ser Gly Ile Tyr Ser Val Asn
305                 310                 315                 320

Ile Asn Lys Phe Asp Asp Ile Phe Lys Lys Leu Tyr Ser Phe Thr Glu

-continued

```
                325                 330                 335
Phe Asp Leu Ala Thr Lys Phe Gln Val Lys Cys Arg Gln Thr Tyr Ile
                340                 345                 350
Gly Gln Tyr Lys Tyr Phe Lys Leu Ser Asn Leu Leu Asn Asn Ser Ile
                355                 360                 365
Tyr Asn Ile Ser Glu Gly Tyr Asn Ile Asn Thr Leu Lys Val Asn Phe
                370                 375                 380
Arg Gly Gln Asn Thr Asn Leu Asn Pro Arg Ile Ile Thr Gln Leu Thr
385                 390                 395                 400
Gly Arg Gly Leu Val Lys Lys Ile Ile Arg Phe Cys Lys Asn Ile Val
                405                 410                 415
Phe Ser Lys Gly Ile Thr Lys Ser Ile Cys Ile Glu Ile Asn Asn Gly
                420                 425                 430
Glu Leu Phe Phe Val Ala Ser Glu Asn Ser Tyr Asn Asp Asp Asn Ile
                435                 440                 445
Asn Thr Pro Lys Glu Ile Asp Asp Thr Val Thr Ser Asn Asn Asn Tyr
                450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
                515                 520                 525
Pro Glu Gly Glu Asn Asn Val Asn Leu Thr Ser Ser Ile Asp Thr Ala
                530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
                580                 585                 590
Val Asp Lys Ile Ala Asp Ile Ser Ile Val Val Pro Tyr Ile Gly Leu
                595                 600                 605
Ala Leu Asn Ile Gly Asn Glu Ala Gln Lys Gly Asn Phe Lys Asp Ala
                610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
                675                 680                 685
Trp Met Thr Lys Ile Asn Thr Gln Phe Asn Lys Arg Lys Glu Gln Met
                690                 695                 700
Tyr Gln Ala Leu Gln Asn Gln Val Asn Ala Leu Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asn Ile Glu Gln Ile Glu Asn Glu Leu Asn Gln Lys Val Ser
                740                 745                 750
```

-continued

Ile Ala Met Asn Asn Ile Glu Ile Phe Leu Thr Glu Ser Ser Ile Ser
            755                 760                 765

Tyr Leu Met Lys Leu Ile Asn Glu Val Lys Ile Asn Lys Leu Arg Glu
        770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Lys Arg Ile Lys
        835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
        900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
            965                 970                 975

Tyr Gly Asn Ala Asn Gly Ile Ser Asp Tyr Ile Asn Lys Trp Ile Phe
        980                 985                 990

Val Thr Ile Thr Asn Asp Arg Leu Gly Asp Ser Lys Leu Tyr Ile Asn
        995                 1000                1005

Gly Asn Leu Ile Asp Lys Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Met Arg Tyr Phe Asn Ile Phe Asp Lys Glu
    1040                1045                1050

Leu Asp Lys Thr Glu Ile Glu Thr Leu Tyr Asn Asn Glu Pro Asn
    1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Val Ile
    1085                1090                1095

Asp Ser Asn Arg Asp Ser Thr Phe Ser Ile His Asn Ile Arg Ser
    1100                1105                1110

Thr Ile Val Leu Ala Asn Lys Leu Tyr Leu Gly Ile Lys Val Lys
    1115                1120                1125

Ile Gln Arg Val Asn Asn Ser Ser Thr Asn Asp Asn Leu Val Arg
    1130                1135                1140

Lys Asn Asp Gln Val Tyr Ile Asn Phe Val Pro Ile Lys Thr His
    1145                1150                1155

-continued

Leu Phe Pro Leu Tyr Ala Asp Thr Asn Thr Asn Lys Glu Lys
    1160            1165            1170

Thr Ile Lys Ser Ser Ser Gly Asn Arg Phe Asn Gln Val Val
    1175            1180            1185

Val Met Asn Ser Val Gly Asn Cys Thr Met Asn Phe Lys Asn
    1190            1195            1200

Asn Asn Gly Asn Asn Ile Gly Met Leu Gly Phe Lys Asp Asn Thr
    1205            1210            1215

Leu Val Ala Ser Thr Trp Tyr Tyr Thr His Met Arg Asp Asn Thr
    1220            1225            1230

Asn Ser Asn Gly Cys Phe Trp Asn Phe Ile Ser Glu Glu His Gly
    1235            1240            1245

Trp Gln Glu Lys
    1250

<210> SEQ ID NO 79
<211> LENGTH: 1252
<212> TYPE: PRT
<213> ORGANISM: Clostridium botulinum

<400> SEQUENCE: 79

Met Pro Lys Ile Asn Ser Phe Asn Tyr Asn Asp Pro Val Asn Asp Lys
1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asn Glu Glu Lys
65                  70                  75                  80

Asp Arg Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Asn Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Arg Ile Thr Thr Lys Tyr Thr Ile Thr Gln Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Tyr Asn Asp Ile Tyr
            260                 265                 270

-continued

Thr Asn Leu Leu Ala Asp Tyr Lys Lys Ile Ala Ser Lys Leu Ser Lys
        275                 280                 285

Val Gln Val Ser Asn Pro Gln Leu Asn Pro Tyr Lys Asp Ile Phe Gln
290                 295                 300

Glu Lys Tyr Gly Leu Asp Lys Asn Ala Ser Gly Ile Tyr Ser Val Asn
305                 310                 315                 320

Ile Asn Lys Phe Asp Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asn Ser Ile
                355                 360                 365

Tyr Asn Ile Ser Glu Gly Tyr Asn Ile Asn Thr Leu Lys Val Asn Phe
                370                 375                 380

Arg Gly Gln Asn Thr Asn Leu Asn Pro Arg Ile Ile Thr Gln Leu Thr
385                 390                 395                 400

Gly Arg Gly Leu Val Lys Lys Ile Ile Arg Phe Cys Lys Asn Ile Val
                405                 410                 415

Phe Ser Lys Gly Ile Thr Lys Ser Ile Cys Ile Glu Ile Asn Asn Gly
                420                 425                 430

Glu Leu Phe Phe Val Ala Ser Glu Asn Ser Tyr Asn Asp Asp Asn Ile
                435                 440                 445

Asn Thr Pro Lys Glu Ile Asp Asp Thr Val Thr Ser Asn Asn Asn Tyr
                450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
                515                 520                 525

Pro Glu Gly Glu Asn Asn Val Asn Leu Thr Ser Ser Ile Asp Thr Ala
                530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
                580                 585                 590

Val Asp Lys Ile Ala Asp Ile Ser Ile Val Val Pro Tyr Ile Gly Leu
                595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
                660                 665                 670

Glu Arg Asp Glu Lys Trp Lys Glu Val Tyr Ser Phe Ile Val Ser Asn
                675                 680                 685

-continued

Trp Met Thr Lys Ile Asn Thr Gln Phe Asn Lys Arg Lys Glu Gln Met
690                     695                     700

Tyr Gln Ala Leu Gln Asn Gln Val Asn Ala Ile Lys Thr Ile Ile Glu
705                     710                     715                 720

Ser Lys Tyr Asn Ser Tyr Thr Leu Glu Glu Lys Asn Glu Leu Thr Asn
                725                     730                     735

Lys Tyr Asp Ile Lys Gln Ile Glu Asn Glu Leu Asn Gln Lys Val Ser
            740                     745                     750

Ile Ala Met Asn Asn Ile Asp Arg Phe Leu Thr Glu Ser Ser Ile Ser
                755                     760                     765

Tyr Leu Met Lys Leu Ile Asn Glu Val Lys Ile Asn Lys Leu Arg Glu
770                     775                     780

Tyr Asp Glu Asn Val Lys Thr Tyr Leu Leu Asn Tyr Ile Ile Gln His
785                     790                     795                 800

Gly Ser Ile Leu Gly Glu Ser Gln Gln Glu Leu Asn Ser Met Val Thr
                805                     810                     815

Asp Thr Leu Asn Asn Ser Ile Pro Phe Lys Leu Ser Ser Tyr Thr Asp
            820                     825                     830

Asp Lys Ile Leu Ile Ser Tyr Phe Asn Lys Phe Phe Lys Arg Ile Lys
            835                     840                     845

Ser Ser Ser Val Leu Asn Met Arg Tyr Lys Asn Asp Lys Tyr Val Asp
850                     855                     860

Thr Ser Gly Tyr Asp Ser Asn Ile Asn Ile Asn Gly Asp Val Tyr Lys
865                     870                     875                 880

Tyr Pro Thr Asn Lys Asn Gln Phe Gly Ile Tyr Asn Asp Lys Leu Ser
                885                     890                     895

Glu Val Asn Ile Ser Gln Asn Asp Tyr Ile Ile Tyr Asp Asn Lys Tyr
                900                     905                     910

Lys Asn Phe Ser Ile Ser Phe Trp Val Arg Ile Pro Asn Tyr Asp Asn
            915                     920                     925

Lys Ile Val Asn Val Asn Asn Glu Tyr Thr Ile Ile Asn Cys Met Arg
930                     935                     940

Asp Asn Asn Ser Gly Trp Lys Val Ser Leu Asn His Asn Glu Ile Ile
945                     950                     955                 960

Trp Thr Leu Gln Asp Asn Ala Gly Ile Asn Gln Lys Leu Ala Phe Asn
                965                     970                     975

Tyr Gly Asn Ala Asn Gly Ile Ser Asp Tyr Ile Asn Lys Trp Ile Phe
            980                     985                     990

Val Thr Ile Thr Asn Asp Arg Leu  Gly Asp Ser Lys Leu  Tyr Ile Asn
                995                     1000                    1005

Gly Asn Leu Ile Asp Gln Lys  Ser Ile Leu Asn Leu  Gly Asn Ile
            1010                    1015                    1020

His Val Ser Asp Asn Ile Leu  Phe Lys Ile Val Asn  Cys Ser Tyr
            1025                    1030                    1035

Thr Arg Tyr Ile Gly Ile Arg  Tyr Phe Asn Ile Phe  Asp Lys Glu
            1040                    1045                    1050

Leu Asp Glu Thr Glu Ile Gln  Thr Leu Tyr Ser Asn  Glu Pro Asn
            1055                    1060                    1065

Thr Asn Ile Leu Lys Asp Phe  Trp Gly Asn Tyr Leu  Leu Tyr Asp
            1070                    1075                    1080

Lys Glu Tyr Tyr Leu Leu Asn  Val Leu Lys Pro Asn  Asn Phe Ile
            1085                    1090                    1095

Asp Arg Arg Lys Asp Ser Thr  Leu Ser Ile Asn Asn  Ile Arg Ser

```
        1100                1105                1110

Thr Ile Leu Leu Ala Asn Arg Leu Tyr Ser Gly Ile Lys Val Lys
        1115                1120                1125

Ile Gln Arg Val Asn Asn Ser Ser Thr Asn Asp Asn Leu Val Arg
        1130                1135                1140

Lys Asn Asp Gln Val Tyr Ile Asn Phe Val Ala Ser Lys Thr His
        1145                1150                1155

Leu Phe Pro Leu Tyr Ala Asp Thr Ala Thr Thr Asn Lys Glu Lys
        1160                1165                1170

Thr Ile Lys Ile Ser Ser Ser Gly Asn Arg Phe Asn Gln Val Val
        1175                1180                1185

Val Met Asn Ser Val Gly Asn Asn Cys Thr Met Asn Phe Lys Asn
        1190                1195                1200

Asn Asn Gly Asn Asn Ile Gly Leu Leu Gly Phe Lys Ala Asp Thr
        1205                1210                1215

Val Val Ala Ser Thr Trp Tyr Tyr Thr His Met Arg Asp His Thr
        1220                1225                1230

Asn Ser Asn Gly Cys Phe Trp Asn Phe Ile Ser Glu Glu His Gly
        1235                1240                1245

Trp Gln Glu Lys
        1250

<210> SEQ ID NO 80
<211> LENGTH: 1252
<212> TYPE: PRT
<213> ORGANISM: Clostridium botulinum

<400> SEQUENCE: 80

Met Pro Lys Ile Asn Ser Phe Asn Tyr Asn Asp Pro Val Asn Asp Lys
1               5                   10                  15

Thr Ile Leu Tyr Ile Lys Pro Gly Gly Cys Gln Gln Phe Tyr Lys Ser
                20                  25                  30

Phe Asn Ile Met Lys Asn Ile Trp Ile Ile Pro Glu Arg Asn Val Ile
            35                  40                  45

Gly Thr Ile Pro Gln Asp Phe Leu Pro Pro Thr Ser Leu Lys Asn Gly
        50                  55                  60

Asp Ser Ser Tyr Tyr Asp Pro Asn Tyr Leu Gln Ser Asn Glu Glu Lys
65                  70                  75                  80

Asp Arg Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Asn Gln Ser Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205
```

```
Thr Leu Met His Glu Leu Ile His Ser Leu His Gly Leu Tyr Gly Ala
    210                 215                 220

Lys Arg Ile Thr Thr Lys Tyr Thr Ile Thr Gln Gln Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Tyr Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Gln Leu Asn Pro Tyr Lys Asp Ile Phe Gln
290                 295                 300

Glu Lys Tyr Gly Leu Asp Lys Asn Ala Ser Gly Ile Tyr Ser Val Asn
305                 310                 315                 320

Ile Asn Lys Phe Asp Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asn Ser Ile
        355                 360                 365

Tyr Asn Ile Ser Glu Gly Tyr Asn Ile Asn Thr Leu Lys Val Asn Phe
370                 375                 380

Arg Gly Gln Asn Thr Asn Leu Asn Pro Arg Ile Ile Thr Gln Leu Thr
385                 390                 395                 400

Gly Arg Gly Leu Val Lys Lys Ile Ile Arg Phe Cys Lys Asn Ile Val
                405                 410                 415

Phe Ser Lys Gly Ile Thr Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Tyr Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560

Asn Asn Val Asn Lys Thr Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
```

```
            625                 630                 635                 640
Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
                660                 665                 670

Glu Arg Asp Glu Lys Trp Lys Glu Val Tyr Ser Phe Ile Val Ser Asn
                675                 680                 685

Trp Met Thr Lys Ile Asn Thr Gln Phe Asn Lys Arg Lys Glu Gln Met
                690                 695                 700

Tyr Gln Ala Leu Gln Asn Gln Val Asn Ala Leu Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asn Ile Glu Gln Ile Glu Asn Glu Leu Asn Gln Lys Val Ser
                740                 745                 750

Ile Ala Met Asn Asn Ile Glu Ile Phe Leu Thr Glu Ser Ser Ile Ser
                755                 760                 765

Tyr Leu Met Lys Leu Ile Asn Glu Val Lys Ile Asn Lys Leu Arg Glu
                770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
                820                 825                 830

Asp Lys Ile Leu Ile Ser Tyr Phe Asn Lys Phe Phe Lys Arg Ile Lys
                835                 840                 845

Ser Ser Ser Val Leu Asn Met Arg Tyr Lys Asn Asp Lys Tyr Val Asp
                850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
                900                 905                 910

Lys Asn Phe Ser Ile Ser Phe Trp Val Arg Ile Pro Asn Tyr Asp Asn
                915                 920                 925

Lys Ile Val Asn Val Asn Asn Glu Tyr Thr Ile Ile Asn Cys Met Arg
                930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
                980                 985                 990

Val Thr Ile Thr Asn Asp Arg Leu Gly Asp Ser Lys Leu Tyr Ile Asn
                995                 1000                1005

Gly Asn Leu Ile Asp Lys Lys Ser Ile Leu Asn Leu Gly Asn Ile
                1010                1015                1020

His Val Ser Asp Asn Ile Leu Phe Lys Ile Val Asn Cys Ser Tyr
                1025                1030                1035

Thr Arg Tyr Ile Gly Ile Arg Tyr Phe Asn Ile Phe Asp Lys Glu
                1040                1045                1050
```

Leu Asp Glu Thr Glu Ile Gln Thr Leu Tyr Asn Asn Glu Pro Asn
    1055               1060               1065

Ala Asn Ile Leu Lys Asp Phe Trp Gly Asn Tyr Leu Leu Tyr Asp
    1070               1075               1080

Lys Glu Tyr Tyr Leu Leu Asn Val Leu Lys Pro Asn Asn Phe Ile
    1085               1090               1095

Asp Arg Arg Thr Asp Ser Thr Leu Ser Ile Asn Asn Ile Arg Ser
    1100               1105               1110

Thr Ile Leu Leu Ala Asn Arg Leu Tyr Ser Gly Ile Lys Val Lys
    1115               1120               1125

Ile Gln Arg Val Asn Asn Ser Ser Thr Asn Asp Asn Leu Val Arg
    1130               1135               1140

Lys Asn Asp Gln Val Tyr Ile Asn Phe Val Ala Ser Lys Thr His
    1145               1150               1155

Leu Phe Pro Leu Tyr Ala Asp Thr Asn Thr Thr Asn Lys Glu Lys
    1160               1165               1170

Thr Ile Lys Ser Ser Ser Ser Gly Asn Arg Phe Asn Gln Val Val
    1175               1180               1185

Val Met Asn Ser Val Gly Asn Asn Cys Thr Met Asn Phe Lys Asn
    1190               1195               1200

Asn Asn Gly Asn Asn Ile Gly Met Leu Gly Phe Lys Asp Asn Thr
    1205               1210               1215

Leu Val Ala Ser Thr Trp Tyr Tyr Thr His Met Arg Asp Asn Thr
    1220               1225               1230

Asn Ser Asn Gly Cys Phe Trp Asn Phe Ile Ser Glu Glu His Gly
    1235               1240               1245

Trp Gln Glu Lys
    1250

<210> SEQ ID NO 81
<211> LENGTH: 1251
<212> TYPE: PRT
<213> ORGANISM: Clostridium botulinum

<400> SEQUENCE: 81

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr

-continued

```
            145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
                180                 185                 190
Arg Phe Asn Asp Asn Ser Met Asn Glu Phe Ile Gln Asp Pro Ala Leu
                195                 200                 205
Thr Leu Met His Glu Leu Ile His Ser Leu His Gly Leu Tyr Gly Ala
                210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
                260                 265                 270
Thr Asn Leu Leu Ala Asp Tyr Lys Lys Ile Ala Ser Lys Leu Ser Lys
                275                 280                 285
Val Gln Val Ser Asn Pro Leu Leu Asn Pro Tyr Lys Asp Val Phe Glu
                290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
                340                 345                 350
Gly Gln Tyr Lys Tyr Phe Lys Leu Ser Asn Leu Leu Asn Asp Ser Ile
                355                 360                 365
Tyr Asn Ile Ser Glu Gly Tyr Asn Ile Asn Asn Leu Lys Val Asn Phe
                370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
                420                 425                 430
Glu Leu Phe Phe Val Ala Ser Glu Asn Ser Tyr Asn Asp Asp Asn Ile
                435                 440                 445
Asn Thr Pro Lys Glu Ile Asp Asp Thr Val Thr Ser Asn Asn Asn Tyr
                450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
                500                 505                 510
Asp Val Asn Glu Leu Asn Val Phe Phe Tyr Leu Asp Ala Gln Lys Val
                515                 520                 525
Pro Glu Gly Glu Asn Asn Val Asn Leu Thr Ser Ser Ile Asp Thr Ala
                530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
```

-continued

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Val Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Leu Lys Thr Ile Ile Glu
705                 710                 715                 720

Phe Lys Tyr Asn Ser Tyr Thr Leu Glu Glu Lys Lys Glu Leu Lys Asn
                725                 730                 735

Asn Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asp Tyr Ile Ile Gln His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Glu Ile Phe Ile
865                 870                 875                 880

Tyr Pro Thr Asn Lys Asn Gln Phe Thr Ile Phe Asn Ser Lys Pro Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Ile Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Arg Ile Asn Gln Lys Leu Val Phe Lys
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
            995                 1000                1005

Gly His Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp
    1070                1075                1080

Lys Gly Tyr Tyr Leu Leu Asn Val Leu Lys Pro Asn Asn Phe Ile
    1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
    1115                1120                1125

Ile Gln Arg Val Asn Asp Ser Ser Thr Asn Asp Arg Phe Val Arg
    1130                1135                1140

Lys Asn Asp Gln Val Tyr Ile Asn Tyr Ile Ser Asn Ser Ser Ser
    1145                1150                1155

Tyr Ser Leu Tyr Ala Asp Thr Asn Thr Thr Asp Lys Glu Lys Thr
    1160                1165                1170

Ile Lys Ser Ser Ser Ser Gly Asn Arg Phe Asn Gln Val Val Val
    1175                1180                1185

Met Asn Ser Val Gly Asn Asn Cys Thr Met Asn Phe Lys Asn Asn
    1190                1195                1200

Asn Gly Asn Asn Ile Gly Leu Leu Gly Phe Lys Ala Asp Thr Val
    1205                1210                1215

Val Ala Ser Thr Trp Tyr Tyr Thr His Met Arg Asp His Thr Asn
    1220                1225                1230

Ser Asn Gly Cys Phe Trp Asn Phe Ile Ser Glu Glu His Gly Trp
    1235                1240                1245

Gln Glu Lys
    1250

<210> SEQ ID NO 82
<211> LENGTH: 1252
<212> TYPE: PRT
<213> ORGANISM: Clostridium botulinum

<400> SEQUENCE: 82

Met Pro Thr Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Tyr Glu Glu Lys
65                  70                  75                  80

Asp Arg Phe Leu Lys Ile Val Thr Lys Ile Phe Asn Arg Ile Asn Asn
                85                  90                  95

```
Asn Leu Ser Gly Gly Ile Leu Glu Glu Leu Ser Lys Ala Asn Pro
                100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Gln Tyr Thr Ile Thr Gln Gln Gln Asn Pro Leu
225                 230                 235                 240

Ile Thr Asn Ile Lys Gly Thr Asn Ile Glu Glu Phe Leu Thr Phe Gly
                245                 250                 255

Gly Thr Asp Leu Asn Ile Ile Thr Ser Ala Gln Tyr Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Lys Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asn Ser Ile
        355                 360                 365

Tyr Asn Ile Ser Glu Gly Tyr Asn Ile Asn Thr Leu Lys Val Asn Phe
370                 375                 380

Arg Gly Gln Asn Thr Asn Leu Asn Pro Arg Ile Ile Thr Pro Leu Thr
385                 390                 395                 400

Gly Arg Gly Leu Val Lys Lys Ile Ile Arg Phe Cys Lys Asn Ile Val
                405                 410                 415

Phe Ser Lys Gly Ile Arg Lys Ser Ile Cys Ile Glu Ile Asn Asn Gly
            420                 425                 430

Glu Leu Phe Phe Val Ala Ser Asp Asn Ser Tyr Asn Asp Asp Asn Ile
        435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510
```

```
Asp Val Asn Glu Leu Asn Val Phe Phe Tyr Leu Asp Ala Gln Lys Val
            515                 520                 525

Pro Glu Gly Glu Asn Asn Ile Asp Phe Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Leu Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asn Ile Glu Gln Ile Glu Asn Glu Leu Asn Gln Lys Val Ser
            740                 745                 750

Ile Ala Met Asn Asn Ile Glu Ile Phe Leu Thr Glu Ser Ser Ile Ser
            755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asn Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
```

```
                930             935             940
Asp Asn Asn Ser Gly Trp Lys Val Ser Leu Asn His Asn Glu Ile Ile
945                 950             955                 960

Trp Thr Leu Gln Asp Asn Ser Gly Ile Asn Gln Lys Leu Ala Phe Asn
                965             970                 975

Tyr Gly Asn Ala Asn Gly Ile Ser Asp Tyr Ile Asn Lys Trp Ile Phe
            980             985             990

Val Thr Ile Thr Asn Asp Arg Leu  Gly Asp Ser Lys Leu  Tyr Ile Asn
        995             1000            1005

Gly Asn  Leu Ile Asp Lys Lys  Ser Ile Leu Asn Leu  Gly Asn Ile
    1010            1015            1020

His Val  Ser Asp Asn Ile Leu  Phe Lys Ile Val Asn  Cys Ser Tyr
    1025            1030            1035

Thr Arg  Tyr Ile Gly Ile Arg  Tyr Phe Asn Ile Phe  Asp Lys Glu
    1040            1045            1050

Leu Asp  Glu Thr Glu Ile Gln  Thr Leu Tyr Asn Asn  Glu Pro Asn
    1055            1060            1065

Ala Asn  Ile Leu Lys Asp Phe  Trp Gly Asn Tyr Leu  Leu Tyr Asp
    1070            1075            1080

Lys Glu  Tyr Tyr Leu Leu Asn  Val Leu Lys Pro Asn  Asn Phe Ile
    1085            1090            1095

Asn Arg  Arg Thr Asp Ser Thr  Leu Ser Ile Asn Asn  Ile Arg Ser
    1100            1105            1110

Thr Ile  Leu Leu Ala Asn Arg  Leu Tyr Ser Gly Ile  Lys Val Lys
    1115            1120            1125

Ile Gln  Arg Val Asn Asn Ser  Ser Thr Asn Asp Asn  Leu Val Arg
    1130            1135            1140

Lys Asn  Asp Gln Val Tyr Ile  Asn Phe Val Asp Ser  Lys Thr His
    1145            1150            1155

Leu Leu  Pro Leu Tyr Ala Asp  Thr Ala Thr Asn Lys  Glu Lys
    1160            1165            1170

Thr Ile  Lys Ile Ser Ser Ser  Gly Asn Arg Phe Asn  Gln Val Val
    1175            1180            1185

Val Met  Asn Ser Val Gly Asn  Asn Cys Thr Met Asn  Phe Lys Asn
    1190            1195            1200

Asn Asn  Gly Asn Asn Ile Gly  Leu Leu Gly Phe Lys  Ala Asp Thr
    1205            1210            1215

Val Val  Ala Ser Thr Trp Tyr  Tyr Thr His Met Arg  Asp Asn Thr
    1220            1225            1230

Asn Ser  Asn Gly Phe Phe Trp  Asn Phe Ile Ser Glu  Glu His Gly
    1235            1240            1245

Trp Gln  Glu Lys
    1250

<210> SEQ ID NO 83
<211> LENGTH: 1252
<212> TYPE: PRT
<213> ORGANISM: Clostridium botulinum

<400> SEQUENCE: 83

Met Pro Thr Ile Asn Ser Phe Asn Tyr Asn Asp Pro Val Asn Asn Arg
1               5                   10                  15

Thr Ile Leu Tyr Ile Lys Pro Gly Gly Cys Gln Gln Phe Tyr Lys Ser
            20                  25                  30
```

-continued

```
Phe Asn Ile Met Lys Asn Ile Trp Ile Ile Pro Glu Arg Asn Val Ile
             35                  40                  45

Gly Thr Ile Pro Gln Asp Phe Leu Pro Pro Thr Ser Leu Lys Asn Gly
 50                  55                  60

Asp Ser Ser Tyr Tyr Asp Pro Asn Tyr Leu Gln Ser Asp Gln Glu Lys
 65                  70                  75                  80

Asp Lys Phe Leu Lys Ile Val Thr Lys Ile Phe Asn Arg Ile Asn Asp
                 85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
            115                 120                 125

Ala Ser Ala Val Pro Ile Gln Phe Ser Asn Gly Ser Gln Ser Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Lys Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
```

```
            450                 455                 460
Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Gly Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Leu Lys Ala Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880
```

-continued

```
Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
        900                 905                 910

Lys Asn Phe Ser Ile Ser Phe Trp Val Arg Ile Pro Asn Tyr Asp Asn
            915                 920                 925

Lys Ile Val Asn Val Asn Glu Tyr Thr Ile Ile Asn Cys Met Arg
        930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
            965                 970                 975

Tyr Gly Asn Ala Asn Gly Ile Ser Asp Tyr Ile Asn Lys Trp Ile Phe
        980                 985                 990

Val Thr Ile Thr Asn Asp Arg Leu Gly Asp Ser Lys Leu Tyr Ile Asn
            995                 1000                1005

Gly Asn Leu Ile Asp Lys Lys Ser Ile Leu Asn Leu Gly Asn Ile
        1010                1015                1020

His Val Ser Asp Asn Ile Leu Phe Lys Ile Val Asn Cys Ser Tyr
        1025                1030                1035

Thr Arg Tyr Ile Gly Ile Arg Tyr Phe Asn Ile Phe Asp Lys Glu
        1040                1045                1050

Leu Asp Glu Thr Glu Ile Gln Thr Leu Tyr Asn Asn Glu Pro Asn
        1055                1060                1065

Ala Asn Ile Leu Lys Asp Phe Trp Gly Asn Tyr Leu Leu Tyr Asp
        1070                1075                1080

Lys Glu Tyr Tyr Leu Leu Asn Val Leu Lys Pro Asn Asn Phe Ile
        1085                1090                1095

Asn Arg Arg Thr Asp Ser Thr Leu Ser Ile Asn Asn Ile Arg Ser
        1100                1105                1110

Thr Ile Leu Leu Ala Asn Arg Leu Tyr Ser Gly Ile Lys Val Lys
        1115                1120                1125

Ile Gln Arg Val Asn Asn Ser Ser Thr Asn Asp Asn Leu Val Arg
        1130                1135                1140

Lys Asn Asp Gln Val Tyr Ile Asn Phe Val Ala Ser Lys Thr His
        1145                1150                1155

Leu Leu Pro Leu Tyr Ala Asp Thr Ala Thr Asn Lys Glu Lys
        1160                1165                1170

Thr Ile Lys Ile Ser Ser Ser Gly Asn Arg Phe Asn Gln Val Val
        1175                1180                1185

Val Met Asn Ser Val Gly Asn Asn Cys Thr Met Asn Phe Lys Asn
        1190                1195                1200

Asn Asn Gly Asn Asn Ile Gly Leu Leu Gly Phe Lys Ala Asp Thr
        1205                1210                1215

Val Val Ala Ser Thr Trp Tyr Tyr Thr His Met Arg Asp Asn Thr
        1220                1225                1230

Asn Ser Asn Gly Phe Phe Trp Asn Phe Ile Ser Glu Glu His Gly
        1235                1240                1245

Trp Gln Glu Lys
        1250

<210> SEQ ID NO 84
<211> LENGTH: 1252
```

<212> TYPE: PRT
<213> ORGANISM: Clostridium botulinum

<400> SEQUENCE: 84

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
                100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln His Ile Leu
        130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Ile Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Thr Cys Ile Ile Thr Gln Gln Asn Pro Leu
225                 230                 235                 240

Ile Thr Asn Arg Lys Gly Ile Asn Ile Glu Glu Phe Leu Thr Phe Gly
                245                 250                 255

Gly Asn Asp Leu Asn Ile Ile Thr Val Ala Gln Tyr Asn Asp Ile Tyr
            260                 265                 270

Thr Asn Leu Leu Asn Asp Tyr Arg Lys Ile Ala Ser Lys Leu Ser Lys
        275                 280                 285

Val Gln Val Ser Asn Pro Gln Leu Asn Pro Tyr Lys Asp Ile Phe Gln
290                 295                 300

Glu Lys Tyr Gly Leu Asp Lys Asp Ala Ser Gly Ile Tyr Ser Val Asn
305                 310                 315                 320

Ile Asn Lys Phe Asp Asp Ile Leu Lys Lys Leu Tyr Ser Phe Thr Glu
                325                 330                 335

Phe Asp Leu Ala Thr Lys Phe Gln Val Lys Cys Arg Glu Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Lys Pro Ile Thr
385                 390                 395                 400

-continued

Gly Arg Gly Leu Val Lys Lys Ile Ile Arg Phe Cys Lys Asn Ile Val
            405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
            450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
            805                 810                 815

```
Asp Thr Leu Asn Asn Ser Ile Pro Phe Lys Leu Ser Ser Tyr Thr Asp
        820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
        900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
        930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
            965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn  Leu Ile Asp Gln Lys  Ser Ile Leu Asn Leu  Gly Asn Ile
    1010                1015                1020

His Val  Ser Asp Asn Ile Leu  Phe Lys Ile Val Asn  Cys Ser Tyr
    1025                1030                1035

Thr Arg  Tyr Ile Gly Ile Arg  Tyr Phe Asn Ile Phe  Asp Lys Glu
    1040                1045                1050

Leu Asp  Glu Thr Glu Ile Gln  Thr Leu Tyr Ser Asn  Glu Pro Asn
    1055                1060                1065

Thr Asn  Ile Leu Lys Asp Phe  Trp Gly Asn Tyr Leu  Leu Tyr Asp
    1070                1075                1080

Lys Glu  Tyr Tyr Leu Leu Asn  Val Leu Lys Pro Asn  Asn Phe Ile
    1085                1090                1095

Asp Arg  Arg Lys Asp Ser Thr  Leu Ser Ile Asn Asn  Ile Arg Ser
    1100                1105                1110

Thr Ile  Leu Leu Ala Asn Arg  Leu Tyr Ser Gly Ile  Lys Val Lys
    1115                1120                1125

Ile Gln  Arg Val Asn Asn Ser  Ser Thr Asn Asp Asn  Leu Val Arg
    1130                1135                1140

Lys Asn  Asp Gln Val Tyr Ile  Asn Phe Val Ala Ser  Lys Thr His
    1145                1150                1155

Leu Phe  Pro Leu Tyr Ala Asp  Thr Ala Thr Thr Asn  Lys Glu Lys
    1160                1165                1170

Thr Ile  Lys Ile Ser Ser Ser  Gly Asn Arg Phe Asn  Gln Val Val
    1175                1180                1185

Val Met  Asn Ser Val Gly Asn  Asn Cys Thr Met Asn  Phe Lys Asn
    1190                1195                1200

Asn Asn  Gly Asn Asn Ile Gly  Leu Leu Gly Phe Lys  Ala Asp Thr
    1205                1210                1215

Val Val  Ala Ser Thr Trp Tyr  Tyr Thr His Met Arg  Asp His Thr
```

-continued

```
                 1220                1225                1230
Asn Ser Asn Gly Cys Phe Trp Asn Phe Ile Ser Glu Glu His Gly
        1235                1240                1245
Trp Gln Glu Lys
        1250

<210> SEQ ID NO 85
<211> LENGTH: 1252
<212> TYPE: PRT
<213> ORGANISM: Clostridium botulinum

<400> SEQUENCE: 85

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ile Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335
```

-continued

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
        435                 440                 445

Asn Thr Pro Lys Glu Ile Asp Asp Thr Val Thr Ser Asn Asn Asn Tyr
    450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
        515                 520                 525

Pro Glu Gly Glu Asn Asn Val Asn Leu Thr Ser Ser Ile Asp Thr Ala
    530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Pro Tyr Ile Gly Leu
        595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser

-continued

```
            755                 760                 765
Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
                820                 825                 830

Asp Lys Ile Leu Ile Ser Tyr Phe Asn Lys Phe Phe Lys Arg Ile Lys
                835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
                900                 905                 910

Lys Asn Phe Ser Ile Ser Phe Trp Val Arg Ile Pro Asn Tyr Asp Asn
                915                 920                 925

Lys Ile Val Asn Val Asn Asn Glu Tyr Thr Ile Ile Asn Cys Met Arg
                930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
                980                 985                 990

Val Thr Ile Thr Asn Asp Arg Leu  Gly Asp Ser Lys Leu  Tyr Ile Asn
                995                 1000                1005

Gly Asn  Leu Ile Asp Gln Lys  Ser Ile Leu Asn Leu  Gly Asn Ile
    1010                1015                1020

His Val  Ser Asp Asn Ile Leu  Phe Lys Ile Val Asn  Cys Ser Tyr
    1025                1030                1035

Thr Arg  Tyr Ile Gly Ile Arg  Tyr Phe Asn Ile Phe  Asp Lys Glu
    1040                1045                1050

Leu Asp  Glu Thr Glu Ile Gln  Thr Leu Tyr Asn Asn  Glu Pro Asn
    1055                1060                1065

Ala Asn  Ile Leu Lys Asp Phe  Trp Gly Asn Tyr Leu  Leu Tyr Asp
    1070                1075                1080

Lys Glu  Tyr Tyr Leu Leu Asn  Val Leu Lys Pro Asn  Asn Phe Ile
    1085                1090                1095

Asp Arg  Arg Thr Asp Ser Thr  Leu Ser Ile Asn Asn  Ile Arg Ser
    1100                1105                1110

Thr Ile  Leu Leu Ala Asn Arg  Leu Tyr Ser Gly Ile  Lys Val Lys
    1115                1120                1125

Ile Gln  Arg Val Asn Asn Ser  Ser Thr Asn Asp Asn  Leu Val Arg
    1130                1135                1140

Lys Asn  Asp Gln Val Tyr Ile  Asn Phe Val Ala Ser  Lys Thr His
    1145                1150                1155

Leu Phe  Pro Leu Tyr Ala Asp  Thr Asn Thr Thr Asn  Lys Glu Lys
    1160                1165                1170
```

```
Thr Ile Lys Ser Ser Ser Gly Asn Arg Phe Asn Gln Val Val
    1175            1180                1185

Val Met Asn Ser Val Gly Asn Asn Cys Thr Met Asn Phe Lys Asn
    1190            1195                1200

Asn Asn Gly Asn Asn Ile Gly Met Leu Gly Phe Lys Asp Asn Thr
    1205            1210                1215

Leu Val Ala Ser Thr Trp Tyr Tyr Thr His Met Arg Asp Asn Thr
    1220            1225                1230

Asn Ser Asn Gly Cys Phe Trp Asn Phe Ile Ser Glu Glu His Gly
    1235            1240                1245

Trp Gln Glu Lys
    1250

<210> SEQ ID NO 86
<211> LENGTH: 1268
<212> TYPE: PRT
<213> ORGANISM: Clostridium botulinum

<400> SEQUENCE: 86

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270

Ser Thr Asn Gln Lys Ile Tyr Asp Asn Leu Leu Ser Asn Tyr Thr Ala
```

-continued

```
                275                 280                 285
Ile Ala Ser Arg Leu Ser Gln Val Asn Ile Asn Asn Ser Ala Leu Asn
290                 295                 300
Thr Thr Tyr Tyr Lys Asn Phe Phe Gln Trp Lys Tyr Gly Leu Asp Gln
305                 310                 315                 320
Asp Ser Asn Gly Asn Tyr Thr Val Asn Ile Ser Lys Phe Asn Ala Ile
                325                 330                 335
Tyr Lys Lys Leu Phe Ser Phe Thr Glu Cys Asp Leu Ala Gln Lys Phe
            340                 345                 350
Gln Val Lys Asn Arg Ser Asn Tyr Leu Phe His Phe Lys Pro Phe Arg
        355                 360                 365
Leu Leu Asp Leu Leu Asp Asp Asn Ile Tyr Ser Ile Ser Glu Gly Phe
370                 375                 380
Asn Ile Gly Ser Leu Arg Val Asn Asn Asn Gly Gln Asn Ile Asn Leu
385                 390                 395                 400
Asn Ser Arg Ile Val Gly Pro Ile Pro Asp Asn Gly Leu Val Glu Arg
                405                 410                 415
Phe Val Gly Leu Cys Lys Ser Ile Val Ser Lys Lys Gly Thr Lys Asn
            420                 425                 430
Ser Leu Cys Ile Lys Val Asn Asn Arg Asp Leu Phe Phe Val Ala Ser
        435                 440                 445
Glu Ser Ser Tyr Asn Glu Asn Gly Ile Asn Ser Pro Lys Glu Ile Asp
450                 455                 460
Asp Thr Thr Ile Thr Asn Asn Asn Tyr Lys Lys Asn Leu Asp Glu Val
465                 470                 475                 480
Ile Leu Asp Tyr Asn Ser Asp Ala Ile Pro Asn Leu Ser Ser Arg Leu
                485                 490                 495
Leu Asn Thr Thr Ala Gln Asn Asp Ser Tyr Val Pro Lys Tyr Asp Ser
            500                 505                 510
Asn Gly Thr Ser Glu Ile Lys Glu Tyr Thr Val Asp Lys Leu Asn Val
        515                 520                 525
Phe Phe Tyr Leu Tyr Ala Gln Lys Ala Pro Glu Gly Glu Ser Ala Ile
530                 535                 540
Ser Leu Thr Ser Ser Val Asn Thr Ala Leu Leu Asp Ala Ser Lys Val
545                 550                 555                 560
Tyr Thr Phe Phe Ser Ser Asp Phe Ile Asn Thr Val Asn Lys Pro Val
                565                 570                 575
Gln Ala Ala Leu Phe Ile Ser Trp Ile Gln Gln Val Ile Asn Asp Phe
            580                 585                 590
Thr Thr Glu Ala Thr Gln Lys Ser Thr Ile Asp Lys Ile Ala Asp Ile
        595                 600                 605
Ser Leu Val Val Pro Tyr Val Gly Leu Ala Leu Asn Ile Gly Asn Glu
610                 615                 620
Val Gln Lys Gly Asn Phe Lys Glu Ala Ile Glu Leu Leu Gly Ala Gly
625                 630                 635                 640
Ile Leu Leu Glu Phe Val Pro Glu Leu Leu Ile Pro Thr Ile Leu Val
                645                 650                 655
Phe Thr Ile Lys Ser Phe Ile Asn Ser Asp Asp Ser Lys Asn Lys Ile
            660                 665                 670
Ile Lys Ala Ile Asn Asn Ala Leu Arg Glu Arg Glu Leu Lys Trp Lys
        675                 680                 685
Glu Val Tyr Ser Trp Ile Val Ser Asn Trp Leu Thr Arg Ile Asn Thr
690                 695                 700
```

```
Gln Phe Asn Lys Arg Lys Glu Gln Met Tyr Gln Ala Leu Gln Asn Gln
705                 710                 715                 720

Val Asp Gly Ile Lys Lys Ile Ile Glu Tyr Lys Tyr Asn Asn Tyr Thr
                725                 730                 735

Leu Asp Glu Lys Asn Arg Leu Lys Ala Glu Tyr Asn Ile Tyr Ser Ile
            740                 745                 750

Lys Glu Glu Leu Asn Lys Lys Val Ser Leu Ala Met Gln Asn Ile Asp
        755                 760                 765

Arg Phe Leu Thr Glu Ser Ser Ile Ser Tyr Leu Met Lys Leu Ile Asn
    770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Gln Glu Leu Asn Asn Leu Val Ser Asn Thr Leu Asn Asn Ser
            820                 825                 830

Ile Pro Phe Glu Leu Ser Glu Tyr Thr Asn Asp Lys Ile Leu Ile Ser
        835                 840                 845

Tyr Phe Asn Arg Phe Tyr Lys Arg Ile Ile Asp Ser Ser Ile Leu Asn
    850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
            900                 905                 910

Asn Asn Thr Ile Ile Tyr Asn Ser Arg Tyr Gln Asn Phe Ser Val Ser
        915                 920                 925

Phe Trp Val Arg Ile Pro Lys Tyr Asn Asn Leu Lys Asn Leu Asn Asn
    930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr Asn Asn Arg
        995                 1000                1005

Leu Gly His Ser Lys Leu Tyr Ile Asn Gly Asn Leu Thr Asp Gln
    1010                1015                1020

Lys Ser Ile Leu Asn Leu Gly Asn Ile His Val Asp Asp Asn Ile
    1025                1030                1035

Leu Phe Lys Ile Val Gly Cys Asn Asp Thr Arg Tyr Val Gly Ile
    1040                1045                1050

Arg Tyr Phe Lys Ile Phe Asn Met Glu Leu Asp Lys Thr Glu Ile
    1055                1060                1065

Glu Thr Leu Tyr His Ser Glu Pro Asp Ser Thr Ile Leu Lys Asp
    1070                1075                1080

Phe Trp Gly Asn Tyr Leu Leu Tyr Asn Lys Lys Tyr Tyr Leu Leu
    1085                1090                1095

Asn Leu Leu Lys Pro Asn Met Ser Val Thr Lys Asn Ser Asp Ile
    1100                1105                1110
```

```
Leu Asn Ile Asn Arg Gln Arg Gly Ile Tyr Ser Lys Thr Asn Ile
    1115                1120                1125

Phe Ser Asn Ala Arg Leu Tyr Thr Gly Val Glu Val Ile Ile Arg
    1130                1135                1140

Lys Val Gly Ser Thr Asp Thr Ser Asn Thr Asp Asn Phe Val Arg
    1145                1150                1155

Lys Asn Asp Thr Val Tyr Ile Asn Val Val Asp Gly Asn Ser Glu
    1160                1165                1170

Tyr Gln Leu Tyr Ala Asp Val Ser Thr Ser Ala Val Glu Lys Thr
    1175                1180                1185

Ile Lys Leu Arg Arg Ile Ser Asn Ser Asn Tyr Asn Ser Asn Gln
    1190                1195                1200

Met Ile Ile Met Asp Ser Ile Gly Asp Asn Cys Thr Met Asn Phe
    1205                1210                1215

Lys Thr Asn Asn Gly Asn Asp Ile Gly Leu Leu Gly Phe His Leu
    1220                1225                1230

Asn Asn Leu Val Ala Ser Ser Trp Tyr Tyr Lys Asn Ile Arg Asn
    1235                1240                1245

Asn Thr Arg Asn Asn Gly Cys Phe Trp Ser Phe Ile Ser Lys Glu
    1250                1255                1260

His Gly Trp Gln Glu
    1265

<210> SEQ ID NO 87
<211> LENGTH: 1277
<212> TYPE: PRT
<213> ORGANISM: Clostridium botulinum

<400> SEQUENCE: 87

Met Pro Val Glu Ile Asn Ser Phe Asn Tyr Asp Asp Leu Val Asn Asp
1               5                   10                  15

Asn Thr Ile Leu Tyr Ile Arg Pro Pro Tyr Tyr Glu Arg Ser Asn Thr
            20                  25                  30

Tyr Phe Lys Ala Phe Asn Ile Met Glu Asn Val Trp Ile Ile Pro Glu
        35                  40                  45

Arg Tyr Arg Leu Gly Ile Glu Ala Ser Lys Phe Asp Pro Pro Asp Ser
    50                  55                  60

Leu Lys Ala Gly Ser Asp Gly Tyr Phe Asp Pro Asn Tyr Leu Ser Thr
65                  70                  75                  80

Asn Thr Glu Lys Asn Arg Tyr Leu Gln Ile Met Ile Lys Leu Phe Lys
                85                  90                  95

Arg Ile Asn Ser Asn Glu Ala Gly Lys Ile Leu Leu Asn Gln Ile Lys
            100                 105                 110

Asp Ala Ile Pro Tyr Leu Gly Asn Ser Tyr Thr Ala Glu Asp Gln Phe
        115                 120                 125

Thr Thr Asn Asn Arg Thr Ile Ser Phe Asn Val Arg Leu Ala Asn Gly
    130                 135                 140

Thr Ile Glu Gln Glu Met Ala Asn Leu Ile Ile Trp Gly Pro Gly Pro
145                 150                 155                 160

Asp Leu Thr Thr Asn Arg Thr Gly Gly Thr Thr Tyr Pro Ala Gln
                165                 170                 175

Ser Leu Glu Ala Ile Pro Tyr Lys Glu Gly Phe Gly Ser Ile Met Thr
            180                 185                 190

Ile Glu Phe Ser Pro Glu Tyr Ala Thr Ala Phe Asn Asp Ile Ser Leu
        195                 200                 205
```

-continued

```
Thr Ser His Ala Pro Ser Leu Phe Ile Lys Asp Pro Ala Leu Ile Leu
    210                 215                 220

Met His Glu Leu Ile His Val Leu His Gly Leu Tyr Gly Thr Tyr Thr
225                 230                 235                 240

Thr Gly Phe Lys Ile Lys Pro Asn Ile Thr Glu Pro Tyr Met Glu Val
                245                 250                 255

Thr Lys Pro Ile Thr Ser Gly Glu Phe Leu Thr Phe Gly Gly Asn Asp
            260                 265                 270

Val Asn Lys Ile Pro Gln Leu Ile Gln Ser Gln Leu Arg Ser Lys Val
        275                 280                 285

Leu Asp Asp Tyr Glu Lys Ile Ala Ser Arg Leu Asn Lys Val Asn Arg
    290                 295                 300

Ala Thr Ala Glu Ile Asn Ile Asp Lys Phe Lys Tyr Ser Tyr Gln Leu
305                 310                 315                 320

Lys Tyr Gln Phe Val Lys Asp Ser Asn Gly Val Tyr Ser Val Asp Leu
                325                 330                 335

Asp Lys Phe Asn Lys Leu Tyr Asp Lys Ile Tyr Ser Phe Thr Glu Phe
            340                 345                 350

Asn Leu Ala His Glu Phe Lys Ile Lys Thr Arg Asn Ser Tyr Leu Ala
        355                 360                 365

Lys Asn Phe Gly Pro Phe Tyr Leu Pro Asn Leu Leu Asp Asn Ser Ile
    370                 375                 380

Tyr Asn Glu Ala Asp Gly Phe Asn Ile Gly Asp Leu Ser Val Asn Tyr
385                 390                 395                 400

Lys Gly Gln Val Ile Gly Ser Asp Ile Asp Ser Ile Lys Lys Leu Glu
                405                 410                 415

Gly Gln Gly Val Val Ser Arg Val Val Arg Leu Cys Leu Asn Ser Ser
            420                 425                 430

Phe Lys Lys Asn Thr Lys Lys Pro Leu Cys Ile Thr Val Asn Asn Gly
        435                 440                 445

Asp Leu Phe Phe Ile Ala Ser Glu Asp Ser Tyr Gly Glu Asp Thr Ile
    450                 455                 460

Asn Thr Pro Lys Glu Ile Asp Asp Thr Thr Leu Val Pro Ser Phe
465                 470                 475                 480

Lys Asn Ile Leu Asp Lys Val Ile Leu Asp Phe Asn Lys Gln Val Thr
                485                 490                 495

Pro Gln Ile Pro Asn Arg Arg Ile Arg Thr Asp Ile Gln Glu Asp Asn
            500                 505                 510

Tyr Ile Pro Glu Tyr Asp Ser Asn Gly Thr Ser Glu Ile Glu Glu Tyr
        515                 520                 525

Asn Val Val Asp Leu Asn Ala Phe Phe Tyr Leu His Ala Gln Lys Val
    530                 535                 540

Pro Glu Gly Glu Thr Asn Ile Ser Leu Thr Ser Ser Ile Asp Thr Ala
545                 550                 555                 560

Leu Ser Glu Glu Ser Lys Val Tyr Thr Phe Phe Ser Ser Glu Phe Ile
                565                 570                 575

Asp Thr Ile Asn Glu Pro Val Asn Ala Ala Leu Phe Ile Asp Trp Ile
            580                 585                 590

Ser Lys Val Ile Arg Asp Phe Thr Thr Glu Ala Thr Gln Lys Ser Thr
        595                 600                 605

Val Asp Lys Ile Ala Asp Ile Ser Leu Ile Val Pro Tyr Val Gly Leu
    610                 615                 620
```

-continued

```
Ala Leu Asn Ile Val Asn Glu Thr Glu Lys Gly Asn Phe Lys Glu Ala
625                 630                 635                 640

Phe Glu Leu Leu Gly Ala Gly Ile Leu Leu Glu Phe Val Pro Glu Leu
                645                 650                 655

Ala Ile Pro Val Ile Leu Val Phe Thr Ile Lys Ser Tyr Ile Asp Ser
            660                 665                 670

Tyr Glu Asn Lys Asn Lys Ile Ile Lys Ala Ile Asn Asn Ser Leu Ile
        675                 680                 685

Glu Arg Glu Ala Lys Trp Lys Glu Ile Tyr Ser Trp Ile Val Ser Asn
    690                 695                 700

Trp Leu Thr Arg Ile Asn Thr Gln Phe Asn Lys Arg Lys Glu Gln Met
705                 710                 715                 720

Tyr Gln Ala Leu Gln Asn Gln Val Asp Ala Ile Lys Thr Ala Ile Glu
                725                 730                 735

Tyr Lys Tyr Asn Asn Tyr Thr Ser Asp Glu Lys Asn Arg Leu Glu Ser
            740                 745                 750

Glu Tyr Asn Ile Asn Asn Ile Glu Glu Leu Asn Lys Lys Val Ser
        755                 760                 765

Leu Ala Met Lys Asn Ile Glu Arg Phe Ile Thr Glu Ser Ser Ile Ser
770                 775                 780

Tyr Leu Met Lys Leu Ile Asn Glu Ala Glu Val Gly Lys Leu Lys Glu
785                 790                 795                 800

Tyr Asp Lys Arg Val Lys Arg His Leu Leu Glu Tyr Ile Phe Asp Tyr
                805                 810                 815

Arg Leu Ile Leu Gly Glu Gln Gly Gly Glu Leu Ile Asp Leu Val Thr
            820                 825                 830

Ser Thr Leu Asn Thr Ser Ile Pro Phe Glu Leu Ser Ser Tyr Thr Asn
        835                 840                 845

Asp Lys Ile Leu Ile Ile Tyr Phe Asn Arg Leu Tyr Lys Lys Ile Lys
    850                 855                 860

Asp Ser Ser Ile Leu Asp Met Arg Tyr Glu Asn Asn Lys Phe Ile Asp
865                 870                 875                 880

Ile Ser Gly Tyr Gly Ser Asn Ile Ser Ile Asn Gly Asn Val Tyr Ile
                885                 890                 895

Tyr Ser Thr Asn Arg Asn Gln Phe Gly Ile Tyr Asp Asp Arg Leu Ser
            900                 905                 910

Glu Val Asn Ile Ala Gln Asn Asn Asp Ile Ile Tyr Asn Ser Arg Tyr
        915                 920                 925

Gln Asn Phe Ser Ile Ser Phe Trp Val Arg Ile Pro Lys His Tyr Arg
    930                 935                 940

Pro Met Asn His Asn Arg Glu Tyr Thr Ile Ile Asn Cys Met Gly Asn
945                 950                 955                 960

Asn Asn Ser Gly Trp Lys Ile Ser Leu Arg Thr Thr Gly Asp Cys Glu
                965                 970                 975

Ile Ile Trp Thr Leu Gln Asp Ser Gly Asn Lys Lys Leu Ile
            980                 985                 990

Phe Arg Tyr Ser Gln Leu Gly Gly Ile Ser Asp Tyr Ile Asn Lys Trp
        995                 1000                1005

Ile Phe Val Thr Ile Thr Asn Asn Arg Leu Gly Asn Ser Arg Ile
    1010                1015                1020

Tyr Ile Asn Gly Asn Leu Ile Val Glu Lys Ser Ile Ser Asn Leu
    1025                1030                1035

Gly Asp Ile His Val Ser Asp Asn Ile Leu Phe Lys Ile Val Gly
```

```
              1040                1045                1050

Cys Asp Asp Lys Met Tyr Val Gly Ile Arg Tyr Phe Lys Val Phe
        1055                1060                1065

Asn Thr Glu Leu Asp Lys Thr Glu Ile Glu Ile Leu Tyr Ser Asn
        1070                1075                1080

Glu Pro Asp Pro Ser Ile Leu Lys Asp Tyr Trp Gly Asn Tyr Leu
        1085                1090                1095

Leu Tyr Asn Lys Lys Tyr Tyr Leu Leu Asn Leu Leu Arg Asn Asp
        1100                1105                1110

Lys Tyr Ile Thr Arg Asn Ser Asp Ile Leu Asn Ile Ser His Gln
        1115                1120                1125

Arg Gly Val Thr Lys Asp Leu Phe Ile Phe Ser Asn Tyr Lys Leu
        1130                1135                1140

Tyr Glu Gly Val Glu Val Ile Ile Arg Lys Asn Gly Pro Ile Asp
        1145                1150                1155

Ile Ser Asn Thr Asp Asn Phe Val Arg Lys Asn Asp Leu Ala Tyr
        1160                1165                1170

Ile Asn Val Val Asp His Gly Val Glu Tyr Arg Leu Tyr Ala Asp
        1175                1180                1185

Ile Ser Ile Thr Lys Pro Glu Lys Ile Ile Lys Leu Ile Arg Arg
        1190                1195                1200

Ser Asn Pro Asp Asp Ser Leu Gly Gln Ile Ile Val Met Asp Ser
        1205                1210                1215

Ile Gly Asn Asn Cys Thr Met Asn Phe Gln Asn Asn Gly Gly
        1220                1225                1230

Asn Ile Gly Leu Leu Gly Phe His Ser Asp Asn Leu Val Ala Ser
        1235                1240                1245

Ser Trp Tyr Tyr Asn Asn Ile Arg Arg Asn Thr Ser Ser Asn Gly
        1250                1255                1260

Cys Phe Trp Ser Phe Ile Ser Lys Glu His Gly Trp Gln Glu
        1265                1270                1275

<210> SEQ ID NO 88
<211> LENGTH: 1277
<212> TYPE: PRT
<213> ORGANISM: Clostridium botulinum

<400> SEQUENCE: 88

Met Pro Val Val Ile Asn Ser Phe Asn Tyr Asp Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Met Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Asp His Thr Pro Ile Asn Glu Phe
        115                 120                 125
```

His Pro Val Thr Arg Thr Thr Ser Val Asn Ile Lys Ser Ser Thr Asn
130                 135                 140

Val Glu Ser Ser Ile Ile Leu Asn Leu Val Leu Gly Ala Gly Pro
145                 150                 155                 160

Asn Ile Phe Glu Asn Ser Ser Tyr Pro Val Arg Lys Leu Met Asn Ser
                165                 170                 175

Gly Glu Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asp Leu Leu Ala Asn Tyr Glu Lys Ile Ala Thr Arg Leu Ser Glu Val
290                 295                 300

Asn Ser Ala Pro Pro Glu Tyr Asp Ile Asn Glu Tyr Lys Asn Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Val Lys Leu Cys Lys Ser Ile
            420                 425                 430

Ile Pro Arg Lys Gly Thr Lys Ala Pro Pro Arg Leu Cys Ile Arg Val
        435                 440                 445

Asn Asn Arg Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Ser Gln Thr Leu Asn Thr Leu Val Gln
            500                 505                 510

Asp Asp Ser Tyr Val Pro Arg Tyr Asp Ser Asn Gly Thr Ser Glu Ile
        515                 520                 525

Glu Glu His Asn Val Val Asp Leu Asn Ala Phe Phe Tyr Leu His Ala
530                 535                 540

Gln Lys Val Pro Glu Gly Glu Thr Asn Ile Ser Leu Thr Ser Ser Ile

-continued

```
545                 550                 555                 560

Asp Thr Ala Leu Ser Glu Glu Ser Lys Val Tyr Thr Phe Phe Ser Ser
                565                 570                 575

Glu Phe Ile Asn Asn Ile Asn Lys Pro Val His Ala Ala Leu Phe Ile
                580                 585                 590

Gly Trp Ile Ser Gln Val Ile Arg Asp Phe Thr Thr Glu Ser Thr Gln
                595                 600                 605

Lys Ser Thr Val Asp Lys Ile Ala Asp Ile Ser Leu Ile Val Pro Tyr
                610                 615                 620

Val Gly Leu Ala Leu Asn Ile Gly Asn Asp Ala Arg Lys Gly Asn Phe
625                 630                 635                 640

Lys Glu Ala Phe Glu Leu Leu Gly Ala Ala Ile Leu Leu Glu Val Val
                645                 650                 655

Pro Glu Leu Leu Ile Pro Val Ile Leu Val Phe Thr Ile Lys Ser Phe
                660                 665                 670

Ile Asp Ser Ser Lys Asn Glu Asp Lys Ile Ile Lys Ala Ile Asn Asn
                675                 680                 685

Ser Leu Ile Glu Arg Glu Ala Lys Trp Lys Glu Val Tyr Ser Trp Ile
                690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
                725                 730                 735

Val Ile Glu Tyr Lys Tyr Asn Ser Tyr Thr Ser Asp Glu Lys Asn Arg
                740                 745                 750

Leu Glu Ser Glu Tyr Asn Ile Asn Asn Ile Glu Glu Glu Leu Asn Lys
                755                 760                 765

Lys Val Ser Leu Ala Met Lys Asn Ile Glu Arg Phe Ile Ala Glu Ser
                770                 775                 780

Ser Ile Ser Tyr Leu Met Lys Leu Ile Asn Glu Ala Lys Val Ser Glu
785                 790                 795                 800

Leu Arg Glu Tyr Asp Glu Gly Val Lys Glu Tyr Leu Leu Asp Tyr Ile
                805                 810                 815

Leu Lys Asn Gly Ser Ile Leu Gly Asp His Val Gln Glu Leu Asn Asp
                820                 825                 830

Leu Val Thr Ser Thr Leu Asn Ser Ser Ile Pro Phe Glu Leu Ser Ser
                835                 840                 845

Tyr Thr Asn Asp Lys Ile Leu Ile Ile Tyr Phe Asn Lys Leu Tyr Lys
                850                 855                 860

Lys Ile Lys Asp Asn Cys Ile Leu Asp Met Arg Tyr Glu Asn Asn Lys
865                 870                 875                 880

Phe Ile Asp Ile Ser Gly Tyr Gly Ser Asn Ile Ser Ile Asn Gly Glu
                885                 890                 895

Leu Tyr Ile Tyr Thr Thr Asn Arg Asn Gln Phe Thr Ile Tyr Ser Gly
                900                 905                 910

Lys Leu Ser Glu Val Asn Ile Ala Gln Asn Asn Asp Ile Ile Tyr Asn
                915                 920                 925

Ser Arg Tyr Gln Asn Phe Ser Ile Ser Phe Trp Val Arg Ile Pro Arg
                930                 935                 940

Tyr Ser Asn Ile Val Asn Leu Asn Asn Glu Tyr Thr Ile Ile Asn Cys
945                 950                 955                 960

Met Gly Asn Asn Asn Ser Gly Trp Lys Ile Ser Leu Asn Tyr Asn Lys
                965                 970                 975
```

Ile Ile Trp Thr Leu Gln Asp Thr Ala Gly Asn Asn Glu Lys Leu Val
            980                 985                 990

Phe Asn Tyr Thr Gln Met Ile Ser Ile Ser Asp Tyr Ile Asn Lys Trp
        995                 1000                1005

Ile Phe Val Thr Ile Thr Asn Asn Arg Leu Gly Asn Ser Arg Ile
    1010                1015                1020

Tyr Ile Asn Gly Asn Leu Ile Asp Gln Lys Ser Ile Ser Asn Leu
    1025                1030                1035

Gly Asp Ile His Val Ser Asp Asn Ile Leu Phe Lys Ile Val Gly
    1040                1045                1050

Cys Asn Asp Thr Arg Tyr Val Gly Ile Arg Tyr Phe Lys Val Phe
    1055                1060                1065

Asp Thr Glu Leu Asp Lys Thr Glu Ile Glu Thr Leu Tyr Ser Asp
    1070                1075                1080

Glu Pro Asp Pro Ser Ile Leu Lys Asp Phe Trp Gly Asn Tyr Leu
    1085                1090                1095

Leu Tyr Asn Lys Arg Tyr Tyr Leu Leu Asn Leu Leu Arg Lys Asp
    1100                1105                1110

Asn Ala Ile Thr Gln Ser Ser Thr Phe Leu Ser Ile Ser Arg Ala
    1115                1120                1125

Arg Gly Val Asp Arg Lys Ala Asn Ile Phe Ser Asn Lys Arg Leu
    1130                1135                1140

Tyr Lys Gly Val Glu Val Ile Ile Arg Lys Asn Glu Pro Ile Asp
    1145                1150                1155

Ile Ser Asn Thr Asp Asn Phe Val Arg Lys Gly Asp Leu Ala Tyr
    1160                1165                1170

Ile Asn Val Val Asp Arg Asp Val Glu Tyr Arg Leu Tyr Ala Asn
    1175                1180                1185

Thr Ser Asn Ala Gln Pro Glu Lys Thr Ile Lys Leu Ile Arg Thr
    1190                1195                1200

Ser Asn Ser Asn Asp Ser Leu Asp Gln Ile Ile Val Met Asp Ser
    1205                1210                1215

Ile Gly Asn Asn Cys Thr Met Asn Phe Gln Asn Asn Asn Gly Gly
    1220                1225                1230

Asn Ile Gly Leu Leu Gly Phe His Ser Asn Thr Leu Val Ala Ser
    1235                1240                1245

Ser Trp Tyr Tyr Asn Asn Ile Arg Arg Asn Thr Ser Ser Asn Gly
    1250                1255                1260

Cys Phe Trp Ser Phe Ile Ser Lys Glu His Gly Trp Gln Glu
    1265                1270                1275

<210> SEQ ID NO 89
<211> LENGTH: 1280
<212> TYPE: PRT
<213> ORGANISM: Clostridium botulinum

<400> SEQUENCE: 89

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser

```
            50                  55                  60
Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Met Ile Lys Leu Phe Asn
                 85                  90                  95

Arg Ile Asn Ser Asn Pro Thr Gly Lys Val Leu Leu Glu Glu Val Ser
                100                 105                 110

Asn Ala Arg Pro Tyr Leu Gly Asp Asp Thr Leu Ile Asn Glu Phe
            115                 120                 125

Phe Pro Val Asn Val Thr Thr Ser Val Asn Ile Lys Phe Ser Thr Asp
        130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asp Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
        435                 440                 445

Asn Asn Arg Glu Leu Phe Phe Val Ala Ser Glu Ser Ser Tyr Asn Glu
    450                 455                 460

Ser Asp Ile Asn Thr Pro Lys Glu Ile Asp Asp Thr Thr Asn Leu Asn
465                 470                 475                 480
```

```
Asn Asn Tyr Arg Asn Asn Leu Asp Glu Val Ile Leu Asp Tyr Asn Ser
            485                 490                 495
Glu Thr Ile Pro Gln Ile Ser Asn Arg Thr Leu Asn Thr Leu Val Gln
        500                 505                 510
Asp Asn Ser Tyr Val Pro Arg Tyr Asp Ser Asn Gly Thr Ser Glu Ile
        515                 520                 525
Glu Glu Tyr Asp Val Val Asp Phe Asn Val Phe Phe Tyr Leu His Ala
    530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Val Tyr Thr Phe Phe Ser Ser
            565                 570                 575
Glu Phe Ile Asp Thr Ile Asn Lys Pro Val Asn Ala Ala Leu Phe Ile
        580                 585                 590
Asp Trp Ile Ser Lys Val Ile Arg Asp Phe Thr Thr Glu Ala Thr Gln
    595                 600                 605
Lys Ser Thr Val Asp Lys Ile Ala Asp Ile Ser Leu Ile Val Pro Tyr
610                 615                 620
Val Gly Leu Ala Leu Asn Ile Val Ile Glu Ala Glu Lys Gly Asn Phe
625                 630                 635                 640
Glu Glu Ala Phe Glu Leu Leu Gly Ala Gly Ile Leu Leu Glu Phe Val
            645                 650                 655
Pro Glu Leu Thr Ile Pro Val Ile Leu Val Phe Thr Ile Lys Ser Tyr
        660                 665                 670
Ile Asp Ser Tyr Glu Asn Lys Asn Lys Ala Ile Lys Ala Ile Asn Asn
        675                 680                 685
Ser Leu Ile Glu Arg Glu Ala Lys Trp Lys Glu Ile Tyr Ser Trp Ile
    690                 695                 700
Val Ser Asn Trp Leu Thr Arg Ile Asn Thr Gln Phe Asn Lys Arg Lys
705                 710                 715                 720
Glu Gln Met Tyr Gln Ala Leu Gln Asn Gln Val Asp Ala Ile Lys Thr
            725                 730                 735
Ala Ile Glu Tyr Lys Tyr Asn Asn Tyr Thr Ser Asp Glu Lys Asn Arg
        740                 745                 750
Leu Glu Ser Lys Tyr Asn Ile Asn Asn Ile Glu Glu Glu Leu Asn Lys
    755                 760                 765
Lys Val Ser Leu Ala Met Lys Asn Ile Glu Arg Phe Met Thr Glu Ser
770                 775                 780
Ser Ile Ser Tyr Leu Met Lys Leu Ile Asn Glu Ala Glu Val Gly Lys
785                 790                 795                 800
Leu Lys Glu Tyr Asp Lys His Val Lys Ser Asp Leu Leu Asp Tyr Ile
            805                 810                 815
Leu Tyr His Lys Leu Ile Leu Gly Glu Gln Thr Lys Glu Leu Ile Asp
        820                 825                 830
Leu Val Thr Ser Thr Leu Asn Ser Ser Ile Pro Phe Glu Leu Ser Ser
    835                 840                 845
Tyr Thr Asn Asp Lys Ile Leu Ile Ile Tyr Phe Asn Arg Leu Tyr Lys
850                 855                 860
Lys Ile Lys Asp Ser Ser Ile Leu Asp Met Arg Tyr Glu Asn Asn Lys
865                 870                 875                 880
Phe Ile Asp Ile Ser Gly Tyr Gly Ser Asn Ile Ser Ile Asn Gly Asn
            885                 890                 895
```

```
Val Tyr Ile Tyr Ser Thr Asn Arg Asn Gln Phe Gly Ile Tyr Ser Gly
            900                 905                 910

Arg Leu Ser Glu Val Asn Ile Ala Gln Asn Asn Asp Ile Ile Tyr Asn
        915                 920                 925

Ser Arg Tyr Gln Asn Phe Ser Ile Ser Phe Trp Val Arg Ile Pro Lys
    930                 935                 940

His Tyr Arg Pro Met Asn Arg Asn Arg Glu Tyr Thr Ile Ile Asn Cys
945                 950                 955                 960

Met Gly Asn Asn Ser Gly Trp Lys Ile Ser Leu Arg Thr Ile Arg
                965                 970                 975

Asp Cys Glu Ile Ile Trp Thr Leu Gln Asp Thr Ser Gly Asn Lys Glu
        980                 985                 990

Lys Leu Ile Phe Arg Tyr Glu Glu Leu Ala Ser Ile Ser Asp Tyr Ile
    995                 1000                1005

Asn Lys Trp Ile Phe Val Thr Ile Thr Asn Asn Arg Leu Gly Asn
    1010            1015                1020

Ser Arg Ile Tyr Ile Asn Gly Asn Leu Ile Val Glu Lys Ser Ile
    1025            1030                1035

Ser Asn Leu Gly Asp Ile His Val Ser Asp Asn Ile Leu Phe Lys
    1040            1045                1050

Ile Val Gly Cys Asp Asp Glu Thr Tyr Val Gly Ile Arg Tyr Phe
    1055            1060                1065

Lys Val Phe Asn Thr Glu Leu Asp Lys Thr Glu Ile Glu Thr Leu
    1070            1075                1080

Tyr Ser Asn Glu Pro Asp Pro Ser Ile Leu Lys Asp Tyr Trp Gly
    1085            1090                1095

Asn Tyr Leu Leu Tyr Asn Lys Lys Tyr Tyr Leu Phe Asn Leu Leu
    1100            1105                1110

Arg Lys Asp Lys Tyr Ile Thr Arg Asn Ser Gly Ile Leu Asn Ile
    1115            1120                1125

Asn Gln Gln Arg Gly Val Thr Gly Gly Ile Ser Val Phe Leu Asn
    1130            1135                1140

Tyr Lys Leu Tyr Glu Gly Val Glu Val Ile Ile Arg Lys Asn Ala
    1145            1150                1155

Pro Ile Asp Ile Ser Asn Thr Asp Asn Phe Val Arg Lys Asn Asp
    1160            1165                1170

Leu Ala Tyr Ile Asn Val Val Asp His Gly Val Glu Tyr Arg Leu
    1175            1180                1185

Tyr Ala Asp Ile Ser Ile Thr Lys Ser Glu Lys Ile Ile Lys Leu
    1190            1195                1200

Ile Arg Thr Ser Asn Pro Asn Asp Ser Leu Gly Gln Ile Ile Val
    1205            1210                1215

Met Asp Ser Ile Gly Asn Asn Cys Thr Met Asn Phe Gln Asn Asn
    1220            1225                1230

Asp Gly Ser Asn Ile Gly Leu Leu Gly Phe His Ser Asp Asp Leu
    1235            1240                1245

Val Ala Ser Ser Trp Tyr Tyr Asn His Ile Arg Arg Asn Thr Ser
    1250            1255                1260

Ser Asn Gly Cys Phe Trp Ser Phe Ile Ser Lys Glu His Gly Trp
    1265            1270                1275

Lys Glu
    1280
```

-continued

```
<210> SEQ ID NO 90
<211> LENGTH: 1279
<212> TYPE: PRT
<213> ORGANISM: Clostridium botulinum

<400> SEQUENCE: 90
```

Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Asp Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Thr Leu Ile Asn Glu Phe
        115                 120                 125

Phe Pro Val Asn Val Thr Thr Ser Val Asn Ile Lys Phe Ser Thr Asp
    130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asp His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Thr Ile Glu Val Lys Arg Gly Pro Leu Met
                245                 250                 255

Ile Ala Glu Lys Pro Ile Arg Leu Glu Glu Phe Leu Thr Phe Gly Gly
            260                 265                 270

Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Glu Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Gly Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asp Leu Leu Asp Asp Asp
    370                 375                 380

```
Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
            405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
            435                 440                 445

Asn Asn Arg Glu Leu Phe Phe Val Ala Ser Glu Ser Ser Tyr Asn Glu
        450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
        530                 535                 540

Gln Lys Val Pro Glu Gly Glu Thr Asn Ile Ser Leu Thr Ser Ser Ile
545                 550                 555                 560

Asp Thr Ala Leu Leu Glu Lys Ser Lys Val Tyr Thr Phe Phe Ser Ser
            565                 570                 575

Glu Phe Ile Asp Thr Ile Asn Glu Ser Val Asn Ala Ala Leu Phe Ile
            580                 585                 590

Asp Trp Ile Asn Lys Val Ile Arg Asp Phe Thr Thr Glu Ala Thr Gln
            595                 600                 605

Lys Ser Thr Val Asp Lys Ile Ala Asp Ile Ser Leu Ile Val Pro Tyr
610                 615                 620

Val Gly Leu Ala Leu Asn Ile Val Ile Asp Ala Glu Lys Gly Asn Phe
625                 630                 635                 640

Gln Glu Ala Phe Glu Leu Leu Gly Ala Gly Ile Leu Leu Glu Phe Val
            645                 650                 655

Pro Glu Leu Thr Ile Pro Val Ile Leu Val Phe Thr Ile Lys Ser Tyr
            660                 665                 670

Ile Asp Ser Tyr Glu Asn Lys Asn Lys Ala Ile Lys Ala Ile Asn Asn
            675                 680                 685

Ala Leu Ile Glu Arg Glu Ala Lys Trp Lys Glu Ile Tyr Ser Trp Ile
            690                 695                 700

Val Ser Asn Trp Leu Thr Lys Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735

Ala Ile Glu Tyr Lys Tyr Asn Asn Tyr Thr Ser Asp Glu Lys Asn Arg
            740                 745                 750

Leu Glu Ser Glu Tyr Asn Ile Asn Asn Ile Glu Glu Glu Leu Asn Lys
            755                 760                 765

Lys Val Ser Leu Ala Met Lys Asn Ile Glu Arg Phe Met Thr Glu Ser
            770                 775                 780

Ser Ile Ser Tyr Leu Met Lys Leu Ile Asn Glu Ala Glu Val Gly Lys
785                 790                 795                 800

Leu Lys Lys Tyr Asp Arg His Val Lys Ser Asp Leu Leu Asp Tyr Ile
```

-continued

```
                805                 810                 815
Leu Tyr His Lys Leu Ile Leu Gly Asp Gln Thr Lys Glu Leu Ile Asp
                820                 825                 830

Leu Val Thr Ser Thr Leu Asn Ser Ser Ile Pro Phe Glu Leu Ser Ser
                835                 840                 845

Tyr Thr Asn Asp Lys Ile Leu Ile Ile Tyr Phe Asn Arg Leu Tyr Lys
        850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
                885                 890                 895

Val Tyr Ile Tyr Ser Thr Asn Arg Asn Gln Phe Gly Ile Tyr Ser Asp
                900                 905                 910

Arg Leu Ser Glu Val Asn Ile Ala Gln Asn Asn Asp Ile Ile Tyr Asn
                915                 920                 925

Ser Arg Tyr Gln Asn Phe Ser Ile Ser Phe Trp Val Arg Ile Pro Lys
        930                 935                 940

His Tyr Gly Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Asn Ile Arg
                965                 970                 975

Asp Cys Glu Ile Ile Trp Thr Leu Gln Asp Thr Ser Gly Asn Lys Glu
                980                 985                 990

Lys Leu Ile Phe Arg Tyr Glu Glu Leu Ala Asn Ile Ser Asp Tyr Ile
                995                 1000                1005

Asn Lys Trp Ile Phe Val Thr Ile Thr Asn Asn Arg Leu Gly Asn
        1010                1015                1020

Ser Arg Ile Tyr Ile Asn Gly Asn Leu Ile Val Glu Lys Ser Ile
        1025                1030                1035

Ser Asn Leu Gly Asp Ile His Val Ser Asp Asn Ile Leu Phe Lys
        1040                1045                1050

Ile Val Gly Cys Asp Asp Lys Thr Tyr Val Gly Ile Arg Tyr Phe
        1055                1060                1065

Lys Val Phe Asn Thr Glu Leu Asp Lys Thr Glu Ile Glu Thr Leu
        1070                1075                1080

Tyr Ser Asn Glu Pro Asp Pro Ser Ile Leu Lys Asp Tyr Trp Gly
        1085                1090                1095

Asn Tyr Leu Leu Tyr Asn Lys Lys Tyr Tyr Leu Phe Asn Leu Leu
        1100                1105                1110

Arg Lys Asp Lys Tyr Ile Thr Arg Asn Ser Gly Ile Leu Asn Ile
        1115                1120                1125

Asn Gln Gln Arg Gly Val Thr Glu Gly Ser Val Phe Leu Asn Tyr
        1130                1135                1140

Lys Leu Tyr Glu Gly Val Glu Val Ile Ile Arg Lys Asn Gly Pro
        1145                1150                1155

Ile Asp Ile Ser Asn Thr Asp Asn Phe Val Arg Lys Asn Asp Leu
        1160                1165                1170

Ala Tyr Ile Asn Val Val Tyr His Asp Val Glu Tyr Arg Leu Tyr
        1175                1180                1185

Ala Asp Ile Ser Ile Thr Lys Pro Glu Lys Ile Ile Lys Leu Ile
        1190                1195                1200

Arg Thr Ser Asn Pro Asn Asp Ser Leu Gly Gln Ile Ile Val Met
        1205                1210                1215
```

-continued

```
Asp Ser Ile Gly Asn Asn Cys Thr Met Asn Phe Gln Asn Asn Asn
    1220                1225                1230

Gly Gly Asn Ile Gly Leu Leu Gly Phe His Ser Asp Asn Leu Val
    1235                1240                1245

Ala Ser Ser Trp Tyr Tyr Asn Asn Ile Arg Arg Asn Thr Ser Ser
    1250                1255                1260

Asn Gly Cys Phe Trp Ser Phe Ile Ser Lys Glu His Gly Trp Gln
    1265                1270                1275

Glu
```

<210> SEQ ID NO 91
<211> LENGTH: 1274
<212> TYPE: PRT
<213> ORGANISM: Clostridium botulinum

<400> SEQUENCE: 91

```
Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300
```

```
Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
                355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
                420                 425                 430

Ile Pro Arg Lys Gly Thr Lys Ala Pro Pro Arg Leu Cys Ile Arg Val
            435                 440                 445

Asn Asn Ser Glu Leu Phe Phe Val Ala Ser Glu Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Gln Thr Ile Pro Gln Ile Ser Asn Arg Thr Leu Asn Thr Leu Val Gln
                500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
            595                 600                 605

Ser Thr Val Asp Lys Ile Ala Asp Ile Ser Leu Ile Val Pro Tyr Val
            610                 615                 620

Gly Leu Ala Leu Asn Ile Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
                660                 665                 670

Asp Ser Tyr Glu Asn Lys Asn Lys Ala Ile Lys Ala Ile Asn Asn Ser
            675                 680                 685

Leu Ile Glu Arg Glu Ala Lys Trp Lys Glu Ile Tyr Ser Trp Ile Val
            690                 695                 700

Ser Asn Trp Leu Thr Arg Ile Asn Thr Gln Phe Asn Lys Arg Lys Glu
705                 710                 715                 720
```

```
Gln Met Tyr Gln Ala Leu Gln Asn Gln Val Asp Ala Ile Lys Thr Ala
            725                 730                 735
Ile Glu Tyr Lys Tyr Asn Asn Tyr Thr Ser Asp Glu Lys Asn Arg Leu
            740                 745                 750
Glu Ser Glu Tyr Asn Ile Asn Ile Glu Glu Leu Asn Lys Lys
            755                 760             765
Val Ser Leu Ala Met Lys Asn Ile Glu Arg Phe Met Thr Glu Ser Ser
            770                 775             780
Ile Ser Tyr Leu Met Lys Leu Ile Asn Glu Ala Lys Val Gly Lys Leu
785                 790                 795                 800
Lys Lys Tyr Asp Asn His Val Lys Ser Asp Leu Leu Asn Tyr Ile Leu
                805                 810                 815
Asp His Arg Ser Ile Leu Gly Glu Gln Thr Asn Glu Leu Ser Asp Leu
            820                 825                 830
Val Thr Ser Thr Leu Asn Ser Ser Ile Pro Phe Glu Leu Ser Ser Tyr
            835                 840                 845
Thr Asn Asp Lys Ile Leu Ile Ile Tyr Phe Asn Arg Leu Tyr Lys Lys
            850                 855                 860
Ile Lys Asp Ser Ser Ile Leu Asp Met Arg Tyr Glu Asn Asn Lys Phe
865                 870                 875                 880
Ile Asp Ile Ser Gly Tyr Gly Ser Asn Ile Ser Ile Asn Gly Asn Val
                885                 890                 895
Tyr Ile Tyr Ser Thr Asn Arg Asn Gln Phe Gly Ile Tyr Asn Ser Arg
            900                 905                 910
Leu Ser Glu Val Asn Ile Ala Gln Asn Asn Asp Ile Ile Tyr Asn Ser
            915                 920                 925
Arg Tyr Gln Asn Phe Ser Ile Ser Phe Trp Val Arg Ile Pro Lys His
            930                 935                 940
Tyr Lys Pro Met Asn His Asn Arg Glu Tyr Thr Ile Ile Asn Cys Met
945                 950                 955                 960
Gly Asn Asn Asn Ser Gly Trp Lys Ile Ser Leu Arg Thr Val Arg Asp
                965                 970                 975
Cys Glu Ile Ile Trp Thr Leu Gln Asp Thr Ser Gly Asn Lys Glu Asn
            980                 985                 990
Leu Ile Phe Arg Tyr Glu Glu Leu Asn Arg Ile Ser Asn Tyr Ile Asn
            995                1000                1005
Lys Trp Ile Phe Val Thr Ile Thr Asn Asn Arg Leu Gly Asn Ser
            1010                1015                1020
Arg Ile Tyr Ile Asn Gly Asn Leu Ile Val Glu Lys Ser Ile Ser
            1025                1030                1035
Asn Leu Gly Asp Ile His Val Ser Asp Asn Ile Leu Phe Lys Ile
            1040                1045                1050
Val Gly Cys Asp Asp Glu Thr Tyr Val Gly Ile Arg Tyr Phe Lys
            1055                1060                1065
Val Phe Asn Thr Glu Leu Asp Lys Thr Glu Ile Glu Thr Leu Tyr
            1070                1075                1080
Ser Asn Glu Pro Asp Pro Ser Ile Leu Lys Asn Tyr Trp Gly Asn
            1085                1090                1095
Tyr Leu Leu Tyr Asn Lys Lys Tyr Tyr Leu Phe Asn Leu Leu Arg
            1100                1105                1110
Lys Asp Lys Tyr Ile Thr Leu Asn Ser Gly Ile Leu Asn Ile Asn
            1115                1120                1125
Gln Gln Arg Gly Val Thr Glu Gly Ser Val Phe Leu Asn Tyr Lys
```

-continued

```
               1130                    1135                    1140
Leu Tyr Glu Gly Val Glu Val Ile Ile Arg Lys Asn Gly Pro Ile
        1145                    1150                    1155

Asp Ile Ser Asn Thr Asp Asn Phe Val Arg Lys Asn Asp Leu Ala
        1160                    1165                    1170

Tyr Ile Asn Val Val Asp Arg Gly Val Glu Tyr Arg Leu Tyr Ala
        1175                    1180                    1185

Asp Thr Lys Ser Glu Lys Glu Lys Ile Ile Arg Thr Ser Asn Leu
        1190                    1195                    1200

Asn Asp Ser Leu Gly Gln Ile Ile Val Met Asp Ser Ile Gly Asn
        1205                    1210                    1215

Asn Cys Thr Met Asn Phe Gln Asn Asn Asn Gly Ser Asn Ile Gly
        1220                    1225                    1230

Leu Leu Gly Phe His Ser Asn Asn Leu Val Ala Ser Ser Trp Tyr
        1235                    1240                    1245

Tyr Asn Asn Ile Arg Arg Asn Thr Ser Ser Asn Gly Cys Phe Trp
        1250                    1255                    1260

Ser Ser Ile Ser Lys Glu Asn Gly Trp Lys Glu
        1265                    1270
```

CHIMERIC NEUROTOXINS

CROSS REFERENCE TO RELATED APPLICATIONS

This application is a U.S. national stage filing of International Patent Application No. PCT/EP 2017/060821, filed May 5, 2017, which claims the priority of United Kingdom Application No. 1607901.4, filed May 5, 2016.

REFERENCE TO SEQUENCE LISTING

The instant application contains a Sequence Listing that has been submitted electronically in ASCII format and is hereby incorporated by reference in its entirety. Said ASCII copy, created on Dec. 4, 2018, is named SequenceListing16094254.txt and is 550,284 bytes in size.

FIELD OF THE INVENTION

The present invention relates to chimeric neurotoxins with enhanced properties and their use in therapy.

BACKGROUND

Bacteria in the genus Clostridia produce highly potent and specific protein toxins, which can poison neurons and other cells to which they are delivered. Examples of such clostridial toxins include the neurotoxins produced by *C. tetani* (TeNT) and by *C. botulinum* (BoNT) serotypes A-G, as well as those produced by *C. baratii* and *C. butyricum*.

Among the clostridial neurotoxins are some of the most potent toxins known. By way of example, botulinum neurotoxins have median lethal dose (LD50) values for mice ranging from 0.5 to 5 ng/kg, depending on the serotype. Both tetanus and botulinum toxins act by inhibiting the function of affected neurons, specifically the release of neurotransmitters. While botulinum toxin acts at the neuromuscular junction and inhibits cholinergic transmission in the peripheral nervous system, tetanus toxin acts in the central nervous system.

In nature, clostridial neurotoxins are synthesised as a single-chain polypeptide that is modified post-translationally by a proteolytic cleavage event to form two polypeptide chains joined together by a disulphide bond. Cleavage occurs at a specific cleavage site, often referred to as the activation site, that is located between the cysteine residues that provide the inter-chain disulphide bond. It is this di-chain form that is the active form of the toxin. The two chains are termed the heavy chain (H-chain), which has a molecular mass of approximately 100 kDa, and the light chain (L-chain), which has a molecular mass of approximately 50 kDa. The H-chain comprises an N-terminal translocation component ($H_N$ domain) and a C-terminal targeting component ($H_C$ domain). The cleavage site is located between the L-chain and the translocation domain components. Following binding of the HC domain to its target neuron and internalisation of the bound toxin into the cell via an endosome, the $H_N$ domain translocates the L-chain across the endosomal membrane and into the cytosol, and the L-chain provides a protease function (also known as a non-cytotoxic protease).

Non-cytotoxic proteases act by proteolytically cleaving intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are integral to intracellular vesicle fusion, and thus to secretion of molecules via vesicle transport from a cell. The protease function is a zinc-dependent endopeptidase activity and exhibits a high substrate specificity for SNARE proteins. Accordingly, once delivered to a desired target cell, the non-cytotoxic protease is capable of inhibiting cellular secretion from the target cell. The L-chain proteases of clostridial neurotoxins are non-cytotoxic proteases that cleave SNARE proteins.

In view of the ubiquitous nature of SNARE proteins, clostridial neurotoxins such as botulinum toxin have been successfully employed in a wide range of therapies.

By way of example, we refer to William J. Lipham, Cosmetic and Clinical Applications of Botulinum Toxin (Slack, Inc., 2004), which describes the use of clostridial neurotoxins, such as botulinum neurotoxins (BoNTs), BoNT/A, BoNT/B, BoNT/C1, BoNT/D, BoNT/E, BoNT/F and BoNT/G, and tetanus neurotoxin (TeNT), to inhibit neuronal transmission in a number of therapeutic and cosmetic or aesthetic applications—for example, marketed botulinum toxin products are currently approved as therapeutics for indications including focal spasticity, upper limb spasticity, lower limb spasticity, cervical dystonia, blepharospasm, hemifacial spasm, hyperhidrosis of the axillae, chronic migraine, neurogenic detrusor overactivity, glabellar lines, and severe lateral canthal lines. In addition, clostridial neurotoxin therapies are described for treating neuromuscular disorders (see U.S. Pat. No. 6,872,397); for treating uterine disorders (see US 2004/0175399); for treating ulcers and gastroesophageal reflux disease (see US 2004/0086531); for treating dystonia (see U.S. Pat. No. 6,319,505); for treating eye disorders (see US 2004/0234532); for treating blepharospasm (see US 2004/0151740); for treating strabismus (see US 2004/0126396); for treating pain (see U.S. Pat. Nos. 6,869,610, 6,641,820, 6,464,986, and U.S. Pat. No. 6,113,915); for treating fibromyalgia (see U.S. Pat. No. 6,623,742, US 2004/0062776); for treating lower back pain (see US 2004/0037852); for treating muscle injuries (see U.S. Pat. No. 6,423,319); for treating sinus headache (see U.S. Pat. No. 6,838,434); for treating tension headache (see U.S. Pat. No. 6,776,992); for treating headache (see U.S. Pat. No. 6,458,365); for reduction of migraine headache pain (see U.S. Pat. No. 5,714,469); for treating cardiovascular diseases (see U.S. Pat. No. 6,767,544); for treating neurological disorders such as Parkinson's disease (see U.S. Pat. Nos. 6,620,415, 6,306,403); for treating neuropsychiatric disorders (see US 2004/0180061, US 2003/0211121); for treating endocrine disorders (see U.S. Pat. No. 6,827,931); for treating thyroid disorders (see U.S. Pat. No. 6,740,321); for treating cholinergic influenced sweat gland disorders (see U.S. Pat. No. 6,683,049); for treating diabetes (see U.S. Pat. Nos. 6,337,075, 6,416,765); for treating a pancreatic disorder (see U.S. Pat. Nos. 6,261,572, 6,143,306); for treating cancers such as bone tumors (see U.S. Pat. Nos. 6,565,870, 6,368,605, 6,139,845, US 2005/0031648); for treating otic disorders (see U.S. Pat. Nos. 6,358,926, 6,265,379); for treating autonomic disorders such as gastrointestinal muscle disorders and other smooth muscle dysfunction (see U.S. Pat. No. 5,437,291); for treatment of skin lesions associated with cutaneous cell-proliferative disorders (see U.S. Pat. No. 5,670,484); for management of neurogenic inflammatory disorders (see U.S. Pat. No. 6,063,768); for reducing hair loss and stimulating hair growth (see U.S. Pat. No. 6,299,893); for treating downturned mouth (see U.S. Pat. No. 6,358,917); for reducing appetite (see US 2004/40253274); for dental therapies and procedures (see US 2004/0115139); for treating neuromuscular disorders and conditions (see US 2002/0010138); for treating various disorders and conditions and associated pain (see US 2004/0013692); for treating conditions resulting from mucus hypersecretion such as asthma and COPD (see WO 00/10598); and for treating non-neuronal conditions such as inflammation, endocrine conditions, exocrine conditions, immunological conditions, cardiovascular conditions, bone conditions (see WO 01/21213). All of the above publications are hereby incorporated by reference in their entirety.

The use of non-cytotoxic proteases such as clostridial neurotoxins (e.g. BoNTs and TeNT) in therapeutic and cosmetic treatments of humans and other mammals is anticipated to expand to an ever-widening range of diseases and ailments that can benefit from the properties of these toxins.

Currently all approved drugs/cosmetic preparations comprising BoNTs contain naturally occurring neurotoxins purified from clostridial strains (BoNT/A in the case of DYSPORT®, BOTOX® or XEOMIN®, and BoNT/B in the case of MYOBLOC®).

Recombinant technology offers the possibility of changing or optimizing the properties of neurotoxins through the introduction of modifications to its sequence and/or structure. In particular, chimeric neurotoxins in which the $H_C$ domain or the $H_{CC}$ subdomain is replaced by a $H_C$ domain or $H_{CC}$ subdomain from a different neurotoxin have been produced.

Rummel et al, 2011 (Exchange of the $H_{CC}$ domain mediating double receptor recognition improves the pharmacodynamic properties of botulinum neurotoxin. FEBS Journal, 278(23), 4506-4515) generated various active full-length hybrid neurotoxins, including AABB, AACC and BBAA chimera (letters represent the serotype origin of each of the four domains: L, $H_N$, $H_{CN}$, $H_{CC}$). The AABB chimera was found to be more potent than BoNT/A in a mouse phrenic nerve hemidiaphragm assay, while the AACC only retained 10% of the potency of BoNT/A. The BBAA chimera retained 85% of the potency of BoNT/A and was equipotent to BoNT/B.

Wang et al, 2008 (Novel chimeras of botulinum neurotoxins A and E unveil contributions from the binding, translocation, and protease domains to their functional characteristics. Journal of Biological Chemistry, 283(25), 16993-17002) generated AE ($LH_N$ from BoNT/A and $H_C$ from BoNT/E) and EA ($LH_N$ from BoNT/E and $H_C$ from BoNT/A) chimeric neurotoxins, adding a linker in the case of the AE chimera between the $LH_N$ and $H_C$ domains to increase flexibility. Both were able to cause a paralysis in a mouse phrenic nerve hemidiaphragm assay as well as in vivo.

Wang et al., 2012a (Longer-acting and highly potent chimaeric inhibitors of excessive exocytosis created with domains from botulinum neurotoxin A and B. Biochemical Journal, 444(1), 59-67) generated AB ($LH_N$ from BoNT/A and $H_C$ from BoNT/B, with a linker to improve folding) and BA ($LH_N$ from BoNT/B and $H_C$ from BoNT/A) chimeric neurotoxins. The AB chimera induced a more prolonged neuromuscular paralysis than BoNT/A in mice. The BA chimera was able to reduce exocytosis from non-neuronal cells.

Wang et al, 2012b (Novel chimeras of botulinum and tetanus neurotoxins yield insights into their distinct sites of neuroparalysis. The FASEB Journal, 26(12), 5035-5048) generated ATx ($LH_N$ from BoNT/A and $H_C$ from TeNT), TxA ($LH_N$ from TeNT and $H_C$ from BoNT/A), ETx ($LH_N$ from BoNT/E and $H_C$ from TeNT) and TxE ($LH_N$ from TeNT and $H_C$ from BoNT/E) chimera. The information provided with respect to the protein sequence of these prior art chimeric neurotoxins is summarised in table 1 below:

TABLE 1

$LH_N$ and $H_C$ domains in prior art chimeric neurotoxins

| | Chimera | $LH_N$ | $H_C$ |
|---|---|---|---|
| Rummel, 2011 | AABB | A | B: 871-1304 |
| | AACC | A | C: 871-1296 |
| | BBAA | B | A: 858-1283 |
| Wang, 2008 | AE | A: 1-874 (+ELGGGGSEL linker) | E: 845-1252 |
| | EA | E: 1-844 (+DI linker) | A: 871-1296 |
| Wang, 2012(a) | AB | A: 1-874 (+ELGGGGSEL linker) | B: 858-1283 |
| | BA | B: 1-861 (+DI linker) | A: 871-1296 |
| Wang, 2012(b) | ATx | A: 1-877 | Tx: 879-1315 |
| | TxA | Tx: 1-882 (+DI linker) | A: 871-1296 |
| | ETx | E: 1-844 (+DI linker) | Tx: 879-1315 |
| | TxE | Tx: 1-882 (+EL linker) | E: 845-1252 |

However, there still exists a need for an optimized design of chimeric neurotoxins allowing for improved therapeutic properties.

The present invention solves the above problem by providing chimeric neurotoxins, as specified in the claims.

SUMMARY OF THE INVENTION

In one aspect, the invention provides a chimeric neurotoxin comprising a $LH_N$ domain from a first neurotoxin covalently linked to a $H_C$ domain from a second neurotoxin, wherein the first and second neurotoxins are different, wherein the C-terminal amino acid residue of the $LH_N$ domain corresponds to the first amino acid residue of the $3_{10}$ helix separating the $LH_N$ and $H_C$ domains in the first neurotoxin, and wherein the N-terminal amino acid residue of the $H_C$ domain corresponds to the second amino acid residue of the $3_{10}$ helix separating the $LH_N$ and $H_C$ domains in the second neurotoxin.

In a second aspect, the invention provides a nucleotide sequence encoding a chimeric neurotoxin according to the invention.

In a third aspect, the invention provides a vector comprising a nucleotide sequence according to the invention.

In a fourth aspect, the invention provides a cell comprising a nucleotide sequence or a vector according to the invention.

In a fifth aspect, the invention provides a pharmaceutical composition comprising a chimeric neurotoxin according to the invention.

In a sixth aspect, the invention provides a chimeric neurotoxin according to the invention for use in therapy.

In a seventh aspect, the invention provides a non-therapeutic use of a chimeric neurotoxin according to the invention for treating an aesthetic or cosmetic condition.

DETAILED DESCRIPTION

In one aspect, the invention provides a chimeric neurotoxin comprising a $LH_N$ domain from a first neurotoxin covalently linked to a $H_C$ domain from a second neurotoxin, wherein the first and second neurotoxins are different,
  wherein the C-terminal amino acid residue of the $LH_N$ domain corresponds to the first amino acid residue of the $3_{10}$ helix separating the $LH_N$ and $H_C$ domains in the first neurotoxin, and wherein the N-terminal amino acid residue of the $H_C$ domain corresponds to the second amino acid residue of the $3_{10}$ helix separating the $LH_N$ and $H_C$ domains in the second neurotoxin.

As used herein, the term "a", "an" and "the" can mean one or more.

The term "neurotoxin" as used herein means any polypeptide that enters a neuron and inhibits neurotransmitter release. This process encompasses the binding of the neurotoxin to a low or high affinity receptor, the internalisation of the neurotoxin, the translocation of the endopeptidase portion of the neurotoxin into the cytoplasm and the enzymatic modification of the neurotoxin substrate. More specifically, the term "neurotoxin" encompasses any polypeptide produced by *Clostridium* bacteria (clostridial neurotoxins) that enters a neuron and inhibits neurotransmitter release, and such polypeptides produced by recombinant technologies or chemical techniques. It is this di-chain form that is the active form of the toxin. The two chains are termed the heavy chain (H-chain), which has a molecular mass of approximately 100 kDa, and the light chain (L-chain), which has a molecular mass of approximately 50 kDa. Preferably, the first and second neurotoxins are clostridial neurotoxins.

An example of a BoNT/A neurotoxin amino acid sequence is provided a SEQ ID NO: 1 (UNIPROT® accession number A5HZZ9). An example of a BoNT/B neurotoxin amino acid sequence is provided as SEQ ID NO: 2 (UNIPROT® accession number B1INP5). An example of a BoNT/C neurotoxin amino acid sequence is provided as SEQ ID NO: 3 (UNIPROT® accession number P18640). An example of a BoNT/D neurotoxin amino acid sequence is provided as SEQ ID NO: 4 (UNIPROT® accession number P19321). An example of a BoNT/E neurotoxin amino acid sequence is provided as SEQ ID NO: 5 (UNIPROT® accession number Q00496). An example of a BoNT/F neurotoxin amino acid sequence is provided as SEQ ID NO: 6 (UNIPROT® accession number Q57236). An example of a BoNT/G neurotoxin amino acid sequence is provided as SEQ ID NO: 7 (UNIPROT® accession number Q60393). An example of a TeNT neurotoxin amino acid sequence is provided as SEQ ID NO: 8 (UNIPROT® accession number P04958). The amino acid sequences of said neurotoxins are shown in the alignment of FIG. 1 below, along with the sequences of other neurotoxins (i.e. SEQ ID NOs: 58 to 91).

The term "chimeric neurotoxin" as used herein means a neurotoxin comprising or consisting of an $LH_N$ domain originating from a first neurotoxin and a $H_C$ domain originating from a second neurotoxin.

The term "$H_C$ domain" as used herein means a functionally distinct region of the neurotoxin heavy chain with a molecular weight of approximately 50 kDa that enables the binding of the neurotoxin to a receptor located on the surface of the target cell. The $H_C$ domain consists of two structurally distinct subdomains, the "$H_{CN}$ subdomain" (N-terminal part of the $H_C$ domain) and the "$H_{CC}$ subdomain" (C-terminal part of the $H_C$ domain), each of which has a molecular weight of approximately 25 kDa.

The term "$LH_N$ domain" as used herein means a neurotoxin that is devoid of the $H_C$ domain and consists of an endopeptidase domain ("L" or "light chain") and the domain responsible for translocation of the endopeptidase into the cytoplasm ($H_N$ domain of the heavy chain).

Reference herein to the "first amino acid residue of the $3_{10}$ helix separating the $LH_N$ and $H_C$ domains in the first neurotoxin" means the N-terminal residue of the $3_{10}$ helix separating the $LH_N$ and $H_C$ domains.

Reference herein to the "second amino acid residue of the $3_{10}$ helix separating the $LH_N$ and $H_C$ domains in the second neurotoxin" means the amino acid residue following the N-terminal residue of the $3_{10}$ helix separating the $LH_N$ and $H_C$ domains.

A "$3_{10}$ helix" is a type of secondary structure found in proteins and polypeptides, along with α-helices, β-sheets and reverse turns. The amino acids in a $3_{10}$ helix are arranged in a right-handed helical structure where each full turn is completed by three residues and ten atoms that separate the intramolecular hydrogen bond between them. Each amino acid corresponds to a 120° turn in the helix (i.e., the helix has three residues per turn), and a translation of 2.0 Å (=0.2 nm) along the helical axis, and has 10 atoms in the ring formed by making the hydrogen bond. Most importantly, the N—H group of an amino acid forms a hydrogen bond with the C=O group of the amino acid three residues earlier; this repeated i+3→i hydrogen bonding defines a $3_{10}$ helix. A $3_{10}$ helix is a standard concept in structural biology with which the skilled person is familiar.

This $3_{10}$ helix corresponds to four residues which form the actual helix and two cap (or transitional) residues, one at each end of these four residues. The term "$3_{10}$ helix separating the $LH_N$ and $H_C$ domains" as used herein consists of those 6 residues.

Through carrying out structural analyses and sequence alignments, the inventor identified a $3_{10}$ helix separating the $LH_N$ and $H_C$ domains in tetanus and botulinum neurotoxins. This $3_{10}$ helix is surrounded by an α-helix at its N-terminus (i.e. at the C-terminal part of the $LH_N$ domain) and by a β-strand at its C-terminus (i.e. at the N-terminal part of the $H_C$ domain). The first (N-terminal) residue (cap or transitional residue) of the $3_{10}$ helix also corresponds to the C-terminal residue of this α-helix.

The $3_{10}$ helix separating the $LH_N$ and $H_C$ domains can be for example determined from publically available crystal structures of botulinum neurotoxins, for example 3BTA and 1EPW from RCSB Protein Data Bank for botulinum neurotoxins A1 and B1 respectively.

In silico modelling and alignment tools which are publically available can also be used to determine the location of the $3_{10}$ helix separating the $LH_N$ and $H_C$ domains in other neurotoxins, for example the homology modelling servers LOOPP (Learning, Observing and Outputting Protein Patterns), PHYRE (Protein Homology/analogY Recognition Engine) and Rosetta, the protein superposition server SuperPose, the alignment program Clustal Omega, and a number of other tools/services listed at the Internet Resources for Molecular and Cell Biologists. The inventor found in particular that the region around the "$H_N$/$H_{CN}$" junction is structurally highly conserved which renders it an ideal region to superimpose different serotypes.

For example, the following methodology was used by the inventor to determine the sequence of this $3_{10}$ helix in other neurotoxins:

1. The structural homology modelling tool LOOP was used to obtain a predicted structure of all BoNT serotypes and TeNT based on the BoNT/A1 crystal structure (3BTA.pdb);
2. The structural (pdb) files thus obtained were edited to include only the N-terminal end of the $H_{CN}$ domain and about 80 residues before it (which are part of the $H_N$ domain), thereby retaining the "$H_N$/$H_{CN}$" region which is structurally highly conserved;
3. The protein superposition server SuperPose was used to superpose each serotype onto the 3BTA.pdb structure;

4. The superposed pdb files were inspected to locate the $3_{10}$ helix at the start of the $H_C$ domain of BoNT/A1 and corresponding residues in the other serotype were then identified.
5. All BoNT serotype sequences were aligned with Clustal Omega in order to check that corresponding residues were correct.

Examples of $LH_N$, $H_C$ and $3_{10}$ helix domains determined by this method are presented in table 2.

TABLE 2

$LH_N$, $H_C$ and $3_{10}$ helix domains

| Neurotoxin | Accession Number | $LH_N$ | $H_C$ | $3_{10}$ helix | SEQ ID NO ($3_{10}$ helix) |
|---|---|---|---|---|---|
| BoNT/A1 | A5HZZ9 | 1-872 | 873-1296 | $^{872}$NIINTS$^{877}$ | 14 |
| BoNT/A2 | X73423 | 1-872 | 873-1296 | $^{872}$NIVNTS$^{877}$ | 15 |
| BoNT/A3 | DQ185900 | 1-872 | 873-1292 | $^{872}$NIVNTS$^{877}$ | 16 |
| BoNT/A4 | EU341307 | 1-872 | 873-1296 | $^{872}$NITNAS$^{877}$ | 17 |
| BoNT/A5 | EU679004 | 1-872 | 873-1296 | $^{872}$NIINTS$^{877}$ | 18 |
| BoNT/A6 | FJ981696 | 1-872 | 873-1296 | $^{872}$NIINTS$^{877}$ | 19 |
| BoNT/A7 | JQ954969 | 1-872 | 873-1296 | $^{872}$NIINTS$^{877}$ | 20 |
| BoNT/A8 | KM233166 | 1-872 | 873-1297 | $^{872}$NITNTS$^{877}$ | 21 |
| BoNT/B1 | B1INP5 | 1-859 | 860-1291 | $^{859}$EILNNI$^{864}$ | 22 |
| BoNT/B2 | AB084152 | 1-859 | 860-1291 | $^{859}$EILNNI$^{864}$ | 23 |
| BoNT/B3 | EF028400 | 1-859 | 860-1291 | $^{859}$EILNNI$^{864}$ | 24 |
| BoNT/B4 | EF051570 | 1-859 | 860-1291 | $^{859}$EILNNI$^{864}$ | 25 |
| BoNT/B5 | EF033130 | 1-859 | 860-1291 | $^{859}$DILNNI$^{864}$ | 26 |
| BoNT/B6 | AB302852 | 1-859 | 860-1291 | $^{859}$EILNNI$^{864}$ | 27 |
| BoNT/B7 | JQ354985 | 1-859 | 860-1291 | $^{859}$EILNNI$^{864}$ | 28 |
| BoNT/B8 | JQ964806 | 1-859 | 860-1292 | $^{859}$EILNNI$^{864}$ | 29 |
| BoNT/C1 | P18640 | 1-867 | 868-1291 | $^{867}$NINDSK$^{872}$ | 30 |
| BoNT/CD | AB200360 | 1-867 | 868-1280 | $^{867}$SINDSK$^{872}$ | 31 |
| BoNT/DC | AB745660 | 1-863 | 864-1276 | $^{863}$SINDSK$^{868}$ | 32 |
| BoNT/D | P19321 | 1-863 | 864-1276 | $^{863}$SINDSK$^{868}$ | 33 |
| BoNT/E1 | Q00496 | 1-846 | 847-1252 | $^{846}$RIKSSS$^{851}$ | 34 |
| BoNT/E2 | EF028404 | 1-846 | 847-1252 | $^{846}$RIKSSS$^{851}$ | 35 |
| BoNT/E3 | EF028403 | 1-846 | 847-1252 | $^{846}$RIKSSS$^{851}$ | 36 |
| BoNT/E4 | AB088207 | 1-846 | 847-1252 | $^{846}$RIKSSS$^{851}$ | 37 |
| BoNT/E5 | AB037711 | 1-846 | 847-1251 | $^{846}$RIKSSS$^{851}$ | 38 |
| BoNT/E6 | AM695759 | 1-846 | 847-1252 | $^{846}$RIKSSS$^{851}$ | 39 |
| BoNT/E7 | JN695729 | 1-846 | 847-1252 | $^{846}$RIKSSS$^{851}$ | 40 |
| BoNT/E8 | JN695730 | 1-846 | 847-1252 | $^{846}$RIKSSS$^{851}$ | 41 |
| BoNT/E9 | JX424534 | 1-846 | 847-1251 | $^{846}$RIKSSS$^{851}$ | 42 |
| BoNT/E10 | KF861917 | 1-846 | 847-1252 | $^{846}$RIKSSS$^{851}$ | 43 |
| BoNT/E11 | KF861875 | 1-846 | 847-1252 | $^{846}$RIKSSS$^{851}$ | 44 |
| BoNT/E12 | KM370319 | 1-846 | 847-1254 | $^{846}$RIKSSS$^{851}$ | 45 |
| BoNT/F1 | Q57236 | 1-865 | 866-1278 | $^{865}$KIKDNS$^{870}$ | 46 |
| BoNT/F2 | GU213209 | 1-865 | 866-1280 | $^{865}$KIKDSS$^{870}$ | 47 |
| BoNT/F3 | GU213227 | 1-865 | 866-1279 | $^{865}$KIKDSS$^{870}$ | 48 |
| BoNT/F4 | GU213214 | 1-865 | 866-1277 | $^{865}$KIKDNC$^{870}$ | 49 |
| BoNT/F5 | GU213211 | 1-862 | 863-1277 | $^{862}$KIKDSS$^{867}$ | 50 |
| BoNT/F6 | M92906 | 1-864 | 865-1274 | $^{864}$KIKDSS$^{869}$ | 51 |
| BoNT/F7 | GU213233 | 1-856 | 857-1268 | $^{856}$KIKDSS$^{861}$ | 52 |
| BoNT/G | Q60393 | 1-864 | 865-1297 | $^{864}$NISSNA$^{869}$ | 53 |
| BoNT/H | KGO15617 | 1-860 | 861-1288 | $^{860}$ELKYNC$^{865}$ | 54 |
| TeNT | P04958 | 1-880 | 881-1315 | $^{880}$ILKKST$^{885}$ | 55 |

Using structural analysis and sequence alignments, the inventor found that the β-strand following the $3_{10}$ helix separating the $LH_N$ and $H_C$ domains is a conserved structure in all botulinum and tetanus neurotoxins and starts at the 8$^{th}$ residue when starting from the first residue of the $3_{10}$ helix separating the $LH_N$ and $H_C$ domains (e.g., at residue 879 for BoNT/A1).

According to an alternative definition, the first aspect of the invention provides a chimeric neurotoxin comprising an $LH_N$ domain from a first neurotoxin covalently linked to a $H_C$ domain from a second neurotoxin, wherein the first and second neurotoxins are different,
wherein the C-terminal amino acid residue of the $LH_N$ domain corresponds to the eighth amino acid residue N-terminally to the β-strand located at the beginning (N-term) of the $H_C$ domain in the first neurotoxin, and
wherein the N-terminal amino acid residue of the $H_C$ domain corresponds to the seventh amino acid residue N-terminally to the β-strand located at the beginning (N-term) of the $H_C$ domain in the second neurotoxin.

According to yet another definition, the first aspect of the invention provides a chimeric neurotoxin comprising a $LH_N$ domain from a first neurotoxin covalently linked to a $H_C$ domain from a second neurotoxin, wherein the first and second neurotoxins are different,
wherein the C-terminal amino acid residue of the $LH_N$ domain corresponds to the C-terminal amino acid residue of the α-helix located at the end (C-term) of $LH_N$ domain in the first neurotoxin, and
wherein the N-terminal amino acid residue of the $H_C$ domain corresponds to the amino acid residue immediately C-terminal to the C-terminal amino acid residue of the α-helix located at the end (C-term) of $LH_N$ domain in the second neurotoxin.

The rationale of the design process of the chimeric neurotoxins according to the invention was to try to ensure that the secondary structure was not compromised and thereby minimise any changes to the tertiary structure and to the function of each domain.

In some of the prior art chimeric neurotoxins, a linker is required between the $LH_N$ and $H_C$ domains (see table 1), presumably to ensure acceptable expression and purification.

Without wishing to be bound by theory, it is hypothesized that structuring chimeric neurotoxins in the form of proteins which have a tertiary structure closely mimicking the tertiary structure of natural neurotoxins will facilitate their solubility.

Without wishing to be bound by theory, it is further hypothesized that the fact of not disrupting the four central amino acid residues of the $3_{10}$ helix in the chimeric neurotoxin ensures an optimal conformation for the chimeric neurotoxin, thereby allowing for the chimeric neurotoxin to exert its functions to their full capacity.

In fact, the inventor has surprisingly found that retaining solely the first amino acid residue of the $3_{10}$ helix of the first neurotoxin and the second amino acid residue of the $3_{10}$ helix onwards of second neurotoxin not only allows the production of soluble and functional chimeric neurotoxins, but further leads to improved properties over other chimeric neurotoxins, in particular an increased potency, an increased safety ratio and/or a longer duration of action.

Undesired effects of a neurotoxin (caused by diffusion of the neurotoxin away from the site of administration) can be assessed experimentally by measuring percentage bodyweight loss in a relevant animal model (e.g. a mouse, where loss of bodyweight is detected within seven days of administration). Conversely, desired on-target effects of a neurotoxin can be assessed experimentally by Digital Abduction Score (DAS) assay, a measurement of muscle paralysis. The DAS assay may be performed by injection of 20 μL of neurotoxin, formulated in Gelatin Phosphate Buffer, into the mouse gastrocnemius/soleus complex, followed by assessment of Digital Abduction Score using the method of Aoki (Aoki KR, Toxicon 39: 1815-1820; 2001).

In the DAS assay, mice are suspended briefly by the tail in order to elicit a characteristic startle response in which the mouse extends its hind limbs and abducts its hind digits. Following neurotoxin injection, the varying degrees of digit abduction are scored on a five-point scale (0=normal to 4=maximal reduction in digit abduction and leg extension).

The Safety Ratio of a neurotoxin may then be expressed as the ratio between the amount of neurotoxin required for a 10% drop in a bodyweight of a mouse (measured at peak effect within the first seven days after dosing in a mouse) and the amount of neurotoxin required for a DAS score of 2. High Safety Ratio scores are therefore desired, and indicate a neurotoxin that is able to effectively paralyse a target muscle with little undesired off-target effects.

A high safety ratio is particularly advantageous in therapy because it represents an increase in the therapeutic index. In other words, this means that reduced dosages can be used compared to known clostridial toxin therapeutics and/or that increased dosages can be used without any additional effects. The possibility to use higher doses of neurotoxin without additional effects is particularly advantageous as higher doses usually lead to a longer duration of action of the neurotoxin.

The Potency of a neurotoxin may be expressed as the minimal dose of neurotoxin which leads to a given DAS score when administered to a mouse gastrocnemius/soleus complex, for example a DAS score of 2 ($ED_{50}$ dose) or a DAS score of 4. The Potency of a neurotoxin may be also expressed as the $EC_{50}$ dose in a cellular assay measuring SNARE cleavage by the neurotoxin, for example the $EC_{50}$ dose in a cellular assay measuring SNAP-25 cleavage by a chimeric BoNT/AB neurotoxin.

The duration of action of a neurotoxin may be expressed as the time required for retrieving a DAS score of 0 after administration of a given dose of neurotoxin, for example the minimal dose of neurotoxin leading to a DAS score of 4, to a mouse gastrocnemius/soleus complex.

In one embodiment, the first neurotoxin is a Botulinum Neurotoxin (BoNT) serotype A, serotype B, serotype C, serotype D, serotype E, serotype F or serotype G or a Tetanus Neurotoxin (TeNT), and the second neurotoxin is a Botulinum Neurotoxin (BoNT) serotype A, serotype B, serotype C, serotype D, serotype E, serotype F or serotype G or a Tetanus Neurotoxin (TeNT). In a preferred embodiment, the first neurotoxin is a Botulinum Neurotoxin (BoNT) serotype A, serotype B or a serotype C, and the second neurotoxin is a Botulinum Neurotoxin (BoNT) serotype A, serotype B or a serotype C.

Different BoNT serotypes can be distinguished based on inactivation by specific neutralising anti-sera, with such classification by serotype correlating with percentage sequence identity at the amino acid level. BoNT proteins of a given serotype are further divided into different subtypes on the basis of amino acid percentage sequence identity.

Preferably, the first and second neurotoxins are Botulinum Neurotoxins from different serotypes. In another embodiment, either the first or second neurotoxin is a Botulinum Neurotoxin and the other neurotoxin is a Tetanus neurotoxin.

Using an "XY" representation according to which X is the $LH_N$ domain and Y is the $H_C$ domain, the following chimeric neurotoxins are embodiments of the present invention:

AB, AC, AD, AE, AF, AG, ATx,
BA, BC, BD, BE, BF, BG, BTx,
CA, CB, CD, CE, CF, CG, CTx,
DA, DB, DC, DE, DF, DG, DTx,
EA, EB, EC, ED, EF, EG, ETx,
FA, FB, FC, FD, FE, FG, FTx,
GA, GB, GC, GD, GE, GF, FTx,
TxA, TxB, TxC, TxD, TxE, TxF, TxG, wherein A, B, C, D, E, F, G and Tx are respectively Botulinum Neurotoxin (BoNT) serotype A, serotype B, serotype C, serotype D, serotype E, serotype F, serotype G and Tetanus Neurotoxin (TeNT).

Yet, using the same "XY" representation as described above, the following chimeric neurotoxins are preferred embodiments of the present invention:

AB, AC,
BA, BC,
CA, CB, wherein A, B, C, are respectively Botulinum Neurotoxin (BoNT) serotype A, serotype B, and serotype C.

In one embodiment, the $LH_N$ domain from the first neurotoxin corresponds to:

amino acid residues 1 to 872 of SEQ ID NO: 1, or a polypeptide sequence having at least 70% sequence identity thereto, amino acid residues 1 to 859 of SEQ ID NO: 2, or a polypeptide sequence having at least 70% sequence identity thereto, amino acid residues 1 to 867 of SEQ ID NO: 3, or a polypeptide sequence having at least 70% sequence identity thereto, amino acid residues 1 to 863 of SEQ ID NO: 4, or a polypeptide sequence having at least 70% sequence identity thereto, amino acid residues 1 to 846 of SEQ ID NO: 5, or a polypeptide sequence having at least 70% sequence identity thereto, amino acid residues 1 to 865 of SEQ ID NO: 6, or a polypeptide sequence having at least 70% sequence identity thereto, amino acid residues 1 to 864 of SEQ ID NO: 7, or a polypeptide sequence having at least 70% sequence identity thereto G, or amino acid residues 1 to 880 of SEQ ID NO: 8, or a polypeptide sequence having at least 70% sequence identity thereto.

and the $H_C$ domain from the second neurotoxin corresponds to:

amino acid residues 873 to 1296 of SEQ ID NO: 1, or a polypeptide sequence having at least 70% sequence identity thereto, amino acid residues 860 to 1291 of SEQ ID NO: 2, or a polypeptide sequence having at least 70% sequence identity thereto, amino acid residues 868 to 1291 of SEQ ID NO: 3, or a polypeptide sequence having at least 70% sequence identity thereto, amino acid residues 864 to 1276 of SEQ ID NO: 4, or a polypeptide sequence having at least 70% sequence identity thereto, amino acid residues 847 to 1251 of SEQ ID NO: 5, or a polypeptide sequence having at least 70% sequence identity thereto, amino acid residues 866 to 1275 of SEQ ID NO: 6, or a polypeptide sequence having at least 70% sequence identity thereto, amino acid residues 865 to 1297 of SEQ ID NO: 7, or a polypeptide sequence having at least 70% sequence identity thereto, or amino acid residues 881 to 1315 of SEQ ID NO: 8, or a polypeptide sequence having at least 70% sequence identity thereto.

The "percent sequence identity" between two or more nucleic acid or amino acid sequences is a function of the number of identical nucleotides/amino acids at identical positions shared by the aligned sequences. Thus, % identity may be calculated as the number of identical nucleotides/ amino acids at each position in an alignment divided by the total number of nucleotides/amino acids in the aligned sequence, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, in particular a global alignment mathematical algorithm (Needleman and Wunsch, J. Mol. Biol. 48(3), 443-453, 1972) such as BLAST, which will be familiar to a skilled person.

The first or second neurotoxin can be a mosaic neurotoxin. The term "mosaic neurotoxin" as used in this context refers to a naturally occurring clostridial neurotoxin that comprises at least one functional domain from another type of clostridial neurotoxins (e.g. a clostridial neurotoxin of a different serotype), said clostridial neurotoxin not usually comprising said at least one functional domain. Examples of mosaic neurotoxins are naturally occurring BoNT/DC and BoNT/CD. BoNT/DC comprises the L chain and $H_N$ domain of serotype D and the $H_C$ domain of serotype C, whereas BoNT/CD consists of the L chain and $H_N$ domain of serotype C and the $H_C$ domain of serotype D.

The first and second neurotoxins can be modified neurotoxins and derivatives thereof, including but not limited to those described below. A modified neurotoxin or derivative may contain one or more amino acids that has been modified as compared to the native (unmodified) form of the neurotoxin, or may contain one or more inserted amino acids that are not present in the native (unmodified) form of the toxin. By way of example, a modified clostridial neurotoxin may have modified amino acid sequences in one or more domains relative to the native (unmodified) clostridial neurotoxin sequence. Such modifications may modify functional aspects of the neurotoxin, for example biological activity or persistence. Thus, in one embodiment, the first neurotoxin and/or the second neurotoxin is a modified neurotoxin, or modified neurotoxin derivative.

A modified neurotoxin retains at least one of the functions of a neurotoxin, selected from the ability to bind to a low or high affinity neurotoxin receptor on a target cell, to translocate the endopeptidase portion of the neurotoxin (light chain) into the cell cytoplasm and to cleave a SNARE protein. Preferably, a modified neurotoxin retains at least two of these functions. More preferably a modified neurotoxin retains these three functions.

A modified neurotoxin may have one or more modifications in the amino acid sequence of the heavy chain (such as a modified $H_C$ domain), wherein said modified heavy chain binds to target nerve cells with a higher or lower affinity than the native (unmodified) neurotoxin. Such modifications in the $H_C$ domain can include modifying residues in the ganglioside binding site of the $H_C$ domain or in the protein (SV2 or synaptotagmin) binding site that alter binding to the ganglioside receptor and/or the protein receptor of the target nerve cell. Examples of such modified neurotoxins are described in WO 2006/027207 and WO 2006/114308, both of which are hereby incorporated by reference in their entirety.

A modified neurotoxin may have one or more modifications in the amino acid sequence of the light chain, for example modifications in the substrate binding or catalytic domain which may alter or modify the SNARE protein specificity of the modified LC. Examples of such modified neurotoxins are described in WO 2010/120766 and US 2011/0318385, both of which are hereby incorporated by reference in their entirety.

A modified neurotoxin may comprise one or more modifications that increases or decreases the biological activity and/or the biological persistence of the modified neurotoxin. For example, a modified neurotoxin may comprise a leucine- or tyrosine-based motif, wherein said motif increases or decreases the biological activity and/or the biological persistence of the modified neurotoxin. Suitable leucine-based motifs include xDxxxLL, xExxxLL, xExxxIL, and xExxxLM (wherein x is any amino acid). Suitable tyrosine-based motifs include Y-x-x-Hy (wherein Hy is a hydrophobic amino acid). Examples of modified neurotoxins comprising leucine- and tyrosine-based motifs are described in WO 2002/08268, which is hereby incorporated by reference in its entirety.

In one embodiment, the first or second neurotoxin is a modified BoNT/A which has an amino acid sequence having at least 70%, preferably at least 75%, 80%, 85%, 90%, 95% or 99% sequence identity to SEQ ID NO: 1.

In one embodiment, the first or second neurotoxin is a modified BoNT/B which has an amino acid sequence having at least 70%, preferably at least 75%, 80%, 85%, 90%, 95% or 99% sequence identity to SEQ ID NO: 2.

In one embodiment, the first or second neurotoxin is a modified BoNT/C which has an amino acid sequence having at least 70%, preferably at least 75%, 80%, 85%, 90%, 95% or 99% sequence identity to SEQ ID NO: 3.

In one embodiment, the first or second neurotoxin is a modified BoNT/D which has an amino acid sequence having at least 70%, preferably at least 75%, 80%, 85%, 90%, 95% or 99% sequence identity to SEQ ID NO: 4.

In one embodiment, the first or second neurotoxin is a modified BoNT/E which has an amino acid sequence having at least 70%, preferably at least 75%, 80%, 85%, 90%, 95% or 99% sequence identity to SEQ ID NO: 5.

In one embodiment, the first or second neurotoxin is a modified BoNT/F which has an amino acid sequence having at least 70%, preferably at least 75%, 80%, 85%, 90%, 95% or 99% sequence identity to SEQ ID NO: 6.

In one embodiment, the first or second neurotoxin is a modified BoNT/G which has an amino acid sequence having at least 70%, preferably at least 75%, 80%, 85%, 90%, 95% or 99% sequence identity to SEQ ID NO: 7.

In one embodiment, the first or second neurotoxin is a modified TeNT which has an amino acid sequence having at least 70%, preferably at least 75%, 80%, 85%, 90%, 95% or 99% sequence identity to SEQ ID NO: 8.

In one embodiment, the second neurotoxin is a BoNT/B. Such a chimeric neurotoxin is referred to herein as a "BoNT/XB neurotoxin".

In a preferred embodiment, the first neurotoxin is a BoNT/A and the second neurotoxin is a BoNT/B. Such a chimeric neurotoxin is referred to herein as a "BoNT/AB neurotoxin". More preferably, the first neurotoxin is a BoNT/A1 and the second neurotoxin is a BoNT/B1. More preferably still, the $LH_N$ domain from a first neurotoxin corresponds to amino acid residues 1 to 872 of BoNT/A1 and the $H_C$ domain from a second neurotoxin corresponds to amino acid residues 860 to 1291 of BoNT/B1. In one preferred embodiment, the $LH_N$ domain from a first neurotoxin corresponds to amino acid residues 1 to 872 of SEQ ID NO: 1 and the $H_C$ domain from a second neurotoxin corresponds to amino acid residues 860 to 1291 of SEQ ID NO: 2. In other words, a preferred chimeric neurotoxin according to the invention comprises or consists of the amino acid sequence SEQ ID NO:13.

Compared to the BoNT/A serotype, natural BoNT/B is much less potent despite a comparatively greater abundance of its receptor on synaptic vesicles. This is due to a unique amino acid change within the toxin binding site in human synaptotagmin II (Syt II) as compared to rodent (rat/mouse) Syt II (Peng, L., et al., J Cell Sci, 125(Pt 13):3233-42 (2012); Rummel, A. et al, FEBS J 278:4506-4515 (2011).13,22. As a result of this residue change, human Syt II has greatly diminished binding to natural BoNT/B, as well as to natural BoNT/D-C, and/G. These findings provide an explanation for the clinical observations that a much higher dose of BoNT/B than BoNT/A (which binds a different receptor) is needed to achieve the same levels of therapeutic effects in patients. In a preferred embodiment of a BoNT/XB or BoNT/AB neurotoxin according to the invention, the $H_C$ domain from a BoNT/B neurotoxin comprises at least one amino acid residue substitution, addition or deletion in the $H_{CC}$ subdomain which has the effect of increasing the binding affinity of BoNT/B neurotoxin for human Syt II as compared to the natural BoNT/B sequence.

Suitable amino acid residue substitution, addition or deletion in the BoNT/B $H_{CC}$ subdomain have been disclosed in WO2013/180799 and in PCT/US2016/024211 which is not yet published (both herein incorporated by reference).

Suitable amino acid residue substitution, addition or deletion in the BoNT/B $H_{CC}$ subdomain include substitution mutations selected from the group consisting of: V1118M; Y1183M; E1191M; E1191I; E1191Q; E1191T; S1199Y; S1199F; S1199L; S1201V; E1191C, E1191V, E1191L, E1191Y, S1199W, S1199E, S1199H, W1178Y, W1178Q, W1178A, W1178S, Y1183C, Y1183P and combinations thereof.

Suitable amino acid residue substitution, addition or deletion in the BoNT/B $H_{CC}$ subdomain further include combinations of two substitution mutations selected from the group consisting of: E1191M and S1199L, E1191M and S1199Y, E1191M and S1199F, E1191Q and S1199L, E1191Q and S1199Y, E1191Q and S1199F, E1191M and S1199W, E1191M and W1178Q, E1191C and S1199W, E1191C and S1199Y, E1191C and W1178Q, E1191Q and S1199W, E1191V and S1199W, E1191V and S1199Y, or E1191V and W1178Q.

Suitable amino acid residue substitution, addition or deletion in the BoNT/B $H_{CC}$ subdomain also include a combination of three substitution mutations which are E1191M, S1199W and W1178Q.

In a preferred embodiment, the suitable amino acid residue substitution, addition or deletion in the BoNT/B $H_{CC}$ subdomain include a combination of two substitution mutations which are E1191M and S1199Y. In other words, a preferred chimeric neurotoxin according to the invention comprises or consists of the amino acid sequence SEQ ID NO: 11 or SEQ ID NO: 12.

In another preferred embodiment, the first neurotoxin is a BoNT/C and the second neurotoxin is a BoNT/B. Such a chimeric neurotoxin is referred to herein as a "BoNT/CB neurotoxin". More preferably, the first neurotoxin is a BoNT/C1 and the second neurotoxin is a BoNT/B1. More preferably still, the $LH_N$ domain from a first neurotoxin corresponds to amino acid residues 1 to 867 of BoNT/C1 and the $H_C$ domain from a second neurotoxin corresponds to amino acid residues 860 to 1291 of BoNT/B1. In one preferred embodiment, the $LH_N$ domain from a first neurotoxin corresponds to amino acid residues 1 to 867 of SEQ ID NO: 3 and the $H_C$ domain from a second neurotoxin corresponds to amino acid residues 860 to 1291 of SEQ ID NO: 2. In a preferred embodiment, the $H_C$ domain from the BoNT/B neurotoxin comprises at least one amino acid residue substitution, addition or deletion in the $H_{CC}$ subdomain which has the effect of increasing the binding affinity of BoNT/B neurotoxin for human Syt II as compared to the natural BoNT/B sequence. Suitable amino acid residue substitution, addition or deletion in the BoNT/B $H_{CC}$ subdomain is as described above.

In a preferred embodiment of a BoNT/XDC neurotoxin (chimeric neurotoxin in which the second neurotoxin is a mosaic BoNT/DC) according to the invention, the $H_C$ domain from a mosaic BoNT/DC neurotoxin comprises at least one amino acid residue substitution, addition or deletion in the $H_{CC}$ subdomain which has the effect of increasing the binding affinity of mosaic BoNT/DC neurotoxin for human Syt II as compared to the natural mosaic BoNT/DC sequence.

In a preferred embodiment of a BoNT/XG neurotoxin according to the invention, the $H_C$ domain from a BoNT/G neurotoxin comprises at least one amino acid residue substitution, addition or deletion in the $H_{CC}$ subdomain which has the effect of increasing the binding affinity of BoNT/G neurotoxin for human Syt II as compared to the natural BoNT/G sequence.

Other preferred neurotoxins according to the invention are as follows.

In a preferred embodiment, the first neurotoxin is a BoNT/A and the second neurotoxin is a BoNT/C. Such a chimeric neurotoxin is referred to herein as a "BoNT/AC neurotoxin". More preferably, the first neurotoxin is a BoNT/A1 and the second neurotoxin is a BoNT/C1. More preferably still, the $LH_N$ domain from a first neurotoxin corresponds to amino acid residues 1 to 872 of BoNT/A1 and the $H_C$ domain from a second neurotoxin corresponds to amino acid residues 868 to 1291 of BoNT/C1. In one preferred embodiment, the $LH_N$ domain from a first neurotoxin corresponds to amino acid residues 1 to 872 of SEQ ID NO: 1 and the $H_C$ domain from a second neurotoxin corresponds to amino acid residues 868 to 1291 of SEQ ID NO: 3.

In another preferred embodiment, the first neurotoxin is a BoNT/B and the second neurotoxin is a BoNT/A. Such a chimeric neurotoxin is referred to herein as a "BoNT/BA neurotoxin". More preferably, the first neurotoxin is a BoNT/B1 and the second neurotoxin is a BoNT/A1. More preferably still, the $LH_N$ domain from a first neurotoxin corresponds to amino acid residues 1 to 859 of BoNT/B1 and the $H_C$ domain from a second neurotoxin corresponds to amino acid residues 873 to 1296 of BoNT/A1. In one preferred embodiment, the $LH_N$ domain from a first neurotoxin corresponds to amino acid residues 1 to 859 of SEQ ID NO: 2 and the $H_C$ domain from a second neurotoxin corresponds to amino acid residues 873 to 1293 of SEQ ID NO: 1.

In another preferred embodiment, the first neurotoxin is a BoNT/B and the second neurotoxin is a BoNT/C. Such a chimeric neurotoxin is referred to herein as a "BoNT/BC neurotoxin". More preferably, the first neurotoxin is a BoNT/B1 and the second neurotoxin is a BoNT/C1. More preferably still, the $LH_N$ domain from a first neurotoxin corresponds to amino acid residues 1 to 859 of BoNT/B1 and the $H_C$ domain from a second neurotoxin corresponds to amino acid residues 868 to 1291 of BoNT/C1. In one preferred embodiment, the $LH_N$ domain from a first neurotoxin corresponds to amino acid residues 1 to 859 of SEQ ID NO: 2 and the $H_C$ domain from a second neurotoxin corresponds to amino acid residues 868 to 1291 of SEQ ID NO: 3. In other words, a preferred chimeric neurotoxin according to the invention comprises or consists of the amino acid sequence SEQ ID NO: 56.

In another preferred embodiment, the first neurotoxin is a BoNT/C and the second neurotoxin is a BoNT/A. Such a chimeric neurotoxin is referred to herein as a "BoNT/CA neurotoxin". More preferably, the first neurotoxin is a BoNT/C1 and the second neurotoxin is a BoNT/A1. More preferably still, the $LH_N$ domain from a first neurotoxin corresponds to amino acid residues 1 to 867 of BoNT/C1 and the $H_C$ domain from a second neurotoxin corresponds to amino acid residues 873 to 1296 of BoNT/A1. In one preferred embodiment, the $LH_N$ domain from a first neurotoxin corresponds to amino acid residues 1 to 867 of SEQ ID NO: 3 and the $H_C$ domain from a second neurotoxin corresponds to amino acid residues 873 to 1296 of SEQ ID NO: 1.

The chimeric neurotoxins of the present invention can be produced using recombinant technologies. Thus, in one embodiment, a chimeric neurotoxin according to the invention is a recombinant chimeric neurotoxin. It shall be readily understood that, according to this preferred embodiment, a nucleotide sequence encoding a recombinant chimeric neurotoxin of the invention, a vector comprising said nucleotide sequence, and a cell comprising said vector, as further described below, can mutatis mutandis be referred as being recombinant.

In another aspect, the invention provides a nucleotide sequence encoding a chimeric neurotoxin according to the invention, for example a DNA or RNA sequence. In a preferred embodiment, the nucleotide sequence is a DNA sequence.

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The DNA sequence of the present invention is preferably designed in silico, and then synthesised by conventional DNA synthesis techniques.

The above-mentioned nucleic acid sequence information is optionally modified for codon-biasing according to the ultimate host cell (e.g. *E. coli*) expression system that is to be employed.

In another aspect, the invention provides a vector comprising a nucleotide sequence according to the invention. In one embodiment, the nucleic acid sequence is prepared as part of a DNA vector comprising a promoter and terminator. In a preferred embodiment, the vector has a promoter selected from Tac, AraBAD, T7-Lac, or T5-Lac.

A vector may be suitable for in vitro and/or in vivo expression of the above-mentioned nucleic acid sequence. The vector can be a vector for transient and/or stable gene expression. The vector may additionally comprise regulatory elements and/or selection markers. Said vector may be of viral origin, of phage origin, or of bacterial origin. For example, said expression vector may be a pET, pJ401, pGEX vector or a derivative thereof.

In another aspect, the invention provides a cell comprising a nucleotide sequence or a vector according to the invention. The term "cell" can herein be used interchangeably with the term "host cell" or "cell line". Suitable cell type includes prokaryotic cells, for example *E. coli*, and eukaryotic cells, such as yeast cells, mammalian cells, insect cells, etc. Preferably, the cell is *E. coli*.

In another aspect, the invention provides a method for producing a chimeric neurotoxin according to the invention, said method comprising the step of culturing a cell as described above, under conditions wherein said chimeric neurotoxin is produced. Said conditions are well-known to the skilled practitioner and therefore need not be further detailed herein. Preferably, said method further comprises the step of recovering the chimeric neurotoxin from the culture.

In another aspect, the invention provides a pharmaceutical composition comprising a chimeric neurotoxin according to the invention. Preferably, the pharmaceutical composition comprises a chimeric neurotoxin together with at least one component selected from a pharmaceutically acceptable carrier, excipient, adjuvant, propellant and/or salt.

In another aspect, the invention provides a chimeric neurotoxin or pharmaceutical composition according to the invention for use in therapy. More precisely, the invention relates to the use of a chimeric neurotoxin or pharmaceutical composition as described herein, for manufacturing a medicament. In other words, the invention relates to a method for treating a subject in need thereof, comprising the step of administering an effective amount of a chimeric neurotoxin or pharmaceutical composition as described herein, to said subject. By "effective amount", it is meant that the chimeric neurotoxin or pharmaceutical composition is administered in a quantity sufficient to provide the effect for which it is indicated. As used herein, the term "subject" preferably refers to a human being or an animal, more preferably to a human being.

A chimeric neurotoxin according to the invention is preferably suitable for use in treating a condition associated with unwanted neuronal activity in a subject in need thereof, for example a condition selected from the group consisting of spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhidrosis, excessive salivation, excessive gastrointestinal secretions, secretory disorders, pain from muscle spasms, headache pain, migraine and dermatological conditions. More precisely, the invention relates to the use of a chimeric neurotoxin or pharmaceutical composition as described herein, for manufacturing a medicament intended to treat a condition associated with unwanted neuronal activity, as described above. In other words, the invention relates to a method for treating a condition associated with unwanted neuronal activity, as described above, in a subject in need thereof, said method comprising the step of administering an effective amount of a chimeric neurotoxin or pharmaceutical composition as described herein, to said subject.

In another aspect, the invention provides a non-therapeutic use of a chimeric neurotoxin according to the invention for treating an aesthetic or cosmetic condition, in a subject in need thereof. In other words, the invention relates to a method for treating an aesthetic or cosmetic condition in a subject in need thereof, comprising the step of administering an effective amount of a chimeric neurotoxin or pharmaceutical composition as described herein, to said subject. According to this aspect of the invention, the subject to be treated is preferably not suffering from a condition associated with unwanted neuronal activity as described above. More preferably, said subject is a healthy subject, i.e. a subject which is not suffering from any disease.

In another aspect, the invention provides a kit for use in a therapeutic or non-therapeutic (cosmetic or aesthetic)

method, or for a therapeutic or non-therapeutic (cosmetic or aesthetic) use, as described above, said kit comprising a pharmaceutical composition of the invention and instructions for performing said method or use. More precisely, the invention relates to a kit comprising a pharmaceutical composition of the invention and instructions for therapeutic or cosmetic administration of said composition to a subject in need thereof. As used herein, the term "instructions" refers to a publication, a recording, a diagram, or any other medium of expression which can be used to communicate how to perform a method or use of the invention, such as therapeutic or cosmetic administration of said composition to a subject in need thereof. Said instructions can, for example, be affixed to a container which comprises said composition or said kit.

The engineered chimeric neurotoxins of the present invention may be formulated for oral, parenteral, continuous infusion, inhalation or topical application. Compositions suitable for injection may be in the form of solutions, suspensions or emulsions, or dry powders which are dissolved or suspended in a suitable vehicle prior to use.

In the case of a chimeric neurotoxin that is to be delivered locally, the chimeric neurotoxin may be formulated as a cream (e.g. for topical application), or for sub-dermal injection.

Local delivery means may include an aerosol, or other spray (e.g. a nebuliser). In this regard, an aerosol formulation of a chimeric neurotoxin enables delivery to the lungs and/or other nasal and/or bronchial or airway passages.

Chimeric neurotoxins of the invention may be administered to a patient by intrathecal or epidural injection in the spinal column at the level of the spinal segment involved in the innervation of an affected organ.

A preferred route of administration is via laparoscopic and/or localised, particularly intramuscular, injection.

The dosage ranges for administration of the chimeric neurotoxins of the present invention are those to produce the desired therapeutic effect. It will be appreciated that the dosage range required depends on the precise nature of the chimeric neurotoxin or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Fluid dosage forms are typically prepared utilising the chimeric neurotoxin and a pyrogen-free sterile vehicle. The engineered clostridial toxin, depending on the vehicle and concentration used, can be either dissolved or suspended in the vehicle. In preparing solutions the chimeric neurotoxin can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively, the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Administration in accordance with the present invention may take advantage of a variety of delivery technologies including microparticle encapsulation, viral delivery systems or high-pressure aerosol impingement.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a clostridial neurotoxin" includes a plurality of such candidate agents and reference to "the clostridial neurotoxin" includes reference to one or more clostridial neurotoxins and equivalents thereof known to those skilled in the art, and so forth.

The invention will now be described, by way of example only, with reference to the following Figures and Examples.

DESCRIPTION OF THE DRAWINGS

Figure 1A:
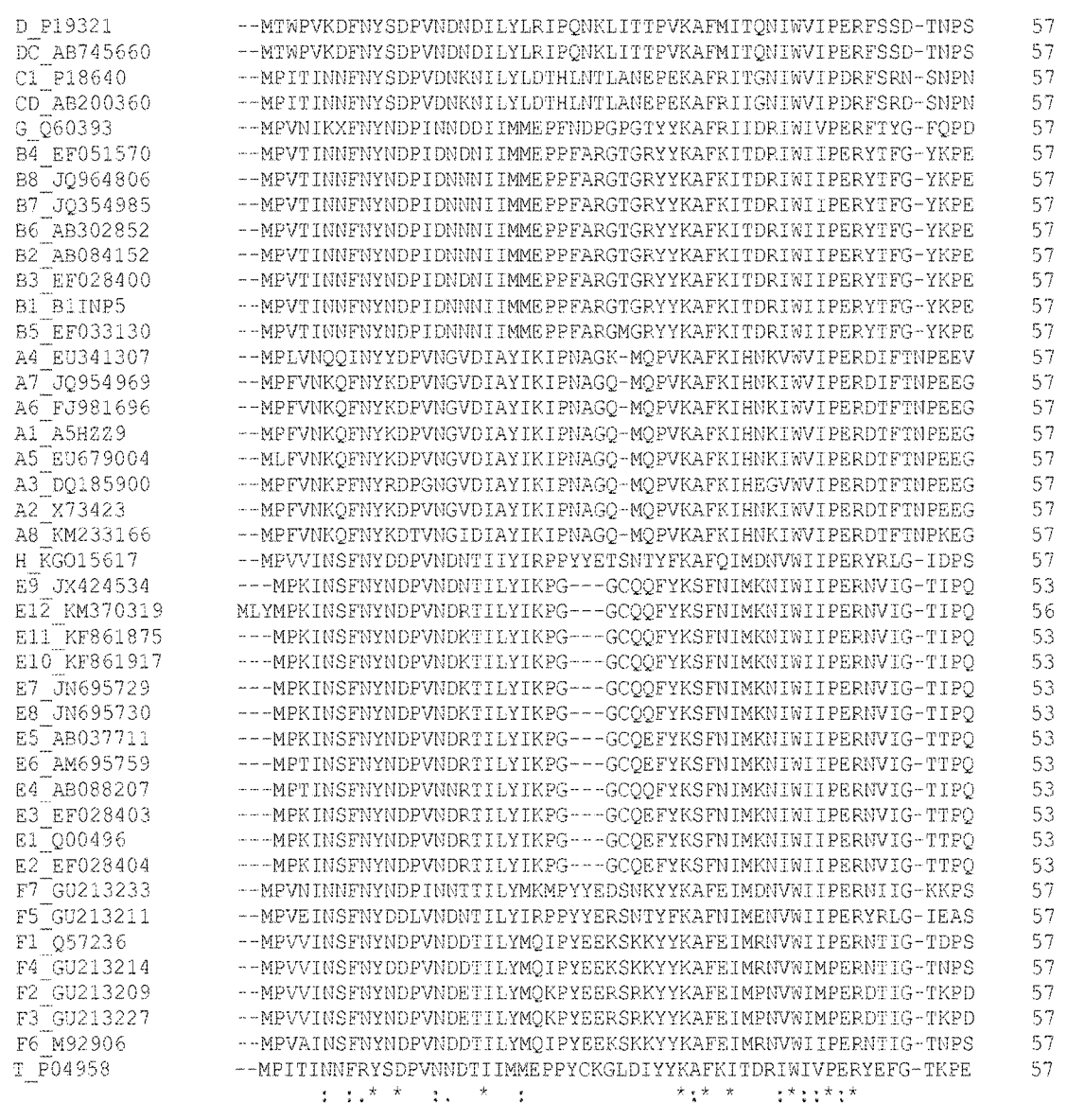
Figure 1C:
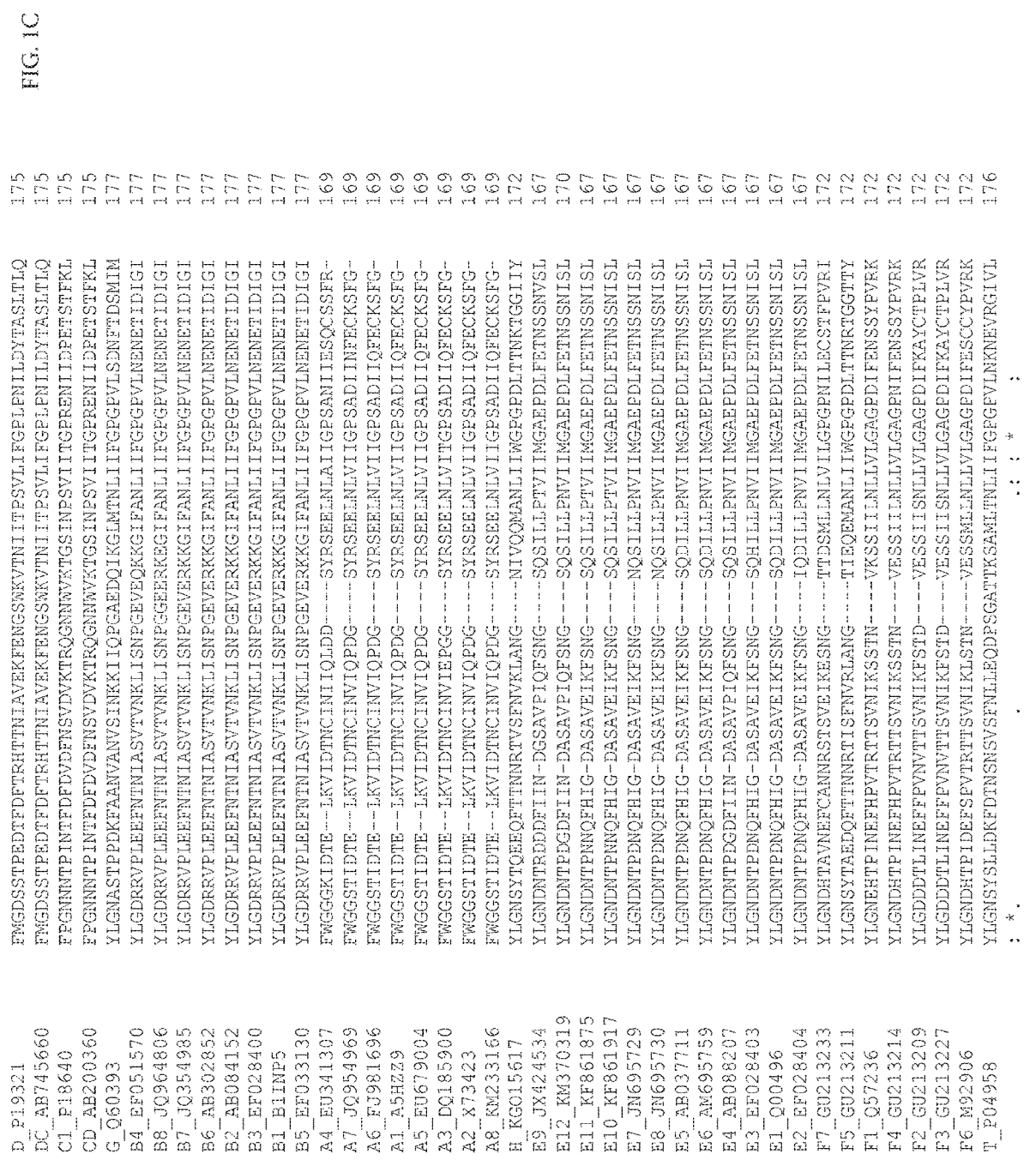
Figure 1D:
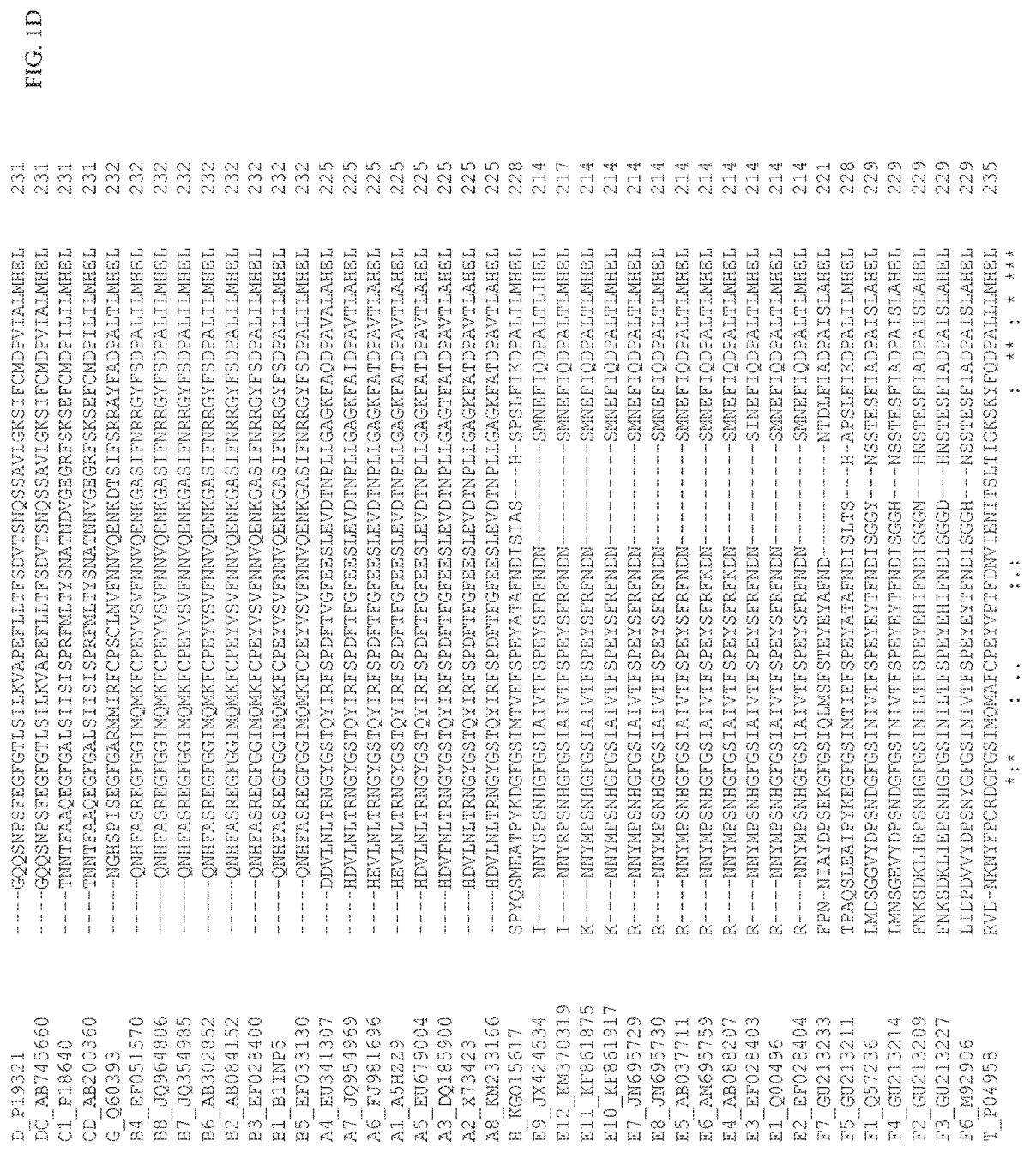
Figure 1E:
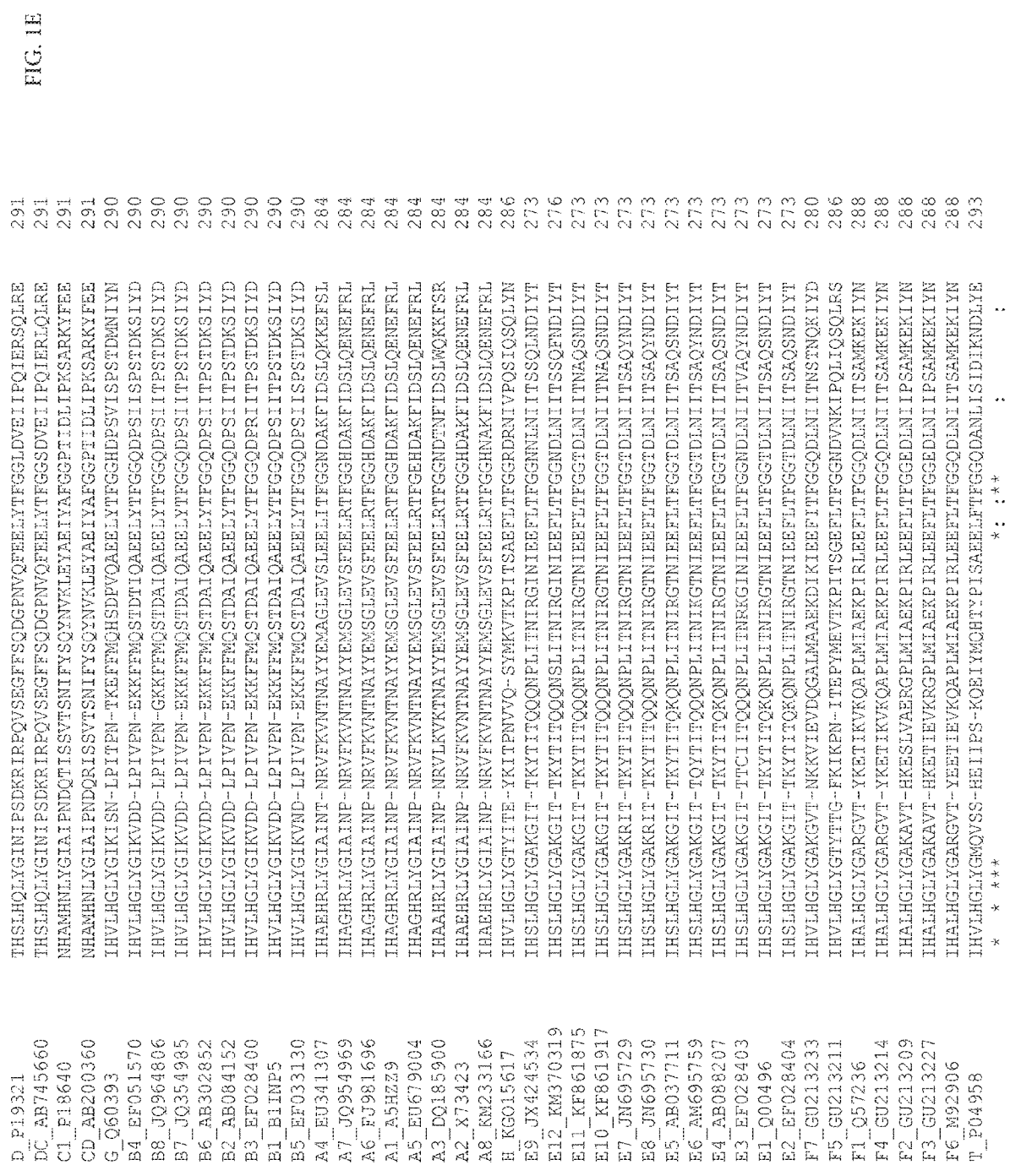
Figure 1F:
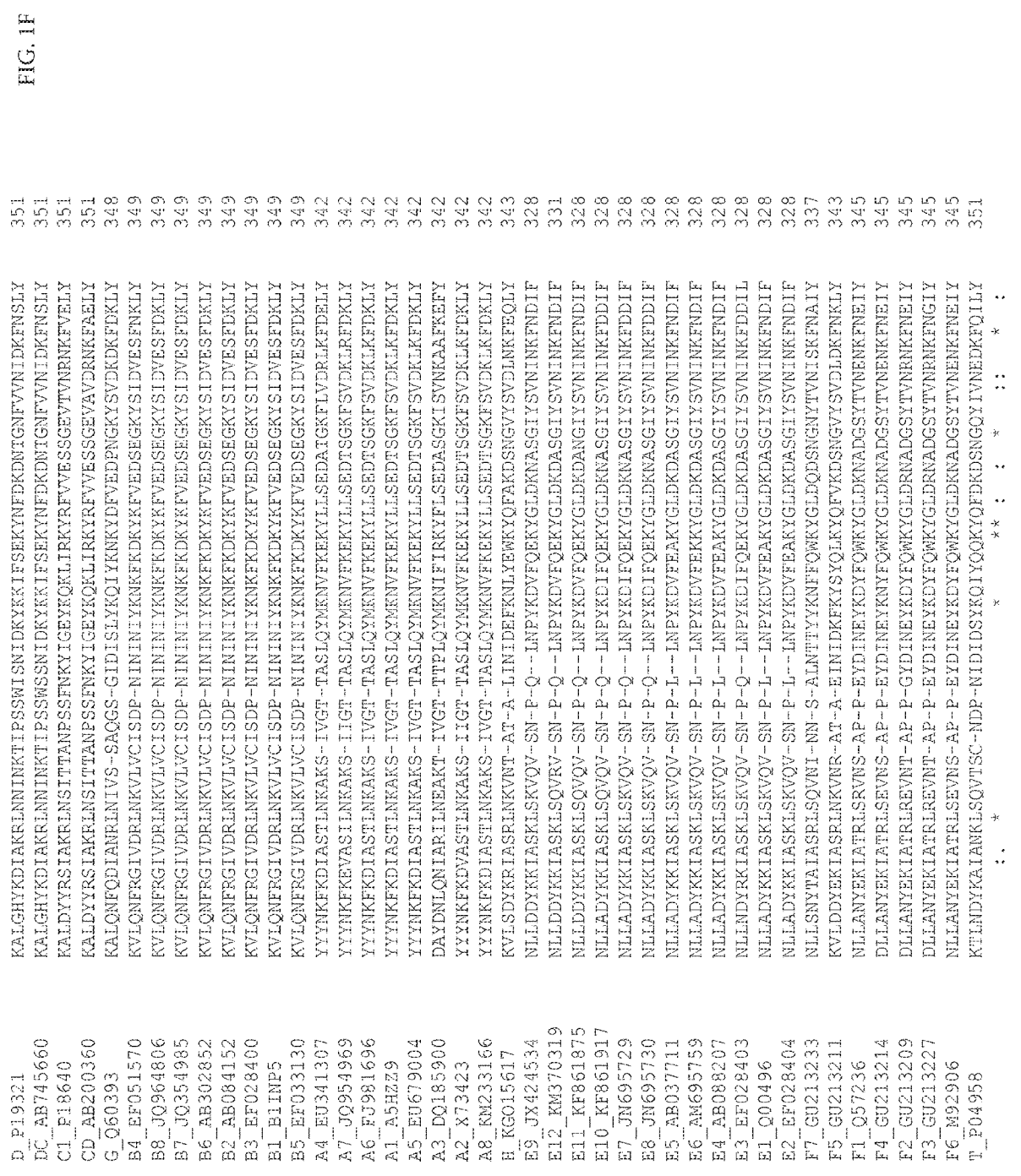
Figure 1G:
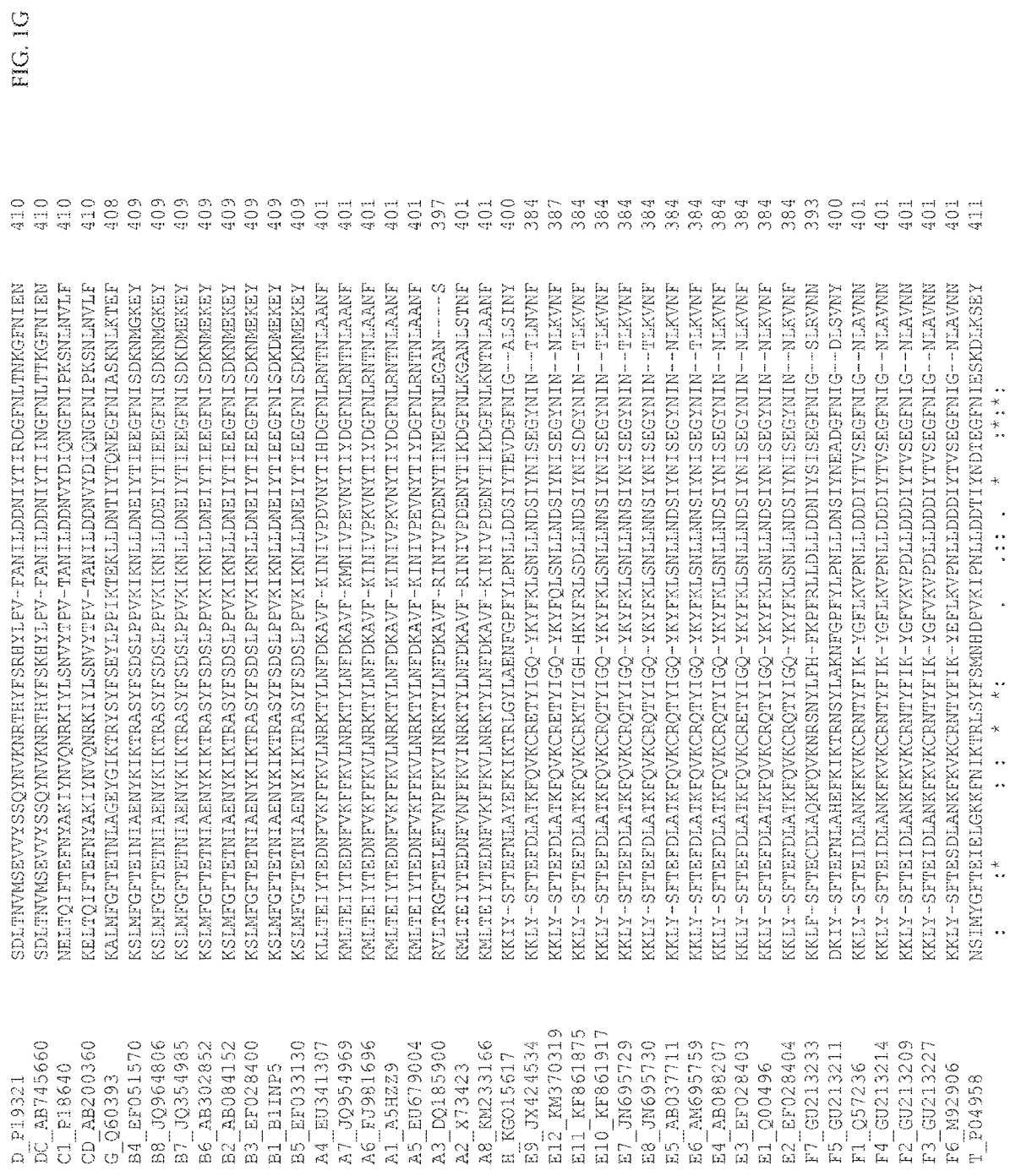
Figure 1H:
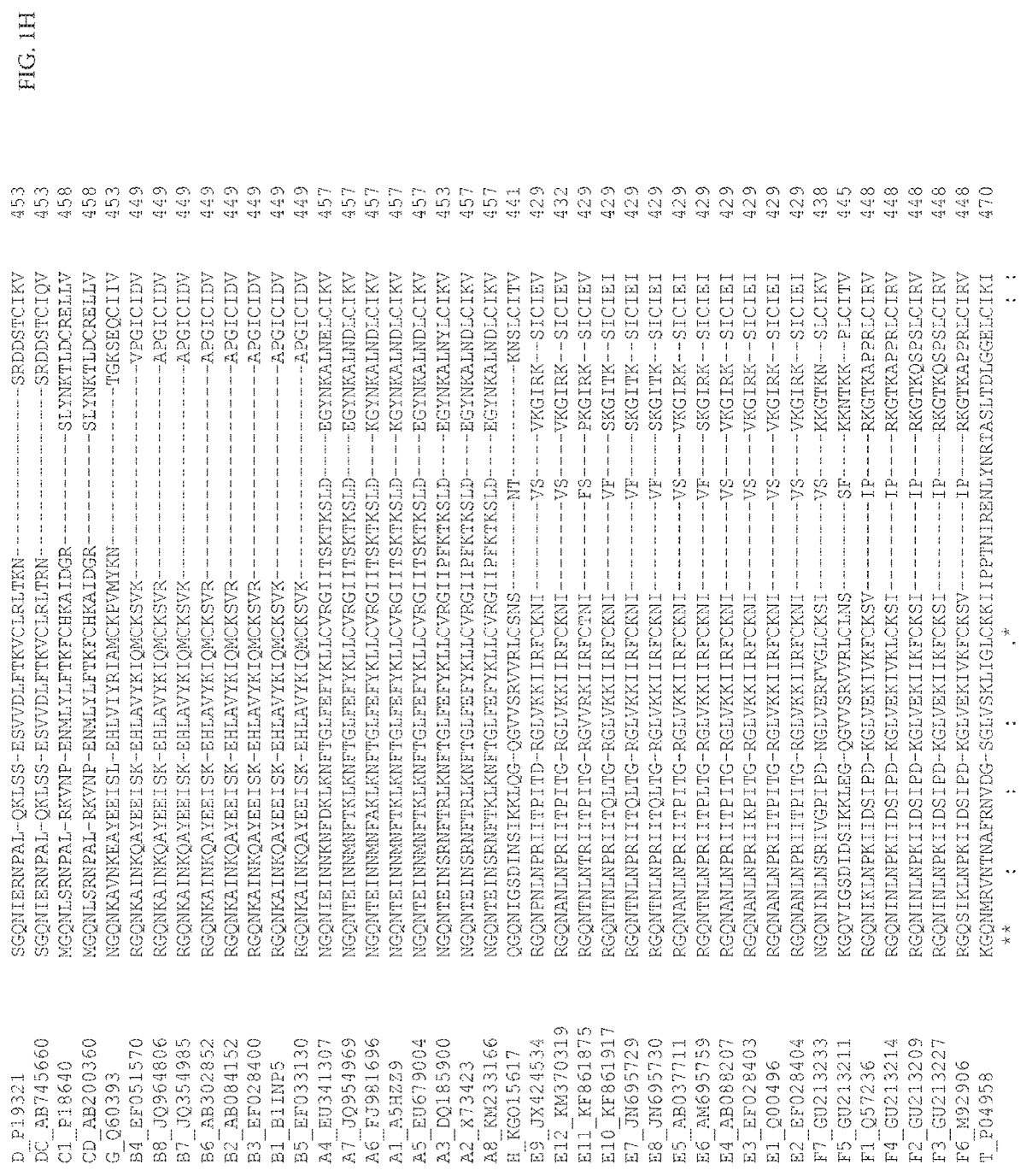
Figure 1J:
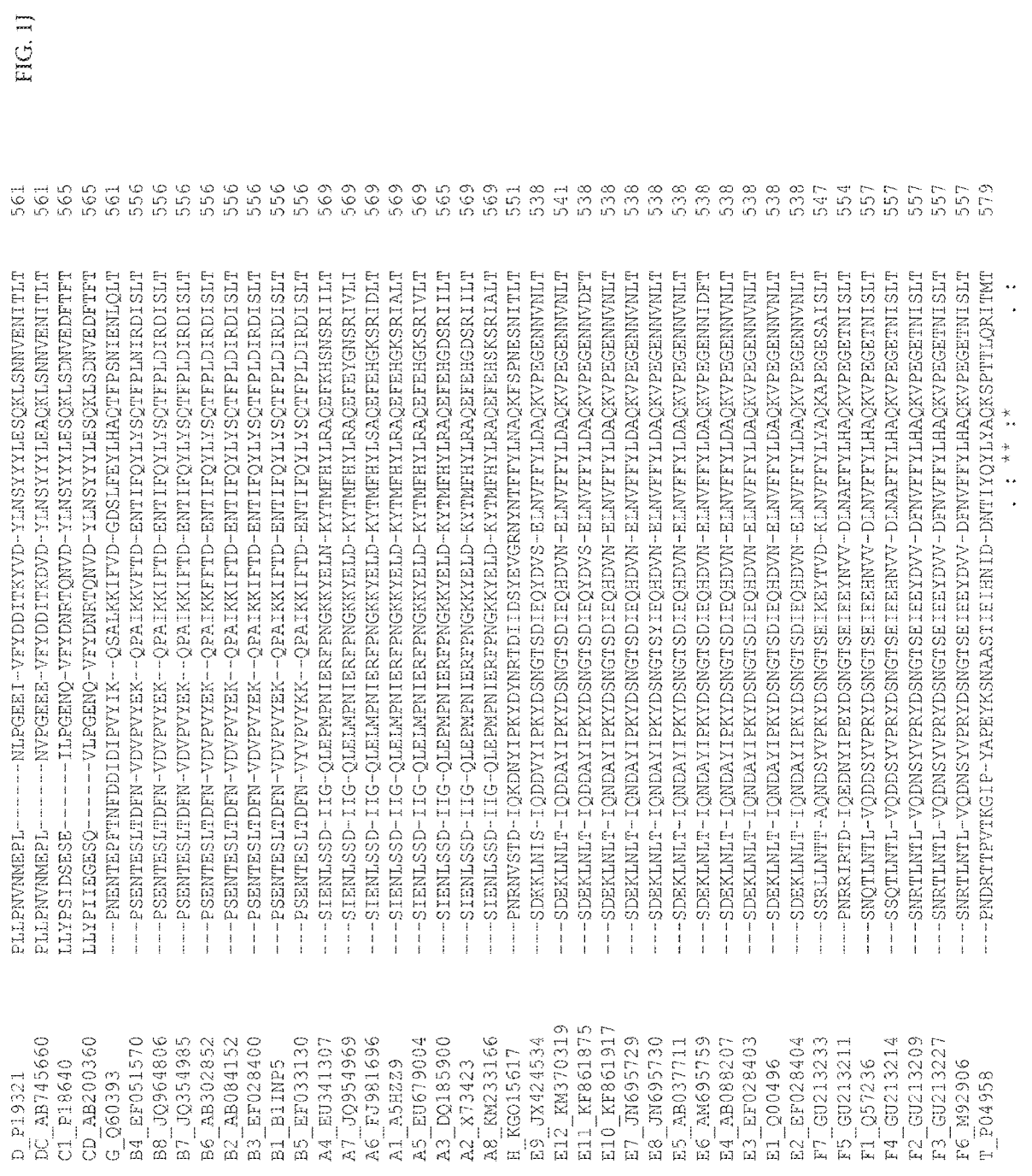
Figure 1K:
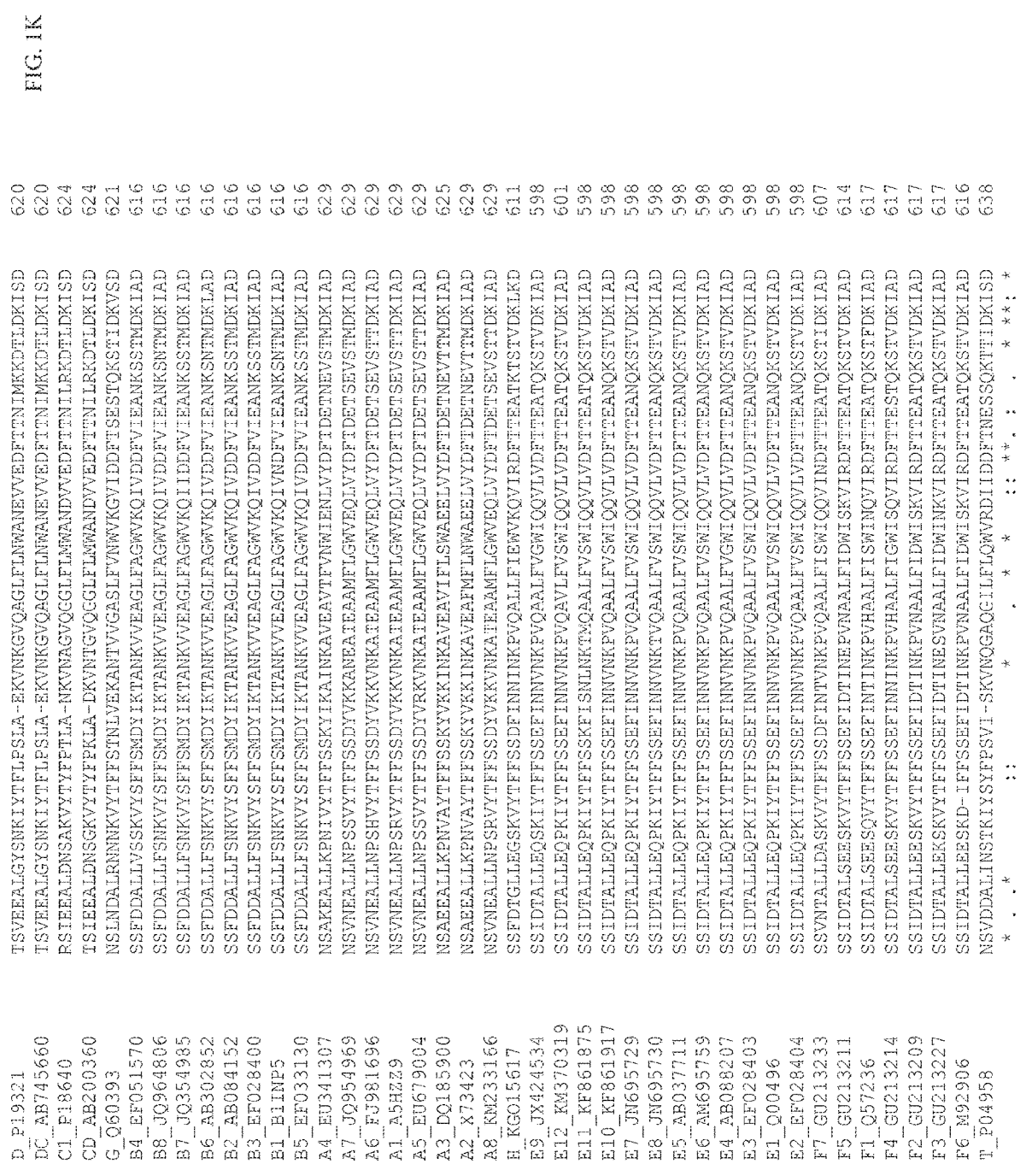
Figure 1E:
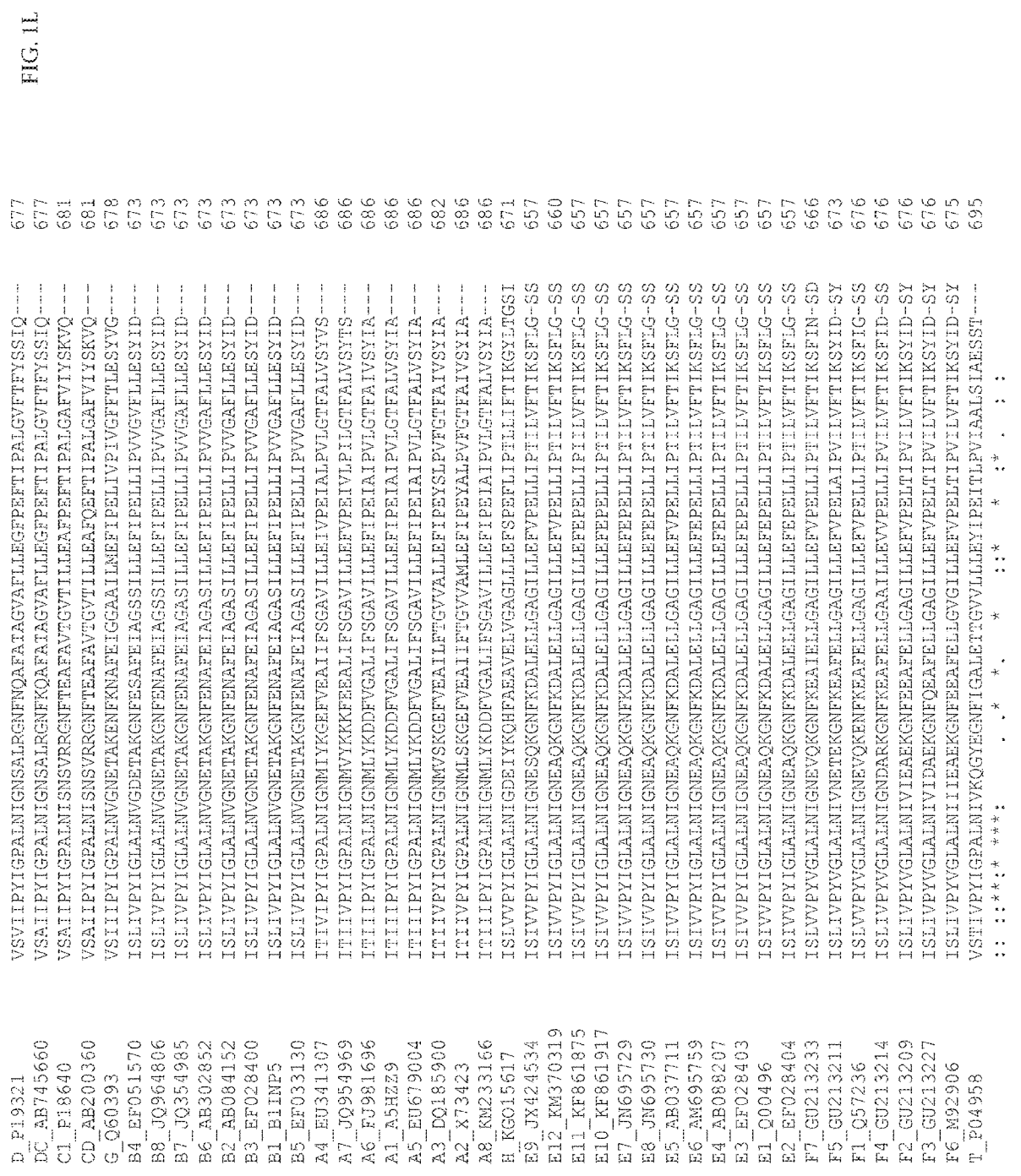
Figure 1M:
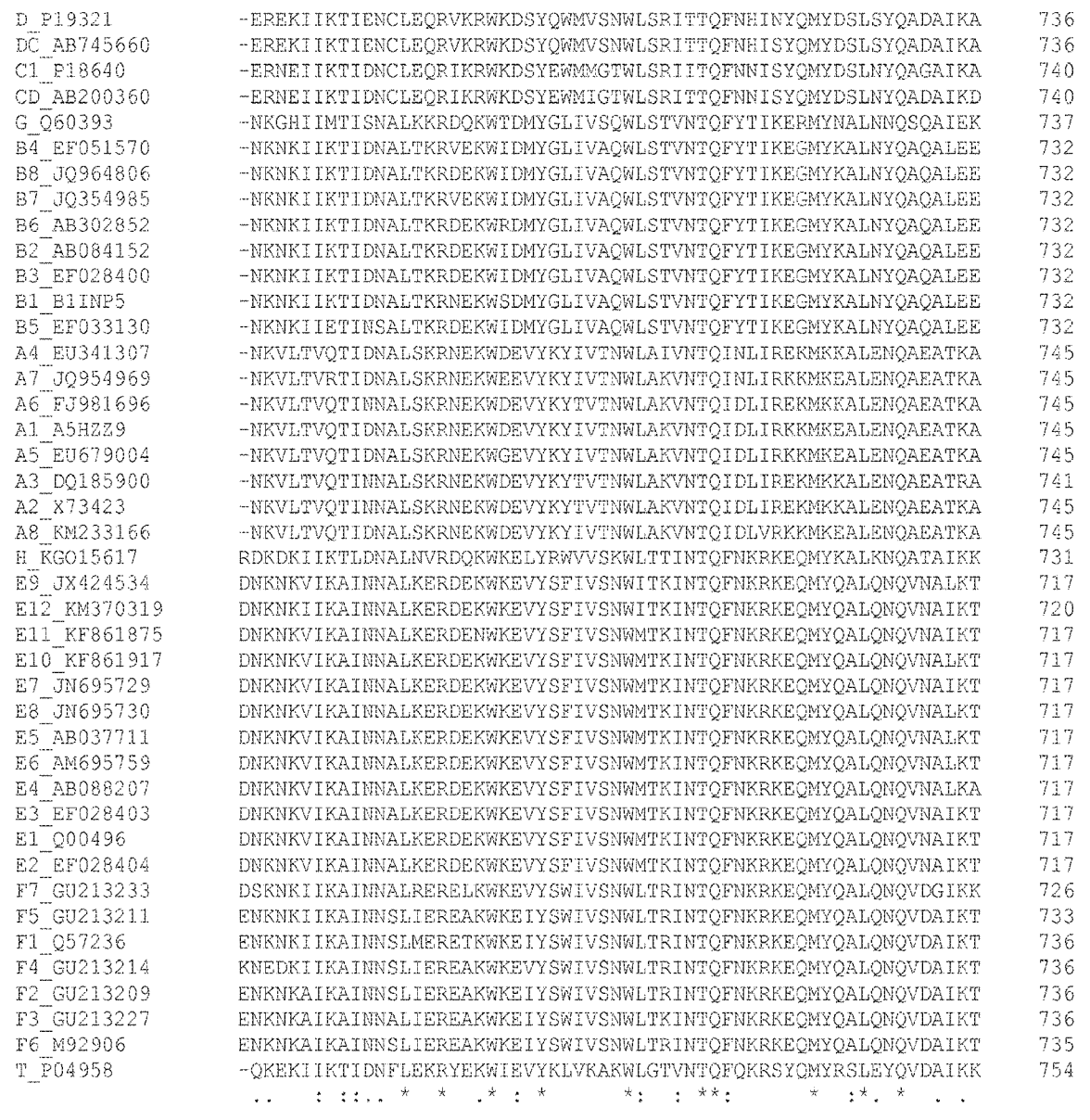
Figure 1N:
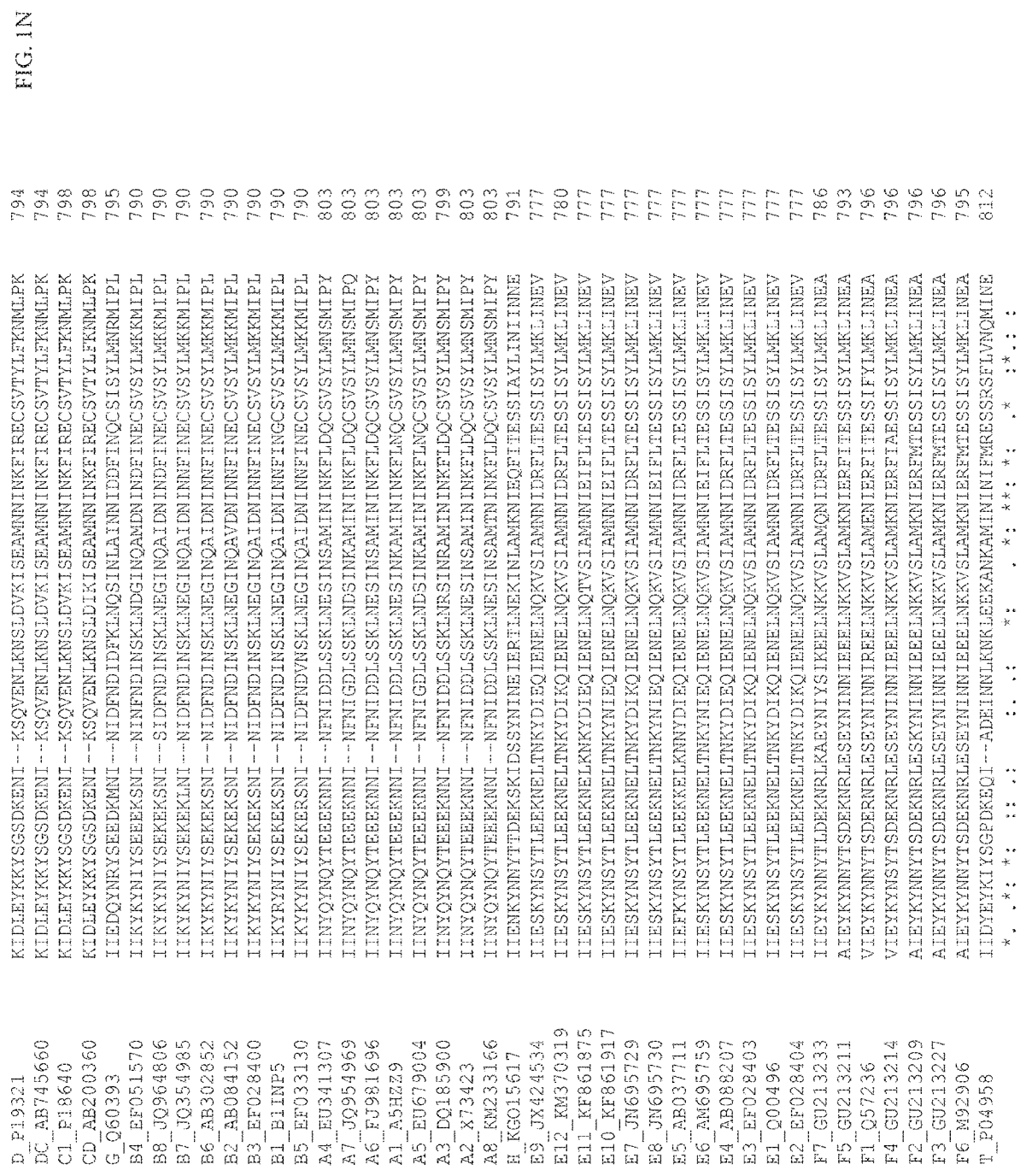
Figure 1P:
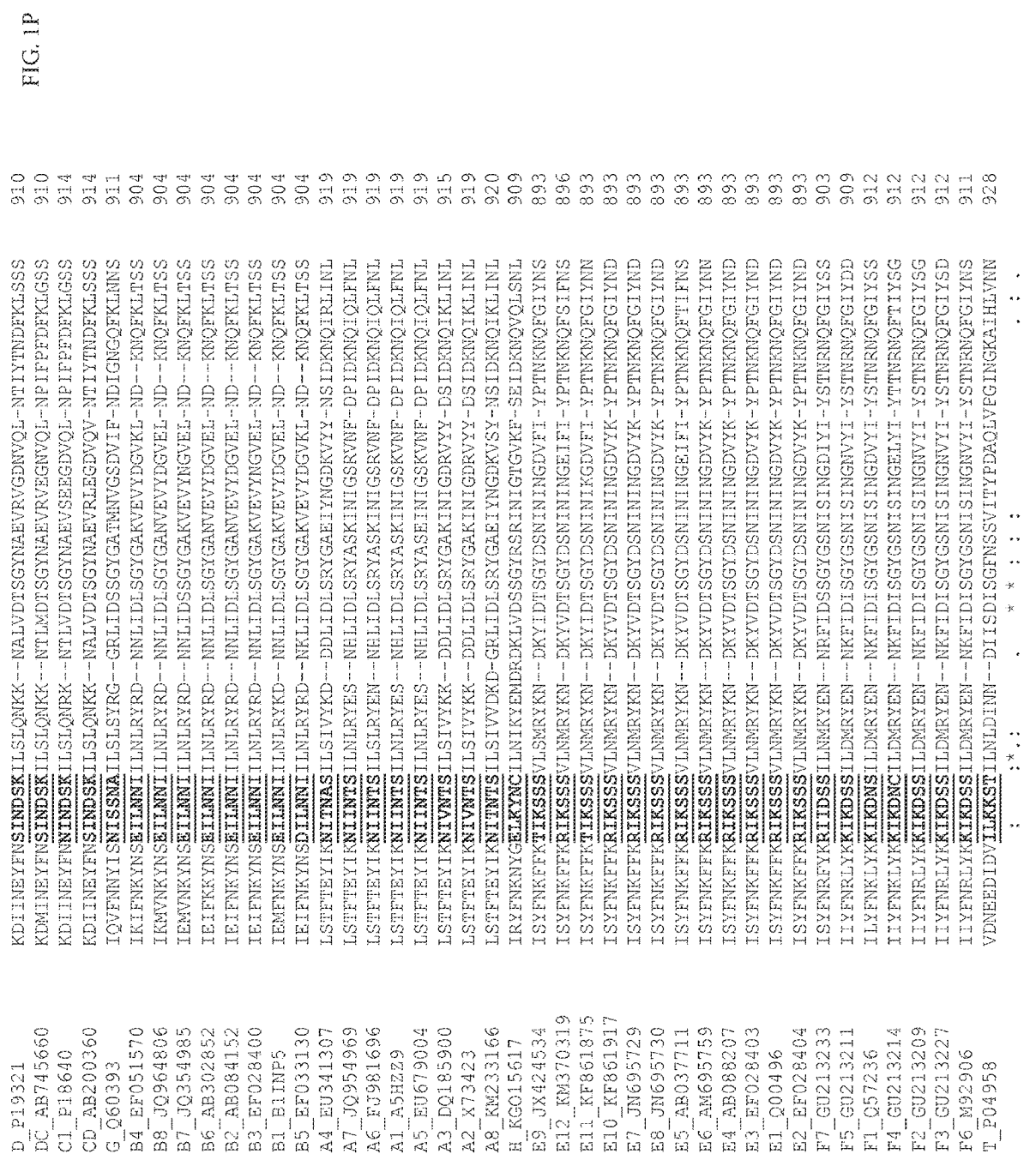
Figure 1Q:
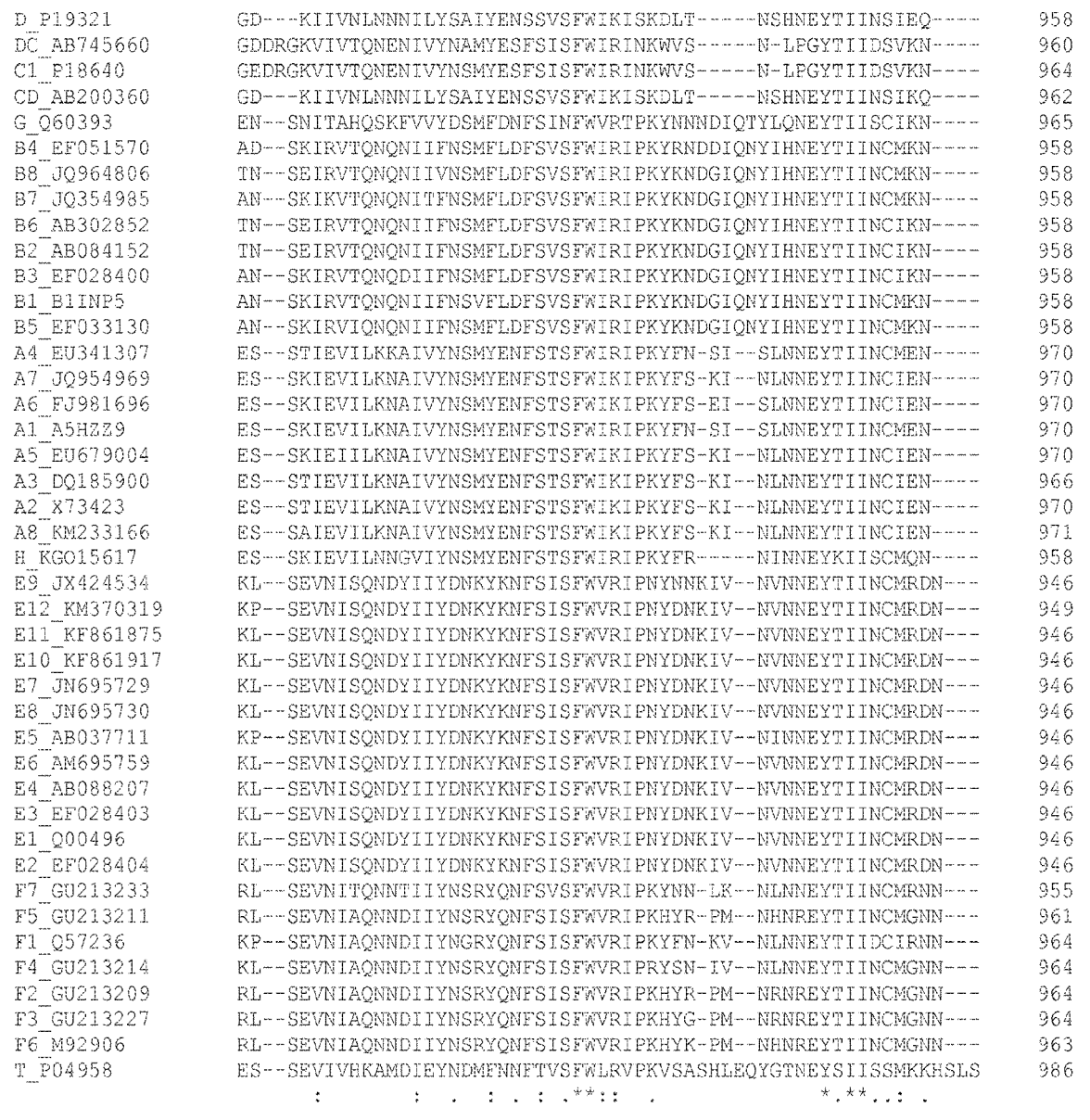
Figure 1R:
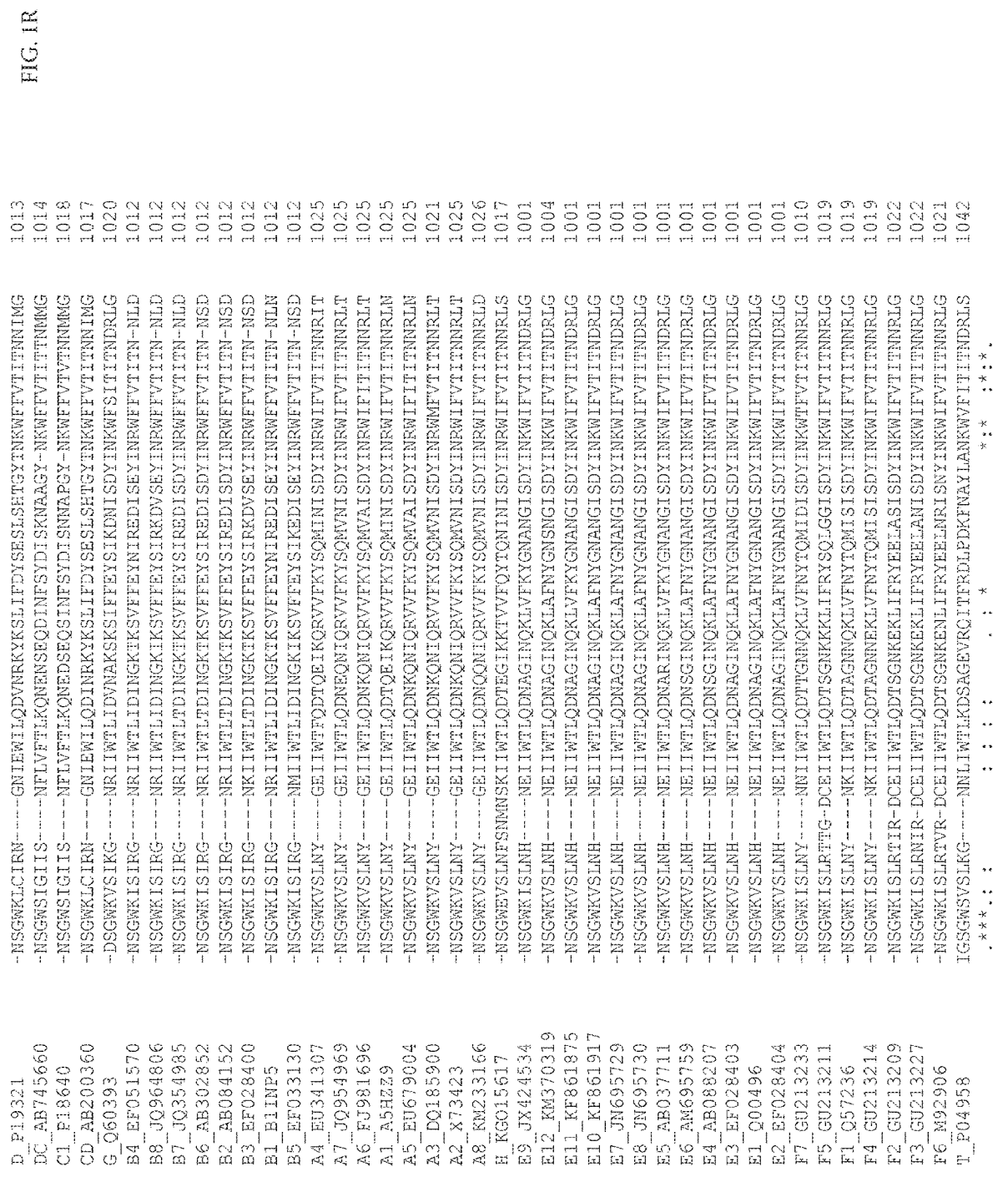
Figure 1S:
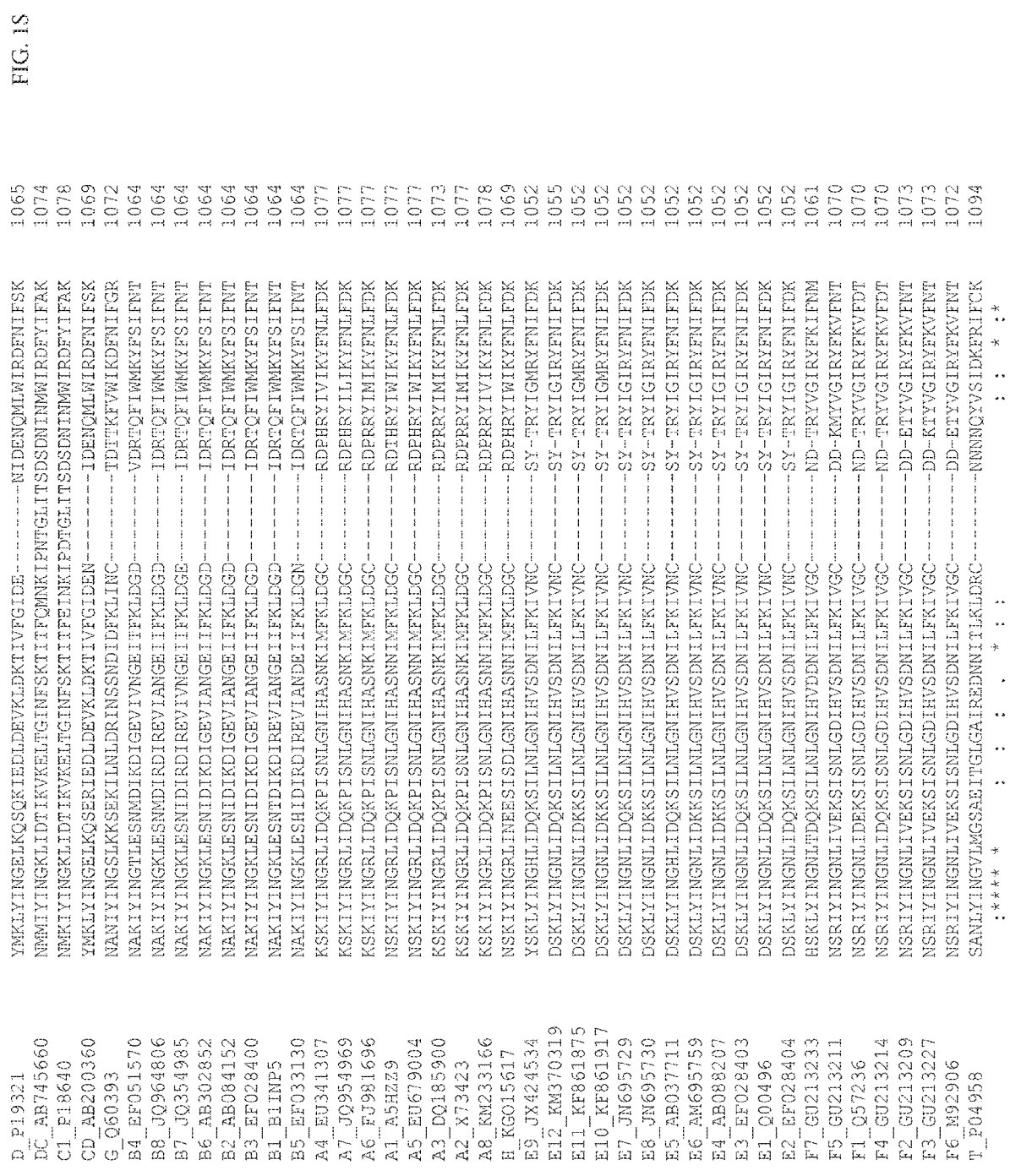
Figure 1T:
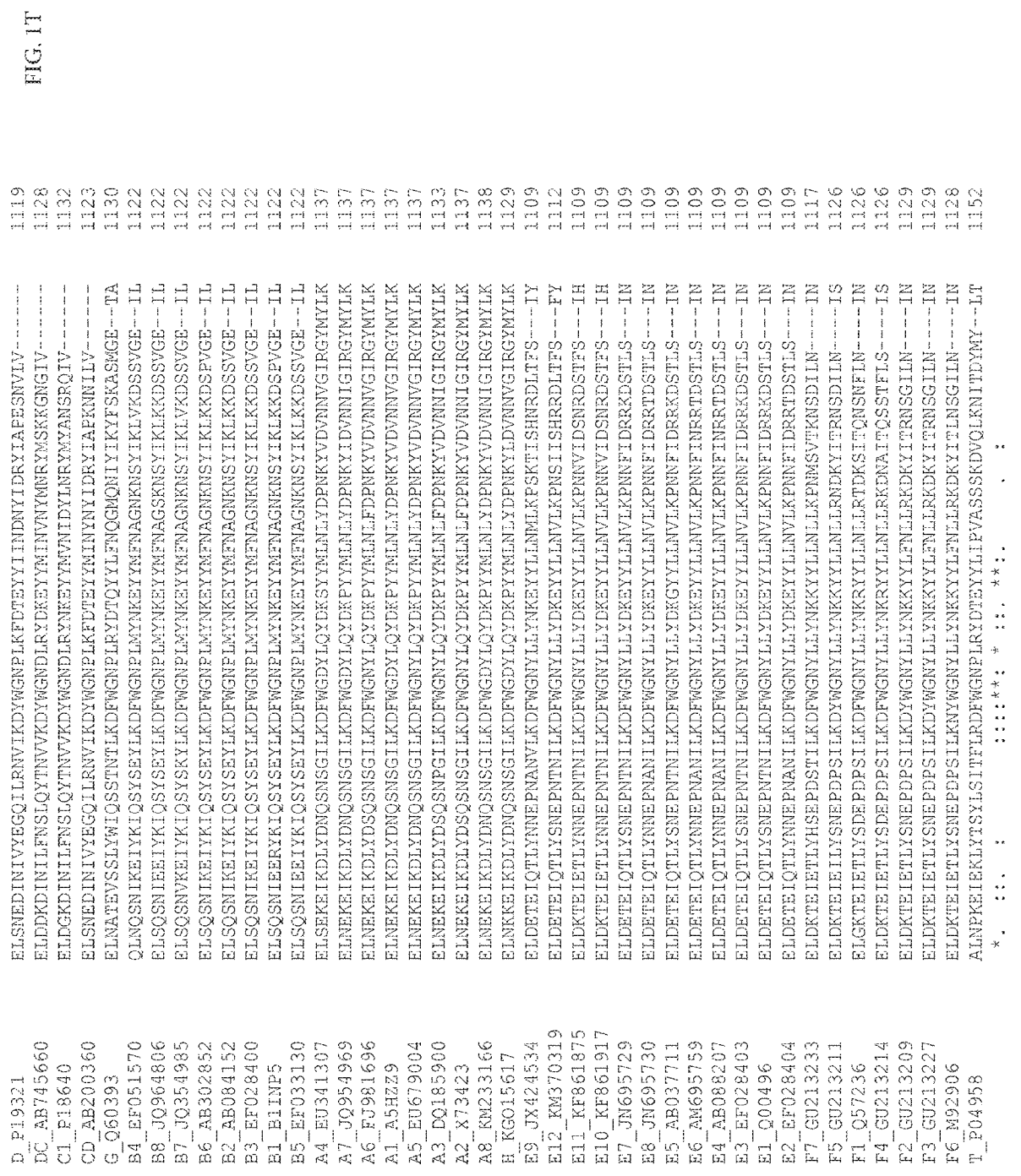
Figure 1U:
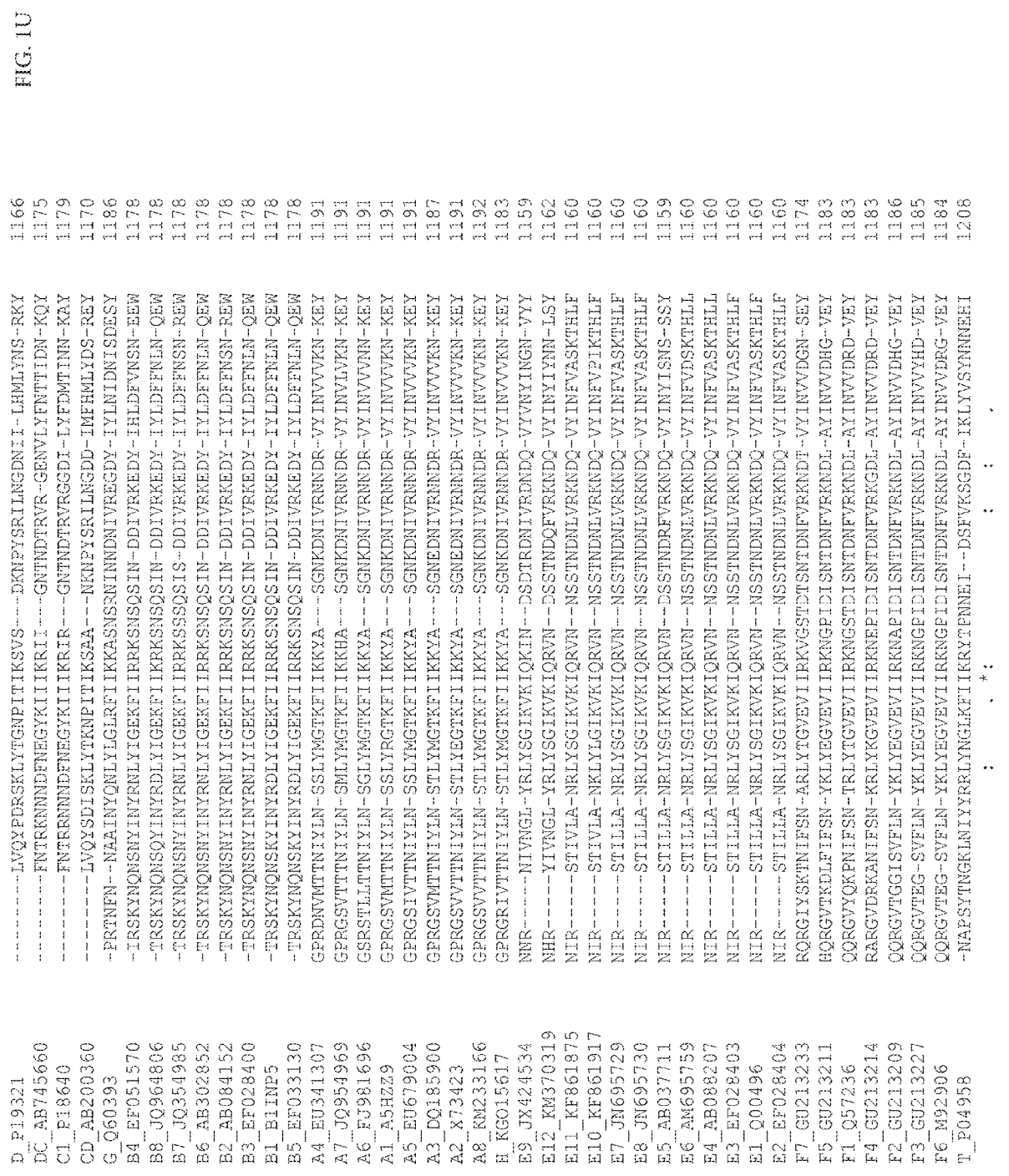
Figure 1V:
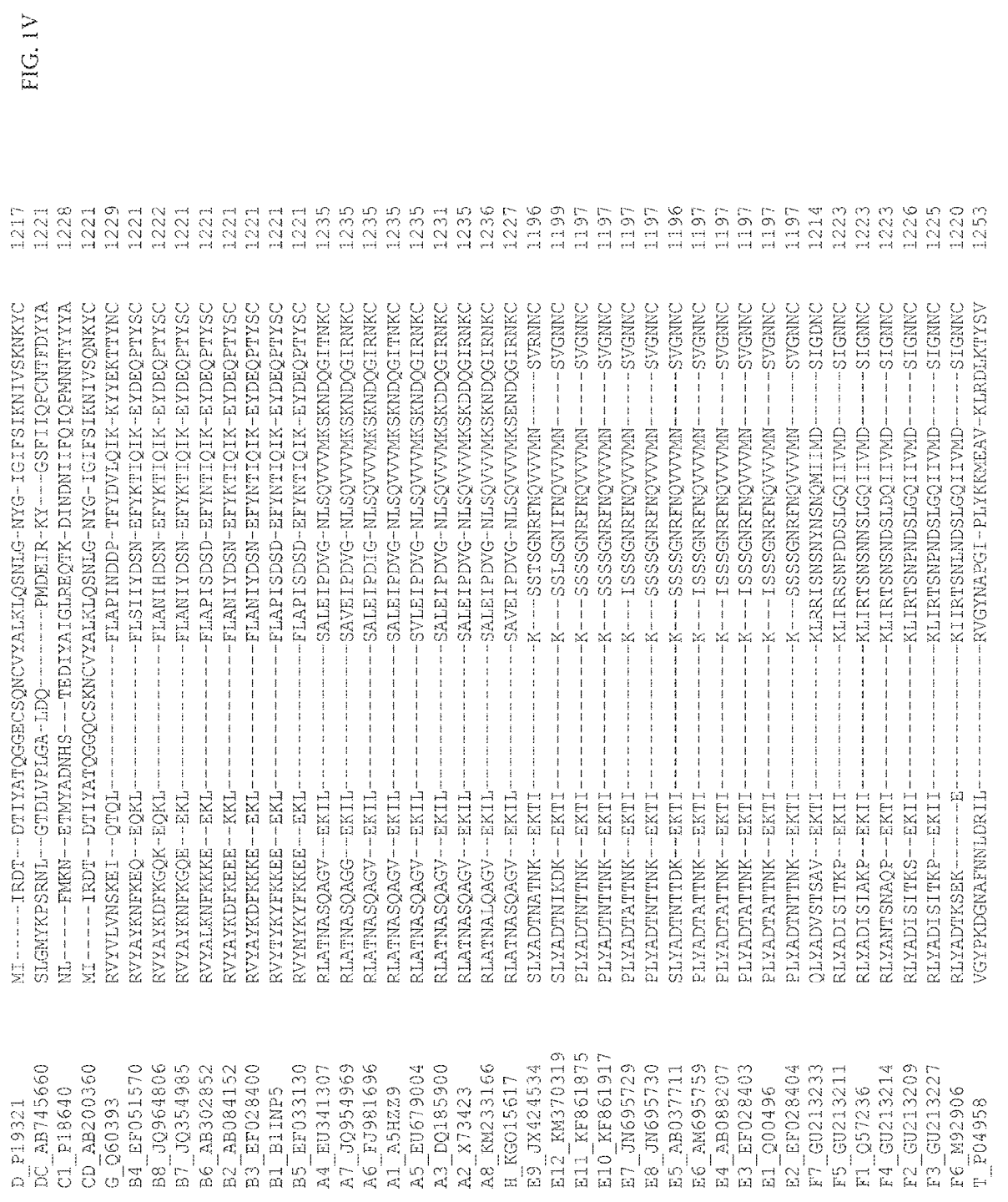
Figure 1W:
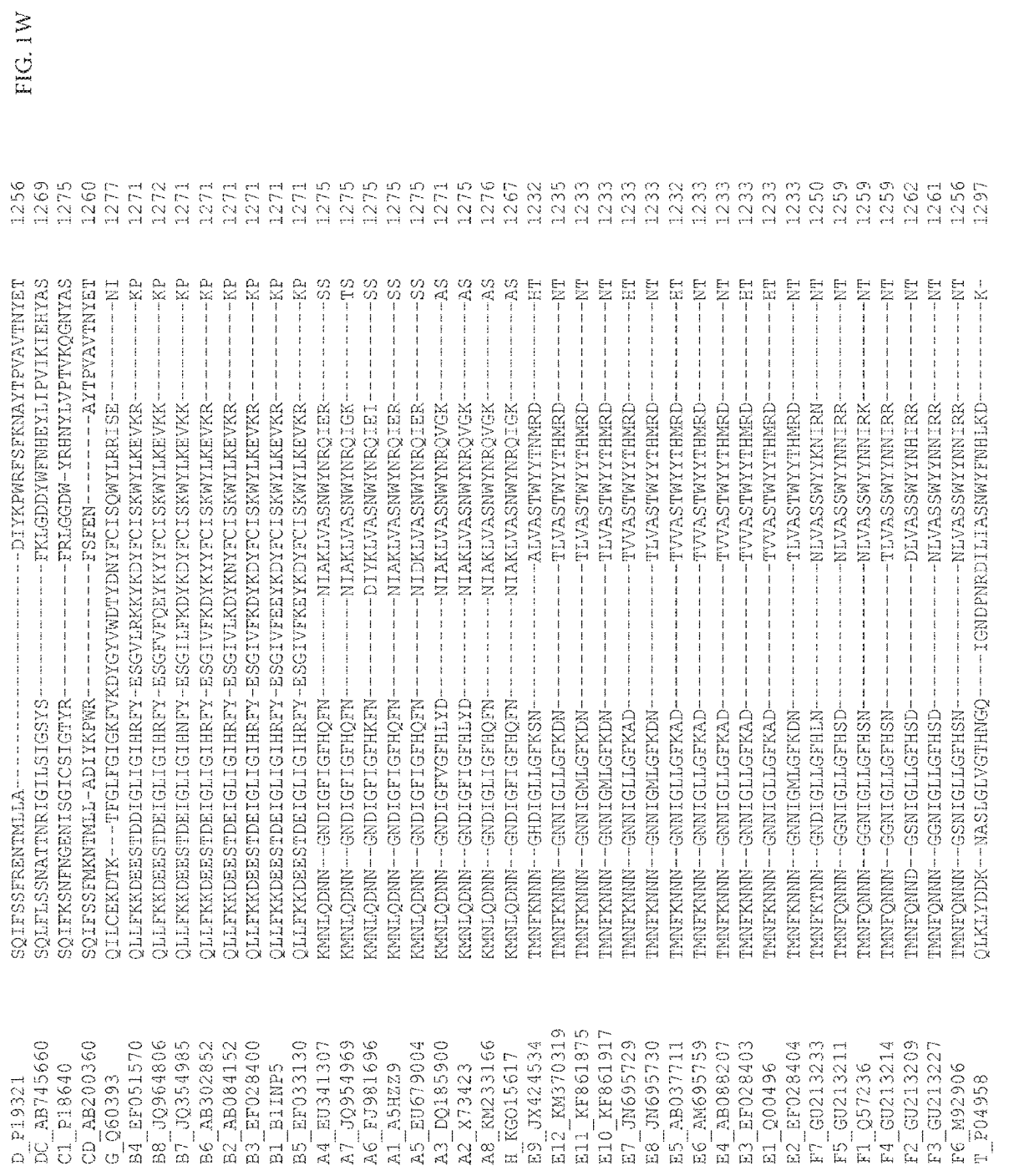

FIG. 1—Sequence alignment of BoNT/A1-8, /B1-8, /C, /D, /E1-12, /F1-7, /G, /"H", and TeNT using CLUSTAL Omega (1.2.1) multiple sequence alignment tool. The location of the putative $3_{10}$ helix separating the $LH_N$ and $H_C$ domains is in bold and underlined characters.

FIG. 2—SDS PAGE of purified recombinant BoNT/AB chimera 1, 2 and 3A (SEQ ID NO: 9, 10 and 11 respectively). Lanes are labelled "Marker" (molecular weight marker), "−DTT" (oxidised BoNT/AB chimera sample), and "+DTT" (reduced BoNT/AB chimera sample).

EXAMPLES

Figure 3:
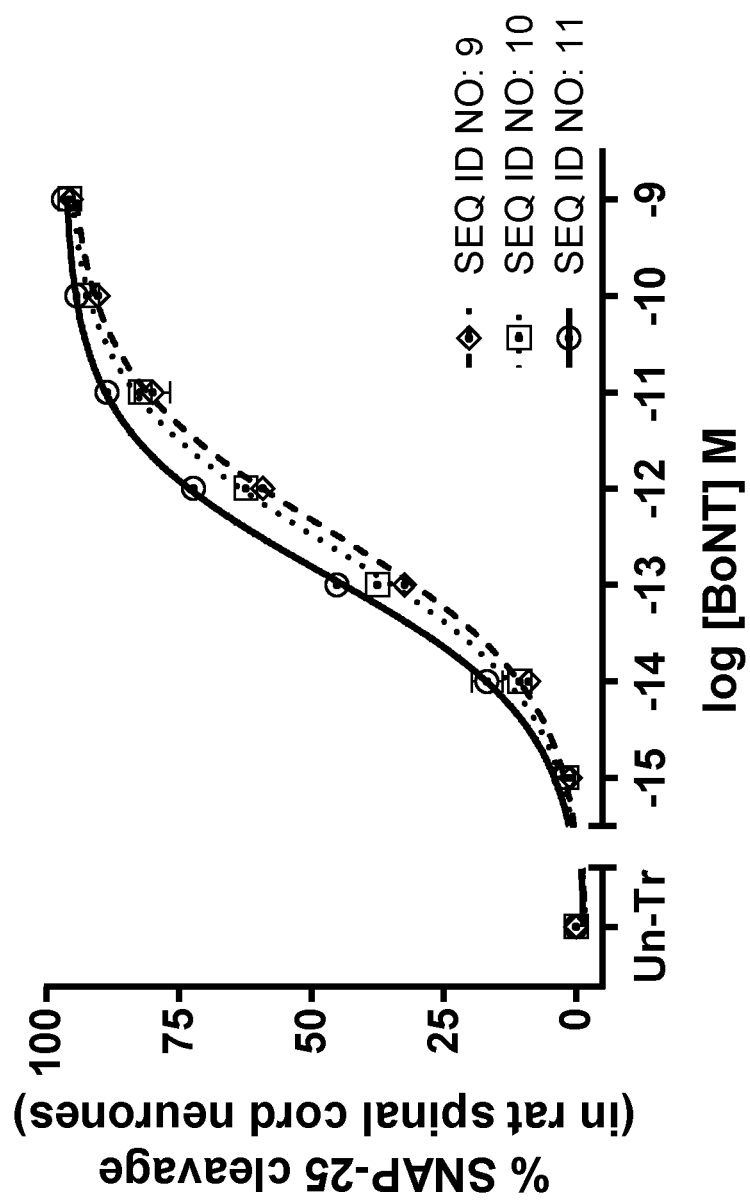
FIG. 3—Cleavage of SNAP-25 in rat spinal cord neurons by recombinant BoNT/AB chimera 1, 2 and 3A (SEQ ID Nos:9, 10 and 11 respectively). Cultured rat primary spinal cord neurons (SCN) were exposed to various concentrations of recombinant BoNT/AB chimera 1, 2 or 3A for 24 hours, at 37° C. in a humidified atmosphere with 10% $C(CO_2)$. Cells were then lysed with 1× NUPAGE™ buffer supplemented with DTT and BENZONASE® nuclease. The samples were transferred to microcentrifuge tubes, heated for 5 min at 90° C. on heat block and stored at −20° C. before analysis of SNAP-25 cleavage by Western blot. SNAP-25 was detected using a polyclonal antibody, that detects both the full length and cleaved forms of SNAP-25 (Sigma #S9684). Anti-rabbit HRP (Sigma #A6154) Vas used as the secondary antibody.

The following Examples serve to illustrate particular embodiments of the invention, and do not limit the scope of the invention defined in the claims in any way.

Example 1

Mapping of $3_{10}$ Helix in Clostridial Neurotoxins

The amino acid sequences of all BoNT serotypes and TeNT were obtained from a public database (e.g., UNI-PROT® or the National Center for Biotechnology Information) NCBI and then modelled onto the known crystal structure of BoNT/A1 (3BTA.pdb) using LOOPP. This yielded a predicted protein structure which was edited to retain only to N-terminal part of the HCN domain and ~80 residues before it (C-terminal part of the $H_N$ domain)—this domain ("$H_N/H_{CN}$") is structurally highly conserved, therefore, making it the best region to superimpose different serotypes. Each edited structure was then superimposed onto 3BTA.pdb using SuperPose and the residues corresponding to a conspicuous $3_{10}$helix at the start of the $H_C$ of BoNT/A1 ($^{872}$NIINTS$^{876}$) and corresponding residues in the other serotype were then identified. These were cross-checked with a sequence alignment of all BoNT serotypes with Clustal Omega (FIG. 1).

By identifying this region of structural equivalence between different neurotoxins, it was possible to identify a specific point at which a C-terminal half of one neurotoxin may transition over to a N-terminal half of another neurotoxin without interrupting the secondary structure of the overall molecule. This point was chosen to be the start of the $3_{10}$ helix.

The results are presented in table 2 above.

Example 2

Cloning, Expression and Purification of BoNT/AB Chimeras

BoNT/AB chimeric constructs 1, 2, 3A, 3B, and 3C (SEQ ID NO: 9 to 13) were constructed from DNA encoding the parent serotype molecule and appropriate oligonucleotides using standard molecular biology techniques. These were then cloned into the pJ401 expression vector with or without a C-terminal His$_{10}$-tag and transformed into BLR (DE3) *E. coli* cells for over-expression. These cells were grown at 37° C. and 225 RPM shaking in 2 L baffled conical flasks containing 1 L modified Terrific Broth (mTB) supplemented with the appropriate antibiotic. Once the $A_{600}$ reached >0.5, the incubator temperature was decreased to 16° C., and then induced with 1 mM IPTG an hour later for 20 h at 225 RPM shaking, to express the recombinant BoNT/AB construct.

Harvested cells were lysed by ultrasonication and clarified by centrifugation at 4500 RPM for 1 h at 4° C. The recombinant BoNT/AB chimeric molecules were then extracted in ammonium sulphate and purified by standard fast protein liquid chromatography (FPLC) techniques. This involved using a hydrophobic interaction resin for capture and an anion-exchange resin for the intermediate purification step. The partially purified molecules were then proteolytically cleaved with endoproteinase Lys-C to yield the active di-chain. This was further purified with a second hydrophobic interaction resin to obtain the final BoNT/AB chimera.

For BoNT/AB chimeric molecules with a decahistadine tag ($H_{10}$) (chimera 1, 2, 3A), the capture step employed the use of an immobilised nickel resin instead of the hydrophobic interaction resin.

The sequence of each chimera is presented in table 3.

TABLE 3 chimeric BoNT/AB constructs

| Molecule | SEQ ID NO | Sequence |
|---|---|---|
| Chimera 1 | 9 | A1: 1-871 + B1: 858-1291 (E1191M/S1199Y) + $His_{10}$-tag |
| Chimera 2 | 10 | A1: 1-874 + ELGGGGSEL + B1: 858-1291 (E1191M/S1199Y) + $His_{10}$-tag |
| Chimera 3A | 11 | A1: 1-872 + B1: 860-1291 (E1191M/S1199Y) + $His_{10}$-tag |
| Chimera 3B | 12 | A1: 1-872 + B1: 860-1291 (E1191M/S1199Y) |
| Chimera 3C | 13 | A1: 1-872 + B1: 860-1291 |

Example 3

Comparison of BoNT/AB Chimera 1, 2 and 3A

BoNT/AB chimera 1, 2 and 3A which have a C-terminal $His_{10}$ tag and E1191M/S1199Y double mutation were purified as described in Example 1 (FIG. 2) and tested for functional activity.

Rat Spinal Cord Neurons SNAP-25 Cleavage Assay

Primary cultures of rat spinal cord neurons (SCN) were prepared and grown, for 3 weeks, in 96 well tissue culture plates (as described in: Masuyer et al., 2011, J. Struct. Biol. Structure and activity of a functional derivative of *Clostridium botulinum* neurotoxin B; and in: Chaddock et al., 2002, Protein Expr. Purif. Expression and purification of catalytically active, non-toxic endopeptidase derivatives of *Clostridium botulinum* toxin type A). Serial dilutions of BoNT/AB were prepared in SCN feeding medium. The growth medium from the wells to be treated was collected and filtered (0.2 µm filter). 125 µL of the filtered medium was added back to each test well. 125 µL of diluted toxin was then added to the plate (triplicate wells). The treated cells were incubated at 37° C., 10% $CO_2$, for 24±1 h).

Analysis of BoNT Activity Using the SNAP-25 Cleavage Assay

Following treatment, BoNT was removed and cells were washed once in PBS (Gibco, UK). Cells were lysed in 1× NUPAGE™ lysis buffer (Life Technologies) supplemented with 0.1 M dithiothreitol (DTT) and 250 units/mL BENZO-NASE® nuclease (Sigma). Lysate proteins were separated by SDS-PAGE and transferred to nitrocellulose membranes. Membranes were probed with a primary antibody specific for SNAP-25 (Sigma #S9684) which recognizes uncleaved SNAP-25 as well as SNAP-25 cleaved by the BoNT/A endopeptidase. The secondary antibody used was an HRP-conjugated anti-rabbit IgG (Sigma #A6154). Bands were detected by enhanced chemiluminescence and imaged using a pXi6 Access (Synoptics, UK). The intensity of bands was determined using GENETOOLS® software (Syngene, Cambridge, UK) and the percentage of SNAP-25 cleaved at each concentration of BoNT calculated. Data were fitted to a 4-parameter logistic equation and $pEC_{50}$ calculated using GRAPHPAD PRISM® version 6 (GraphPad).

Table 4 below provides the $pEC_{50}$ values determined for Chimera 1, 2 and 3A in the rat SCN SNAP-25 cleavage assay. These results show that the three BoNT/AB chimeras retained the ability to enter rat spinal cord neurons and cleave their target substrate. However, chimera 3A was more potent than chimera 1 and 2 in this assay (see also FIG. 3).

TABLE 4

| | $pEC_{50}$ ± SEM |
|---|---|
| Chimera 1 | 12.42 ± 0.04 |
| Chimera 2 | 12.57 ± 0.01 |
| Chimera 3A | 12.89 ± 0.04 |

Digit Abduction Scoring (DAS) Assay

The method to measure the activity of BoNT/AB chimera 1, 2 and 3A in the DAS assay is based on the startled response toe spreading reflex of mice, when suspended briefly by the tail. This reflex is scored as Digit Abduction Score (DAS) and is inhibited after administration of BoNT into the gastrocnemius-soleus muscles of the hind paw. Mice are suspended briefly by the tail to elicit a characteristic startled response in which the animal extends its hind limb and abducts its hind digits. (Aoki et al. 1999, Eur. J. Neurol.; 6 (suppl. 4) S3-S10)

On the day of injection, mice were anaesthetized in an induction chamber receiving isoflurane 3% in oxygen. Each mouse received an intramuscular injection of BoNT/AB chimera or vehicle (phosphate buffer containing 0.2% gelatine) in the gastrocnemius-soleus muscles of the right hind paw.

Following neurotoxin injection, the varying degrees of digit abduction were scored on a scale from zero to four, where 0=normal and 4=maximal reduction in digit abduction and leg extension. $ED_{50}$ was determined by nonlinear adjustment analysis using average of maximal effect at each dose. The mathematical model used was the 4 parameters logistic model.

DAS was performed every 2 hours during the first day after dosing; thereafter it was performed 3 times a day for 4 days.

Figure 4:
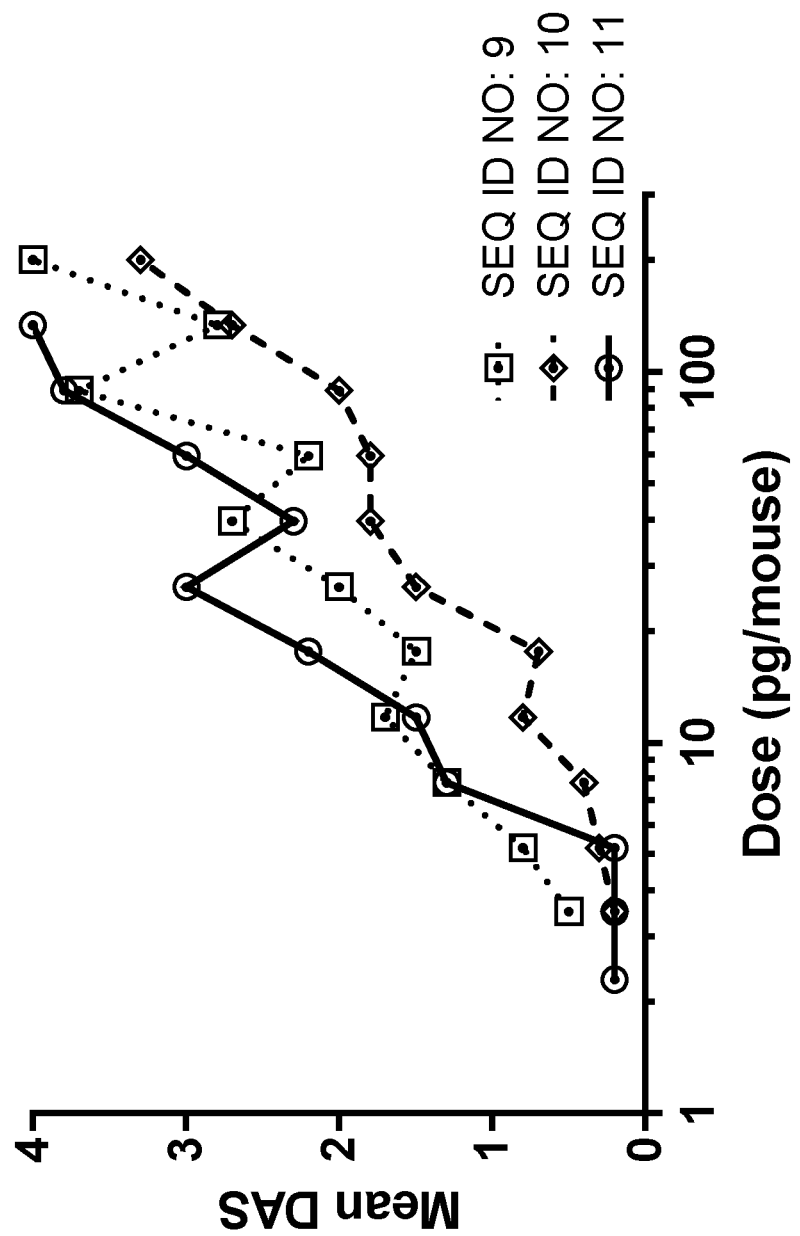
FIG. 4—Mouse digit abduction scoring assay. Mice were injected into the gastrocnemius-soleus complex muscles of one hind limb, under short general anaesthesia; muscle weakening was measured on a 0-4 scale using the digit abduction score (DAS). DAS max values were determined for each dose and plotted against dose and the data were fitted to a 4-parameter logistic equation, $ED_{50}$ and dose leading to DAS 4 (DAS 4 dose) values were determined.

FIG. 4 shows the fitted curves for chimera 1, 2 and 3A (SEQ ID NO: 9, 10 and 11 respectively). The chimera 3A curve is shifted to the left, meaning lower doses of chimera 3A achieved a similar DAS response compared to chimera 1 and 2, therefore showing that chimera 3A is more potent than the others in the mouse DAS assay; see also the table below (table 5) that provides the values for the calculated $ED_{50}$ and the dose leading to DAS 4 (highest score) for each chimera.

Table 5 below provides the $ED_{50}$ and DAS 4 doses determined for recombinant BoNT/A1 (rBoNT/A1) and chimeras 1, 2 and 3A in the mouse DAS assay. These results show that of the three chimeras, chimera 3A has the highest in vivo potency in inducing muscle weakening. Studies shown in FIG. 4 and table 5 were performed in mice obtained from Charles River laboratories.

TABLE 5

| | $ED_{50}$ (pg/mouse) | DAS 4 dose (pg/mouse) |
|---|---|---|
| rBoNT/A1 | 1 | 5 |
| Chimera 1 | 23 | 200 |

TABLE 5-continued

|  | ED$_{50}$ (pg/mouse) | DAS 4 dose (pg/mouse) |
|---|---|---|
| Chimera 2 | 89 | >300 |
| Chimera 3A | 18 | 133 |

Example 4

Comparison of BoNT/AB Chimera 3B, 3C and BoNT/A1

Figure 5:
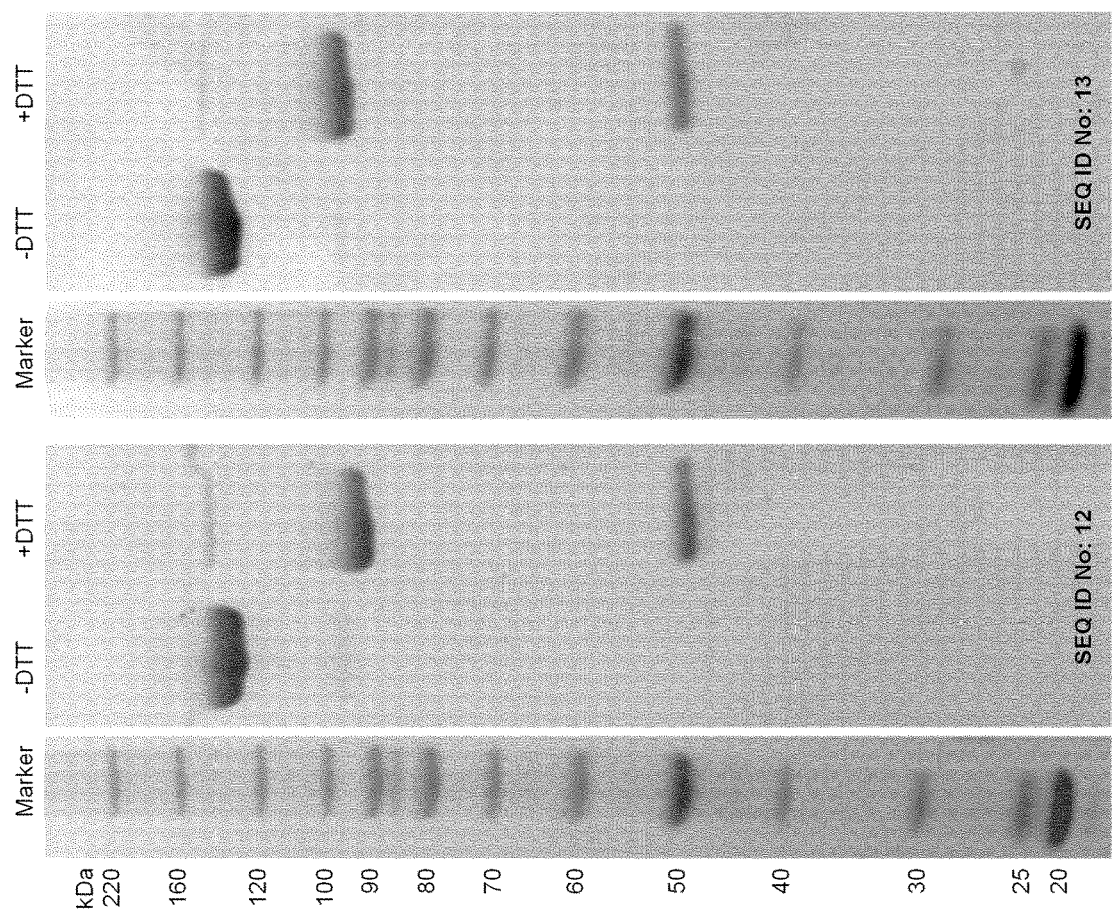
FIG. 5—SDS PAGE of purified recombinant BoNT/AB chimera 3B and 3C (SEQ ID NO: 12 and 13 respectively). Lanes are labelled "Marker" (molecular weight marker), "−DTT" (oxidised BoNT/AB chimera sample), and "+DTT" (reduced BoNT/AB chimera sample).

Untagged BoNT/AB chimera 3B and 3C, respectively with and without the presence of the E1191M/S1199Y double mutation (SEQ ID NO: 12 and 13) were purified as described in Example 1 (FIG. 5), and tested for functional activity using recombinant BoNT/A1 (SEQ ID NO: 1) as a reference.

Human Pluripotent Stem Cells SNAP-25 Cleavage Assay

Cryopreserved PERI.4U-cells were purchased from Axiogenesis (Cologne, Germany). Thawing and plating of the cells were performed as recommended by the manufacturer. Briefly, cryovials containing the cells were thawed in a water bath at 37° C. for 2 minutes. After gentle resuspension the cells were transferred to a 50 mL tube. The cryovial was washed with 1 mL of PERI.4U® thawing medium supplied by the manufacturer and the medium was transferred drop-wise to the cell suspension to the 50 mL tube, prior to adding a further 2 mL of PERI.4U® thawing medium drop-wise to the 50 mL tube. Cells were then counted using a hemocytometer. After this, a further 6 mL of PERI.4U® thawing medium was added to the cell suspension. A cell pellet was obtained by centrifugation at 260 xg (e.g. 1,100 RPM) for 6 minutes at room temperature. Cells were then resuspended in complete PERI.4U® culture medium supplied by the manufacturer. Cells were plated at a density of 50,000 to 150,000 cells per cm$^2$ on cell culture plates coated with poly-L-ornithine and laminin. Cells were cultured at 37° C. in a humidified $CO_2$ atmosphere, and medium was changed completely every 2-3 days during culture.

For toxin treatment, serial dilutions of BoNTs were prepared in PERI.4U® culture medium. The medium from the wells to be treated was collected and filtered (0.2 µm filter). 125 µL of the filtered medium was added back to each test well. 125 µL of diluted toxin was then added to the plate (triplicate wells). The treated cells were incubated at 37° C., 10% $CO_2$, for 48±1 h).

Analysis of BoNT Activity Using the SNAP-25 Cleavage Assay

Following treatment, BoNT was removed and cells were washed once in PBS (Gibco, UK). Cells were lysed in 1× NUPAGE™ lysis buffer (Life Technologies) supplemented with 0.1 M dithiothiolol (DTT) and 250 units/mL BENZO-NASE® nuclease (Sigma). Lysate proteins were separated by SDS-PAGE and transferred to nitrocellulose membranes. Membranes were probed with a primary antibody specific for SNAP-25 (Sigma #S9684) which recognizes uncleaved SNAP-25 as well as SNAP-25 cleaved by the BoNT/A endopeptidase. The secondary antibody used was an HRP-conjugated anti-rabbit IgG (Sigma #A6154). Bands were detected by enhanced chemiluminescence and imaged using a pXi6 Access (Synoptics, UK). The intensity of bands was determined using GENETOOLS® software (Syngene, Cambridge, UK) and the percentage of SNAP-25 cleaved at each concentration of BoNT calculated. Data were fitted to a 4-parameter logistic equation and pEC$_{50}$ calculated using GRAPHPAD PRISM® version 6 (GraphPad).

Figure 6:
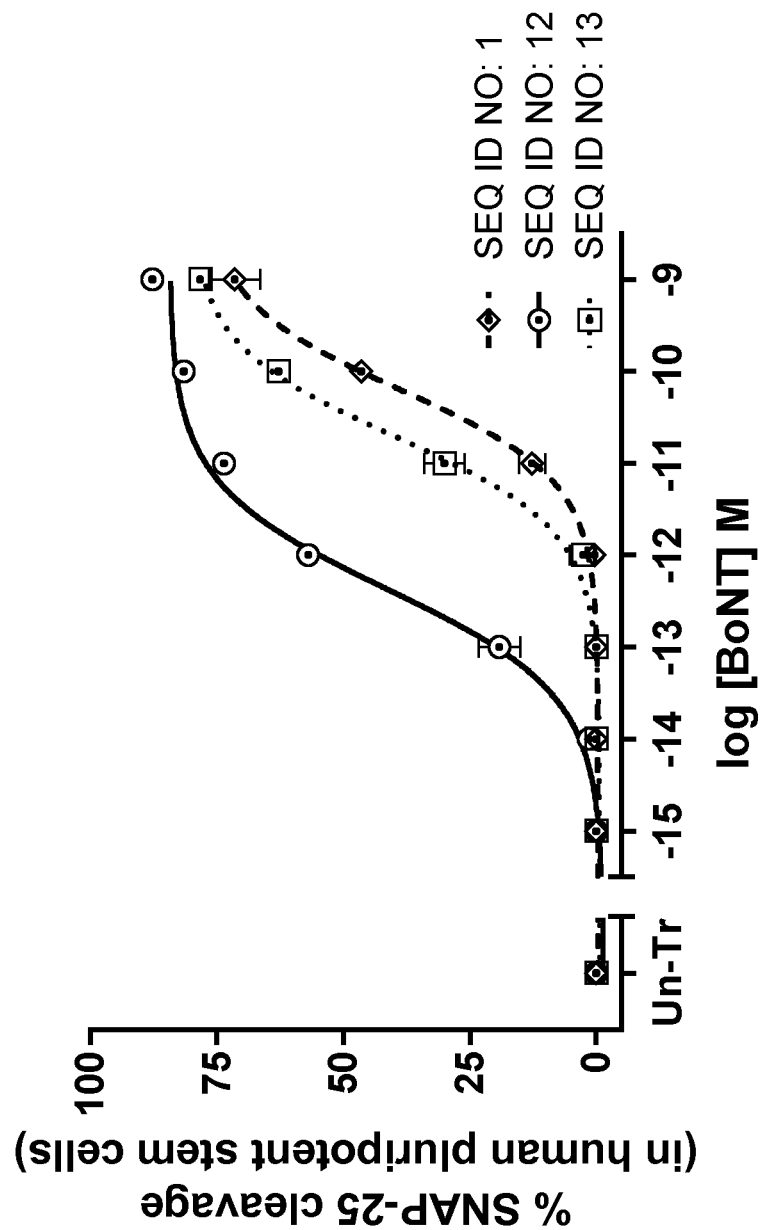
FIG. 6—Cleavage of SNAP-25 by recombinant BoNT/A and BoNT/AB chimera 3B and 3C (SEQ ID NOs: 1, 12 and 13 respectively) in human induced pluripotent stem cell derived peripheral neurons (PERL4U-Axiogenesis, Germany). PERL4U cells were exposed to various concentrations of recombinant BoNT/A, or BoNT/AB chimera 3B or 3C for 24 hours, at 37° C. in a humidified $CO_2$ atmosphere containing 5% $CO_2$. Cells were then lysed with 1× NUPAGE™ buffer supplemented with DTT and BENZO-NASE® nuclease. The samples were transferred to microcentrifuge tubes, heated for 5 main at 90° C. on heat block and stored at −20° C., before analysis of SNAP-25 cleavage by Western blot. SNAP-25 was detected using a polyclonal antibody, that detects both the full length and cleaved forms of SNAP-25 (Sigma #S9684). Anti-rabbit HRP (Sigma #A6154) was used as the secondary antibody.

FIG. 6 shows that chimera 3B and 3C displayed greater potency than rBoNT/A1 in cleaving SNAP-25 in induced human pluripotent stem cells but the former significantly more so. This can be explained by the double mutation which increases the affinity of chimera 3B for the human synaptotagmin II protein receptor present in these cells (FIG. 6, table 6).

TABLE 6

|  | pEC$_{50}$ ± SEM |
|---|---|
| rBoNT/A1 | 10.21 ± 0.05 |
| Chimera 3B | 12.38 ± 0.06 |
| Chimera 3C | 10.72 ± 0.08 |

Digit Abduction Scoring (DAS) Assay—Safety Ratio

The method to measure the activity of BoNTs in the DAS assay is based on the startled response toe spreading reflex of mice, when suspended briefly by the tail. This reflex is scored as Digit Abduction Score (DAS) and is inhibited after administration of BoNT into the gastrocnemius-soleus muscles of the hind paw. Mice are suspended briefly by the tail to elicit a characteristic startled response in which the animal extends its hind limb and abducts its hind digits. (Aoki et al. 1999, Eur. J. Neurol.; 6 (suppl. 4) S3-S10)

On the day of injection, mice were anaesthetized in an induction chamber receiving isoflurane 3% in oxygen. Each mouse received an intramuscular injection of BoNT or vehicle (phosphate buffer containing 0.2% gelatine) in the gastrocnemius-soleus muscles of the right hind paw.

Following neurotoxin injection, the varying degrees of digit abduction were scored on a scale from zero to four, where 0=normal and 4=maximal reduction in digit abduction and leg extension. ED$_{50}$ was determined by nonlinear adjustment analysis using average of maximal effect at each dose. The mathematical model used was the 4 parameters logistic model.

DAS was performed every 2 hours during the first day after dosing; thereafter it was performed 3 times a day for 4 days for all doses. Animals of the groups injected with vehicle and the lowest dose that induced during the first four days of injection a DAS of 4 were thereafter monitored until complete recovery of the muscle weakness to a DAS of 0 (no observed muscle weakness).

For calculation of the safety ratio all animals were weighed the day before toxin injection (D0) and thereafter once daily throughout the duration of the study. The average body weight, its standard deviation, and the standard error mean were calculated daily for each dose-group. To obtain the safety ratio for a BoNT (−10%ΔBW/ED$_{50}$), the dose at which at any time during the study the average weight of a dose-group was lower than 10% of the average weight at D0 of that same dose-group was divided by the ED$_{50}$ for the BoNT studied. The lethal dose was defined as the dose at which one or more of the animals within that dose-group died.

Figure 7:
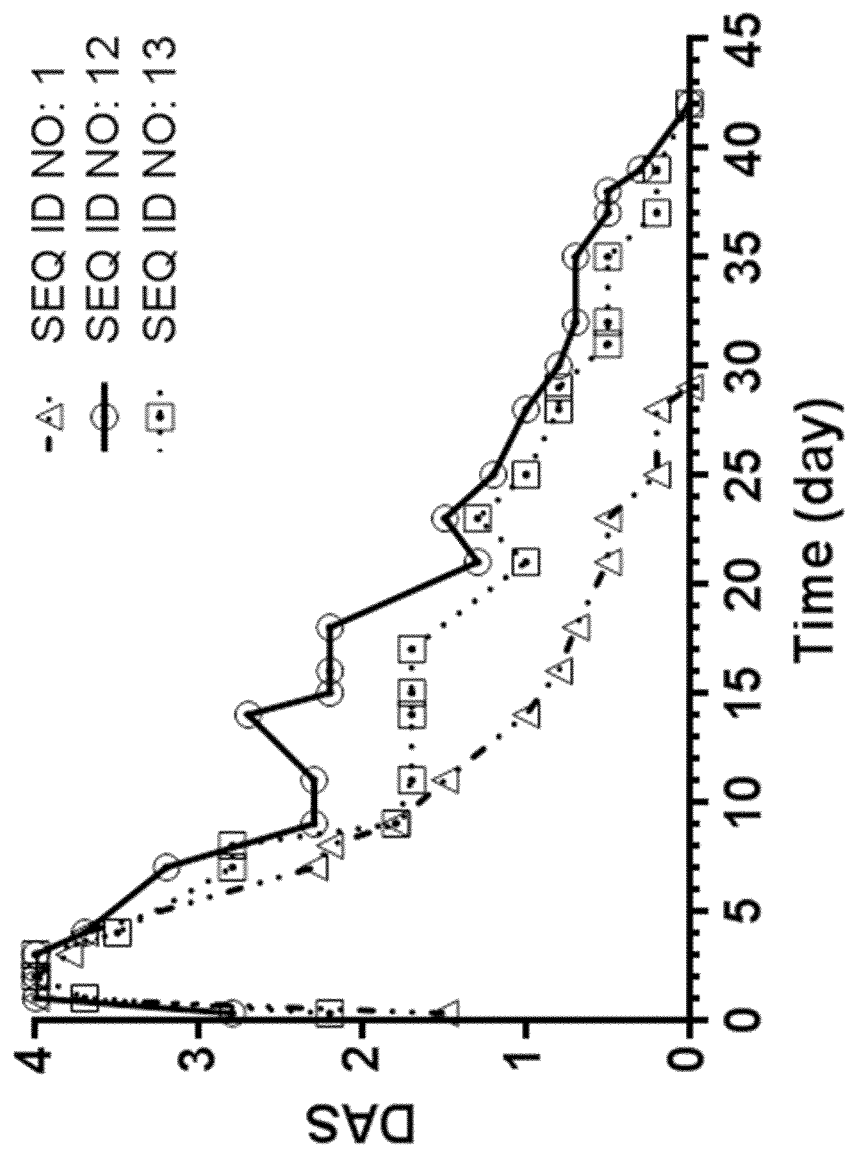
FIG. 7—Duration of muscle weakening over time in the mouse digit abduction scoring assay. Mice were injected into the gastrocnemius-soleus complex muscles of one hind limb, under short general anaesthesia; muscle weakening was measured on a 0-4 scale using the digit abduction score (DAS). Animals of the group injected with the lowest dose that induced during the first four days of injection a DAS of 4 were monitored until complete recovery of the muscle weakness to a DAS of 0 (no observed muscle weakness).

FIG. 7 shows the duration of muscle weakening over time in the mouse digit abduction scoring assay for rBoNT/A1, chimera 3B and chimera 3C (SEQ ID NO: 1, 12 and 13), showing that the chimera has longer duration of action.

Table 7 below provides the ED$_{50}$ and DAS 4 doses determined for rBoNT/A1 and chimeras 3B and 3C in the mouse DAS assay. The table also provide the total duration of action for the DAS 4 dose until complete recovery of the muscle weakness to a DAS of 0 (no observed muscle weakness). In addition, the table shows the mouse lethal dose and the safety ratio (−10%, ΔBW/ED$_{50}$), as defined in the text above. In comparison to rBoNT/A1, chimeras 3B and 3C have longer duration of action, a better safety ratio, and a higher lethal dose. Studies shown in FIG. 7 and table 7 were performed in mice obtained from Janvier laboratories.

TABLE 7

|  | ED$_{50}$ (DAS 2) Dose (pg/ mouse) | DAS 4 dose (pg/ mouse) | Total duration of action (day) with lowest DAS 4 dose | Mouse lethal dose (pg) | Safety ratio (−10% ΔBW/ED$_{50}$) |
| --- | --- | --- | --- | --- | --- |
| rBoNT/A1 | 0.9 | 2.3 | 29 | 18 | 4.5 |
| Chimera 3B | 8.0 | 89 | 42 | 200 | 14.1 |
| Chimera 3C | 5.0 | 26 | 42 | 8.9 | 7.4 |

Example 5

Figure 8:
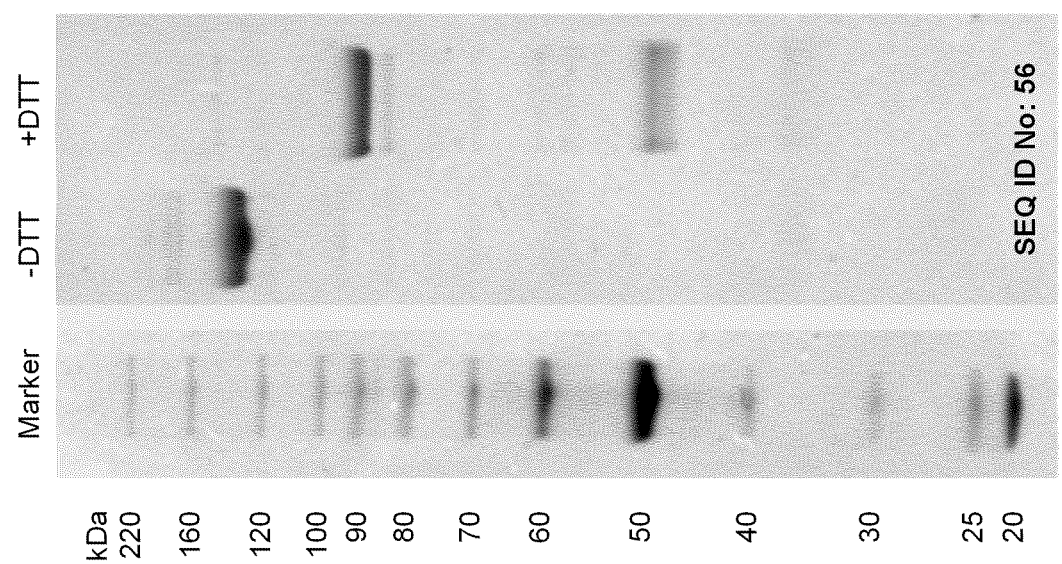
FIG. 8—SDS PAGE of purified recombinant BoNT/BC (SEQ ID NO: 56). Lanes are labelled "Marker" (molecular weight marker), "−DTT" (oxidised BoNT/BC chimera sample), and "+DTT" (reduced BoNT/BC chimera sample).

Expression and Purification of BoNT/BC Chimera and Confirmation of Functional Activity BoNT/BC chimera 4 (SEQ ID NO: 56) was cloned, expressed and purified as described in Example 2 except for the use of a different expression cell strain (BL21) and proteolytic cleavage with trypsin rather than endoproteinase Lys-C (FIG. 8).

TABLE 8

| chimeric BoNT/BC construct | | |
| --- | --- | --- |
| Molecule | SEQ ID NO | Sequence |
| Chimera 4 | 56 | B1: 1-859 + C1: 868-1291 |

This chimera was tested for functional activity in a VAMP-2 cleavage assay.

Rat Cortical Neuron VAMP-2 Cleavage Assay

Rat cortical neurons were prepared and maintained on poly-L-ornithine (PLO) coated 96-well plates at a density of 20000 cells/well in 125 μL NEUROBASAL® media containing 2% B27 supplement, 0.5 mM GLUTAMAX™ supplement, 1% foetal bovine serum (FBS) and 100 U/mL penicillin/streptomycin, at 37° C. in a humidified atmosphere containing 5% CO$_2$. A further 125 μL NEUROBASAL® medium containing 2% B27, 0.5 mM GLUTAMAX™ supplement was added on DIV 4. Cells were maintained by replacement of half the medium every 3-4 days. On DIV 11, 1.5 μM cytosine β-D-arabinofuranoside (AraC) was added to the medium to prevent proliferation of non-neuronal cells. Cortical neurons at DIV 19-21 were treated with a concentration range of BoNT (30 fM-3 nM) for 24 hours at 37° C.

Analysis of BoNT Activity Using the VAMP-2 Cleavage Assay

Cells were briefly washed in assay medium (NEUROBASAL® media w/o phenol red, 2% B27, 0.5 mM GLUTAMAX™ supplement, 10 μM TFB-TBOA ((3S)-3-[[3-[[4-(Trifluoromethyl) benzoyl] amino] phenyl] methoxy]-L-aspartic acid, before lysis in 100 μL lysis buffer (NUPAGE® LDS sample buffer, 1 mM DTT and 1:500 BENZONASE® nuclease) and heated at 90° C. for 5 minutes. 15 μL lysates were run in 12% Bis-Tris gels at 200 V for 50 minutes with MES buffer. Proteins were transferred onto nitrocellulose membranes via a TRANS-BLOT® TURBO™ transfer system (Biorad) using the low MW program Membranes were blocked with 5% low fat milk in PBST and then probed with rabbit anti-VAMP-2 (Abcam ab3347, 1:1000) primary antibody and then HRP-conjugated anti-rabbit secondary antibody (Sigma #A6154). Membranes were developed with SUPERSIGNAL® West Dura chemiluminescent substrate and visualized using a SYNGENE® PXi system. Band densitometry was analyzed using GENETOOLS® software (Syngene) and VAMP-2 percentage cleavage at each concentration of BoNT was determined relative to the control wells. Data was fit to a 4-parameter logistic equation and the pEC$_{50}$ calculated using GRAPHPAD PRISM® software (GraphPad).

Figure 9:
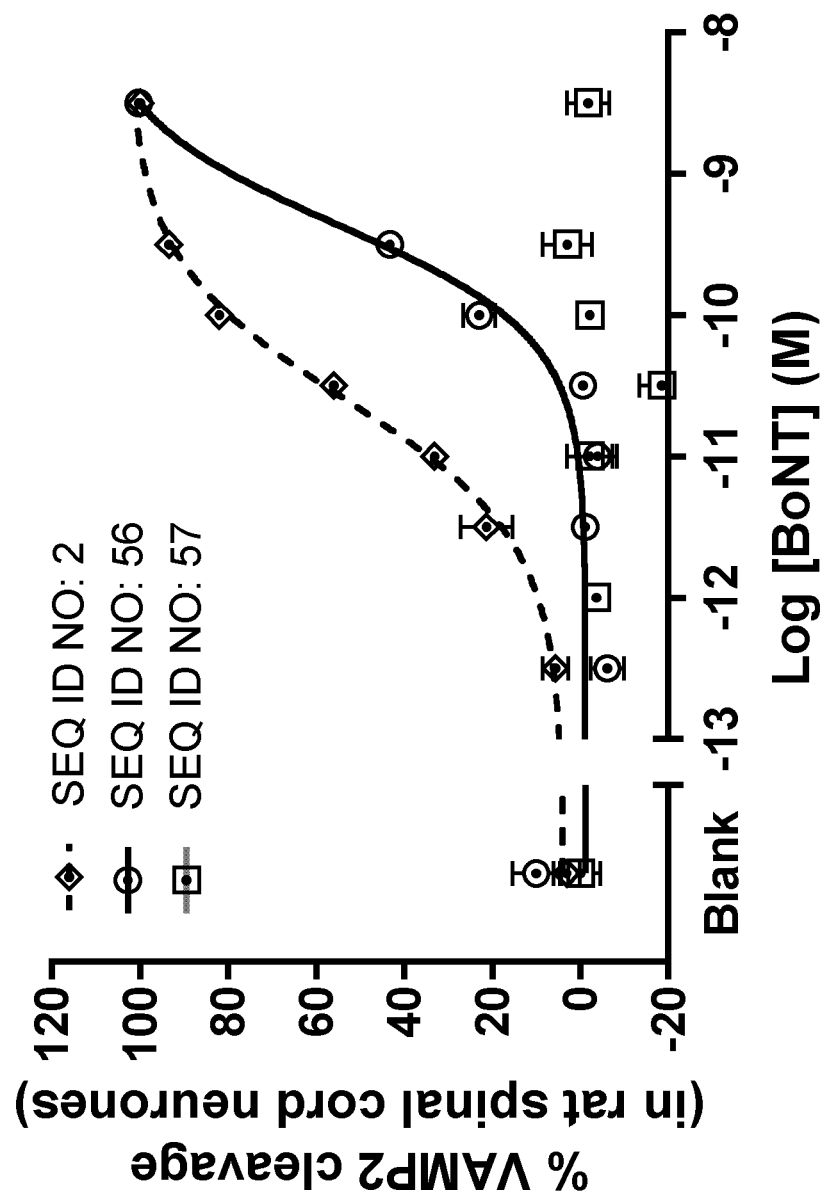
FIG. 9—Cleavage of VAMP-2 by native BoNT/B, BoNT/BC chimera, and inactive recombinant BoNT/B (SEQ ID NOs: 56 and 57, respectively) in rat cortical neurons. Cells were exposed to various concentrations of BoNT for 24 hours, at 37° C. in a humidified $CO_2$ atmosphere containing 5% $CO_2$. Cells were lysed with 1× NUPAGE™ buffer supplemented with DTT and BENZONASE® nuclease, and heated for 5 min at 90° C. before storage at −20° C. Samples were analysed for VAMP-2 cleavage by Western blot using a polyclonal rabbit anti-VAMP-2 (Abeam ab3347, 1:1000) primary antibody, and an HRP-conjugated anti-rabbit secondary antibody (Sigma #A6154).

FIG. 9 shows that chimera 4 is able to bind to rat spinal cord neurones, translocate into the cytoplasm, and specifically cleave its substrate VAMP-2. As a point of reference, this chimera is clearly functional compared an inactive recombinant BoNT/B1 molecule (having a double mutation at E231Q and H234Y, and also referred herein as BoNT/B1 (0)) (SEQ ID NO: 57), and is almost as active as the native BoNT/B1 molecule (SEQ ID NO: 2) (Table 9). This may be explained by the high affinity binding of BoNT/B to synaptotagmin and various gangliosides present on the rat cell surface, whereas the binding domain of C in chimera 4, is only known to bind with lower affinity to gangliosides. This is supported by data from the light chain protease activity assay, as shown further below.

TABLE 9

| | pEC50 ± SEM (VAMP-2 cleavage assay in rat cortical cells) |
| --- | --- |
| native BoNT/B1 | 10.60 ± 0.06 |
| Chimera 4 | 9.36 ± 0.15 |
| BoNT/B1(0) | inactive |

Light Chain Protease Activity Assay

The light chain activity of serotype B was assessed using the BOTEST® (BioSentinel A1009) cell-free assay according to the manufacturer's instructions. For example, BoNTs were diluted to 1.39 nM in BOTEST® Reaction Buffer (50 mM HEPES-NaOH, 5 mM NaCl, 10 μM ZnCl$_2$, 0.1% Tween-20, 0.1 mg/ml BSA, pH 7.1) and reduced with 5 mM DTT for 30 minutes at room temperature. VAMP-2 peptide reporter (CFP-VAMP-2 (33-94)-YFP in 50 mM HEPES-NaOH, 10 mM NaCl, 15% glycerol) at a final concentration of 200 nM was combined with a concentration range of BoNTs (500 fM-1.25 nM, final) in black MAXISORP® plates (Nunc) in a final assay volume of 100 μL/well. The plates were sealed and incubated at 30° C. for 18 hours away from light. The loss of CFP to YFP FRET fluorescence at 528 nm and gain of GFP fluorescence at 485 nm following excitation at 440 nm was measured using a BIOTEK® SYNGERY® HT plate reader. The fluorescence emission ratio of uncleaved:cleaved reporter substrate at each BoNT concentration was fit to a 4-parameter logistic equation and the pEC$_{50}$ calculated using GRAPHPAD PRISM® software.

Figure 10:
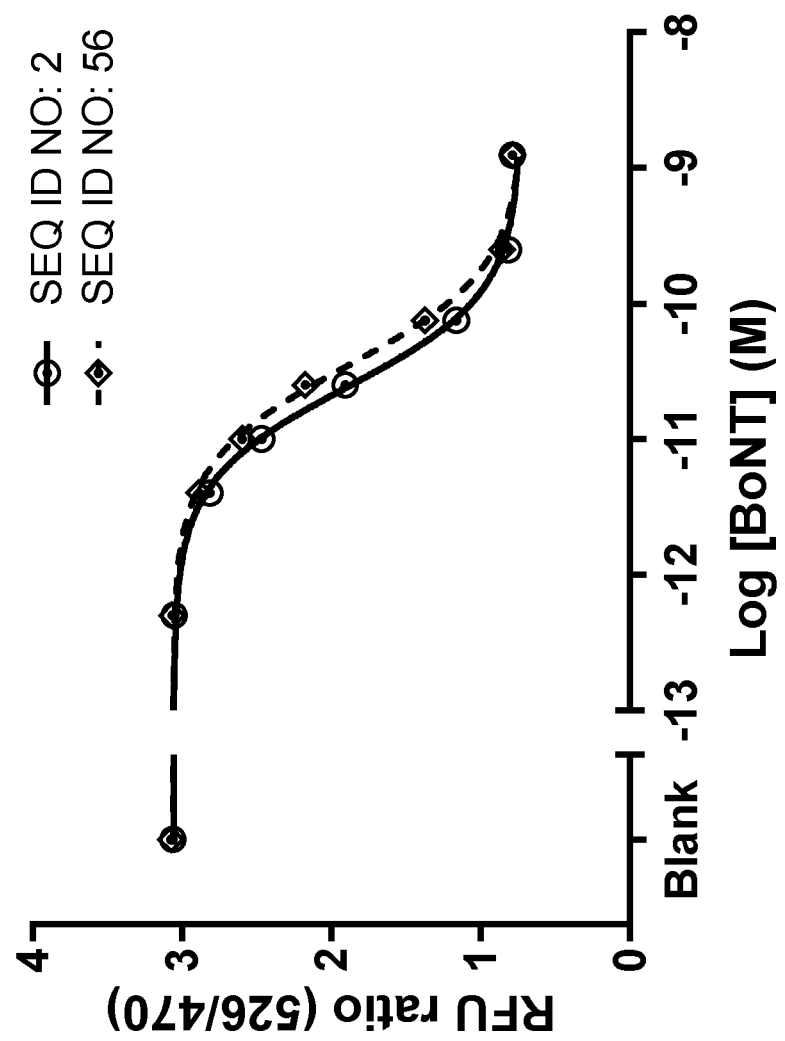
FIG. 10—Cleavage of VAMP-2 peptide reporter by native BoNT/B and BoNT/BC chimera (SEQ ID NO: 2 and 56, respectively) using the BOTEST® BoNT detection kit (Bio-Sentinel). Various concentrations of BoNT were incubated at 30° C. for 18 hours with a VAMP-2 peptide with a CFP-YFP FRET pair as a reporter and the proportion of uncleaved: cleaved reporter substrate was measured as a loss of YFP fluorescence intensity at 528 nm and gain of CFP fluorescence at 485 nm following excitation at 440 nm.

The light chain protease activity assay confirms that the light chain of chimera 4 is as active as the one of native BoNT/B1 (see FIG. 10, and Table 10), and therefore that, as explained above, the results of the VAMP-2 cleavage assay may be explained by the fact that BoNT/B has a higher affinity to synaptotagmin and various gangliosides present on the rat cell surface, compared to the binding domain of C in chimera 4 which only binds to gangliosides.

TABLE 10

|  | pEC50 ± SEM (VAMP-2 peptide cleavage assay in vitro) |
| --- | --- |
| native BoNT/B1 | 10.62 ± 0.01 |
| Chimera 4 | 10.46 ± 0.01 |
| BoNT/B1(0) | NA |

The invention claimed is:

1. A chimeric neurotoxin comprising a $LH_N$ domain from a first neurotoxin covalently linked to a $H_C$ domain from a second neurotoxin, wherein:
   the first and second neurotoxins are different;
   the C-terminal amino acid residue of the $LH_N$ domain corresponds to the first amino acid residue of the $3_{10}$ helix separating the $LH_N$ and $H_C$ domains in the first neurotoxin; and
   the N-terminal amino acid residue of the $H_C$ domain corresponds to the second amino acid residue of the $3_{10}$ helix separating the $LH_N$ and $H_C$ domains in the second neurotoxin.

2. The chimeric neurotoxin of claim 1, wherein the first and second neurotoxins are each individually selected from botulinum neurotoxin (BoNT) serotypes A, B, C, D, E, F, or G, or Tetanus neurotoxin (TeNT).

3. The chimeric neurotoxin of claim 1, wherein the $LH_N$ domain corresponds to:
   amino acid residues 1 to 872 of SEQ ID NO: 1, or a sequence having at least 70% sequence identity thereto;
   amino acid residues 1 to 859 of SEQ ID NO: 2, or a sequence having at least 70% sequence identity thereto;
   amino acid residues 1 to 867 of SEQ ID NO: 3, or a sequence having at least 70% sequence identity thereto;
   amino acid residues 1 to 863 of SEQ ID NO: 4, or a sequence having at least 70% sequence identity thereto;
   amino acid residues 1 to 846 of SEQ ID NO: 5, or a sequence having at least 70% sequence identity thereto;
   amino acid residues 1 to 865 of SEQ ID NO: 6, or a sequence having at least 70% sequence identity thereto;
   amino acid residues 1 to 864 of SEQ ID NO: 7, or a sequence having at least 70% sequence identity thereto; or
   amino acid residues 1 to 880 of SEQ ID NO: 8, or a sequence having at least 70% sequence identity thereto;
   and wherein the $H_C$ domain corresponds to:
   amino acid residues 873 to 1296 of SEQ ID NO: 1, or a sequence having at least 70% sequence identity thereto;
   amino acid residues 860 to 1291 of SEQ ID NO: 2, or a sequence having at least 70% sequence identity thereto;
   amino acid residues 868 to 1291 of SEQ ID NO: 3, or a sequence having at least 70% sequence identity thereto;
   amino acid residues 864 to 1276 of SEQ ID NO: 4, or a sequence having at least 70% sequence identity thereto;
   amino acid residues 847 to 1251 of SEQ ID NO: 5, or a sequence having at least 70% sequence identity thereto;
   amino acid residues 866 to 1275 of SEQ ID NO: 6, or a sequence having at least 70% sequence identity thereto;
   amino acid residues 865 to 1297 of SEQ ID NO: 7, or a sequence having at least 70% sequence identity thereto; or
   amino acid residues 881 to 1315 of SEQ ID NO: 8, or a sequence having at least 70% sequence identity thereto.

4. The chimeric neurotoxin of claim 1, wherein the first neurotoxin is a BoNT/A and wherein the second neurotoxin is a BoNT/B.

5. The chimeric neurotoxin of claim 4, wherein the first neurotoxin is a BoNT/A1 and the second neurotoxin is a BoNT/B1.

6. The chimeric neurotoxin of claim 5, wherein the $LH_N$ domain corresponds to amino acid residues 1 to 872 of SEQ ID NO: 1, or a sequence having at least 70% sequence identity thereto, and the $H_C$ domain corresponds to amino acid residues 860 to 1291 of SEQ ID NO: 2, or a sequence having at least 70% sequence identity thereto.

7. The chimeric neurotoxin of claim 4, wherein the $H_C$ domain comprises at least one amino acid residue substitution, addition or deletion in the $H_{CC}$ subdomain that has the effect of increasing the binding affinity of the $H_C$ domain for the human Syt II receptor as compared to the natural sequence.

8. The chimeric neurotoxin of claim 7, wherein the $H_C$ domain corresponds to amino acid residues 860 to 1291 of SEQ ID NO: 2, or a sequence having at least 70% sequence identity thereto, and comprises an amino acid substitution selected from the group consisting of: V1118M; Y1183M; E1191M; E1191I; E1191Q; E1191T; S1199Y; S1199F; S1199L; S1201V; E1191C; E1191V, E1191L; E1191Y;

S1199W; S1199E; S1199H; W1178Y; W1178Q; W1178A; W1178S; Y1183C; and Y1183P.

9. The chimeric neurotoxin of claim 7, wherein the $H_C$ domain corresponds to amino acid residues 860 to 1291 of SEQ ID NO: 2, or a sequence having at least 70% sequence identity thereto, and comprises two amino acid substitutions selected from the group consisting of: E1191M and S1199L; E1191M and S1199Y; E1191M and S1199F; E1191Q and S1199L; E1191Q and S1199Y; E1191Q and S1199F; E1191M and S1199W; E1191M and W1178Q; E1191C and S1199W; E1191C and S1199Y; E1191C and W1178Q; E1191Q and S1199W; E1191V and S1199W; E1191V and S1199Y; and E1191V and W1178Q.

10. The chimeric neurotoxin of claim 9, wherein the substitutions are E1191M and S1199Y.

11. The chimeric neurotoxin of claim 7, wherein the $H_C$ domain corresponds to amino acid residues 860 to 1291 of SEQ ID NO: 2, or a sequence having at least 70% sequence identity thereto, and comprises the following substitutions: E1191M; S1199W; and W1178Q.

12. The chimeric neurotoxin of claim 1, wherein the first neurotoxin is a BoNT/B and the second neurotoxin is a BoNT/C.

13. The chimeric neurotoxin of claim 12, wherein the first neurotoxin is a BoNT/B1 and the second neurotoxin is a BoNT/C1.

14. The chimeric neurotoxin of claim 13, wherein the $LH_N$ domain corresponds to amino acid residues 1 to 859 of SEQ ID NO: 2, or a sequence having at least 70% sequence identity thereto, and the $H_C$ domain corresponds to amino acid residues 868 to 1291 of SEQ ID NO: 3, or a sequence having at least 70% sequence identity thereto.

15. A pharmaceutical composition comprising the chimeric neurotoxin of claim 1, and a pharmaceutically acceptable carrier, an excipient, an adjuvant, a propellant, and/or a salt.

16. A kit comprising the pharmaceutical composition of claim 15 and instructions for therapeutic or cosmetic administration of the composition to a subject in need thereof.

17. A method for producing the chimeric neurotoxin of claim 1, the method comprising the step of culturing a cell comprising a nucleotide sequence encoding the chimeric neurotoxin under conditions wherein the chimeric neurotoxin is produced.

* * * * *